(12) United States Patent
Baker-Glenn et al.

(10) Patent No.: US 8,815,882 B2
(45) Date of Patent: Aug. 26, 2014

(54) PYRAZOLE AMINOPYRIMIDINE DERIVATIVES AS LRRK2 MODULATORS

(75) Inventors: Charles Baker-Glenn, St. Neots (GB); Daniel Jon Burdick, Burlingame, CA (US); Mark Chambers, Puckeridge (GB); Bryan K. Chan, San Carlos, CA (US); Huifen Chen, Burlingame, CA (US); Anthony Estrada, San Carlos, CA (US); Zachary Kevin Sweeney, Redwood City, CA (US)

(73) Assignee: Genentech, Inc., South San Francisco, CA (US)

(\*) Notice: Subject to any disclaimer, the term of this patent is extended or adjusted under 35 U.S.C. 154(b) by 0 days.

(21) Appl. No.: 13/292,668

(22) Filed: Nov. 9, 2011

(65) Prior Publication Data

US 2012/0157427 A1 Jun. 21, 2012

Related U.S. Application Data

(60) Provisional application No. 61/546,613, filed on Oct. 13, 2011, provisional application No. 61/412,273, filed on Nov. 10, 2010.

(51) Int. Cl.
*A01N 43/54* (2006.01)
*A61K 31/505* (2006.01)

(52) U.S. Cl.
USPC ............ 514/272; 514/275; 544/320; 544/324

(58) Field of Classification Search
USPC ........... 544/320, 321, 324, 331; 514/272, 275
See application file for complete search history.

(56) References Cited

U.S. PATENT DOCUMENTS

| | | | |
|---|---|---|---|
| 6,107,301 A | 8/2000 | Aldrich et al. | |
| 6,172,222 B1 | 1/2001 | Gilbert et al. | |
| 6,197,779 B1 | 3/2001 | Andries et al. | |
| 6,342,503 B1 | 1/2002 | Aldrich et al. | |
| 6,440,986 B2 | 8/2002 | Andries et al. | |
| 6,664,247 B2 | 12/2003 | Bebbington et al. | |
| 6,878,697 B2 | 4/2005 | Metcalf et al. | |
| 6,903,213 B2 | 6/2005 | Andries et al. | |
| 6,908,920 B2 | 6/2005 | Thomas et al. | |
| 6,939,872 B2 | 9/2005 | Newcombe et al. | |
| 6,969,714 B2 | 11/2005 | Breault et al. | |
| 7,115,739 B2 | 10/2006 | Bebbington et al. | |
| 7,166,599 B2 | 1/2007 | Bornemann et al. | |
| 7,173,028 B2 | 2/2007 | Dahmann et al. | |
| 7,235,561 B2 | 6/2007 | Brumby et al. | |
| 7,235,562 B2 | 6/2007 | Kath et al. | |
| 7,241,769 B2 | 7/2007 | Stadtmueller et al. | |
| 7,253,174 B2 | 8/2007 | Ahmed et al. | |
| 7,262,203 B2 | 8/2007 | Boloor et al. | |
| 7,276,510 B2 | 10/2007 | Kukla et al. | |
| 7,288,547 B2 | 10/2007 | Lucking et al. | |
| 7,291,624 B2 | 11/2007 | Brumby et al. | |
| 7,338,958 B2 | 3/2008 | Luecking et al. | |
| 7,427,681 B2 | 9/2008 | Bebbington et al. | |
| 7,435,814 B2 | 10/2008 | Singh et al. | |
| 7,456,191 B2 | 11/2008 | Lucking et al. | |
| 7,479,495 B2 | 1/2009 | Moriarty et al. | |
| 7,485,638 B2 | 2/2009 | Newcombe et al. | |
| 7,485,724 B2 | 2/2009 | Singh et al. | |
| 7,498,435 B2 | 3/2009 | Singh et al. | |
| 7,504,410 B2 | 3/2009 | Bryant et al. | |
| 7,521,457 B2 | 4/2009 | Stadtmueller et al. | |
| 7,550,473 B2 | 6/2009 | Cardozo et al. | |
| 7,557,207 B2 | 7/2009 | Cooper et al. | |
| 7,557,210 B2 | 7/2009 | Singh et al. | |
| 7,576,053 B2 | 8/2009 | Masuda et al. | |
| 7,589,197 B2 | 9/2009 | Yen et al. | |
| 7,598,260 B2 | 10/2009 | Brumby et al. | |
| 7,601,714 B2 | 10/2009 | Barbosa et al. | |
| 7,709,480 B2 | 5/2010 | Dahmann et al. | |
| 7,943,629 B2 | 5/2011 | Luecking et al. | |
| 8,354,420 B2 * | 1/2013 | Baker-Glenn et al. ........ 514/269 |
| 2002/0032198 A1 | 3/2002 | Gilbert et al. | |
| 2003/0004164 A1 | 1/2003 | Bebbington et al. | |
| 2003/0055044 A1 | 3/2003 | Davies et al. | |
| 2003/0064981 A1 | 4/2003 | Knegtel et al. | |
| 2003/0064982 A1 | 4/2003 | Davies et al. | |

(Continued)

FOREIGN PATENT DOCUMENTS

EP 2161259 A1 3/2010
EP 1841760 B1 8/2011

(Continued)

OTHER PUBLICATIONS

Z. Liu et al., 20 Human Molecular Genetics, 3933-3942 (2011).*
R. J. Nichols et al., 424 Biochemical Journal 47-60 (2009).*
J.H. Poupaert, Drug Design: Basic Principles and Applications, in 2 Encyclopedia of Pharmaceutical Technology 1362-1369 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403 (L.L. Brunton et al., eds., 11th ed., 2006).*

*Primary Examiner* — Deepak Rao
*Assistant Examiner* — Alexander R Pagano
(74) *Attorney, Agent, or Firm* — Robert C. Hall

(57) ABSTRACT

Compounds of the formula I:

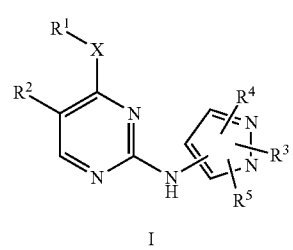

I or pharmaceutically acceptable salts thereof,
wherein X, $R^1$, $R^2$, $R^3$, $R^4$ and $R^5$ are as defined herein. Also disclosed are methods of making the compounds and using the compounds for treatment of diseases associated with LRRK2 receptor, such as Parkinson's disease.

22 Claims, No Drawings

(56) References Cited

U.S. PATENT DOCUMENTS

| | | |
|---|---|---|
| 2003/0078166 A1 | 4/2003 | Davies et al. |
| 2003/0105090 A1 | 6/2003 | Bebbington et al. |
| 2003/0171359 A1 | 9/2003 | Dahmann et al. |
| 2004/0167141 A1 | 8/2004 | Bebbington et al. |
| 2005/0256111 A1 | 11/2005 | Kath et al. |
| 2006/0252748 A1 | 11/2006 | Lindenthal et al. |
| 2007/0032514 A1 | 2/2007 | Zahn et al. |
| 2008/0249079 A1 | 10/2008 | Chen et al. |
| 2009/0041786 A1 | 2/2009 | Li et al. |
| 2009/0163467 A1 | 6/2009 | Zahn et al. |
| 2009/0181995 A1 | 7/2009 | Djung et al. |
| 2009/0318405 A1 | 12/2009 | Li et al. |
| 2010/0069357 A1 | 3/2010 | Bergeron et al. |
| 2010/0081679 A1 | 4/2010 | Greul et al. |
| 2010/0130486 A1 | 5/2010 | Singh et al. |
| 2010/0137313 A1 | 6/2010 | Boriack-sjodin et al. |
| 2010/0152266 A1 | 6/2010 | Dunkel et al. |
| 2010/0204229 A1 | 8/2010 | Beier et al. |
| 2011/0046093 A1 | 2/2011 | Hollick et al. |
| 2011/0105472 A1 | 5/2011 | Greul et al. |
| 2011/0112063 A1 | 5/2011 | Marsilje et al. |
| 2011/0112096 A1 | 5/2011 | Marsilje et al. |
| 2011/0159019 A1 | 6/2011 | Tanaka et al. |
| 2011/0195968 A1 | 8/2011 | Greul et al. |
| 2011/0230478 A1 | 9/2011 | Greul et al. |
| 2011/0245242 A1 | 10/2011 | Greul et al. |
| 2011/0245249 A1 | 10/2011 | Wasnaire et al. |
| 2011/0251174 A1 | 10/2011 | Zahn et al. |
| 2011/0301141 A1* | 12/2011 | Baker-Glenn et al. ... 514/210.16 |
| 2013/0096102 A1* | 4/2013 | Baker-Glenn et al. ... 514/210.18 |
| 2013/0156700 A1* | 6/2013 | Marik et al. ............ 424/1.89 |
| 2013/0157999 A1* | 6/2013 | Baker-Glenn et al. ... 514/210.18 |
| 2013/0158006 A1* | 6/2013 | Baker-Glenn et al. ... 514/211.05 |
| 2013/0158032 A1* | 6/2013 | Baker-Glenn et al. ..... 514/235.8 |
| 2013/0158057 A1* | 6/2013 | Baker-Glenn et al. ........ 514/275 |

FOREIGN PATENT DOCUMENTS

| | | |
|---|---|---|
| GB | 2388596 A1 | 11/2003 |
| WO | 95/10506 | 4/1995 |
| WO | 00/27825 | 5/2000 |
| WO | 01/12621 A1 | 2/2001 |
| WO | 01/22938 A1 | 4/2001 |
| WO | 01/85700 A2 | 11/2001 |
| WO | 02/04429 A1 | 1/2002 |
| WO | 02/22608 A1 | 3/2002 |
| WO | 02/46171 A2 | 6/2002 |
| WO | 02/46184 A1 | 6/2002 |
| WO | 02/50065 A2 | 6/2002 |
| WO | 02/50066 A2 | 6/2002 |
| WO | 02/059112 A2 | 8/2002 |
| WO | 02/062789 A1 | 8/2002 |
| WO | 02/066461 A1 | 8/2002 |
| WO | 02/092573 A2 | 11/2002 |
| WO | 02/102313 A2 | 12/2002 |
| WO | 03/002544 A1 | 1/2003 |
| WO | 03/030909 A1 | 4/2003 |
| WO | 03/040141 A1 | 5/2003 |
| WO | 03/055489 A1 | 7/2003 |
| WO | 03/063794 A2 | 8/2003 |
| WO | 03/094920 A1 | 11/2003 |
| WO | 2004/005282 A1 | 1/2004 |
| WO | 2004/048343 A1 | 6/2004 |
| WO | 2005/009977 A1 | 2/2005 |
| WO | 2005/012298 A1 | 2/2005 |
| WO | 2005/013996 A2 | 2/2005 |
| WO | 2005/016893 A2 | 2/2005 |
| WO | WO 2005012294 A1 * | 2/2005 |
| WO | 2005/075468 A2 | 8/2005 |
| WO | 2005/118544 A2 | 12/2005 |
| WO | 2006/028833 A1 | 3/2006 |
| WO | 2006/053109 A1 | 5/2006 |
| WO | 2006/064251 A1 | 6/2006 |
| WO | 2006/074057 A2 | 7/2006 |
| WO | WO 2006074057 A2 * | 7/2006 |
| WO | 2006/117560 A1 | 11/2006 |
| WO | 2007/023382 A2 | 3/2007 |
| WO | 2007/030362 A1 | 3/2007 |
| WO | 2007/035309 A1 | 3/2007 |
| WO | 2007/129195 A2 | 11/2007 |
| WO | 2007/140957 A1 | 12/2007 |
| WO | 2008/016675 A1 | 2/2008 |
| WO | 2008/025556 A1 | 3/2008 |
| WO | 2008/040548 A2 | 4/2008 |
| WO | 2008/064866 A1 | 6/2008 |
| WO | 2008/073687 A2 | 6/2008 |
| WO | 2008/074515 A1 | 6/2008 |
| WO | 2008/074982 A1 | 6/2008 |
| WO | 2008/077885 A2 | 7/2008 |
| WO | 2008/079719 A1 | 7/2008 |
| WO | 2008/099210 A2 | 8/2008 |
| WO | 2008/107096 A1 | 9/2008 |
| WO | 2008/132502 A1 | 11/2008 |
| WO | 2009/040556 A1 | 4/2009 |
| WO | 2009/048751 A1 | 4/2009 |
| WO | 2009/064835 A1 | 5/2009 |
| WO | 2009/071535 A1 | 6/2009 |
| WO | 2009/071701 A1 | 6/2009 |
| WO | 2009/103032 A1 | 8/2009 |
| WO | 2009/115267 A2 | 9/2009 |
| WO | 2009/122180 A1 | 10/2009 |
| WO | 2009/127642 A2 | 10/2009 |
| WO | 2009/143389 A1 | 11/2009 |
| WO | 2009/158348 A1 | 12/2009 |
| WO | 2010/028179 A1 | 3/2010 |
| WO | 2010/055117 A1 | 5/2010 |
| WO | 2010/057833 A1 | 5/2010 |
| WO | 2010/080712 A2 | 7/2010 |
| WO | 2010/106097 A1 | 9/2010 |
| WO | 2010/118986 A1 | 10/2010 |
| WO | WO 2010113834 A1 * | 10/2010 |
| WO | 2010/129053 A2 | 11/2010 |
| WO | 2010/141406 A2 | 12/2010 |
| WO | 2010/142752 A1 | 12/2010 |
| WO | 2010/142766 A2 | 12/2010 |
| WO | 2010/144468 A1 | 12/2010 |
| WO | 2010/146132 A1 | 12/2010 |
| WO | 2010/146133 A1 | 12/2010 |
| WO | 2011/034907 A2 | 3/2011 |
| WO | 2011/038572 A1 | 4/2011 |
| WO | 2011/053861 A2 | 5/2011 |
| WO | 2011/060295 A1 | 5/2011 |
| WO | 2011/089132 A1 | 7/2011 |
| WO | 2011/090760 A4 | 7/2011 |
| WO | 2011/090761 A1 | 7/2011 |

* cited by examiner

PYRAZOLE AMINOPYRIMIDINE DERIVATIVES AS LRRK2 MODULATORS

FIELD OF THE INVENTION

This invention pertains to compounds that modulate the function of LRRK2 and are useful for treatment of LRRK2-mediated diseases and conditions such as Parkinson's disease.

BACKGROUND OF THE INVENTION

Neurodegenerative diseases such as Parkinson's disease, Lewy body dementia and Huntington's disease affect millions of individuals. Parkinson's disease is a chronic, progressive motor system disorder that afflicts approximately one out of every 1000 people, with hereditary Parkinson's disease accounting for 5-10% of all of patients. Parkinson's disease is caused by progressive loss of mid-brain dopamine neurons, leaving patients with impaired ability to direct and control their movements. The primary Parkinson's disease symptoms are trembling, rigidity, slowness of movement, and impaired balance. Many Parkinson's disease patients also experience other symptoms such as emotional changes, memory loss, speech problems, and sleeping disorders.

The gene encoding the leucine-rich repeat kinase 2 protein (LRRK2) has been identified in association with hereditary Parkinson's disease (Paisan-Ruiz et al., *Neuron*, Vol. 44(4), 2004, pp 595-600; Zimprich et al., *Neuron*, Vol. 44(4), 2004, 601-607). In-vitro studies show that Parkinson's disease-associated mutation leads to increased LRRK2 kinase activity and decreased rate of GTP hydrolysis compared to wild-type (Guo et al., *Experimental Cell Research*, Vol. 313(16), 2007, pp. 3658-3670. Anti-LRRK2 antibodies have been used to label brainstem Lewy bodies associated with Parkinson's disease and cortical antibodies associated with Lewis body-dementia suggesting that LRRK2 may play an important role in Lewie body formation and pathogenesis associated with these diseases (Zhou et al., *Molecular Degeneration*, 2006, 1:17 doi:10.1186/1750-1326-1-17). LRRK2 has also been identified as a gene potentially associated with increased susceptibility to Crohn's disease and susceptibility to leprosy (Zhang et al., *New England J. Med*. Vol. 361 (2009) pp. 2609-2618.

LRRK2 has also been associated with the transition of mild cognitive impairment to Alzheimer's disease (WO2007/149789); L-Dopa induced dyskinesia (Hurley et al., *Eur. J. Neurosci.*, Vol. 26, 2007, pp. 171-177; CNS disorders associated with neuronal progenitor differentiation (Milosevic et al., *Neurodegen.*, Vol. 4, 2009, p. 25); cancers such as kidney, breast, prostate, blood and lung cancers and acute myelogenous leukemia (WO2011/038572); papillary renal and thyroid carcinomas (Looyenga et al., www.pnas.org/cgi/doi/10.1073/pnas.1012500108); multiple myeloma (Chapman et al., *Nature* Vol. 471, 2011, pp. 467-472); amyotrophic lateral sclerosis (Shtilbans et al., *Amyotrophic Lateral Sclerosis* "Early Online 2011, pp. 1-7); rheumatoid arthritis (Nakamura et al., *DNA Res*. Vol. 13(4), 2006, pp. 169-183); and ankylosing spondylytis (Danoy et al., *PLoS Genetics*, Vol. 6(12), 2010, e1001195, pp. 1-5).

Accordingly, compounds and compositions effective at modulating LRRK2 activity may provide a treatment for neurodegenerative diseases such as Parkinson's disease and Lewie body dementia, for CNS disorders such as Alzheimer's disease and L-Dopa induced dyskinesia, for cancers such as kidney, breast, prostate, blood, papillary and lung cancers, acute myelogenous leukemia and multiple myeloma, and for inflammatory diseases such as leprosy, Crohn's disease, amyotrophic lateral sclerosis, rheumatoid arthritis, and ankylosing spondylytis. Particularly, there is a need for compounds with LRRK2 affinity that are selective for LRRK2 over other kinases, such as JAK2, which can provide effective drugs for treatment of neurodegenerative disorders such as PD.

SUMMARY OF THE INVENTION

The invention provides compounds of the formula I:

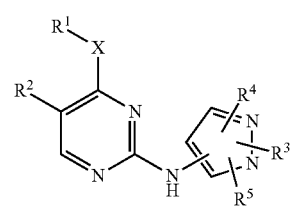

or pharmaceutically acceptable salts thereof,
wherein:
X is: —NR$^a$—; or —O— wherein R$^a$ is hydrogen or C$_{1-6}$alkyl;
R$^1$ is: C$_{1-6}$alkyl; C$_{2-6}$alkenyl; C$_{2-6}$alkynyl; halo-C$_{1-6}$alkyl; C$_{1-6}$alkoxy-C$_{1-6}$alkyl; hydroxy-C$_{1-6}$alkyl; amino-C$_{1-6}$alkyl; C$_{1-6}$alkylsulfonyl-C$_{1-6}$alkyl; C$_{3-6}$cycloalkyl optionally substituted one or more times with C$_{1-6}$alkyl; C$_{3-6}$cycloalkyl-C$_{1-6}$ alkyl wherein the C$_{3-6}$cycloalkyl portion is optionally substituted one or more times with C$_{1-6}$alkyl; heterocyclyl optionally substituted one or more times with R$^7$; or heterocyclyl-C$_{1-6}$alkyl optionally substituted one or more times with R$^7$;
or X and R$^1$ together form C$_{1-6}$alkyl; C$_{1-6}$alkoxy-C$_{1-6}$alkyl; C$_{3-6}$cycloalkyl optionally substituted one or more times with R$^6$; or C$_{3-6}$cycloalkyl-C$_{1-6}$alkyl wherein the C$_{3-6}$cycloalkyl portion is optionally substituted one or more times with R$^6$;
or R$^1$ and R$^a$ together with the atoms to which they are attached may form a three- to six-membered heterocyclic ring optionally substituted one or more times with R$^7$;
R$^2$ is: C$_{1-6}$alkyl; halo; C$_{1-6}$alkoxy; cyano; C$_{2-6}$alkynyl; C$_{2-6}$alkenyl; halo-C$_{1-6}$alkyl; halo-C$_{1-6}$alkoxy; C$_{3-6}$cycloalkyl optionally substituted one or more times with R$^6$; C$_{3-6}$cycloalkyl-C$_{1-6}$alkyl wherein the C$_{3-6}$cycloalkyl portion is optionally substituted one or more times with R$^6$; —OR$^b$ wherein R$^b$ is C$_{1-6}$alkyl, C$_{3-6}$cycloalkyl optionally substituted one or more times with R$^6$, or C$_{3-6}$cycloalkyl-C$_{1-6}$alkyl wherein the C$_{3-6}$cycloalkyl portion is optionally substituted one or more times with R$^6$; or —C(O)—R$^c$ wherein R$^c$ is C$_{1-6}$alkyl, C$_{1-6}$alkoxy, amino, or heterocyclyl optionally substituted one or more times with R$^7$;
R$^3$ is: hydrogen; C$_{1-6}$alkyl; halo-C$_{1-6}$alkyl; C$_{2-6}$alkenyl; C$_{2-6}$alkynyl; hydroxy-C$_{1-6}$alkyl; C$_{1-6}$alkoxy-C$_{1-6}$alkyl; cyano-C$_{1-6}$alkyl; C$_{1-6}$alkylsulfonyl; C$_{1-6}$alkylsulfonylC$_{1-6}$alkyl; amino-C$_{1-6}$alkyl; C$_{3-6}$cycloalkyl optionally substituted one or more times with R$^6$; C$_{3-6}$cycloalkyl-C$_{1-6}$alkyl wherein the C$_{3-6}$cycloalkyl portion is optionally substituted one or more times with R$^6$; C$_{3-6}$cycloalkyl-sulfonyl wherein the C$_{3-6}$cycloalkyl portion is optionally substituted one or more times with R$^6$; heterocyclyl optionally substituted one or more times with R$^7$; heterocyclyl-C$_{1-6}$alkyl wherein the heterocyclyl portion is optionally substituted one or more times with R$^7$; aryl optionally substituted one or more times with R$^8$; aryl-C$_{1-6}$alkyl wherein the aryl portion is optionally substituted one or more times with $R^8$; heteroaryl optionally substituted one or more times with $R^8$; heteroaryl-$C_{1-6}$alkyl wherein the heteroaryl portion is optionally substituted one or more times with $R^8$; or —Y—C(O)—$R^d$;

Y is $C_{2-6}$alkylene or a bond;

$R^d$ is $C_{1-6}$alkyl, $C_{1-6}$alkoxy, amino, $C_{1-6}$alkyl-amino, di-$C_{1-6}$alkyl-amino, halo-$C_{1-6}$alkyl-amino, di-halo-$C_{1-6}$alkyl-amino, halo-$C_{1-6}$alkyl, hydroxy-$C_{1-6}$alkyl, hydroxy, $C_{1-6}$alkoxy-$C_{1-6}$alkyl, cyano-$C_{1-6}$alkyl, $C_{1-6}$alkylsulfonyl$C_{1-6}$ alkyl, amino-$C_{1-6}$alkyl, $C_{3-6}$cycloalkyl optionally substituted one or more times with $R^6$, $C_{3-6}$cycloalkyl-$C_{1-6}$alkyl wherein the $C_{3-6}$cycloalkyl portion is optionally substituted one or more times with $R^6$ heterocyclyl optionally substituted one or more times with $R^7$, or heterocyclyl-$C_{1-6}$alkyl wherein the heterocyclyl portion is optionally substituted one or more times with $R^7$;

$R^4$ is: hydrogen; $C_{1-6}$alkyl; halo; cyano; halo-$C_{1-6}$alkyl; $C_{2-6}$alkenyl; $C_{2-6}$alkynyl; $C_{1-6}$alkoxy; $C_{1-6}$alkoxy-$C_{1-6}$alkyl; hydroxy-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; or —Y—C(O)—$R^d$;

$R^5$ is: hydrogen; or $C_{1-6}$alkyl;

each $R^6$ is independently: $C_{1-6}$alkyl; halo-$C_{1-6}$alkyl; $C_{1-6}$alkoxy; oxo; cyano; halo; or Y—C(O)—$R^d$;

each $R^7$ is independently: $C_{1-6}$alkyl; halo-$C_{1-6}$alkyl; halo; oxo; $C_{1-6}$alkoxy; $C_{1-6}$alkylsulfonyl; $C_{1-6}$alkoxy-$C_{1-6}$alkyl; cyano; —Y—C(O)—$R^d$; heterocyclyl; heterocyclyl-$C_{1-6}$alkyl; $C_{3-6}$cycloalkyl; $C_{3-6}$cycloalkyl-$C_{1-6}$alkyl; or $C_{3-6}$cycloalkylsulfonyl; and each $R^8$ is independently: oxo; $C_{1-6}$alkyl; halo-$C_{1-6}$alkyl; halo; $C_{1-6}$alkyl-sulfonyl; $C_{1-6}$alkoxy; $C_{1-6}$alkoxy-$C_{1-6}$alkyl; cyano; hetoeryclyl; heterocyclyl-$C_{1-6}$alkyl; —Y—C(O)—$R^d$; $C_{3-6}$cycloalkyl, $C_{3-6}$cycloalkyl-$C_{1-6}$alkyl, or $C_{3-6}$cycloalkyl-sulfonyl.

The invention also provides pharmaceutical compositions comprising the compounds, methods of using the compounds, and methods of preparing the compounds.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy" means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —$SO_2$—R, wherein R is alkyl as defined herein.

"Alkylsulfonylalkyl means a moiety of the formula —R'—$SO_2$—R" where R' is alkylene and R" is alkyl as defined herein.

"Alkylsulfonylalkoxy" means a group of the formula —O—R—$SO_2$—R' wherein R is alkylene and R' is alkyl as defined herein.

"Amino means a moiety of the formula —NRR' wherein R and R' each independently is hydrogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

"Arylalkyl" and "Aralkyl", which may be used interchangeably, mean a radical-R$^a$R$^b$ where R$^a$ is an alkylene group and R$^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" "means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof "Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each optionally substituted.

Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R''' wherein R', R" and R''' each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R''' each independently is hydrogen or alkyl.

"Optionally substituted", when used in association with "aryl", phenyl", "heteroaryl" "cycloalkyl" or "heterocyclyl", means an aryl, phenyl, heteroaryl, cycloalkyl or heterocyclyl which is optionally substituted independently with one to four substituents, for example one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —SO$_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain particular optional substituents for "aryl", phenyl", "heteroaryl" "cycloalkyl" or "heterocyclyl" include alkyl, halo, haloalkyl, alkoxy, cyano, amino and alkylsulfonyl. In one embodiment substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Parkinson's disease" means a degenerative disorder of the central nervous system that impairs motor skills, speech, and/or cognitive function. Symptoms of Parkinson's disease may include, for example, muscle rigidity, tremor, slowing of physical movement (bradykinesia) and loss of physical movement (akinesia).

"Lewie (Lewy) body disease" also called "Lewie body dementia", diffuse Lewie body disease", cortical Lewie body disease", means a neurogenerative disorder characterized anatomically by the presence of Lewie bodies in the brain.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where one or more chiral centers exists in a structure but no specific stereochemistry is shown for the chiral centers, both enantiomers associated with each such chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes.

All patents and publications identified herein are incorporated herein by reference in their entirety.

Compounds of the Invention

The invention provides compounds of the formula I:

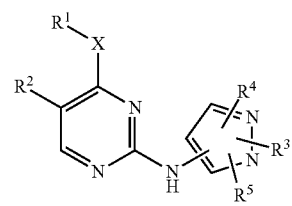

I or pharmaceutically acceptable salts thereof,
wherein:
X is: —$NR^a$—; or —O— wherein $R^a$ is hydrogen or $C_{1-6}$alkyl;
$R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted one or more times with $C_{1-6}$alkyl; $C_{3-6}$cycloalkyl-$C_{1-6}$ alkyl wherein the $C_{3-6}$cycloalkyl portion is optionally substituted one or more times with $C_{1-6}$alkyl; heterocyclyl optionally substituted one or more times with $R^7$; or heterocyclyl-$C_{1-6}$alkyl optionally substituted one or more times with $R^7$;
or X and $R^1$ together form $C_{1-6}$alkyl; $C_{1-6}$alkoxy-$C_{1-6}$alkyl; $C_{3-6}$cycloalkyl optionally substituted one or more times with $R^6$; or $C_{3-6}$cycloalkyl-$C_{1-6}$alkyl wherein the $C_{3-6}$cycloalkyl portion is optionally substituted one or more times with $R^6$;
or $R^1$ and $R^a$ together with the atoms to which they are attached may form a three- to six-membered heterocyclic ring optionally substituted one or more times with $R^7$;
$R^2$ is: $C_{1-6}$alkyl; halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; —$OR^b$ wherein $R^b$ is $C_{1-6}$alkyl, $C_{3-6}$cycloalkyl optionally substituted one or more times with $R^6$, or $C_{3-6}$cycloalkyl-$C_{1-6}$alkyl wherein the $C_{3-6}$cycloalkyl portion is optionally substituted one or more times with $R^6$; or —C(O)—$R^c$ wherein $R^c$ is $C_{1-6}$alkyl, $C_{1-6}$alkoxy, amino, or heterocyclyl optionally substituted one or more times with $R^7$;

$R^3$ is: hydrogen; $C_{1-6}$alkyl; halo-$C_{1-6}$alkyl; $C_{2-6}$alkenyl; $C_{2-6}$alkynyl; hydroxy-$C_{1-6}$alkyl; $C_{1-6}$alkoxy-$C_{1-6}$alkyl; cyano-$C_{1-6}$alkyl; $C_{1-6}$alkylsulfonyl; $C_{1-6}$alkylsulfonyl$C_{1-6}$alkyl; amino-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; $C_{3-6}$cycloalkyl-sulfonyl wherein the $C_{3-6}$cycloalkyl portion is optionally substituted one or more times with $R^6$; heterocyclyl optionally substituted one or more times with $R^7$; heterocyclyl-$C_{1-6}$alkyl wherein the heterocyclyl portion is optionally substituted one or more times with $R^7$; aryl optionally substituted one or more times with $R^8$; aryl-$C_{1-6}$alkyl wherein the aryl portion is optionally substituted one or more times with $R^8$; heteroaryl optionally substituted one or more times with $R^8$; heteroaryl-$C_{1-6}$alkyl wherein the heteroaryl portion is optionally substituted one or more times with $R^8$; or —Y—C(O)—$R^d$;

Y is $C_{2-6}$alkylene or a bond;

$R^d$ is $C_{1-6}$alkyl, $C_{1-6}$alkoxy, amino, $C_{1-6}$alkyl-amino, di-$C_{1-6}$alkyl-amino, halo-$C_{1-6}$alkyl-amino, di-halo-$C_{1-6}$alkyl-amino, halo-$C_{1-6}$alkyl, hydroxy-$C_{1-6}$alkyl, hydroxy, $C_{1-6}$alkoxy-$C_{1-6}$alkyl, cyano-$C_{1-6}$alkyl, $C_{1-6}$alkylsulfonyl$C_{1-6}$ alkyl, amino-$C_{1-6}$alkyl, $C_{3-6}$cycloalkyl optionally substituted one or more times with $R^6$, $C_{3-6}$cycloalkyl-$C_{1-6}$alkyl wherein the $C_{3-6}$cycloalkyl portion is optionally substituted one or more times with $R^6$ heterocyclyl optionally substituted one or more times with $R^7$, or heterocyclyl-$C_{1-6}$alkyl wherein the heterocyclyl portion is optionally substituted one or more times with $R^7$;

$R^4$ is: hydrogen; $C_{1-6}$alkyl; halo; cyano; halo-$C_{1-6}$alkyl; $C_{2-6}$alkenyl; $C_{2-6}$alkynyl; $C_{1-6}$alkoxy; $C_{1-6}$alkoxy-$C_{1-6}$alkyl; hydroxy-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; or —Y—C(O)—$R^d$;

$R^5$ is: hydrogen; or $C_{1-6}$alkyl;

each $R^6$ is independently: $C_{1-6}$alkyl; halo-$C_{1-6}$alkyl; $C_{1-6}$alkoxy; oxo; cyano; halo; or Y—C(O)—$R^d$;

each $R^7$ is independently: $C_{1-6}$alkyl; halo-$C_{1-6}$alkyl; halo; oxo; $C_{1-6}$alkoxy; $C_{1-6}$alkylsulfonyl; $C_{1-6}$alkoxy-$C_{1-6}$alkyl; cyano; —Y—C(O)—$R^d$; heterocyclyl; heterocyclyl-$C_{1-6}$alkyl; $C_{3-6}$cycloalkyl; $C_{3-6}$cycloalkyl-$C_{1-6}$alkyl; or $C_{3-6}$cycloalkylsulfonyl; and each $R^8$ is independently: oxo; $C_{1-6}$alkyl; halo-$C_{1-6}$alkyl; halo; $C_{1-6}$alkyl-sulfonyl; $C_{1-6}$alkoxy; $C_{1-6}$alkoxy-$C_{1-6}$alkyl; cyano; hetoeryclyl; heterocyclyl-$C_{1-6}$alkyl; —Y—C(O)—$R^d$; $C_{3-6}$cycloalkyl, $C_{3-6}$cycloalkyl-$C_{1-6}$alkyl, or $C_{3-6}$cycloalkyl-sulfonyl.

In certain embodiments the invention provides compounds of the formula II:

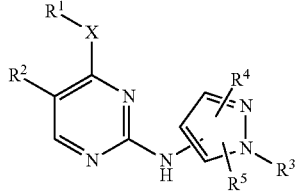

II or pharmaceutically acceptable salts thereof, wherein:

X is: —$NR^a$—; or —O— wherein $R^a$ is hydrogen or $C_{1-6}$alkyl;

$R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; or heterocyclyl-$C_{1-6}$alkyl;

or X and $R^1$ together form $C_{1-6}$alkyl; $C_{3-6}$cycloalkyl optionally substituted with $C_{1-6}$alkyl; or $C_{3-6}$cycloalkyl-$C_{1-6}$alkyl wherein the $C_{3-6}$cycloalkyl portion is optionally substituted with $C_{1-6}$alkyl;

or $R^1$ and $R^a$ together with the atoms to which they are attached may form a three- to six-membered heterocyclic ring.

$R^2$ is: $C_{1-6}$alkyl; halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; —$OR^b$ wherein $R^b$ is $C_{1-6}$alkyl, $C_{3-6}$cycloalkyl optionally substituted with $C_{1-6}$alkyl, or $C_{3-6}$cycloalkyl-$C_{1-6}$alkyl wherein the $C_{3-6}$cycloalkyl portion is optionally substituted with $C_{1-6}$alkyl; or —C(O)—$R^c$ wherein $R^c$ is $C_{1-6}$alkyl, $C_{1-6}$alkoxy, amino, or heterocyclyl;

$R^3$ is: hydrogen; $C_{1-6}$alkyl; halo-$C_{1-6}$alkyl; $C_{2-6}$alkenyl; $C_{2-6}$alkynyl; hydroxy-$C_{1-6}$alkyl; $C_{1-6}$alkoxy-$C_{1-6}$alkyl; cyano-$C_{1-6}$alkyl; $C_{1-6}$alkylsulfonyl; $C_{1-6}$alkylsulfonylalkyl; amino-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; heterocyclyl-$C_{1-6}$alkyl; aryl; heteroaryl; or —C(O)—$R^c$ wherein $R^c$ is $C_{1-6}$alkyl, $C_{1-6}$alkoxy, amino, or heterocyclyl;

$R^4$ is: hydrogen; $C_{1-6}$alkyl; halo; cyano; halo-$C_{1-6}$alkyl; $C_{2-6}$alkenyl; $C_{2-6}$alkynyl; $C_{1-6}$alkoxy-$C_{1-6}$alkyl; hydroxy-$C_{1-6}$ alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; or —C(O)—$R^c$ wherein $R^c$ is $C_{1-6}$alkyl, $C_{1-6}$alkoxy, amino, or heterocyclyl; and $R^5$ is: hydrogen; or $C_{1-6}$alkyl.

In certain embodiments of formula I or formula II, X is —$NR^a$— or —O—.

In certain embodiments of formula I or formula II, X is —$NR^a$.

In certain embodiments of formula I or formula II, X is —O—.

In certain embodiments of formula I or formula II, X is —NH— or —O—.

In certain embodiments of formula I or formula II, X is —NH—.

In certain embodiments of formula I or formula II, X is —O—.

In certain embodiments of formula I or formula II, $R^a$ is hydrogen.

In certain embodiments of formula I or formula II, $R^a$ is $C_{1-6}$alkyl.

In certain embodiments of formula I or formula II, $R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; or heterocyclyl-$C_{1-6}$alkyl.

In certain embodiments of formula I or formula II, $R^1$ is: $C_{1-6}$alkyl; halo-$C_{1-6}$alkyl; $C_{1-6}$alkoxy-$C_{1-6}$alkyl; amino-$C_{1-6}$alkyl; $C_{1-6}$alkylsulfonyl-$C_{1-6}$alkyl; $C_{3-6}$cycloalkyl; or $C_{3-6}$cycloalkyl-$C_{1-6}$alkyl.

In certain embodiments of formula I or formula II, $R^1$ is: $C_{1-6}$alkyl; $C_{3-6}$cycloalkyl optionally substituted with $C_{1-6}$alkyl; or $C_{3-6}$cycloalkyl-$C_{1-6}$alkyl wherein the $C_{3-6}$cycloalkyl portion is optionally substituted with $C_{1-6}$alkyl.

In certain embodiments of formula I or formula II, $R^1$ is: $C_{1-6}$alkyl; halo-$C_{1-6}$alkyl; $C_{1-6}$alkoxy-$C_{1-6}$alkyl; amino-$C_{1-6}$alkyl; $C_{1-6}$alkylsulfonyl-$C_{1-6}$alkyl; tetrahydrofuranyl; tetrahydrofuranyl-$C_{1-6}$alkyl; oxetanyl; or oxetan-$C_{1-6}$alkyl.

In certain embodiments of formula I or formula II, $R^1$ is: $C_{1-6}$alkyl; halo-$C_{1-6}$alkyl; $C_{1-6}$alkoxy-$C_{1-6}$alkyl; amino-$C_{1-6}$alkyl; or $C_{1-6}$alkylsulfonyl-$C_{1-6}$alkyl.

In certain embodiments of formula I or formula II, $R^1$ is $C_{1-6}$alkyl or halo-$C_{1-6}$alkyl.

In certain embodiments of formula I or formula II, $R^1$ is $C_{1-6}$alkyl.

In certain embodiments of formula I or formula II, $R^1$ is halo-$C_{1-6}$alkyl.

In certain embodiments of formula I or formula II, $R^1$ is $C_{1-6}$alkoxy-$C_{1-6}$alkyl.

In certain embodiments of formula I or formula II, $R^1$ is amino-$C_{1-6}$alkyl.

In certain embodiments of formula I or formula II, $R^1$ is $C_{1-6}$alkylsulfonyl-$C_{1-6}$alkyl.

In certain embodiments of formula I or formula II, $R^1$ is $C_{3-6}$cycloalkyl optionally substituted with $C_{1-6}$alkyl.

In certain embodiments of formula I or formula II, $R^1$ is $C_{3-6}$cycloalkyl-$C_{1-6}$alkyl wherein the $C_{3-6}$cycloalkyl portion is optionally substituted with $C_{1-6}$alkyl.

In certain embodiments of formula I or formula II, $R^1$ is heterocyclyl or heterocyclyl-$C_{1-6}$alkyl.

In embodiments of formula I or formula II wherein $R^1$ is heterocyclyl or heterocyclyl-$C_{1-6}$alkyl, such heterocyclyl may be piperidinyl, piperazinyl, morpholinyl, tetrahydropyranyl, pyrrolidinyl, tetrahydrofuranyl or oxetanyl, each optionally substituted as defined herein.

In embodiments of formula I or formula II wherein $R^1$ is heterocyclyl or heterocyclyl-$C_{1-6}$alkyl, such heterocyclyl may be tetrahydropyranyl, piperidinyl, tetrahydrofuranyl or oxetanyl, each optionally substituted as defined herein.

In certain embodiments of formula I or formula II, $R^1$ is tetrahydrofuranyl.

In certain embodiments of formula I or formula II, $R^1$ is tetrahydropyranyl.

In certain embodiments of formula I or formula II, $R^1$ is tetrahydrofuranyl-$C_{1-6}$alkyl or oxetanyl.

In certain embodiments of formula I or formula II, $R^1$ is tetrahydrofuranyl-$C_{1-6}$alkyl.

In certain embodiments of formula I or formula II, $R^1$ is oxetanyl.

In certain embodiments of formula I or formula II, $R^1$ is or oxetan-$C_{1-6}$alkyl.

In certain embodiments of formula I or formula II, $R^1$ is: methyl; ethyl; n-propyl; isopropyl; isobutyl; 3,3-dimethylpropyl; cyclopropyl; cyclobutyl; cyclopentyl; cyclohexyl; cyclopropylmethyl; cyclobutylmethyl; cyclopentylmethyl; cyclopropylethyl; methoxyethyl; oxetanyl; tetrahydropyranyl; 2,2-difluoroethyl; or tetrahydrofuranylmethyl.

In certain embodiments of formula I or formula II, $R^1$ is: methyl; ethyl; n-propyl; isopropyl; isobutyl; 3,3-dimethylpropyl; cyclopentyl; cyclohexyl; cyclopropylmethyl; cyclobutylmethyl; cyclopentylmethyl; cyclopropylethyl; methoxyethyl; oxetanyl; tetrahydropyranyl; 2,2-difluoroethyl; or tetrahydrofuranylmethyl.

In certain embodiments of formula I or formula II, $R^1$ is: methyl; ethyl; n-propyl; isopropyl; isobutyl; 3,3-dimethylpropyl; cyclopentyl; cyclohexyl; cyclopentylmethyl; methoxyethyl; oxetanyl; tetrahydropyranyl; or tetrahydrofuranylmethyl.

In certain embodiments of formula I or formula II, $R^1$ is 2,2-difluoroethyl.

In certain embodiments of formula I or formula II, $R^1$ is: methyl; ethyl; n-propyl; isopropyl; or isobutyl.

In certain embodiments of formula I or formula II, $R^1$ is methyl or ethyl.

In certain embodiments of formula I or formula II, $R^1$ is methyl.

In certain embodiments of formula I or formula II, $R^1$ is ethyl.

In certain embodiments of formula I or formula II, $R^1$ is: cyclopropyl; cyclobutyl; cyclopentyl; cyclohexyl; cyclopropylmethyl; cyclobutylmethyl; cyclopentylmethyl; or cyclopropylethyl.

In certain embodiments of formula I or formula II, $R^1$ is: cyclopentyl; cyclohexyl; or cyclopentylmethyl.

In certain embodiments of formula I or formula II, $R^1$ is: cyclopropyl.

In certain embodiments of formula I or formula II, $R^1$ and $R^a$ together with the atoms to which they are attached may form a three- to six-membered heterocyclic ring.

In certain embodiments of formula I or formula II, $R^1$ and $R^a$ together with the atoms to which they are attached may form a three-membered heterocyclic ring.

In certain embodiments of formula I or formula II, $R^1$ and $R^a$ together with the atoms to which they are attached may form a four-membered heterocyclic ring.

In certain embodiments of formula I or formula II, $R^1$ and $R^a$ together with the atoms to which they are attached may form a five-membered heterocyclic ring.

In certain embodiments of formula I or formula II, $R^1$ and $R^a$ together with the atoms to which they are attached may form a six-membered heterocyclic ring.

In certain embodiments of formula I or formula II, X and $R^1$ together form $C_{1-6}$alkyl; $C_{3-6}$cycloalkyl optionally substituted with $C_{1-6}$alkyl; or $C_{3-6}$cycloalkyl-$C_{1-6}$alkyl wherein the $C_{3-6}$cycloalkyl portion is optionally substituted with $C_{1-6}$alkyl.

In certain embodiments of formula I or formula II, X and $R^1$ together form $C_{1-6}$alkyl.

In certain embodiments of formula I or formula II, X and $R^1$ together form $C_{3-6}$cycloalkyl optionally substituted with $C_{1-6}$alkyl.

In certain embodiments of formula I or formula II, X and $R^1$ together form $C_{3-6}$cycloalkyl-$C_{1-6}$alkyl wherein the $C_{3-6}$cycloalkyl portion is optionally substituted with $C_{1-6}$alkyl.

In certain embodiments of formula I or formula II, $R^2$ is: $C_{1-6}$alkyl; halo; $C_{1-6}$alkoxy; cyano; $C_{2-6}$alkynyl; $C_{2-6}$alkenyl; halo-$C_{1-6}$alkyl; halo-$C_{1-6}$alkoxy; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; —$OR^b$ wherein $R^b$ is $C_{1-6}$alkyl, $C_{3-6}$cycloalkyl optionally substituted with $C_{1-6}$alkyl, or $C_{3-6}$cycloalkyl-$C_{1-6}$alkyl wherein the $C_{3-6}$cycloalkyl portion is optionally substituted with $C_{1-6}$alkyl; or —C(O)—$R^c$.

In certain embodiments of formula I or formula II, $R^2$ is: halo; $C_{1-6}$alkoxy; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the In certain embodiments of formula I or formula II, $R^2$ is: halo; $C_{1-6}$alkoxy; halo-$C_{1-6}$alkyl; cyano; $C_{2-6}$alkynyl; $C_{2-6}$alkenyl; $C_{3-6}$cycloalkyl; or $C_{3-6}$cycloalkyl-$C_{1-6}$alkyl.

In certain embodiments of formula I or formula II, $R^2$ is: halo; $C_{1-6}$alkoxy; halo-$C_{1-6}$alkyl; cyano; $C_{3-6}$cycloalkyl; or $C_{3-6}$cycloalkyl-$C_{1-6}$alkyl.

In certain embodiments of formula I or formula II, $R^2$ is: halo; $C_{1-6}$alkoxy; halo-$C_{1-6}$alkyl; $C_{3-6}$cycloalkyl; or $C_{3-6}$cycloalkyl-$C_{1-6}$alkyl.

In certain embodiments of formula I or formula II, $R^2$ is: halo; halo-$C_{1-6}$alkyl or cyano.

In certain embodiments of formula I or formula II, $R^2$ is: fluoro; bromo; chloro; iodo; trifluoromethyl; or cyano.

In certain embodiments of formula I or formula II, $R^2$ is: chloro; trifluoromethyl; or cyano.

In certain embodiments of formula I or formula II, $R^2$ is: halo; or halo-$C_{1-6}$alkyl.

In certain embodiments of formula I or formula II, $R^2$ is $C_{1-6}$alkyl.

In certain embodiments of formula I or formula II, $R^2$ is halo.

In certain embodiments of formula I or formula II, $R^2$ is $C_{1-6}$alkoxy.

In certain embodiments of formula I or formula II, $R^2$ is halo-$C_{1-6}$alkoxy.

In certain embodiments of formula I or formula II, $R^2$ is halo-$C_{1-6}$alkyl.

In certain embodiments of formula I or formula II, $R^2$ is $C_{3-6}$cycloalkyl.

In certain embodiments of formula I or formula II, $R^2$ is $C_{3-6}$cycloalkyl-$C_{1-6}$alkyl.

In certain embodiments of formula I or formula II, $R^2$ is tetrahydrofuranyl.

In certain embodiments of formula I or formula II, $R^2$ is tetrahydrofuranyl-$C_{1-6}$alkyl.

In certain embodiments of formula I or formula II, $R^2$ is oxetanyl.

In certain embodiments of formula I or formula II, $R^2$ is oxetan-$C_{1-6}$alkyl.

In certain embodiments of formula I or formula II, $R^2$ is fluoro, chloro or bromo.

In certain embodiments of formula I or formula II, $R^2$ is chloro.

In certain embodiments of formula I or formula II, $R^2$ is fluoro.

In certain embodiments of formula I or formula II, $R^2$ is bromo.

In certain embodiments of formula I or formula II, $R^2$ is bromo.

In certain embodiments of formula I or formula II, $R^2$ is iodo.

In certain embodiments of formula I or formula II, $R^2$ is trifluoromethyl.

In certain embodiments of formula I or formula II, $R^2$ is methoxy.

In certain embodiments of formula I or formula II, $R^2$ is cyano.

In certain embodiments of formula I or formula II, $R^2$ is $C_{2-6}$alkynyl.

In certain embodiments of formula I or formula II, $R^2$ is $C_{2-6}$alkenyl.

In certain embodiments of formula I or formula II, $R^2$ is —$OR^b$ wherein $R^b$ is $C_{1-6}$alkyl, $C_{3-6}$cycloalkyl optionally substituted with $C_{1-6}$alkyl, or $C_{3-6}$cycloalkyl-$C_{1-6}$alkyl wherein the $C_{3-6}$cycloalkyl portion is optionally substituted with $C_{1-6}$alkyl.

In certain embodiments of formula I, $R^2$ is —$C(O)$—$R^c$ wherein $R^c$ is $C_{1-6}$alkyl, $C_{1-6}$alkoxy, amino, or heterocyclyl.

In certain embodiments of formula I or formula II, $R^3$ is: $C_{1-6}$alkyl; halo-$C_{1-6}$alkyl; $C_{2-6}$alkenyl; $C_{2-6}$alkynyl; hydroxy-$C_{1-6}$alkyl; $C_{1-6}$alkoxy-$C_{1-6}$alkyl; cyano-$C_{1-6}$alkyl; $C_{1-6}$alkylsulfonyl; $C_{1-6}$alkylsulfonyl$C_{1-6}$alkyl; amino-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; heterocyclyl optionally substituted one or more times with $R^7$; heterocyclyl-$C_{1-6}$alkyl wherein the heterocyclyl portion is optionally substituted one or more times with $R^7$; aryl optionally substituted one or more times with $R^8$; heteroaryl optionally substituted one or more times with $R^8$; or —Y—$C(O)$—$R^d$.

In certain embodiments of formula I or formula II, $R^3$ is: hydrogen; $C_{1-6}$alkyl; halo-$C_{1-6}$alkyl; $C_{2-6}$alkenyl; $C_{2-6}$alkynyl; hydroxy-$C_{1-6}$alkyl; $C_{1-6}$alkoxy-$C_{1-6}$alkyl; cyano-$C_{1-6}$alkyl; $C_{1-6}$alkylsulfonyl; $C_{1-6}$alkylsulfonylalkyl; amino-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; heterocyclyl-$C_{1-6}$alkyl; aryl; heteroaryl; or —$C(O)$—$R^c$.

In certain embodiments of formula I or formula II, $R^3$ is: $C_{1-6}$alkyl; halo-$C_{1-6}$alkyl; hydroxy-$C_{1-6}$alkyl; $C_{1-6}$alkoxy-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; heterocyclyl-$C_{1-6}$alkyl; or —$C(O)$—$R^b$ wherein $R^b$ is $C_{1-6}$alkyl, $C_{1-6}$alkoxy, amino, or heterocyclyl.

In certain embodiments of formula I or formula II, $R^3$ is: $C_{1-6}$alkyl; hydroxy-$C_{1-6}$alkyl; $C_{1-6}$alkoxy-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; heterocyclyl; heterocyclyl-$C_{1-6}$alkyl; or —$C(O)$—$R^c$ wherein $R^c$ is $C_{1-6}$alkyl, $C_{1-6}$alkoxy, amino, or heterocyclyl.

In certain embodiments of formula I or formula II, $R^3$ is: $C_{1-6}$alkyl; hydroxy-$C_{1-6}$alkyl; $C_{1-6}$alkoxy-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; heterocyclyl optionally substituted one or more times with $R^7$; heterocyclyl-$C_{1-6}$alkyl wherein the heterocyclyl portion is optionally substituted one or more times with $R^7$; or —$C(O)$—$R^d$.

In certain embodiments of formula I or formula II, $R^3$ is: $C_{1-6}$alkyl; hydroxy-$C_{1-6}$alkyl; $C_{1-6}$alkoxy-$C_{1-6}$alkyl; heterocyclyl; heterocyclyl-$C_{1-6}$alkyl; or —$C(O)$—$R^c$ wherein $R^c$ is $C_{1-6}$alkyl, $C_{1-6}$alkoxy, amino, or heterocyclyl.

In certain embodiments of formula I or formula II, $R^3$ is: $C_{1-6}$alkyl; hydroxy-$C_{1-6}$alkyl; $C_{1-6}$alkoxy-$C_{1-6}$alkyl; heterocyclyl; or heterocyclyl-$C_{1-6}$alkyl.

In certain embodiments of formula I or formula II, $R^3$ is: $C_{1-6}$alkyl; hydroxy-$C_{1-6}$alkyl; or $C_{1-6}$alkoxy-$C_{1-6}$alkyl.

In embodiments of formula I or formula II wherein $R^3$ is heterocyclyl or heterocyclyl-$C_{1-6}$alkyl, such heterocyclyl may be piperidinyl, piperazinyl, morpholinyl, tetrahydropyranyl, pyrrolidinyl, tetrahydrofuranyl or oxetanyl.

In embodiments of formula I or formula II wherein $R^3$ is heterocyclyl or heterocyclyl-$C_{1-6}$alkyl, such heterocyclyl may be piperidinyl, piperazinyl, morpholinyl, tetrahydropyranyl, pyrrolidinyl, azetidinyl, tetrahydrofuranyl or oxetanyl, each optionally substituted one or more times, or one or two times, with $R^7$ as defined herein.

In embodiments of formula I or formula II wherein $R^3$ is heterocyclyl or heterocyclyl-$C_{1-6}$alkyl, such heterocyclyl may be piperidinyl, morpholinyl, tetrahydropyranyl, tetrahydrofuranyl or oxetanyl.

In embodiments of formula I or formula II wherein $R^3$ is heterocyclyl or heterocyclyl-$C_{1-6}$alkyl, such heterocyclyl may be piperidinyl, pyrrolidinyl, azetidinyl, morpholinyl, tetrahydropyranyl, tetrahydrofuranyl or oxetanyl, each optionally substituted one or more times, or one or two times, with $R^7$ as defined herein.

In certain embodiments of formula I or formula II, $R^3$ is: methyl; ethyl; n-propyl; isopropyl; 2-methoxy-ethyl; oxetan-3-yl; 2-(morpholin-4-yl)-ethyl; 2-hydroxy-2-methyl-propan-1-yl; tetrahydropyran-4-yl; or morpholin-4-yl-carbonyl.

In certain embodiments of formula I, $R^3$ is: methyl; ethyl; n-propyl; isopropyl; 2-methoxy-ethyl; oxetan-3-yl; 2-(morpholin-4-yl)-ethyl; 2-hydroxy-2-methyl-propan-1-yl; or tetrahydropyran-4-yl.

In certain embodiments of formula I or formula II, $R^3$ is hydrogen.

In certain embodiments of formula I or formula II, $R^3$ is $C_{1-6}$alkyl.

In certain embodiments of formula I or formula II, $R^3$ is halo-$C_{1-6}$alkyl.

In certain embodiments of formula I or formula II, $R^3$ is $C_{2-6}$alkenyl.

In certain embodiments of formula I or formula II, $R^3$ is $C_{2-6}$alkynyl.

In certain embodiments of formula I or formula II, $R^3$ is hydroxy-$C_{1-6}$alkyl.

In certain embodiments of formula I or formula II, $R^3$ is $C_{1-6}$alkoxy-$C_{1-6}$alkyl.

In certain embodiments of formula I or formula II, $R^3$ is $C_{3-6}$cycloalkyl optionally substituted one or more times with $R^6$.

In certain embodiments of formula I or formula II, $R^3$ is $C_{3-6}$cycloalkyl optionally substituted with $C_{1-6}$alkyl.

In certain embodiments of formula I or formula II, $R^3$ is $C_{3-6}$cycloalkyl-$C_{1-6}$alkyl wherein the $C_{3-6}$cycloalkyl portion is optionally substituted one or more times with $R^6$.

In certain embodiments of formula I or formula II, $R^3$ is $C_{3-6}$cycloalkyl-$C_{1-6}$alkyl wherein the $C_{3-6}$cycloalkyl portion is optionally substituted with $C_{1-6}$alkyl.

In certain embodiments of formula I or formula II, $R^3$ is heterocyclyl optionally substituted one or more times with $R^7$.

In certain embodiments of formula I or formula II, $R^3$ is heterocyclyl.

In certain embodiments of formula I or formula II, $R^3$ is heterocyclyl-$C_{1-6}$alkyl wherein the heterocyclyl portion is optionally substituted one or more times with $R^7$.

In certain embodiments of formula I or formula II, $R^3$ is heterocyclyl-$C_{1-6}$alkyl.

In certain embodiments of formula I or formula II, $R^3$ is —C(O)—$R^c$.

In certain embodiments of formula I or formula II, $R^3$ is cyano-$C_{1-6}$alkyl.

In certain embodiments of formula I or formula II, $R^3$ is $C_{1-6}$alkylsulfonyl.

In certain embodiments of formula I or formula II, $R^3$ is $C_{1-6}$alkylsulfonyl-$C_{1-6}$alkyl.

In certain embodiments of formula I or formula II, $R^3$ is amino-$C_{1-6}$alkyl.

In certain embodiments of formula I or formula II, $R^3$ is aryl optionally substituted one or more times with $R^8$.

In certain embodiments of formula I or formula II, $R^3$ is aryl.

In certain embodiments of formula I or formula II, $R^3$ is phenyl optionally substituted one or more times, or one or two times, with $R^8$.

In certain embodiments of formula I or formula II, $R^3$ is heteroaryl optionally substituted one or more times, or one or two times, with $R^8$.

In certain embodiments of formula I or formula II, $R^3$ is heteroaryl.

In certain embodiments of formula I or formula II, $R^3$ is $C_{3-6}$cycloalkyl-sulfonyl wherein the $C_{3-6}$cycloalkyl portion is optionally substituted one or more times with $R^6$ In certain embodiments of formula I or formula II, $R^3$ is: hydrogen; methyl; ethyl; propyl; isopropyl; butyl; cyclopropyl; cyclopropylmethyl; cyclobutyl; methanesulfonyl; ethylsulfonyl; cyclopropylsulfonyl; sec-butylsulfonyl; morpholin-4-yl-ethyl; oxetan-3-yl; 2-methoxyethyl; 2-hydroxy-2-methyl-propyl; 3-hydroxy-2-methyl-propan-2-yl; 2-methoxy-propyl; tetrahydro-2H-pyran-4-yl; tetrahydrofuran-3-yl; 2,6-dimethyltetrahydro-2H-pyran-4-yl; tetrahydro-2H-pyran-3-yl); phenyl; 4-(methylsulfonyl)phenyl); 4-cyano-phenyl; 4-fluoro-phenyl; 4-chloro-phenyl; 3,5-difluorophenyl; 4-(dimethylamino-carbonyl)-phenyl); 4-(cyclopropylsulfonyl)phenyl; 2,2,2-trifluoroethyl; 2-fluoroethyl; difluoromethyl; 2-dimethyl-1,3-dioxan-5-yl; 1-methyl-cyclopropyl-carbonyl; 3-methylpyridin-4-yl; 2-methylpyridin-4-yl; pyridin-2-yl; pyrimidin-2-yl; pyrimidin-5-yl; pyridin-2-ylmethyl; 1-(pyridin-2-yl)ethyl; cyclopropylsulfonyl; 1-cyano-1-methyl-ethyl (also called 2-cyano-propan-2-yl); 2-cyano-ethyl; 1-cyano-ethyl; 2-cyano-2-methyl-propyl; 1-(2,2,2-trifluoroethyl)piperidin-4-yl; 1-(methylsulfonyl)azetidin-3-yl; (3-methyloxetan-3-yl)methyl; (1S,5S)-8-oxabicyclo[3.2.1]octan-3-yl; 1-(oxetan-3-yl)piperidin-4-yl; 1-acetyl-piperidin-4-yl; 1-(cyclopropyl-carbonyl)-piperidin-4-yl; 1-methyl-piperidin-4-yl; 1-methyl-2-oxo-piperidin-5-yl; 2-oxo-piperidin-5-yl; 1-(isopropyl-carbonyl)-piperidin-4-yl; 1-(oxetan-3-yl)azetidin-3-yl; 1-(cyclopropyl-carbonyl)-piperidin-4-yl; 2-methoxycyclopentyl; 3-methoxycyclopentyl; 1-methoxy-2-methylpropan-2-yl; tetrahydro-2H-1,1-dioxo-thiopyran-4-yl; 3-fluoro-1-(oxetan-3-yl)piperidin-4-yl; 1-methoxypropan-2-yl; 1-(2,2,2-trifluoroethyl)azetidin-3-yl); 1-(oxetan-3-yl)pyrrolidin-3-yl; 1-isopropylazetidin-3-yl; 3-fluoro-1-methylpiperidin-4-yl; 1-ethyl-3-fluoropiperidin-4-yl; 1-methylpyrrolidin-3-yl; 2-methoxyethyl)piperidin-4-yl); 1-methyl-1-(methylamino-carbonyl)-ethyl; 2-methyl-2-morpholino-propyl; 4,4-difluorocyclohexyl; morpholin-4-yl-carbonyl; dimethylamino-carbonyl-methyl; methylamino-carbonyl-methyl; 1-methyl-1-(dimethylamino-carbonyl)-ethyl; pyrrolidin-'-yl-carbonyl; 1-cyamo-cyclopropyl; 1-(pyrrolidin-'-yl-carbonyl)-ethyl; 1-(dimethylamino-carbonyl)-ethyl; 1-(methoxy-carbonyl)-ethyl; 1-(tert-butylamino-carbonyl)-1-methyl-ethyl; 1-(2,2,2-trifluoroethyllamino-carbonyl)-1-methyl-ethyl; 1-(ethylamino-carbonyl)-1-methyl-ethyl; 1-(cyclopropylmethylamino-carbonyl)-1-methyl-ethyl; 1-(ethylamino-carbonyl)-cyclobutyl; 1-(isopropylamino-carbonyl)-1-methyl-ethyl; 1-cyano-cyclobutyl; 2-methoxy-1-methyl-ethyl; 1-methyl-1-(methoxy-carbonyl)-ethyl; 2-methoxy-2-methyl-propan-1-yl; 1-(oxetan-3-yl)-pyrrolidin-3-yl; isopropylsulfonyl; butane-2-sulfonyl; 1-(2-fluoroethyl)-piperidin-4-yl; 3-fluoro-1-methyl-piperidin-4-yl; 1-ethyl-3-fluoro-piperidin-4-yl; pyridin-3-ylmethyl; 6-methyl-pyridin-2-ylmethyl; 2-(morpholin-1-yl)-1,1,dimethyl-ethyl; pyrimdin-2-yl-methyl; 3-fluoro-1-(oxetan-3-yl)-piperidin-4-yl; 1-(oxetan-3-yl)-piperidin-3-yl; 1-([1,3]Dioxolan-2-ylmethyl)-piperidin-4-yl; pyridazin-3-ylmethyl;

piperidin-3-yl; pyrazin-2-ylmethyl; 2-hydroxy-3-methyl-butan-1-yl; 1-([1,3]Dioxolan-2-ylmethyl)-pyrrolidin-3-yl; pyrimidin-4-ylmethyl; 1-methyl-1H-pyrazol-3-ylmethyl; 1-methyl-1-(4H-[1,2,4]triazol-3-yl)-ethyl; 1-methyl-1-(5-methyl-4H-[1,2,4]triazol-3-yl)-ethyl; 3-fluoro-piperidin-4-yl; 2-hydroxy-cyclopentyl; dimethyl-[1,3]dioxan-5-yl; 2-(5-methyl-1,3,4-oxadiazol-2-yl)propan-2-yl; 2-(4-methyl-4H-1,2,4-triazol-3-yl)propan-2-yl; 2-(1-methyl-1H-1,2,4-triazol-3-yl)propan-2-yl; 2-(1-methyl-1H-pyrazol-4-yl)propan-2-yl; 2-(1-methyl-1H-pyrazol-3-yl)propan-2-yl; 2-(1-methyl-1H-pyrazol-5-yl; 2-(4H-1,2,4-triazol-3-yl)propan-2-yl; or 1-methyl-1H-pyrazole-4-yl.

In certain embodiments of formula I or formula II, $R^3$ is: methyl; ethyl; propyl; isopropyl; butyl; cyclopropyl; cyclopropylmethyl; cyclobutyl; methanesulfonyl; ethylsulfonyl; cyclopropylsulfonyl; sec-butylsulfonyl; morpholin-4-yl-ethyl; oxetan-3-yl; 2-methoxyethyl; 2-hydroxy-2-methyl-propyl; 3-hydroxy-2-methyl-propan-2-yl; 2-methoxy-propyl; tetrahydro-2H-pyran-4-yl; tetrahydrofuran-3-yl; 2,6-dimethyltetrahydro-2H-pyran-4-yl; tetrahydro-2H-pyran-3-yl); phenyl; 4-(methylsulfonyl)phenyl); 4-cyano-phenyl; 4-fluoro-phenyl; 4-chloro-phenyl; 3,5-difluorophenyl; 4-(dimethylamino-carbonyl)-phenyl); 4-(cyclopropylsulfonyl)phenyl; 2,2,2-trifluoroethyl; 2-fluoroethyl; difluoromethyl; 2-dimethyl-1,3-dioxan-5-yl; 1-methyl-cyclopropyl-carbonyl; 3-methylpyridin-4-yl; 2-methylpyridin-4-yl; pyridin-2-yl; pyrimidin-2-yl; pyrimidin-5-yl; pyridin-2-ylmethyl; 1-(pyridin-2-yl)ethyl; cyclopropylsulfonyl; 1-cyano-1-methyl-ethyl (also called 2-cyano-propan-2-yl); 2-cyano-ethyl; 1-cyano-ethyl; 2-cyano-2-methyl-propyl; 1-(2,2,2-trifluoroethyl)piperidin-4-yl; 1-(methylsulfonyl)azetidin-3-yl; (3-methyloxetan-3-yl)methyl; (1S,5S)-8-oxabicyclo[3.2.1]octan-3-yl; 1-(oxetan-3-yl)piperidin-4-yl; 1-acetyl-piperidin-4-yl; 1-(cyclopropyl-carbonyl)-piperidin-4-yl; 1-methyl-piperidin-4-yl; 1-methyl-2-oxo-piperidin-5-yl; 2-oxo-piperidin-5-yl; 1-(isopropyl-carbonyl)-piperidin-4-yl; 1-(oxetan-3-yl)azetidin-3-yl; 1-(cyclopropyl-carbonyl)-piperidin-4-yl; 2-methoxycyclopentyl; 3-methoxycyclopentyl; 1-methoxy-2-methylpropan-2-yl; tetrahydro-2H-1,1-dioxo-thiopyran-4-yl; 3-fluoro-1-(oxetan-3-yl)piperidin-4-yl; 1-methoxypropan-2-yl; 1-(2,2,2-trifluoroethyl)azetidin-3-yl); 1-(oxetan-3-yl)pyrrolidin-3-yl; 1-isopropylazetidin-3-yl; 3-fluoro-1-methylpiperidin-4-yl; 1-ethyl-3-fluoropiperidin-4-yl; 1-methylpyrrolidin-3-yl; 2-methoxyethyl)piperidin-4-yl); 1-methyl-1-(methylamino-carbonyl)-ethyl; 2-methyl-2-morpholino-propyl; 4,4-difluorocyclohexyl; morpholin-4-yl-carbonyl; dimethylamino-carbonyl-methyl; methylamino-carbonyl-methyl; 1-methyl-1-(dimethylamino-carbonyl)-ethyl; pyrrolidin-'-yl-carbonyl; 1-cyamo-cyclopropyl; 1-(pyrrolidin-'-yl-carbonyl)-ethyl; 1-(dimethylamino-carbonyl)-ethyl; 1-(methoxy-carbonyl)-ethyl; 1-(tert-butylamino-carbonyl)-1-methyl-ethyl; 1-(2,2,2-trifluoroethylamino-carbonyl)-1-methyl-ethyl; 1-(ethylamino-carbonyl)-1-methyl-ethyl; 1-(cyclopropylmethylamino-carbonyl)-1-methyl-ethyl; 1-(ethylamino-carbonyl)-cyclobutyl; 1-(isopropylamino-carbonyl)-1-methyl-ethyl; 1-cyano-cyclobutyl; 2-methoxy-1-methyl-ethyl; 1-methyl-1-(methoxy-carbonyl)-ethyl; 2-methoxy-2-methyl-propan-1-yl; 1-(oxetan-3-yl)-pyrrolidin-3-yl; isopropylsulfonyl; butane-2-sulfonyl; 1-(2-fluoroethyl)-piperidin-4-yl; 3-fluoro-1-methyl-piperidin-4-yl; 1-ethyl-3-fluoro-piperidin-4-yl; pyridin-3-ylmethyl; 6-methyl-pyridin-2-ylmethyl; 2-(morpholin-1-yl)-1,1,dimethyl-ethyl; pyrimdin-2-yl-methyl; 3-fluoro-1-(oxetan-3-yl)-piperidin-4-yl; 1-(oxetan-3-yl)-piperidin-3-yl; 1-([1,3]Dioxolan-2-ylmethyl)-piperidin-3-yl; pyridazin-3-ylmethyl; piperidin-3-yl; pyrazin-2-ylmethyl; 2-hydroxy-3-methyl-butan-1-yl; 1-([1,3]Dioxolan-2-ylmethyl)-pyrrolidin-3-yl; pyrimidin-4-ylmethyl; 1-methyl-1H-pyrazol-3-ylmethyl; 1-methyl-1-(4H-[1,2,4]triazol-3-yl)-ethyl; 1-methyl-1-(5-methyl-4H-[1,2,4]triazol-3-yl)-ethyl; 3-fluoro-piperidin-4-yl; 2-hydroxy-cyclopentyl; dimethyl-[1,3]dioxan-5-yl; 2-(5-methyl-1,3,4-oxadiazol-2-yl)propan-2-yl; 2-(4-methyl-4H-1,2,4-triazol-3-yl)propan-2-yl; 2-(1-methyl-1H-1,2,4-triazol-3-yl)propan-2-yl; 2-(1-methyl-1H-pyrazol-4-yl)propan-2-yl; 2-(1-methyl-1H-pyrazol-3-yl)propan-2-yl; 2-(1-methyl-1H-pyrazol-5-yl; 2-(4H-1,2,4-triazol-3-yl)propan-2-yl; or 1-methyl-1H-pyrazole-4-yl.

In certain embodiments of formula I or formula II, $R^3$ is: hydrogen; methyl; ethyl; n-propyl; isopropyl; 2-methoxy-ethyl; oxetan-3-yl; 2-hydroxy-2-methyl-propan-1-yl; tetrahydropyran-4-yl; or morpholin-4-yl-carbonyl.

In certain embodiments of formula I or formula II, $R^3$ is: methyl; ethyl; n-propyl; isopropyl; 2-methoxy-ethyl; oxetan-3-yl; 2-hydroxy-2-methyl-propan-1-yl; or tetrahydropyran-4-yl.

In certain embodiments of formula I or formula II, $R^3$ is: methyl; ethyl; isopropyl; 2-methoxy-ethyl; oxetan-3-yl; or 2-hydroxy-2-methyl-propan-1-yl.

In certain embodiments of formula I or formula II, $R^3$ is: methyl; ethyl; isopropyl; 2-methoxy-ethyl; oxetan-3-yl; or 2-hydroxy-2-methyl-propan-1-yl.

In certain embodiments of formula I or formula II, $R^3$ is: methyl; ethyl; or isopropyl.

In certain embodiments of formula I or formula II, $R^3$ is hydrogen.

In certain embodiments of formula I or formula II, $R^3$ is methyl.

In certain embodiments of formula I or formula II, $R^3$ is ethyl.

In certain embodiments of formula I or formula II, $R^3$ is n-propyl.

In certain embodiments of formula I or formula II, $R^3$ is isopropyl.

In certain embodiments of formula I or formula II, $R^3$ is 2-methoxy-ethyl.

In certain embodiments of formula I or formula II, $R^3$ is oxetan-3-yl.

In certain embodiments of formula I or formula II, $R^3$ is 2-hydroxy-2-methyl-propan-1-yl.

In certain embodiments of formula I or formula II, $R^3$ is tetrahydropyran-4-yl.

In certain embodiments of formula I or formula II, $R^3$ is morpholin-4-yl-carbonyl.

In certain embodiments of formula I or formula II, $R^3$ is butyl.

In certain embodiments of formula I or formula II, $R^3$ is cyclopropyl.

In certain embodiments of formula I or formula II, $R^3$ is cyclopropylmethyl.

In certain embodiments of formula I or formula II, $R^3$ is cyclobutyl.

In certain embodiments of formula I or formula II, $R^3$ is methanesulfonyl.

In certain embodiments of formula I or formula II, $R^3$ is ethylsulfonyl.

In certain embodiments of formula I or formula II, $R^3$ is cyclopropylsulfonyl.

In certain embodiments of formula I or formula II, $R^3$ is sec-butylsulfonyl.

In certain embodiments of formula I or formula II, $R^3$ is morpholin-4-yl-ethyl.

In certain embodiments of formula I or formula II, $R^3$ is 2-hydroxy-2-methyl-propyl.

In certain embodiments of formula I or formula II, $R^3$ is 3-hydroxy-2-methyl-propan-2-yl.

In certain embodiments of formula I or formula II, $R^3$ is 2-methoxy-propyl.

In certain embodiments of formula I or formula II, $R^3$ is tetrahydro-2H-pyran-4-yl.

In certain embodiments of formula I or formula II, $R^3$ is tetrahydrofuran-3-yl.

In certain embodiments of formula I or formula II, $R^3$ is 2,6-dimethyltetrahydro-2H-pyran-4-yl.

In certain embodiments of formula I or formula II, $R^3$ is tetrahydro-2H-pyran-3-yl).

In certain embodiments of formula I or formula II, $R^3$ is phenyl.

In certain embodiments of formula I or formula II, $R^3$ is 4-(methylsulfonyl)phenyl).

In certain embodiments of formula I or formula II, $R^3$ is 4-cyano-phenyl.

In certain embodiments of formula I or formula II, $R^3$ is 4-fluoro-phenyl.

In certain embodiments of formula Iv, $R^3$ is 4-chloro-phenyl.

In certain embodiments of formula I or formula II, $R^3$ is 3,5-difluorophenyl.

In certain embodiments of formula I or formula II, $R^3$ is 4-(dimethylamino-carbonyl)-phenyl).

In certain embodiments of formula I or formula II, $R^3$ is 4-(cyclopropylsulfonyl)phenyl.

In certain embodiments of formula I or formula II, $R^3$ is 2,2,2-trifluoroethyl.

In certain embodiments of formula I or formula II, $R^3$ is 2-fluoroethyl.

In certain embodiments of formula I or formula II, $R^3$ is difluoromethyl.

In certain embodiments of formula I or formula II, $R^3$ is 2-dimethyl-1,3-dioxan-5-yl.

In certain embodiments of formula I or formula II, $R^3$ is 1-methyl-cyclopropyl-carbonyl.

In certain embodiments of formula I or formula II, $R^3$ is 3-methylpyridin-4-yl.

In certain embodiments of formula I or formula II, $R^3$ is 2-methylpyridin-4-yl.

In certain embodiments of formula I or formula II, $R^3$ is pyridin-2-yl.

In certain embodiments of formula I or formula II, $R^3$ is pyrimidin-2-yl.

In certain embodiments of formula I or formula II, $R^3$ is pyrimidin-5-yl.

In certain embodiments of formula I or formula II, $R^3$ is pyridin-2-ylmethyl.

In certain embodiments of formula I or formula II, $R^3$ is 1-(pyridin-2-yl)ethyl.

In certain embodiments of formula I or formula II, $R^3$ is cyclopropylsulfonyl.

In certain embodiments of formula I or formula II, $R^3$ is 1-cyano-1-methyl-ethyl (also called 2-cyano-propan-2-yl).

In certain embodiments of formula I or formula II, $R^3$ is 2-cyano-ethyl.

In certain embodiments of formula I or formula II, $R^3$ is 1-cyano-ethyl.

In certain embodiments of formula I or formula II, $R^3$ is 2-cyano-2-methyl-propyl.

In certain embodiments of formula I or formula II, $R^3$ is 1-(2,2,2-trifluoroethyl)piperidin-4-yl.

In certain embodiments of formula I or formula II, $R^3$ is 1-(methylsulfonyl)azetidin-3-yl.

In certain embodiments of formula I or formula II, $R^3$ is (3-methyloxetan-3-yl)methyl.

In certain embodiments of formula I or formula II, $R^3$ is (1S,5S)-8-oxabicyclo[3.2.1]octan-3-yl.

In certain embodiments of formula I or formula II, $R^3$ is 1-(oxetan-3-yl)piperidin-4-yl.

In certain embodiments of formula I or formula II, $R^3$ is 1-acetyl-piperidin-4-yl.

In certain embodiments of formula I or formula II, $R^3$ is 1-(cyclopropyl-carbonyl)-piperidin-4-yl.

In certain embodiments of formula I or formula II, $R^3$ is 1-methyl-piperidin-4-yl.

In certain embodiments of formula I or formula II, $R^3$ is 1-methyl-2-oxo-piperidin-5-yl.

In certain embodiments of formula I or formula II, $R^3$ is 2-oxo-piperidin-5-yl.

In certain embodiments of formula I or formula II, $R^3$ is 1-(isopropyl-carbonyl)-piperidin-4-yl.

In certain embodiments of formula I or formula II, $R^3$ is 1-(oxetan-3-yl)azetidin-3-yl.

In certain embodiments of formula I or formula II, $R^3$ is 1-(cyclopropyl-carbonyl)-piperidin-4-yl.

In certain embodiments of formula I or formula II, $R^3$ is 2-methoxycyclopentyl.

In certain embodiments of formula I or formula II, $R^3$ is 3-methoxycyclopentyl.

In certain embodiments of formula I or formula II, $R^3$ is 1-methoxy-2-methylpropan-2-yl.

In certain embodiments of formula I or formula II, $R^3$ is tetrahydro-2H-1,1-dioxo-thiopyran-4-yl.

In certain embodiments of formula I or formula II, $R^3$ is 3-fluoro-1-(oxetan-3-yl)piperidin-4-yl.

In certain embodiments of formula I or formula II, $R^3$ is 1-methoxypropan-2-yl.

In certain embodiments of formula I or formula II, $R^3$ is 1-(2,2,2-trifluoroethyl)azetidin-3-yl).

In certain embodiments of formula I or formula II, $R^3$ is 1-(oxetan-3-yl)pyrrolidin-3-yl.

In certain embodiments of formula I or formula II, $R^3$ is 1-isopropylazetidin-3-yl.

In certain embodiments of formula I or formula II, $R^3$ is 3-fluoro-1-methylpiperidin-4-yl.

In certain embodiments of formula I or formula II, $R^3$ is 1-ethyl-3-fluoropiperidin-4-yl.

In certain embodiments of formula I or formula II, $R^3$ is 1-methylpyrrolidin-3-yl.

In certain embodiments of formula I or formula II, $R^3$ is 2-methoxyethyl)piperidin-4-yl).

In certain embodiments of formula I or formula II, $R^3$ is 1-methyl-1-(methylamino-carbonyl)-ethyl.

In certain embodiments of formula I or formula II, $R^3$ is 2-methyl-2-morpholino-propyl.

In certain embodiments of formula I or formula II, $R^3$ is 4,4-difluorocyclohexyl.

In certain embodiments of formula I or formula II, $R^3$ is dimethylamino-carbonyl-methyl.

In certain embodiments of formula I or formula II, $R^3$ is methylamino-carbonyl-methyl.

In certain embodiments of formula I or formula II, $R^3$ is 1-methyl-1-(dimethylamino-carbonyl)-ethyl.

In certain embodiments of formula I or formula II, $R^3$ is pyrrolidin-'-yl-carbonyl.

In certain embodiments of formula I or formula II, $R^3$ is 1-cyano-cyclopropyl.

In certain embodiments of formula I or formula II, $R^3$ is 1-(pyrrolidin-'-yl-carbonyl)-ethyl.

In certain embodiments of formula I or formula II, $R^3$ is 1-(dimethylamino-carbonyl)-ethyl.

In certain embodiments of formula I or formula II, $R^3$ is 1-(methoxy-carbonyl)-ethyl.

In certain embodiments of formula I or formula II, $R^3$ is 1-(tert-butylamino-carbonyl)-1-methyl-ethyl.

In certain embodiments of formula I or formula II, $R^3$ is 1-(2,2,2-trifluoroethyllamino-carbonyl)-1-methyl-ethyl.

In certain embodiments of formula I or formula II, $R^3$ is 1-(ethylamino-carbonyl)-1-methyl-ethyl.

In certain embodiments of formula I or formula II, $R^3$ is 1-(cyclopropylmethylamino-carbonyl)-1-methyl-ethyl.

In certain embodiments of formula I or formula II, $R^3$ is 1-(ethylamino-carbonyl)-cyclobutyl.

In certain embodiments of formula I or formula II, $R^3$ is 1-(isopropylamino-carbonyl)-1-methyl-ethyl.

In certain embodiments of formula I or formula II, $R^3$ is 1-cyano-cyclobutyl.

In certain embodiments of formula I or formula II, $R^3$ is dimethyl-[1,3]dioxan-5-yl.

In certain embodiments of formula I or formula II, $R^3$ is 2-methoxy-2-methyl-propan-1-yl.

In certain embodiments of formula I or formula II, $R^3$ is 2-methoxy-1-methyl-ethyl.

In certain embodiments of formula I or formula II, $R^3$ is 1-methyl-1-(methoxy-carbonyl)-ethyl.

In certain embodiments of formula I or formula II, $R^3$ is 1-oxetan-3-yl-pyrrolidin-3-yl.

In certain embodiments of formula I or formula II, $R^3$ is isopropylsulfonyl.

In certain embodiments of formula I or formula II, $R^3$ is butane-2-sulfonyl.

In certain embodiments of formula I or formula II, $R^3$ is 1-(2-fluoroethyl)-piperidin-4-yl.

In certain embodiments of formula I or formula II, $R^3$ is 3-fluoro-1-methyl-piperidin-4-yl.

In certain embodiments of formula I or formula II, $R^3$ is 1-ethyl-3-fluoro-piperidin-4-yl. In certain embodiments of formula I or formula II, $R^3$ is pyridin-3-ylmethyl.

In certain embodiments of formula I or formula II, $R^3$ is 6-methyl-pyridin-2-ylmethyl.

In certain embodiments of formula I or formula II, $R^3$ is 2-(morpholin-1-yl)-1,1,dimethyl-ethyl.

In certain embodiments of formula I or formula II, $R^3$ is pyrimdin-2-yl-methyl.

In certain embodiments of formula I or formula II, $R^3$ is 3-fluoro-1-(oxetan-3-yl)-piperidin-4-yl.

In certain embodiments of formula I or formula II, $R^3$ is 1-(oxetan-3-yl)-piperidin-3-yl.

In certain embodiments of formula I or formula II, $R^3$ is 1-([1,3]Dioxolan-2-ylmethyl)-piperidin-4-yl.

In certain embodiments of formula I or formula II, $R^3$ is pyridazin-3-ylmethyl.

In certain embodiments of formula I or formula II, $R^3$ is piperidin-3-yl.

In certain embodiments of formula I or formula II, $R^3$ is pyrazin-2-ylmethyl.

In certain embodiments of formula I or formula II, $R^3$ is 2-hydroxy-3-methyl-butan-1-yl.

In certain embodiments of formula I or formula II, $R^3$ is 1-([1,3]dioxolan-2-ylmethyl)-pyrrolidin-3-yl.

In certain embodiments of formula I or formula II, $R^3$ is pyrimidin-4-ylmethyl.

In certain embodiments of formula I or formula II, $R^3$ is 1-methyl-1H-pyrazol-3-ylmethyl.

In certain embodiments of formula I or formula II, $R^3$ is 1-methyl-1-(5-methyl-4H-[1,2,4]triazol-3-yl)-ethyl.

In certain embodiments of formula I or formula II, $R^3$ is 1-methyl-1-(4H-[1,2,4]triazol-3-yl)-ethyl.

In certain embodiments of formula I or formula II, $R^3$ is 3-fluoro-piperidin-4-yl; 2-hydroxy-cyclopentyl.

In certain embodiments of formula I or formula II, $R^3$ is 2-(5-methyl-1,3,4-oxadiazol-2-yl)propan-2-yl.

In certain embodiments of formula I or formula II, $R^3$ is 2-(4-methyl-4H-1,2,4-triazol-3-yl)propan-2-yl.

In certain embodiments of formula I or formula II, $R^3$ is 2-(1-methyl-1H-1,2,4-triazol-3-yl)propan-2-yl.

In certain embodiments of formula I or formula II, $R^3$ is 2-(1-methyl-1H-pyrazol-4-yl)propan-2-yl; 2-(1-methyl-1H-pyrazol-3-yl)propan-2-yl.

In certain embodiments of formula I or formula II, $R^3$ is 2-(1-methyl-1H-pyrazol-5-yl.

In certain embodiments of formula I or formula II, $R^3$ is 2-(4H-1,2,4-triazol-3-yl)propan-2-yl.

In certain embodiments of formula I or formula II, $R^3$ is 1-methyl-1H-pyrazole-4-yl.

In embodiments of formula I or formula II wherein $R^3$ is aryl, such aryl may be unsubstituted phenyl or phenyl substituted one or more times with $R^8$, or in certain embodiments, once, twice or three times with a group or groups independently selected from $C_{1-6}$alkyl, halo, halo-$C_{1-6}$alkyl, $C_{1-6}$alkoxy, hydroxy or cyano.

In embodiments of formula I or formula II wherein $R^3$ is heteroaryl or heteroaryl-$C_{1-6}$alkyl, such heteroaryl moiety may be pyrrolyl, pyrazolyl, imidazolyl, thiazolyl, oxazolyl, pyridinyl, pyrimidinyl, pyrazinyl, pyridazinyl, isoxazolyl, isothiazolyl, triazolyl, oxadiaolyl, thiadiazolyl or tetrazolyl, each being unsubstituted or substituted once or twice with $R^8$, or in certain embodiments, substituted once or twice with $C_{1-6}$alkyl.

In embodiments of formula I or formula II wherein $R^3$ is heteroaryl or heteroaryl-$C_{1-6}$alkyl, such heteroaryl moiety may be pyrazolyl, pyridinyl, pyrimidinyl, pyrazinyl, pyridazinyl, triazolyl or oxadiaolyl each being unsubstituted or substituted once or twice with $R^8$, or in certain embodiments, substituted once or twice with $C_{1-6}$alkyl.

In embodiments of formula I or formula II wherein $R^3$ is heteroaryl or heteroaryl-$C_{1-6}$alkyl, such heteroaryl moiety may be pyrrolyl, pyrazolyl, imidazolyl, thiazolyl, oxazolyl, pyridinyl, pyrimidinyl, pyrazinyl or pyridazinyl, each being unsubstituted or substituted one or more times with $R^8$ In embodiments of formula I or formula II wherein $R^3$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with $R^7$.

In embodiments of formula I or formula II wherein $R^3$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with $R^7$.

In certain embodiments of formula I or formula II, $R^3$ is —Y—C(O)—$R^d$.

In certain embodiments of formula I or formula II, Y is a bond.

In certain embodiments of formula I or formula II, Y is $C_{2-6}$alkylene.

In certain embodiments of formula I or formula II, Y is isopropylidine.

In certain embodiments of formula I or formula II, Y is methylene.

In certain embodiments of formula I or formula II, Y is ethylene.

In certain embodiments of formula I or formula II, Y is —C(CH$_3$)$_2$—.

In certain embodiments of formula I or formula II, Y is —CH$_2$—.

In certain embodiments of formula I or formula II, Y is —CH(CH$_3$)—.

In certain embodiments of formula I or formula II, Y is —CH$_2$—C(CH$_3$)$_2$—.

In certain embodiments of formula I or formula II, Y is —C(CH$_3$)$_2$—CH$_2$—.

In certain embodiments of formula I or formula II, R$^d$ is C$_{1-6}$alkyl, C$_{1-6}$alkoxy, amino, or heterocyclyl.

In certain embodiments of formula I or formula II, R$^d$ is C$_{1-6}$alkyl.

In certain embodiments of formula I or formula II, R$^d$ is C$_{1-6}$alkoxy.

In certain embodiments of formula I or formula II, R$^d$ is amino

In certain embodiments of formula I or formula II, R$^d$ is halo-C$_{1-6}$alkyl.

In certain embodiments of formula I or formula II, R$^d$ is hydroxy-C$_{1-6}$alkyl.

In certain embodiments of formula I or formula II, R$^d$ is C$_{1-6}$alkoxy-C$_{1-6}$alkyl.

In certain embodiments of formula I or formula II, R$^d$ is cyano-C$_{1-6}$alkyl.

In certain embodiments of formula I or formula II, R$^d$ is C$_{1-6}$alkylsulfonylC$_{1-6}$alkyl.

In certain embodiments of formula I or formula II, R$^d$ is amino-C$_{1-6}$alkyl.

In certain embodiments of formula I or formula II, R$^d$ is C$_{3-6}$cycloalkyl optionally substituted one or more times with R$^6$.

In certain embodiments of formula I or formula II, R$^d$ is C$_{3-6}$cycloalkyl-C$_{1-6}$alkyl wherein the C$_{3-6}$cycloalkyl portion is optionally substituted one or more times with R$^6$.

In certain embodiments of formula I or formula II, R$^d$ is heterocyclyl optionally substituted one or more times with R$^7$.

In certain embodiments of formula I or formula II, R$^d$ is heterocyclyl-C$_{1-6}$alkyl wherein the heterocyclyl portion is optionally substituted one or more times with R$^7$.

In certain embodiments of formula I or formula II, R$^d$ is 1-methyl-cyclopropyl; methylamino; dimethylamino; pyrrolidin-1-yl; methoxy; cyclopropyl-methyl; ethyl; 2,2,2-trifluoro-ethyl; tert-butyl; or isopropyl.

In certain embodiments of formula I or formula II, R$^d$ is 1-methyl-cyclopropyl.

In certain embodiments of formula I or formula II, R$^d$ is methylamino.

In certain embodiments of formula I or formula II, R$^d$ is dimethylamino

In certain embodiments of formula I or formula II, R$^d$ is pyrrolidin-1-yl.

In certain embodiments of formula I or formula II, R$^d$ is methoxy.

In certain embodiments of formula I or formula II, R$^d$ is cyclopropyl-methyl.

In certain embodiments of formula I or formula II, R$^d$ is ethyl.

In certain embodiments of formula I or formula II, R$^d$ is 2,2,2-trifluoro-ethyl.

In certain embodiments of formula I or formula II, R$^d$ is tert-butyl.

In certain embodiments of formula I or formula II, R$^d$ is isopropyl.

In embodiments of formula I or formula II wherein R$^d$ is heterocyclyl or heterocyclyl-C$_{1-6}$alkyl, such heterocyclyl may be piperidinyl, piperazinyl, morpholinyl, tetrahydropyranyl, pyrrolidinyl, azetidinyl, tetrahydrofuranyl or oxetanyl, each optionally substituted one or more times, or one or two times, with R$^7$ as defined herein.

In embodiments of formula I or formula II wherein R$^d$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with R$^7$.

In embodiments of formula I or formula II wherein R$^d$ is heterocyclyl-C$_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl, each being unsubstituted or substituted one or more times with R$^7$.

In certain embodiments of formula I or formula II, R$^4$ is: hydrogen; C$_{1-6}$alkyl; halo; halo-C$_{1-6}$alkyl; C$_{1-6}$alkoxy-C$_{1-6}$alkyl; hydroxy-C$_{1-6}$alkyl; C$_{3-6}$cycloalkyl optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; or —C(O)—R$^c$ wherein R$^c$ is C$_{1-6}$alkyl, C$_{1-6}$alkoxy, amino, or heterocyclyl.

In certain embodiments of formula I or formula II, R$^4$ is: C$_{1-6}$alkyl; halo; halo-C$_{1-6}$alkyl; C$_{1-6}$alkoxy-C$_{1-6}$alkyl; hydroxy-C$_{1-6}$alkyl; C$_{3-6}$cycloalkyl optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; or —C(O)—R$^c$ wherein R$^c$ is C$_{1-6}$alkyl, C$_{1-6}$alkoxy, amino, or heterocyclyl.

In certain embodiments of formula I or formula II, R$^4$ is: hydrogen; C$_{1-6}$alkyl; halo; C$_{3-6}$cycloalkyl optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; or —C(O)—R$^c$ wherein R$^c$ is C$_{1-6}$alkyl, C$_{1-6}$alkoxy, amino, or heterocyclyl.

In certain embodiments of formula I or formula II, R$^4$ is: hydrogen; C$_{1-6}$alkyl; halo; or C$_{3-6}$cycloalkyl optionally substituted with C$_{1-6}$alkyl.

In certain embodiments of formula I or formula II, R$^4$ is hydrogen or C$_{1-6}$alkyl.

In certain embodiments of formula I or formula II, R$^4$ is hydrogen.

In certain embodiments of formula I or formula II, R$^4$ is C$_{1-6}$alkyl.

In certain embodiments of formula I or formula II, R$^4$ is halo.

In certain embodiments of formula I or formula II, R$^4$ is cyano.

In certain embodiments of formula I or formula II, R$^4$ is halo-C$_{1-6}$alkyl.

In certain embodiments of formula I or formula II, R$^4$ is C$_{1-6}$alkoxy-C$_{1-6}$alkyl.

In certain embodiments of formula I or formula II, R$^4$ is hydroxy-C$_{1-6}$alkyl.

In certain embodiments of formula I or formula II, R$^4$ is C$_{3-6}$cycloalkyl optionally substituted with C$_{1-6}$alkyl.

In certain embodiments of formula I or formula II, R$^4$ is hydrogen or methyl.

In certain embodiments of formula I or formula II, R$^4$ is C$_{3-6}$cycloalkyl-C$_{1-6}$alkyl wherein the C$_{3-6}$cycloalkyl portion is optionally substituted with C$_{1-6}$alkyl.

In certain embodiments of formula I or formula II, R$^4$ is —C(O)—R$^c$ wherein R$^c$ is C$_{1-6}$alkyl, C$_{1-6}$alkoxy, amino, or heterocyclyl.

In certain embodiments of formula I or formula II, $R^4$ is —C(O)—$R^c$ wherein $R^c$ is heterocyclyl.

In embodiments of formula I or formula II wherein $R^c$ is heterocyclyl, such heterocyclyl may be pyrrolidinyl, piperidinyl, piperazinyl or morpholinyl.

In embodiments of formula I or formula II wherein $R^c$ is heterocyclyl, such heterocyclyl may be piperidinyl, piperazinyl or morpholinyl.

In certain embodiments of formula I or formula II, $R^4$ is: hydrogen; methyl; isopropyl; cyclopropyl; chloro; or morpholin-4-yl-carbonyl.

In certain embodiments of formula I or formula II, $R^4$ is: hydrogen; methyl; isopropyl; cyclopropyl; or chloro.

In certain embodiments of formula I or formula II, $R^4$ is hydrogen.

In certain embodiments of formula I or formula II, $R^4$ is methyl.

In certain embodiments of formula I or formula II, $R^4$ is isopropyl.

In certain embodiments of formula I or formula II, $R^4$ is cyclopropyl.

In certain embodiments of formula I or formula II, $R^4$ is chloro.

In certain embodiments of formula I or formula II, $R^4$ is morpholin-4-yl-carbonyl.

In certain embodiments of formula I or formula II, $R^4$ is 2-fluoro-ethyl.

In certain embodiments of formula I or formula II, $R^4$ is $C_{3-6}$cycloalkyl optionally substituted one or more times, or one or two times, with $R^6$.

In certain embodiments of formula I or formula II, $R^4$ is $C_{3-6}$cycloalkyl-$C_{1-6}$alkyl wherein the $C_{3-6}$cycloalkyl portion is optionally substituted one or more times, or one or two times, with $R^6$.

In certain embodiments of formula I or formula II, $R^4$ is —Y—C(O)—$R^d$.

In certain embodiments of formula I or formula II, or $R^3$ and $R^4$ together with the atoms to which they are attached may form a 5- or 6-membered ring that optionally includes a heteroatom selected from O, N and S.

In certain embodiments of formula I or formula II, $R^5$ is hydrogen.

In certain embodiments of formula I or formula II, $R^5$ is $C_{1-6}$alkyl.

In certain embodiments of formula I or formula II, $R^5$ is methyl.

In certain embodiments of formula I or formula II, each $R^6$ is independently $C_{1-6}$alkyl; halo-$C_{1-6}$alkyl; $C_{1-6}$alkoxy; cyano; or halo.

In certain embodiments of formula I or formula II, $R^6$ is $C_{1-6}$alkyl; halo-$C_{1-6}$alkyl; $C_{1-6}$alkoxy; or halo.

In certain embodiments of formula I or formula II, $R^6$ is $C_{1-6}$alkyl; halo-$C_{1-6}$alkyl; or halo.

In certain embodiments of formula I or formula II, $R^6$ is $C_{1-6}$alkyl.

In certain embodiments of formula I or formula II, $R^6$ is halo-$C_{1-6}$alkyl. In certain embodiments of formula I or formula II, $R^6$ is $C_{1-6}$alkoxy.

In certain embodiments of formula I or formula II, $R^6$ is cyano.

In certain embodiments of formula I or formula II, $R^6$ is halo.

In certain embodiments of formula I or formula II, $R^6$ is Y—C(O)—$R^d$.

In certain embodiments of formula I or formula II, $R^6$ is oxo.

In certain embodiments of formula I or formula II, each $R^7$ is independently $C_{1-6}$alkyl; halo-$C_{1-6}$alkyl; halo; $C_{1-6}$alkylsulfonyl; $C_{1-6}$alkoxy-$C_{1-6}$alkyl; cyano; heterocyclyl; or $C_{3-6}$cycloalkylsulfonyl wherein the $C_{3-6}$cycloalkyl portion is optionally substituted one or more times with $R^6$.

In certain embodiments of formula I or formula II, $R^7$ is $C_{1-6}$alkyl.

In certain embodiments of formula I or formula II, $R^7$ is halo-$C_{1-6}$alkyl.

In certain embodiments of formula I or formula II, $R^7$ is halo.

In certain embodiments of formula I or formula II, $R^7$ is $C_{1-6}$alkylsulfonyl.

In certain embodiments of formula I or formula II, $R^7$ is $C_{1-6}$alkoxy-$C_{1-6}$alkyl.

In certain embodiments of formula I or formula II, $R^7$ is cyano.

In certain embodiments of formula I or formula II, $R^7$ is —Y—C(O)—$R^d$.

In certain embodiments of formula I or formula II, $R^7$ is heterocyclyl.

In certain embodiments of formula I or formula II, $R^7$ is $C_{3-6}$cycloalkylsulfonyl wherein the $C_{3-6}$cycloalkyl portion is optionally substituted one or more times with $R^6$.

In certain embodiments of formula I or formula II, $R^7$ is oxo.

In certain embodiments of formula I or formula II, $R^7$ is $C_{1-6}$alkoxy.

In certain embodiments of formula I or formula II, $R^7$ is heterocyclyl-$C_{1-6}$alkyl.

In certain embodiments of formula I or formula II, $R^7$ is $C_{3-6}$cycloalkyl.

In certain embodiments of formula I or formula II, $R^7$ is $C_{3-6}$cycloalkyl-$C_{1-6}$alkyl.

In embodiments of formula I or formula II wherein $R^7$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl.

In embodiments of formula I or formula II wherein $R^7$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl.

In certain embodiments of formula I or formula II, each $R^8$ is independently oxo; $C_{1-6}$alkyl; halo-$C_{1-6}$alkyl; halo; $C_{1-6}$alkoxy; $C_{1-6}$alkoxy-$C_{1-6}$alkyl; cyano; $C_{3-6}$cycloalkyl optionally substituted one or more times with $R^6$, $C_{3-6}$cycloalkyl-$C_{1-6}$alkyl wherein the $C_{3-6}$cycloalkyl portion is optionally substituted one or more times with $R^6$, or $C_{3-6}$cycloalkyl-sulfonyl wherein the $C_{3-6}$cycloalkyl portion is optionally substituted one or more times with $R^6$.

In certain embodiments of formula I or formula II, $R^8$ is oxo. In certain embodiments of formula I or formula II, $R^7$ is $C_{1-6}$alkyl.

In certain embodiments of formula I or formula II, $R^7$ is halo-$C_{1-6}$alkyl In certain embodiments of formula I or formula II, $R^7$ is halo. In certain embodiments of formula I or formula II, $R^7$ is $C_{1-6}$alkoxy.

In certain embodiments of formula I or formula II, $R^7$ is $C_{1-6}$alkoxy-$C_{1-6}$alkyl.

In certain embodiments of formula I or formula II, $R^7$ is cyano.

In certain embodiments of formula I or formula II, $R^7$ is hetoeryclyl.

In certain embodiments of formula I or formula II, $R^7$ is —Y—C(O)—$R^d$.

In certain embodiments of formula I or formula II, $R^7$ is $C_{3-6}$cycloalkyl optionally substituted one or more times with $R^6$.

In certain embodiments of formula I or formula II, $R^7$ is $C_{3-6}$cycloalkyl-$C_{1-6}$alkyl wherein the $C_{3-6}$cycloalkyl portion is optionally substituted one or more times with $R^6$.

In certain embodiments of formula I or formula II, $R^7$ is $C_{3-6}$cycloalkyl-sulfonyl wherein the $C_{3-6}$cycloalkyl portion is optionally substituted one or more times with $R^6$.

In certain embodiments of formula I or formula II, $R^8$ is oxo.

In certain embodiments of formula I or formula II, $R^8$ is $C_{1-6}$alkyl.

In certain embodiments of formula I or formula II, $R^8$ is halo-$C_{1-6}$alkyl.

In certain embodiments of formula I or formula II, $R^8$ is halo.

In certain embodiments of formula I or formula II, $R^8$ is $C_{1-6}$alkyl-sulfonyl.

In certain embodiments of formula I or formula II, $R^8$ is $C_{1-6}$alkoxy.

In certain embodiments of formula I or formula II, $R^8$ is $C_{1-6}$alkoxy-$C_{1-6}$alkyl.

In certain embodiments of formula I or formula II, $R^8$ is cyano; hetoeryclyl.

In certain embodiments of formula I or formula II, $R^8$ is heterocyclyl-$C_{1-6}$alkyl.

In certain embodiments of formula I or formula II, $R^8$ is —Y—C(O)—$R^d$.

In certain embodiments of formula I or formula II, $R^8$ is $C_{3-6}$cycloalkyl.

In certain embodiments of formula I or formula II, $R^8$ is $C_{3-6}$cycloalkyl-$C_{1-6}$alkyl-$C_{3-6}$cycloalkyl-sulfonyl.

In embodiments of formula I or formula II wherein $R^8$ is heterocyclyl, such heterocyclyl moiety may be piperidinyl, pyrrolidinyl, oxetanyl, tetrahydropyranyl, tetrahydrofuranyl, azetidinyl, [1,3]dioxolanyl or tetrahydrothiopyranyl.

In embodiments of formula I or formula II wherein $R^8$ is heterocyclyl-$C_{1-6}$alkyl, such heterocyclyl moiety may be piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl.

In certain embodiments of the invention, compounds of formulas III, IV and V are provided:

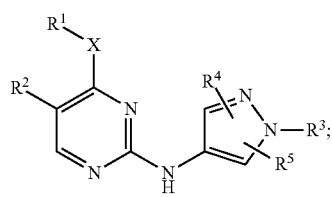

III

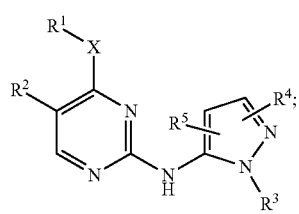

IV

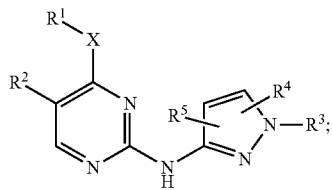

V wherein X, $R^1$, R, $R^2$, $R^3$, $R^4$ and $R^5$ are as defined herein.

In certain embodiments of the invention, the subject compounds are of formula III.

In certain embodiments of the invention, the subject compounds are of formula IV.

In certain embodiments of the invention, the subject compounds are of formula V.

Where any of $R^1$, $R^2$, R' $R^4$, $R^5$, $R^6$, $R^7$, $R^8$ $R^a$, $R^b$, $R^c$ and $R^d$ is alkyl or contains an alkyl moiety, such alkyl may be lower alkyl, i.e. $C_1$-$C_6$alkyl, and in many embodiments may be $C_1$-$C_4$alkyl.

The invention also provides a method for treating a disease or condition mediated by or otherwise associated with the LRRK2 receptor, the method comprising administering to a subject in need thereof an effective amount of a compound of the invention.

The disease may be a neurodegenerative disease such as Parkinson's disease, Huntington's disease or Lewie body dementia.

The disease may be a CNS disorder such as Alzheimer's disease or L-Dopa induced dyskinesia.

The disease may be a cancer or proliferative disorder such as kidney, breast, prostate, blood, papillary or lung cancer, acute myelogenous leukemia, or multiple myeloma.

The disease may be an inflammatory disease such as leprosy, Crohn's disease, amyotrophic lateral sclerosis, rheumatoid arthritis, or ankylosing spondylytis.

The invention also provides a method for enhancing cognitive memory, the method comprising administering to a subject in need thereof an effective amount of a compound of the invention.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I, wherein X, $R^1$, $R^2$, $R^3$, $R^4$ and $R^5$ are as defined herein.

individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and in some embodiments 1-30 mg daily, depending upon numerous factors such as the severity of the disease to be treated, the age and relative health

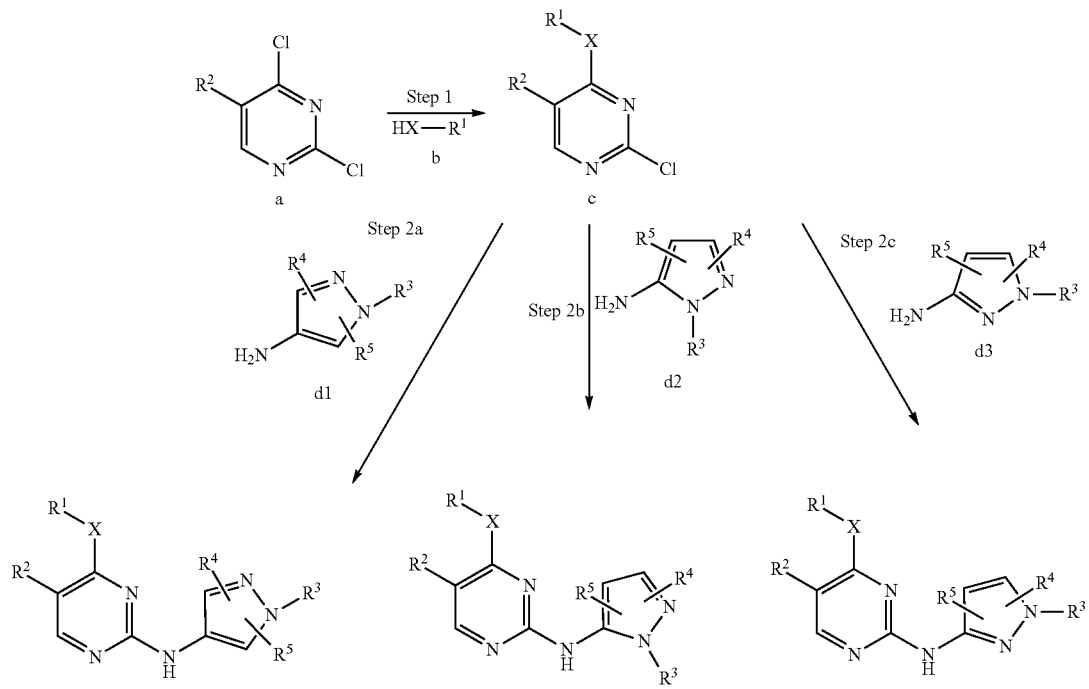

SCHEME A

In step 1 of Scheme A, dichloropyrimidine compound a is reacted with reagent b to afford pyrimidine compound c. The reaction of step 1 may take place under polar solvent conditions. In embodiments of the invention where X is —O— (reagent b is an alcohol), the reaction of step 1 may be carried out in the presence of base.

Following step 1, one of steps 2a, 2b and 2c is carried out. In step 2a, pyrimidine compound c undergoes reaction with 4-amino-pyrazole compound d1 to provide an aminopyrimidine compound of formula III. In step 2b, pyrimidine compound c is reacted with 5-amino-pyrazole compound d2 to afford an aminopyrimidine compound of formula IV. In step 2c, pyrimidine compound c is treated with 3-amino-pyrazole compound d3 to yield an aminopyrimidine compound of formula V. The reaction of steps 2a-2c may take place in polar protic solvent and in the presence of acid such as HCl.

Many variations on the procedure of Scheme A are possible and will suggest themselves to those skilled in the art. Specific details for producing compounds of the invention are described in the Examples below.

Administration and Pharmaceutical Composition

The invention includes pharmaceutical compositions comprising at least one compound of the present invention, or an of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of LRRK2-mediated diseases or conditions, including neurodegenerative diseases such as Parkinson's disease, Lewy body dementia and Huntington's disease, and for enhancement of cognitive memory generally in subjects in need thereof.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

ABBREVIATIONS

AcOH Acetic acid
AIBN 2,2'-Azobis(2-methylpropionitrile)
Atm. Atmosphere
(BOC)$_2$O di-tent-Butyl dicarbonate
dba tris(dibenzylideneacetone)
DCM Dichloromethane/Methylene chloride
DIAD Diisopropyl azodicarboxylate
DIPEA Diisopropylethylamine
DMAP 4-Dimethylaminopyridine
DME 1,2-Dimethoxyethane
DMF N,N-Dimethylformamide
DMSO Dimethyl sulfoxide
DPPF 1,1'-Bis(diphenylphosphino)ferrocene
Et$_2$O Diethyl ether
EtOH Ethanol/Ethyl alcohol
EtOAc Ethyl acetate
HATU 2-(1H-7-Azabenzotriazol-1-yl)-1,1,3,3-tetramethyl uronium hexafluorophosphate Methanaminium
HBTU O-Benzotriazol-1-yl-N,N,N',N'-tetramethyluronium hexafluorophosphate
HOBT 1-Hydroxybenzotriazole
HPLC High pressure liquid chromatography
HPLC Reverse phase high pressure liquid chromatography
i-PrOH Isopropanol/isopropyl alcohol
LCMS Liquid Chromatograph/Mass Spectroscopy
MeOH Methanol/Methyl alcohol
MW Microwaves
NBS N-Bromosuccinimide
NMP 1-Methyl-2-pyrrolidinone
PSI Pound per square inch
RT Room temperature
SFC Supercritical fluid chromatography
TBDMS tert-Butyldimethylsilyl
TFA Trifluoroacetic acid
THF Tetrahydrofuran
TLC Thin layer chromatography
Xphos 2-Dicyclohexylphosphino-2',4',6'-triisopropylbiphenyl Liquid Chromatography-Mass Spectrometry Method A LC-MS was performed on an Agilent 1200 Series LC coupled to an Agilent 6140 quadrupole mass spectrometer using an Agilent SD-C18 column (1.8 μm, 2.1×30 mm) with a linear gradient of 3-95% acetonitrile/water (with 0.05% trifluoroacetic acid in each mobile phase) within 8.5 minutes and held at 95% for 2.5 minutes.

Liquid Chromatography-Mass Spectrometry Method B

LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 um, 100×4.6 mm plus guard cartridge) with a linear gradient of 5-95% acetonitrile/water (with 0.1% formic acid in each mobile phase) within 3.5 minutes and held at 95% for 2.0 minutes.

Liquid Chromatography-Mass Spectrometry Method C

LC-MS was performed on a Waters 2795 Alliance HT HPLC with Waters 2996 Diode Array Detector coupled to a Micromass ZQ, single quadrapole mass spectrometer using a Waters Xterra MS C18 column (5 um, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.

Analytical Methods $^1$H Nuclear magnetic resonance (NMR) spectroscopy was carried out using a Bruker instrument operating at 400 or 500 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad. Where thin layer chromatography (TLC) has been used it refers to silica gel TLC using silica gel MK6F 60 Å plates, $R_f$ is the distance traveled by the compound divided by the distance traveled by the solvent on a TLC plate. Flash chromatography refers to silica gel chromatography and is carried out using an SP4 or an Isolara 4 MPLC system (manufactured by Biotage); pre-packed silica gel cartridges (supplied by Biotage); or using conventional glass column chromatography.

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is an Initiator 60 supplied by Biotage. The actual power supplied varies during the course of the reaction in order to maintain a constant temperature.

Compounds made in the following examples are summarized in the Tables below, which shows affinity values for LRRK2 (Ki, micromolar) for representative compounds together with LCMS method (M), LC retention time (RT) in minutes, and Mass Spec m/z values (molecular weight).

Intermediate 1

2,5-Dichloro-4-methoxypyrimidine

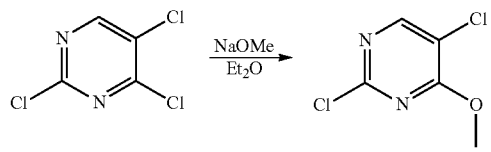

To a 250 mL round bottom flask equipped with a stir bar was added 2,4,5-trichloro-pyrimidine (1 g), and diethyl ether (15 mL). The mixture was cooled to 0° C. in an ice bath and then 1 equivalent of sodium methoxide in methanol (prepared from reacting 120 mg of sodium with 4 mL of methanol at room temperature) was slowly added. The reaction was stirred over night at room temperature and checked by LCMS. The white precipitate was filtered and the solid washed with cold methanol. After drying, 0.98 g of pure 2,5-dichloro-4-methoxypyrimidine was obtained and this material was used without further purification. $^1$H-NMR (DMSO): δ 8.61 (s, 1H), 4.05 (s, 3H).

Intermediate 2

2,5-Dichloro-N-methylpyrimidin-4-amine

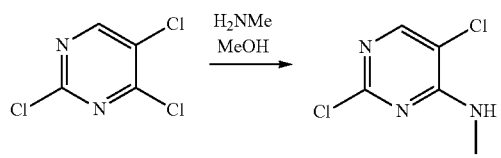

To a cooled (0° C.) solution of 2,4,5-trichloropyrimidine (2.0 g, 11 mmol) in methanol (30 mL) was added dropwise a 2 M solution of methylamine in methanol (6.3 mL). The reaction was allowed to warm to room temperature and stirred overnight. The reaction was then concentrated and redissolved in DCM. The solution was washed with sat. NaHCO$_3$, brine, dried over Na$_2$SO$_4$, filtered and concentrated. The crude product was purified by column chromatography (0-40% EtOAc in heptane) to give 2,5-dichloro-N-methylpyrimidin-4-amine (0.9 g, 50%). $^1$H-NMR (DMSO): δ 8.13 (s, 1H), 7.89 (s, 1H), 2.86 (d, J=4.5, 3H).

Intermediate 3

5-Bromo-2-chloro-N-methylpyrimidin-4-amine

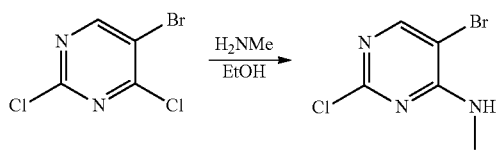

To a cooled (0° C.) solution of 5-bromo-2,4-dichloropyrimidine (5.0 g, 22 mmol) in methanol (42 mL) was added dropwise a 33 wt % solution of methylamine in ethanol (3.3 mL). The reaction was allowed to warm to room temperature. The reaction was then concentrated. The crude product was purified by column chromatography (0-10% methanol in DCM) to give 5-bromo-2-chloro-N-methylpyrimidin-4-amine (1.8 g, 39%). $^1$H-NMR (DMSO): δ 8.22 (s, 1H), 7.75 (s, 1H), 2.85 (d, J=3.9, 3H).

Intermediate 4

5-Bromo-2-chloro-4-methoxypyrimidine

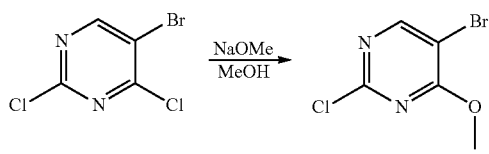

To a cooled (−78° C.) solution of 5-bromo-2,4-dichloropyrimidine (1.7 g, 7.3 mmol) in THF (30 mL) was added dropwise a 25 wt % solution of methylamine in ethanol (1.7 mL). The reaction was allowed to warm to 0° C. and stirred for 1 h. The reaction was then concentrated and re-dissolved in EtOAc. The solution was washed with brine, dried over Na$_2$SO$_4$, filtered and concentrated to give 5-bromo-2-chloro-4-methoxypyrimidine (1.25 g, 76%). $^1$H-NMR (CDCl$_3$): δ 8.43 (s, 1H), 4.10 (s, 3H).

Intermediate 5

2-chloro-5-fluoro-N-methylpyrimidin-4-amine

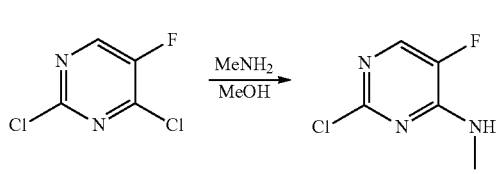

To a 250 mL round bottom flask equipped with a stir bar was added 5-fluoro-2,4-dichloro-pyrimidine (9 g), methanol (40 mL) and 8M methylamine in ethanol (15 mL). The reaction heated up (mild exo-therm) and was allowed to stir at room temperature for 30 minutes. A check by TLC (1:1 EtOAc:heptane) and LCMS showed complete reaction. The reaction was concentrated down to give 9.77 g crude material which was purified on a silica column running a gradient of 1% to 10% MeOH in DCM over 35 minutes to give 2-chloro-5-fluoro-N-methylpyrimidin-4-amine (6.77 g).

Intermediate 6

2-Chloro-5-iodo-N-methylpyrimidin-4-amine

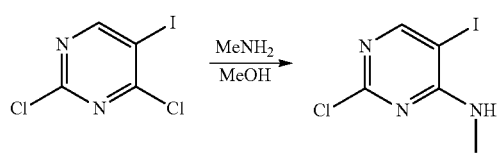

2-chloro-5-iodo-N-methylpyrimidin-4-amine was prepared following the procedure of Intermediate 5 but using 2,4-dichloro-5-iodopyrimidine. $^1$H-NMR (DMSO): δ 8.26 (s, 1H), 5.47 (s, 1H), 3.07 (d, J=4.9, 3H).

Intermediate 7

2-Chloro-N-methyl-5-(trifluoromethyl)pyrimidin-4-amine

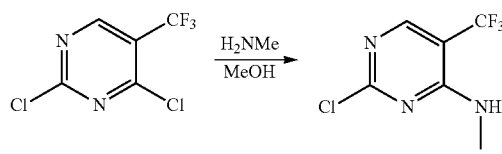

To a cooled (−10° C.) solution of 2,4-dichloro-5-trifluoromethylpyrimidine (20 g, 0.089 mol) in methanol (100 mL) was added triethylamine (12.5 mL, 0.089 mol) and a 2 M solution of methylamine in methanol (45 mL). The reaction was allowed to warm to room temperature and stirred overnight. The reaction was then concentrated and re-dissolved in ethyl acetate. The solution was washed with sat. NaHCO$_3$, brine, dried over MgSO$_4$, filtered and concentrated. The crude product was purified by column chromatography (5-25% EtOAc in heptane) to give 2-chloro-N-methyl-5-(trifluoromethyl)pyrimidin-4-amine (8.6 g, 45%). $^1$H-NMR (DMSO): δ 8.37 (s, 1H), 7.90 (s, 1H), 2.90 (s, 3H).

Intermediate 8

2-chloro-4-(pyrrolidin-1-yl)-5-(trifluoromethyl)pyrimidine

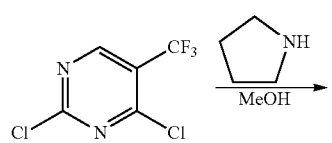

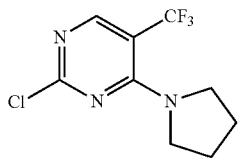

2-Chloro-4-(pyrrolidin-1-yl)-5-(trifluoromethyl)pyrimidine was prepared according to the procedure described for intermediate 7 using pyrrolidine.

Intermediate 9

2,5-Dichloro-4-(tetrahydro-2H-pyran-4-yloxy)pyrimidine

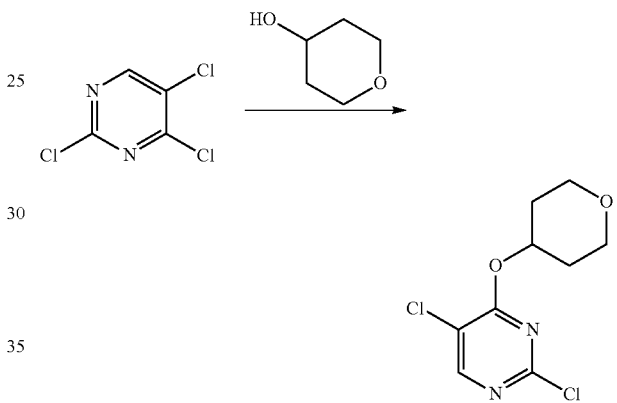

To a solution of tetrahydro-4-pyranol (0.36 g, 3.54 mmol) in DMF (5 mL) was added sodium hydride (60% dispersion, 0.17 g, 4.25 mmol). The resulting mixture was added to a solution of 2,4,5-trichloropyrimidine (650 mg, 3.5 mmol) in THF at 0° C. The combined mixture was then allowed to warm to room temperature. To the reaction was then added water and the product was extracted with a 1:1 EtOAc-Heptane mixture. The extract was then dried over Na$_2$SO$_4$, filtered and concentrated. The crude product was purified by column chromatography (0-30% EtOAc in heptane) to give 2,5-dichloro-4-(tetrahydro-2H-pyran-4-yloxy)pyrimidine.
$^1$H-NMR (CDCl$_3$): δ 8.33 (s, 1H), 5.42 (m, 1H), 4.09-3.90 (m, 2H), 3.65 (m, 2H), 2.19-1.99 (m, 2H), 1.87 (m, 2H).

Additional intermediates prepared using similar methods as described above are listed in Table 1 below:

TABLE 1

| 10 | 2-chloro-N-ethyl-5-(trifluoromethyl)pyrimidin-4-amine | |
|---|---|---|

TABLE 1-continued

| | | |
|---|---|---|
| 11 | 2-chloro-N-(2,2-difluoroethyl)-5-(trifluoromethyl)pyrimidin-4-amine | 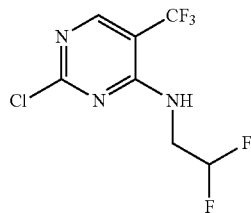 [SMILES: FC(F)CNc1nc(Cl)ncc1C(F)(F)F] |
| 12 | 2-chloro-N-((tetrahydro-2H-pyran-4-yl)methyl)-5-(trifluoromethyl)pyrimidin-4-amine | 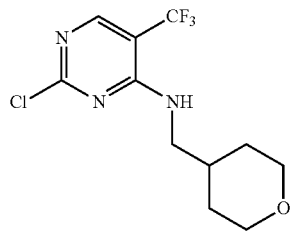 [SMILES: FC(F)(F)c1cnc(Cl)nc1NCC1CCOCC1] |
| 13 | 2,5-dichloro-4-ethoxypyrimidine | 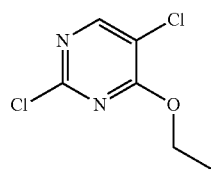 |
| 14 | 2-chloro-4-(2,2,2-trifluoroethoxy)-5-(trifluoromethyl)pyrimidine |  |
| 15 | 2-chloro-4-(2,2-difluoroethoxy)-5-(trifluoromethyl)pyrimidine | 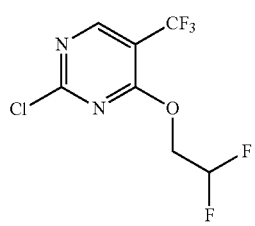 |
| 16 | 2,5-dichloro-4-(2,2-difluoroethoxy)pyrimidine | 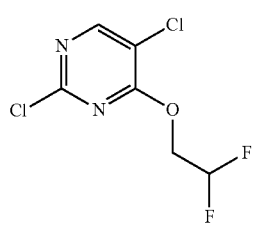 [SMILES: FC(F)COc1nc(Cl)ncc1Cl] |
| 17 | 2,5-dichloro-4-(oxetan-3-yloxy)pyrimidine | 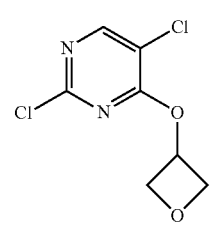 [SMILES: Clc1ncc(Cl)c(OC2COC2)n1] |
| 18 | 2-chloro-N-cyclopropyl-5-(trifluoromethyl)pyrimidin-4-amine | 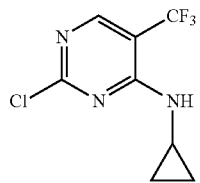 [SMILES: FC(F)(F)c1cnc(Cl)nc1NC1CC1] |

Intermediates 19 and 20

5-Methyl-1-(oxetan-3-yl)-1H-pyrazol-4-amine and 3-methyl-1-(oxetan-3-yl)-1H-pyrazol-4-amine

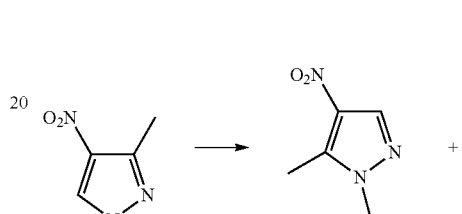

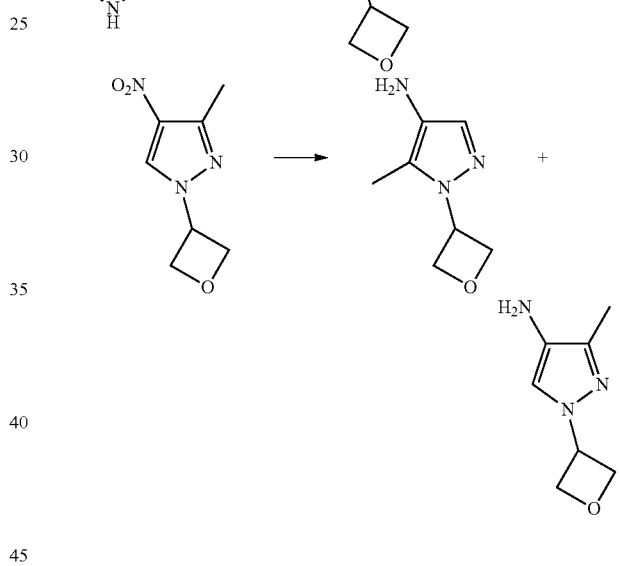

Step 1 5-Methyl-4-nitro-1-(oxetan-3-yl)-1H-pyrazole and 3-methyl-4-nitro-1-(oxetan-3-yl)-1H-pyrazole To a mixture of 3-methyl-4-nitro-pyrazole (0.80 g, 6.3 mmol), cesium carbonate (4.1 g, 12 mmol) in DMF (10 mL) was added 3-iodo-oxetane (3.47 g, 19 mmol). The mixture was stirred at 100° C. for 3 h. The reaction was diluted with water and extracted with ethyl acetate (3×). The combined extracts were washed with brine, dried over $Na_2SO_4$, filtered and concentrated. The crude product was purified by column chromatography (20-100% EtOAc-heptane) to give a mixture of 5-methyl-4-nitro-1-(oxetan-3-yl)-1H-pyrazole and 3-methyl-4-nitro-1-(oxetan-3-yl)-1H-pyrazole (0.85 g, 74%).

Step 2 5-Methyl-1-(oxetan-3-yl)-1H-pyrazol-4-amine and 3-methyl-1-(oxetan-3-yl)-1H-pyrazol-4-amine To a solution of 5-methyl-4-nitro-1-(oxetan-3-yl)-1H-pyrazole and 3-methyl-4-nitro-1-(oxetan-3-yl)-1H-pyrazole (0.137 g, 0.75 mmol) in ethanol (2 mL) was added Pd—C (10 wt %, 0.10 g). The mixture was stirred under a hydrogen atmosphere for 24 hours. The reaction was filtered through Celite® and concentrated to give a mixture of 5-methyl-1-(oxetan-3-yl)-1H-pyrazol-4-amine and 3-methyl-1-(oxetan-3-yl)-1H-pyrazol-4-amine (83 mg, 73%), which were used together in the following Examples.

Additional intermediates made using the above procedure are shown in Table 2 below.

TABLE 2

| | | |
|---|---|---|
| 21 | 1-(2-methoxyethyl)-5-methyl-1H-pyrazol-4-amine | |
| 22 | 1-(2-methoxyethyl)-3-methyl-1H-pyrazol-4-amine | |
| 23 | 1-(4-Amino-5-methyl-1H-pyrazol-1-yl)-2-methylpropan-2-ol | |
| 24 | 1-(4-amino-3-methyl-1H-pyrazol-1-yl)-2-methylpropan-2-ol | |
| 25 | 5-Methyl-1-(tetrahydro-2H-pyran-4-yl)-1H-pyrazol-4-amine | |

TABLE 2-continued

| | | |
|---|---|---|
| 26 | 3-Methyl-1-(tetrahydro-2H-pyran-4-yl)-1H-pyrazol-4-amine | |
| 27 | 3-methyl-1-(2,2,2-trifluoroethyl)-1H-pyrazol-4-amine | |
| 28 | 5-methyl-1-(2,2,2-trifluoroethyl)-1H-pyrazol-4-amine | |
| 29 | 3-methyl-1-(tetrahydrofuran-3-yl)-1H-pyrazol-4-amine | |
| 30 | 5-methyl-1-(tetrahydrofuran-3-yl)-1H-pyrazol-4-amine | |
| 31 | 5-(4-amino-5-methyl-1H-pyrazol-1-yl)-1-methylpiperidin-2-one | |

TABLE 2-continued

| # | Name |
|---|---|
| 32 | 5-(4-amino-3-methyl-1H-pyrazol-1-yl)-1-methylpiperidin-2-one |
| 33 | 5-(4-amino-3-methyl-1H-pyrazol-1-yl)piperidin-2-one |
| 34 | 5-(4-amino-5-methyl-1H-pyrazol-1-yl)piperidin-2-one |
| 35 | 1-(1-methoxy-2-methylpropan-2-yl)-5-methyl-1H-pyrazol-4-amine |
| 36 | 1-(2-methoxy-2-methylpropyl)-5-methyl-1H-pyrazol-4-amine |
| 37 | 1-(2-methoxypropyl)-5-methyl-1H-pyrazol-4-amine |
| 38 | 1-(1-methoxypropan-2-yl)-5-methyl-1H-pyrazol-4-amine |
| 39 | 3-methyl-1-(methylsulfonyl)-1H-pyrazol-4-amine |
| 40 | 1-(isopropylsulfonyl)-3-methyl-1H-pyrazol-4-amine |
| 41 | 1-(cyclopropylsulfonyl)-3-methyl-1H-pyrazol-4-amine |
| 42 | 1-(isopropylsulfonyl)-5-methyl-1H-pyrazol-4-amine |
| 43 | 1-(cyclopropylsulfonyl)-5-methyl-1H-pyrazol-4-amine |

TABLE 2-continued

| | | |
|---|---|---|
| 44 | 1-(sec-butylsulfonyl)-5-methyl-1H-pyrazol-4-amine | 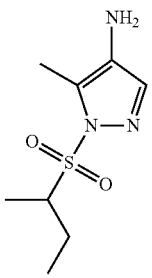 |
| 45 | 1-(2,2-dimethyl-1,3-dioxan-5-yl)-5-methyl-1H-pyrazol-4-amine | 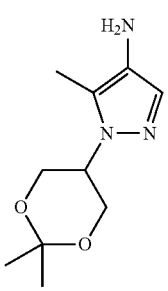 |
| 46 | 5-methyl-1-((3-methyloxetan-3-yl)methyl)-1H-pyrazol-4-amine | 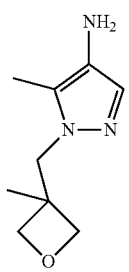 |
| 47 | 1-(2-fluoroethyl)-5-methyl-1H-pyrazol-4-amine | 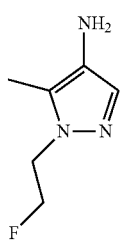 |
| 48 | 1-isopropyl-5-methyl-1H-pyrazol-4-amine | 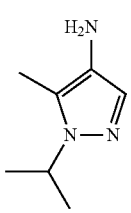 |

Intermediate 49

5-Chloro-1-methyl-1H-pyrazol-4-amine

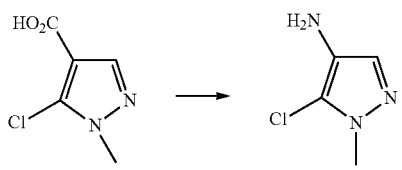

To a suspension of 5-chloro-1-methyl-1H-pyrazole-4-carboxylic acid (1.0 g, 6.2 mmol) in toluene (15 mL) was added triethylamine (1.7 mL, 12 mmol) and diphenylphosphonic azide (2 mL, 9.3 mmol). The resulting solution was stirred at room temperature for 30 minutes before heating at 95° C. for 1 h. After cooling to room temperature, the reaction was diluted with water and extracted with ethyl acetate (3×). The combined extracts were washed with brine, dried over Na$_2$SO$_4$, filtered and concentrated to give a yellow syrup. The crude product was purified by column chromatography (0-50% EtOAc in heptane) to give 5-chloro-1-methyl-1H-pyrazol-4-amine $^1$H-NMR (CDCl$_3$): δ 7.90 (s, 1H), 3.88 (s, 2H), 1.55 (s, 3H).

Intermediates 50 and 51

(S)-3-methyl-1-(1-(oxetan-3-yl)pyrrolidin-3-yl)-1H-pyrazol-4-amine and (S)-5-methyl-1-(1-(oxetan-3-yl)pyrrolidin-3-yl)-1H-pyrazol-4-amine

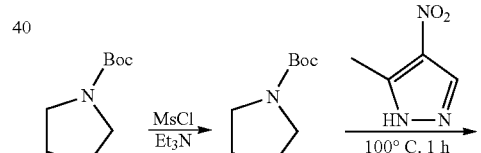
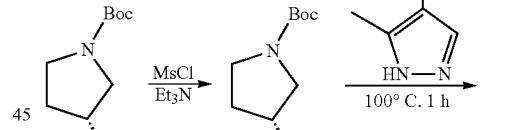
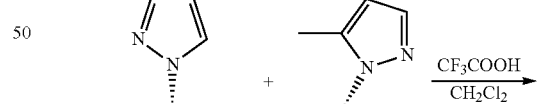
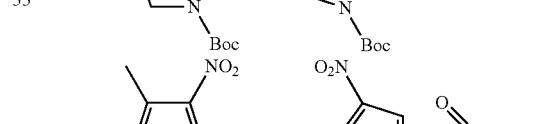
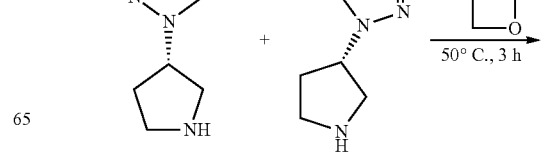

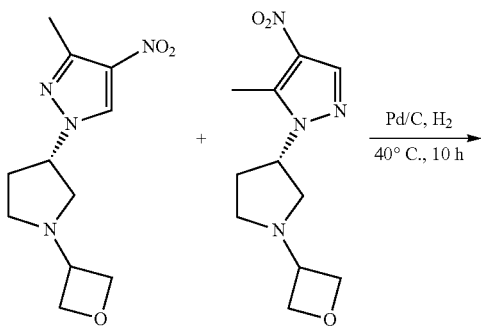

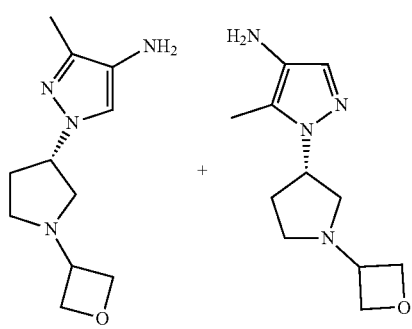

Step 1: (R)-tert-butyl 3-(methylsulfonyloxy)pyrrolidine-1-carboxylate (R)-tert-butyl 3-hydroxypyrrolidine-1-carboxylate (5.0 g, 26.7 mmol) and Et$_3$N (8.0 g, 80.2 mmol) were dissolved in dichloromethane (50 mL). The mixture was stirred at 0° C. for 30 minutes, then methanesulfonyl chloride (4.5 g, 40.1 mmol) was added dropwise. It was stirred at room temperature for 2 h and concentrated under reduced pressure. DCM (50 mL) and water (50 mL) were added. The organic phase was washed with saturated NaHCO$_3$ (30 mL) and H$_2$O (2×30 mL), and concentrated to afford the title compound as oil (6 g, 100%).

Step 2: (5)-tert-butyl 3-(3-methyl-4-nitro-1H-pyrazol-1-yl)pyrrolidine-1-carboxylate and (5)-tert-butyl 3-(5-methyl-4-nitro-1H-pyrazol-1-yl)pyrrolidine-1-carboxylate A microwave vial equipped with a magnetic stirrer was charged with (R)-tert-butyl 3-(methylsulfonyloxy)pyrrolidine-1-carboxylate (6.0 g, 22.5 mmol), 5-methyl-4-nitro-1H-pyrazole (2 g, 15.1 mmol), K$_2$CO$_3$ (6.2 g, 45.3 mmol) and DMF (50 mL). The reaction mixture was heated at 100° C. for 1 h under microwave irradiation. It was then filtered to get rid of K$_2$CO$_3$ and the filtrate was concentrated. The residue was purified by silica gel chromatography eluting with petroleum ether/ethyl acetate (2:1) to afford the mixture of the two title compounds as brown oil (5 g, 100%). m/z (ES+APCI)$^+$: [M+H]+ 241.

Alternatively, (5)-tert-butyl 3-(3-methyl-4-nitro-1H-pyrazol-1-yl)pyrrolidine-1-carboxylate (049-3) and (S)-tert-butyl 3-(5-methyl-4-nitro-1H-pyrazol-1-yl)pyrrolidine-1-carboxylate or related analogs, such as tert-butyl 3-fluoro-4-(3-methyl-4-nitro-1H-pyrazol-1-yl)piperidine-1-carboxylate, can be prepared by the following procedure: To a solution of 5-methyl-4-nitro-1H-pyrazole (0.99 g, 7.8 mmol), tert-butyl 3-fluoro-4-hydroxypiperidine-1-carboxylate (1.7 g, 7.8 mmol) and triphenylphosphine (2.3 g, 8.5 mmol) in THF (8 mL) was added diisopropyl azodicarboxylate (2 g, 9.3 mmol). The reaction was stirred at room temperature for 2 hours before being diluted with water and extracted with EtOAc (4×). The organic extracts were washed with brine, dried over sodium sulfate, filtered and concentrated. The crude product was purified by chromatography to give tert-butyl 3-fluoro-4-(3-methyl-4-nitro-1H-pyrazol-1-yl)piperidine-1-carboxylate (2.25 g, 88%).

Step 3: (S)-3-methyl-4-nitro-1-(pyrrolidin-3-yl)-1H-pyrazole and (S)-5-methyl-4-nitro-1-(pyrrolidin-3-yl)-1H-pyrazole The mixture of (S)-tert-butyl 3-(3-methyl-4-nitro-1H-pyrazol-1-yl)pyrrolidine-1-carboxylate and (5)-tert-butyl 3-(5-methyl-4-nitro-1H-pyrazol-1-yl)pyrrolidine-1-carboxylate (5 g, 16.9 mmol) was dissolved in dichloromethane (40 mL). CF$_3$COOH (10 mL) was added and the mixture was stirred at room temperature for overnight. The solvent was removed under reduced pressure to afford the mixture of the two title compounds as brown oil (4.0 g, 100%). m/z (ES+ APCI)$^+$: [M+H]+ 197.

Step 4: (S)-3-methyl-4-nitro-1-(1-(oxetan-3-yl)pyrrolidin-3-yl)-1H-pyrazole and (S)-5-methyl-4-nitro-1-(1-(oxetan-3-yl)pyrrolidin-3-yl)-1H-pyrazole To the mixture of (S)-3-methyl-4-nitro-1-(pyrrolidin-3-yl)-1H-pyrazole and (S)-5-methyl-4-nitro-1-(pyrrolidin-3-yl)-1H-pyrazole (4 g, 20.4 mmol), oxetan-3-one (4.4 g, 61.2 mmol), and ZnCl$_2$ (8.3 g, 61.2 mmol) in MeOH (50 mL) was added NaBH$_4$ (3.8 g, 61.2 mmol). The mixture was stirred at 50° C. for 5 h. Then the solvent was removed in vacuum. Dichloromethane (100 mL) was added and the mixture was washed with water (2×50 mL). It was then concentrated in vacuo and purified by silica gel chromatography eluting with dichloromethane/methanol (25/1) to afford the mixture of the two title compounds as yellow oil (3.8 g, 75%). m/z (ES+ APCI)$^+$: [M+H]+ 253.

Step 5: (S)-3-methyl-1-(1-(oxetan-3-yl)pyrrolidin-3-yl)-1H-pyrazol-4-amine and (S)-5-methyl-1-(1-(oxetan-3-yl)pyrrolidin-3-yl)-1H-pyrazol-4-amine To the mixture of (S)-3-methyl-4-nitro-1-(1-(oxetan-3-yl)pyrrolidin-3-yl)-1H-pyrazole and (S)-5-methyl-4-nitro-1-(1-(oxetan-3-yl)pyrrolidin-3-yl)-1H-pyrazole (500 mg, 1.98 mmol), and Zn (506 mg, 7.94 mmol) in methanol (20 mL) was added THF (20 mL) and NH$_4$Cl (841 mg, 15.9 mmol). The mixture was stirred at 50° C. for 2 h. It was then concentrated and purified by reverse-phase prep-HPLC to afford the mixture of the two title compounds as yellow solid (200 mg, 45%). m/z (ES+APCI)$^+$: [M+H]+ 223.

Additional intermediates made using the above procedure are shown in Table 3 below.

TABLE 3

| | | |
|---|---|---|
| 52 | 5-methyl-1-(1-(2,2,2-trifluoroethyl)piperidin-4-yl)-1H-pyrazol-4-amine | 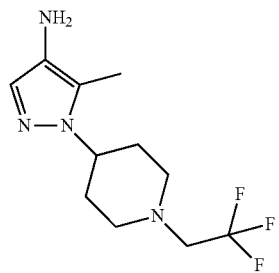 [SMILES: Cc1c(N)cnn1C1CCN(CC(F)(F)F)CC1] |
| 53 | 3-methyl-1-(1-(2,2,2-trifluoroethyl)piperidin-4-yl)-1H-pyrazol-4-amine | 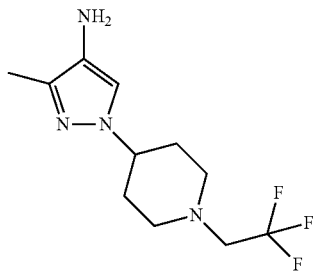 [SMILES: Cc1nn(C2CCN(CC(F)(F)F)CC2)cc1N] |
| 54 | 3-methyl-1-(1-(oxetan-3-yl)piperidin-4-yl)-1H-pyrazol-4-amine | 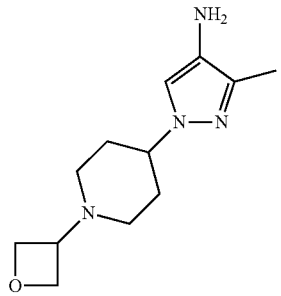 [SMILES: Cc1nn(C2CCN(C3COC3)CC2)cc1N] |
| 55 | 5-methyl-1-(1-(oxetan-3-yl)piperidin-4-yl)-1H-pyrazol-4-amine | 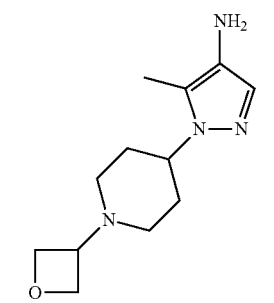 [SMILES: Cc1c(N)cnn1C1CCN(C2COC2)CC1] |
| 56 | 1-(1-methylpiperidin-4-yl)-1H-pyrazol-4-amine | 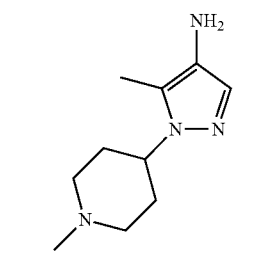 |

TABLE 3-continued

| | | |
|---|---|---|
| 57 | 3-methyl-1-(1-methylpiperidin-4-yl)-1H-pyrazol-4-amine | 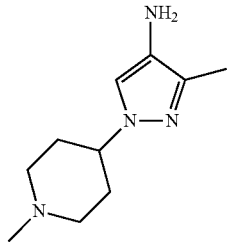 |
| 58 | 1-(4-(4-amino-3-methyl-1H-pyrazol-1-yl)piperidin-1-yl)ethanone | 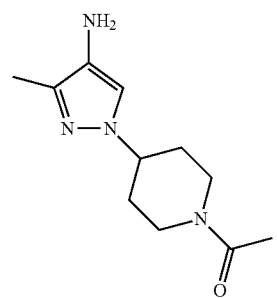 [SMILES: CC(=O)N1CCC(n2cc(N)c(C)n2)CC1] |
| 59 | 1-(4-(4-amino-5-methyl-1H-pyrazol-1-yl)piperidin-1-yl)ethanone | 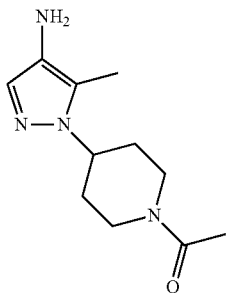 [SMILES: CC(=O)N1CCC(n2ncc(N)c2C)CC1] |
| 60 | (4-(4-amino-5-methyl-1H-pyrazol-1-yl)piperidin-1-yl)(cyclopropyl)methanone | 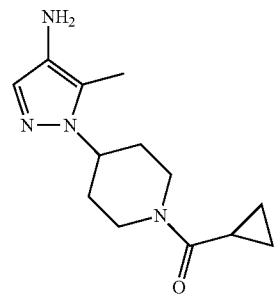 [SMILES: Cc1c(N)cnn1C1CCN(C(=O)C2CC2)CC1] |
| 61 | (4-(4-amino-3-methyl-1H-pyrazol-1-yl)piperidin-1-yl)(cyclopropyl)methanone | 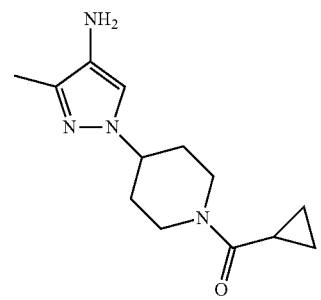 [SMILES: Cc1nn(C2CCN(C(=O)C3CC3)CC2)cc1N] |

TABLE 3-continued

| | | |
|---|---|---|
| 62 | (4-(4-amino-3-methyl-1H-pyrazol-1-yl)piperidin-1-yl)(1-methylcyclopropyl)methanone | 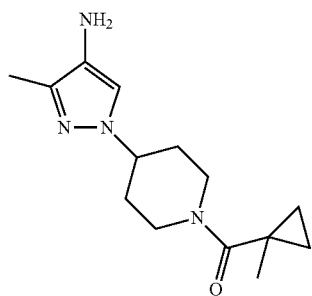 [SMILES: Cc1nn(C2CCN(C(=O)C3(C)CC3)CC2)cc1N] |
| 63 | 3-methyl-1-(1-methylpiperidin-4-yl)-1H-pyrazol-4-amine | 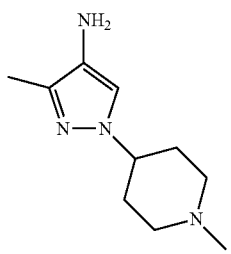 |
| 64 | 1-(3-fluoro-1-methylpiperidin-4-yl)-3-methyl-1H-pyrazol-4-amine | 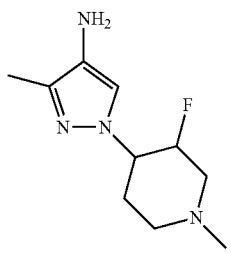 |
| 65 | 1-(1-ethyl-3-fluoropiperidin-4-yl)-3-methyl-1H-pyrazol-4-amine | 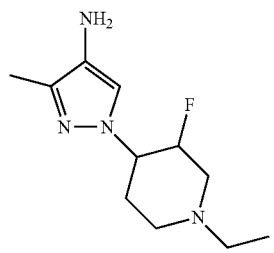 [SMILES: CCN1CCC(n2cc(N)c(C)n2)C(F)C1] |
| 66 | 3-methyl-1-(1-methylpyrrolidin-3-yl)-1H-pyrazol-4-amine | 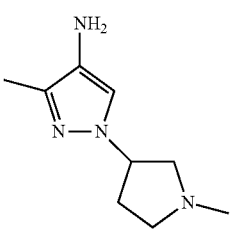 |

Intermediates 67 and 68

3-Methyl-1-(4-(methylsulfonyl)phenyl)-4-nitro-1H-pyrazole compound with 5-methyl-1-(4-(methylsulfonyl)phenyl)-4-nitro-1H-pyrazole

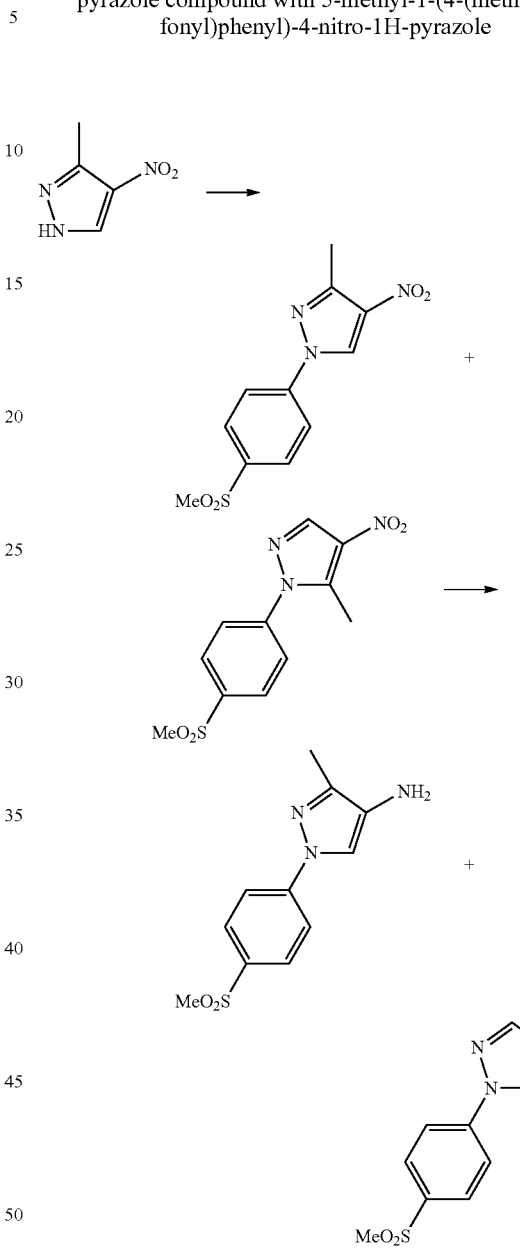

Step 1: 3-Methyl-1-(4-(methylsulfonyl)phenyl)-4-nitro-1H-pyrazole compound and 5-methyl-1-(4-(methylsulfonyl)phenyl)-4-nitro-1H-pyrazole A mixture of 3-methyl-4-nitro-1H-pyrazole (2.1 g, 17 mmol) and 4-methylsulfonylphenylboronic acid (5.0 g, 25 mmol), copper (II) acetate monohydrate (0.91 g, 5.0 mmol) and pyridine (0.5 g, 6.6 mmol) in DMF was stirred at 95° C. under an oxygen atmosphere for 7 hours. The reaction was diluted with water, extracted with EtOAc (3×). The combined extracts were washed with brine, dried over sodium sulfate, filtered and concentrated. The crude product was purified by flash chromatography to give a mixture of 3-methyl-1-(4-

(methylsulfonyl)phenyl)-4-nitro-1H-pyrazole compound and 5-methyl-1-(4-(methylsulfonyl)phenyl)-4-nitro-1H-pyrazole (1.3 g, 28%).

Step 2: 3-Methyl-1-(4-(methylsulfonyl)phenyl)-4-nitro-1H-pyrazole compound with 5-methyl-1-(4-(methylsulfonyl)phenyl)-4-nitro-1H-pyrazole A suspension of 3-methyl-1-(4-(methylsulfonyl)phenyl)-4-nitro-1H-pyrazole compound and 5-methyl-1-(4-(methylsulfonyl)phenyl)-4-nitro-1H-pyrazole (0.57 g, 2.0 mmol) and palladium on carbon (10 wt %, 0.2 g) in ethanol was stirred under a hydrogen atmosphere at 55° C. for 18 hours. The reaction mixture was filtered through celite and concentrated to give the title compounds as a mixture of regioisomers (446 mg, 87%).

Additional intermediates made using the above procedure are shown in Table 4 below

TABLE 4

| 69 | 3-methyl-1-phenyl-1H-pyrazol-4-amine | 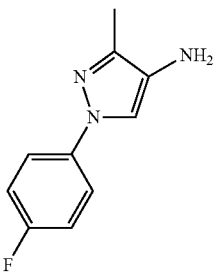 |
| 70 | 5-methyl-1-phenyl-1H-pyrazol-4-amine | 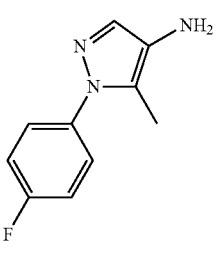 |
| 71 | 1-(4-chlorophenyl)-5-methyl-1H-pyrazol-4-amine | 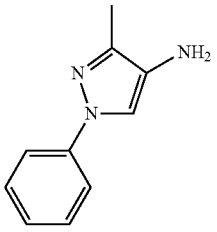 |
| 72 | 1-(4-chlorophenyl)-3-methyl-1H-pyrazol-4-amine | 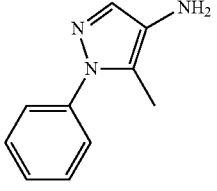 |

TABLE 4-continued

| 73 | 1-(4-fluorophenyl)-3-methyl-1H-pyrazol-4-amine | 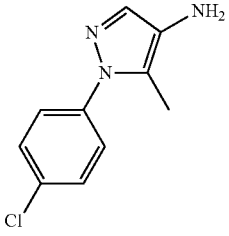 |
| 74 | 1-(4-fluorophenyl)-5-methyl-1H-pyrazol-4-amine | 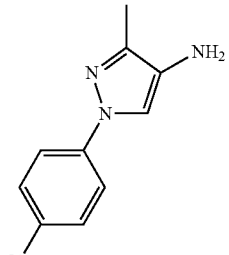 |
| 75 | 4-(4-amino-5-methyl-1H-pyrazol-1-yl)benzonitrile | 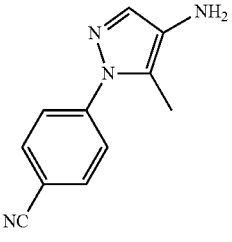 |
| 76 | 4-(4-amino-3-methyl-1H-pyrazol-1-yl)benzonitrile | 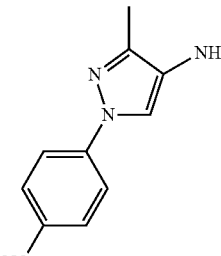 |
| 77 | 4-(4-amino-3-methyl-1H-pyrazol-1-yl)-N,N-dimethylbenzamide | 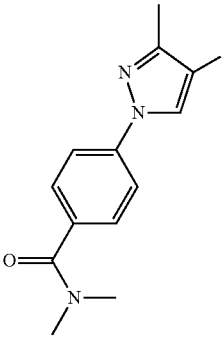 |

TABLE 4-continued

| | | |
|---|---|---|
| 78 | 4-(4-amino-5-methyl-1H-pyrazol-1-yl)-N,N-dimethylbenzamide | 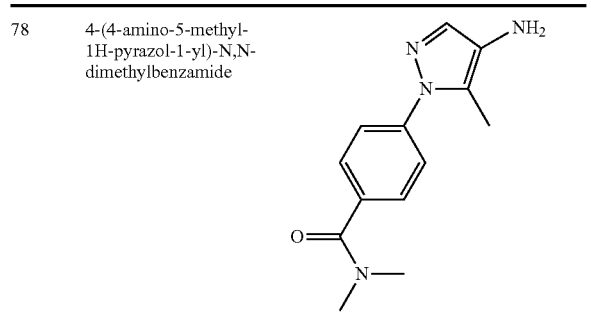 |
| 79 | 1-(3,5-difluorophenyl)-5-methyl-1H-pyrazol-4-amine | 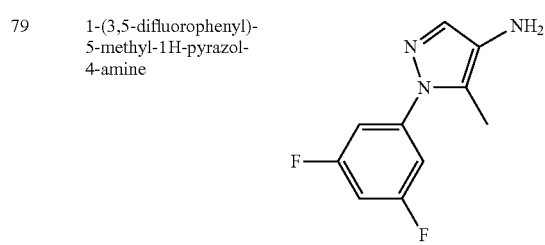 |
| 80 | 1-(3,5-difluorophenyl)-3-methyl-1H-pyrazol-4-amine | 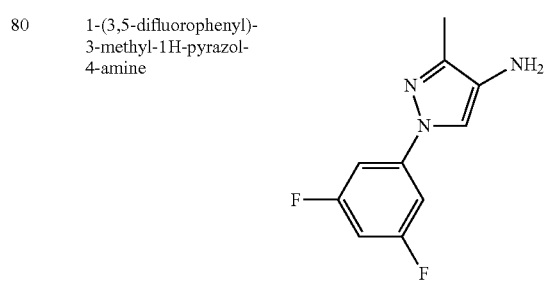 |
| 81 | 3-methyl-1-(pyridin-2-yl)-1H-pyrazol-4-amine | 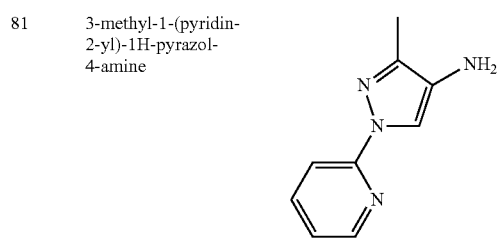 |
| 82 | 3-methyl-1-(pyrimidin-5-yl)-1H-pyrazol-4-amine | 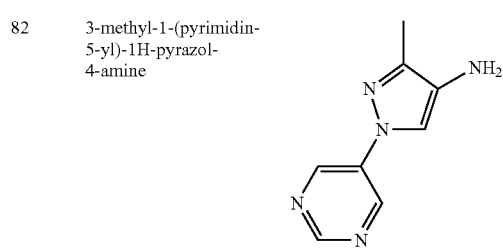 |
| 83 | 3-methyl-1-(2-methylpyridin-4-yl)-1H-pyrazol-4-amine | 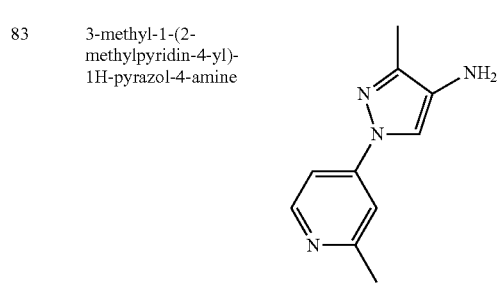 |
| 84 | 5-methyl-1-(2-methylpyridin-4-yl)-1H-pyrazol-4-amine | 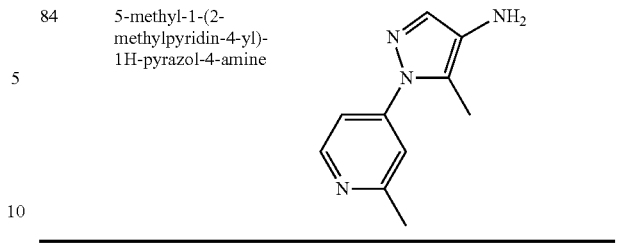 |

Intermediate 85

5-Chloro-1-(tetrahydro-2H-pyran-4-yl)-1H-pyrazol-4-amine

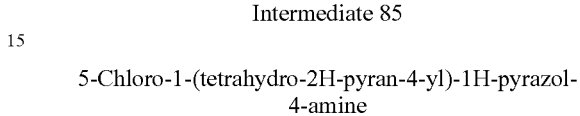

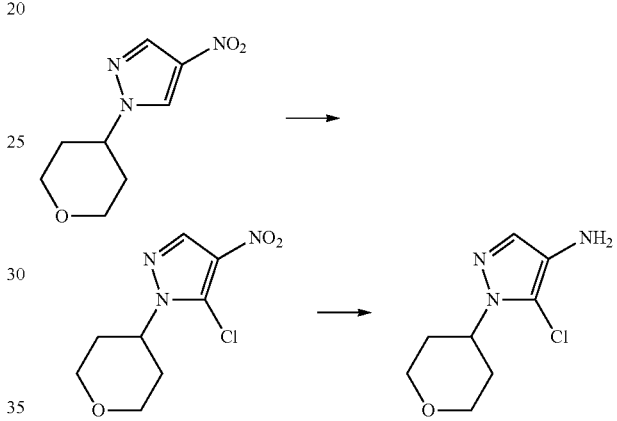

Step 1: 5-Chloro-4-nitro-1-(tetrahydro-2H-pyran-4-yl)-1H-pyrazole

To a solution of 4-nitro-1-tetrahydropyran-4-yl-pyrazole (1.32 g; 6.69 mmol) in THF (15 mL) was added dropwise LHMDS (1 mol/L) in THF (2.0 equiv.; 13.4 mmol) at −78° C. The reaction was stirred at −78° C. for 30 minutes before the addition of hexachloroethane (2.4 g, 10 mmol) in THF (5 mL). The reaction was stirred at −78° C. before warming to room temperature. The reaction was diluted with sat. NaCl and extracted with EtOAc (3×). The combined extracts were washed with brine, dried over sodium sulfate, filtered and concentrated. The crude product was purified by flash chromatography to give 5-chloro-4-nitro-1-(tetrahydro-2H-pyran-4-yl)-1H-pyrazole (0.98 g, 63%).

Step 2: 5-Chloro-1-(tetrahydro-2H-pyran-4-yl)-1H-pyrazol-4-amine

To a solution of 5-chloro-4-nitro-1-(tetrahydro-2H-pyran-4-yl)-1H-pyrazole (0.4 g, 2 mmol) in ethanol (10 mL) was added ammonium chloride (0.3 g, 5 mmol) and iron (0.3 g). The reaction was stirred at 90° C. for 30 minutes before filtered through celite and concentrated. The residue was triturated in EtOAc and filtered. The filtrated was concentrated to give the title compound (0.34 g, quant.)

Additional intermediates made using the above procedure are shown in Table 5 below.

TABLE 5

| | | |
|---|---|---|
| 86 | 1-(4-amino-5-chloro-1H-pyrazol-1-yl)-2-methylpropan-2-ol | 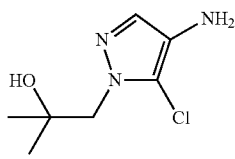 |
| 87 | methyl 2-(4-amino-5-chloro-1H-pyrazol-1-yl)-2-methylpropanoate | 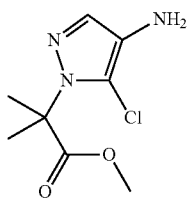 |
| 88 | 5-chloro-1-(oxetan-3-yl)-1H-pyrazol-4-amine | 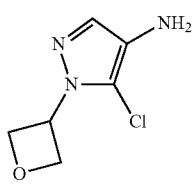 [SMILES: Nc1cnn(C2COC2)c1Cl] |
| 89 | 5-chloro-1-(cyclopropylmethyl)-1H-pyrazol-4-amine | 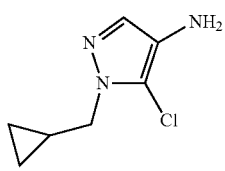 [SMILES: Nc1cnn(CC2CC2)c1Cl] |
| 90 | 5-chloro-1-(1-methylpiperidin-4-yl)-1H-pyrazol-4-amine | 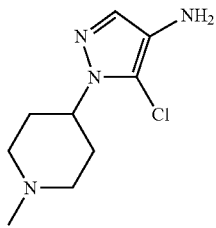 |
| 91 | 5-chloro-1-(3-fluoro-1-methylpiperidin-4-yl)-1H-pyrazol-4-amine | 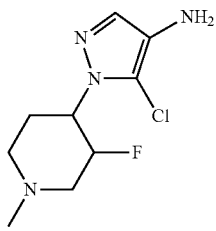 |
| 92 | 5-chloro-1-ethyl-1H-pyrazol-4-amine | 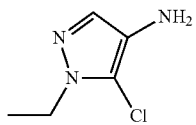 |
| 93 | 5-chloro-1-(1-ethyl-3-fluoropiperidin-4-yl)-1H-pyrazol-4-amine | 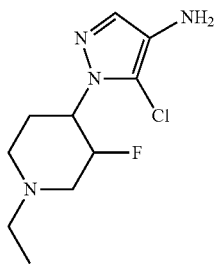 [SMILES: CCN1CCC(n2ncc(N)c2Cl)C(F)C1] |

TABLE 5-continued

| | | |
|---|---|---|
| 94 | 5-chloro-1-isopropyl-1H-pyrazol-4-amine | 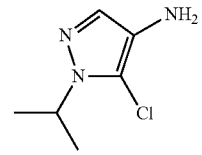 |
| 95 | 2-(4-amino-5-chloro-1H-pyrazol-1-yl)-2-methylpropan-1-ol | 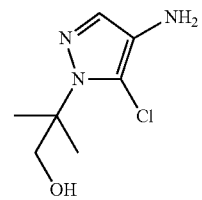 |

Intermediates 96

3-Cyclopropyl-4-nitro-1H-pyrazole

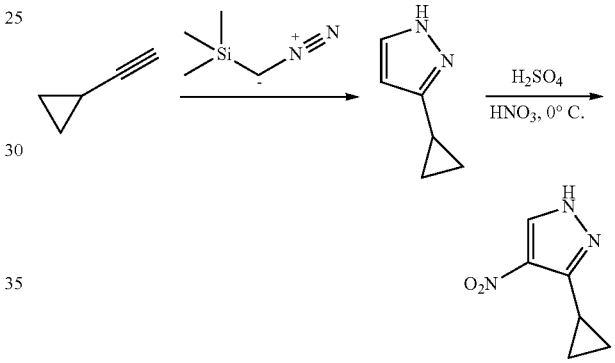

Step 1: 3-cyclopropyl-1H-pyrazole

Ethynylcyclopropane (660 mg, 10 mmol) mixed with (diazomethyl)trimethylsilane (5 mL, 2M in hexane) in a 30 mL microwave tube was microwaved at 135° C. for 1 h. Then this reaction was concentrated in vacuo to give a light yellow oil product (1.02 g, 94%). This product was pure enough to be used to the next step reaction without further purification. MS: [M+H]$^+$109.

Step 2: 3-Cyclopropyl-4-nitro-1H-pyrazole

To a cooling (0° C.) solution of 3-cyclopropyl-1H-pyrazole (1.5 g, 13.89 mmol) in concentrated H$_2$SO$_4$ (20 mL, 98%) was added concentrated HNO$_3$ (20 mL, 65%) over 2 min. The reaction mixture was stirred over 1 hr at this temperature. It was then diluted with ice-water and extracted with EA (30 mL×4). The organic phase was combined and washed with saturated sodium bicarbonate (50 mL). It was dried over Na$_2$SO$_4$ and concentrated in vacuo to give a crude product (1.5 g, 70%). This crude product was pure enough to be delivered or used to the next step reaction. MS: [M+H]$^+$154. $^1$H NMR (500 MHz, CDCl$_3$) δ 0.97 (m, 2H), 1.22 (m, 2H), 2.66 (m, 1H), 8.20 (s, 1H), 8.38 (s, 1H).

Intermediates made using the above procedure are shown in Table 6 below

TABLE 6

| | | |
|---|---|---|
| 97 | 5-isopropyl-4-nitro-1H-pyrazole | 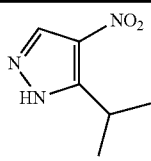 |
| 98 | 5-cyclobutyl-4-nitro-1H-pyrazole | 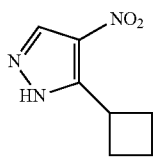 [SMILES: O=[N+]([O-])c1cn[nH]c1C1CCC1] |
| 99 | 5-tert-butyl-4-nitro-1H-pyrazole | 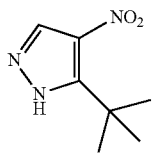 |
| 100 | 4-nitro-5-(trifluoromethyl)-1H-pyrazole | 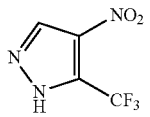 |

Example 1

N²-(1-isopropyl-1H-pyrazol-4-yl)-N⁴-methyl-5-(trifluoromethyl)pyrimidine-2,4-diamine

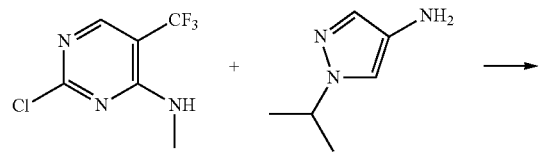

To a microwave tube was added 2-chloro-N-methyl-5-(trifluoromethyl)pyrimidin-4-amine (112 mg, 0.53 mmol), 1-isopropyl-1H-pyrazol-4-amine (55 mg, 0.44 mmol), cesium carbonate (0.287 g, 0.88 mmol), XPhos (21 mg, 0.044 mmol), $Pd_2(dba)_3$ (20 mg, 0.02 mmol) and dioxane (2.5 mL). The tube was sealed and the reaction was irradiated in the microwave at 140° C. for 30 minutes. The reaction mixture was then filtered and concentrated. The crude product was purified by reverse phase HPLC to give $N^2$-(1-isopropyl-1H-pyrazol-4-yl)-$N^4$-methyl-5-(trifluoromethyl)pyrimidine-2,4-diamine (22 mg, 16%). LCMS (Method A): [MH⁺]=301.1 at 3.2 min. ¹H-NMR (DMSO): δ 9.43 (m, 2H), 8.08 (s, 1H), 7.89 (s, 1H), 7.54 (s, 1H), 6.96 (m, 2H), 4.43 (m, 1H), 2.92 (d, J=8.0, 3H), 1.39 (d, J=6.6, 6H).

Compounds made using the above procedure are shown in Table 7 below, together with low resolution mass spectrometry (M+H), proton NMR, and LRRK2 $K_i$ (micromolar) data for selected compounds determined from the assay described below.

TABLE 7

| | Name | Structure | ¹H NMR | M + H⁺ | $K_I$ |
|---|---|---|---|---|---|
| 2 | N²-(1,5-dimethyl-1H-pyrazol-4-yl)-N⁴-methyl-5-(trifluoromethyl)pyrimidine-2,4-diamine | 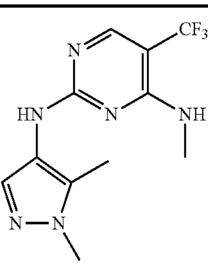 | ¹H-NMR (DMSO): δ 8.87 (s, 1 H), 8.04 (s, 1 H), 7.64 (s, 1 H), 6.90 (s, 2 H), 3.69 (s, 3 H), 2.84 (s, 3 H), 2.17 (s, 3 H). | 287.0 | |
| 3 | N⁴-methyl-N²-(1-(2-morpholinoethyl)-1H-pyrazol-4-yl)-5-(trifluoromethyl)pyrimidine-2,4-diamine | 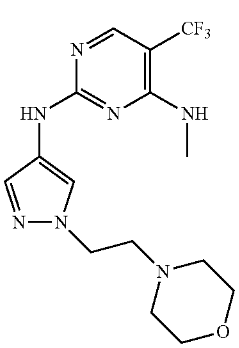 [SMILES: CNc1nc(Nc2cnn(CCN3CCOCC3)c2)ncc1C(F)(F)F] | ¹H-NMR (DMSO): δ 9.53 (s, 1 H), 8.08 (s, 1 H), 7.88 (s, 1 H), 7.55 (s, 1 H), 7.04 (s, 1 H), 4.17 (t, J = 6.0, 2 H), 3.61-3.49 (m, 4 H), 2.96 (s, 3 H), 2.67 (t, J = 6.4, 2 H), 2.39 (s, 3 H). | 372.1 | 0.015 |

TABLE 7-continued

| | Name | Structure | ¹H NMR | M + H⁺ | $K_I$ |
|---|---|---|---|---|---|
| 4 | N⁴-methyl-N²-(1-methyl-1H-pyrazol-4-yl)-5-(trifluoromethyl)pyrimidine-2,4-diamine | 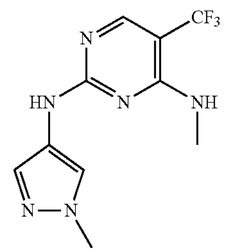 [SMILES: CNc1nc(Nc2cnn(C)c2)ncc1C(F)(F)F] | ¹H-NMR (DMSO): δ 9.53 (s, 1 H), 8.08 (s, 1 H), 7.81 (s, 1 H), 7.53 (s, 1 H), 7.06 (s, 1 H), 3.79 (s, 3 H), 2.95 (s, 3 H). | 273.0 | 0.0097 |
| 5 | 5-chloro-N²-(1-isopropyl-1H-pyrazol-4-yl)-N⁴-methyl-pyrimidine-2,4-diamine | 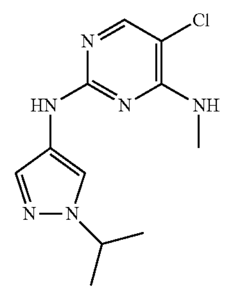 [SMILES: CNc1nc(Nc2cnn(C(C)C)c2)ncc1Cl] | ¹H-NMR (DMSO): δ 9.00 (s, 1 H), 7.5 (s, 2 H), 7.47 (s, 1 H), 7.06 (s, 1 H), 4.47-4.32 (m, 1 H), 2.91 (s, 3 H), 1.38 (d, J = 6.6, 6 H). | 267.0 | |
| 6 | N⁴-methyl-N²-(1-methyl-1H-pyrazol-5-yl)-5-(trifluoromethyl)pyrimidine-2,4-diamine | 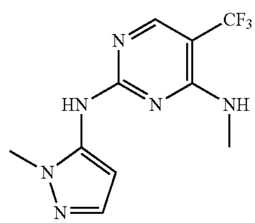 [SMILES: CNc1nc(Nc2ccnn2C)ncc1C(F)(F)F] | ¹H-NMR (DMSO): δ 9.40 (s, 1 H), 8.14 (s, 1 H), 7.32 (s, 1 H), 7.13 (s, 1 H), 6.23 (s, 1 H), 3.66 (s, 3 H), 2.84 (d, J = 3.8, 3 H). | 273.0 | 0.016 |
| 7 | N⁴-methyl-N²-(1-methyl-1H-pyrazol-3-yl)-5-(trifluoromethyl)pyrimidine-2,4-diamine | 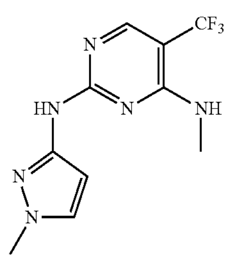 [SMILES: CNc1nc(Nc2ccn(C)n2)ncc1C(F)(F)F] | ¹H-NMR (DMSO): δ 9.69 (s, 1 H), 8.10 (s, 1 H), 7.53 (s, 1 H), 7.02 (s, 1 H), 6.60 (s, 1 H), 3.73 (s, 3 H), 2.91 (s, 3 H). | 273.0 | 0.018 |
| 8 | N²-(1,3-dimethyl-1H-pyrazol-4-yl)-N⁴-methyl-5-(trifluoromethyl)pyrimidine-2,4-diamine | 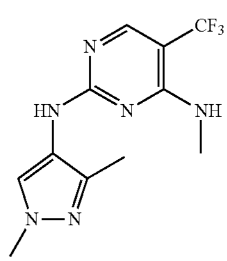 [SMILES: CNc1nc(Nc2cn(C)nc2C)ncc1C(F)(F)F] | ¹H-NMR (DMSO): δ 8.86 (s, 1 H), 8.07 (s, 1 H), 7.79 (s, 1 H), 6.94 (s, 1 H), 3.72 (s, 3 H), 2.88 (s, 3 H), 2.10 (s, 3 H). | 287.0 | |
| 9 | 5-Chloro-N-(1,5-dimethyl-1H-pyrazol-4-yl)-4-(tetrahydro-2H-pyran-4-yloxy)pyrimidin-2-amine | 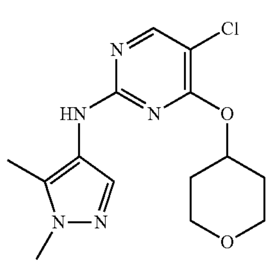 [SMILES: Cc1c(Nc2ncc(Cl)c(OC3CCOCC3)n2)cnn1C] | ¹H-NMR (DMSO): δ 8.78 (s, 1 H), 8.15 (s, 1 H), 7.44 (s, 1 H), 5.20 (s, 1 H), 3.85 (m, 2 H), 3.69 (s, 3 H), 3.47 (m, 2 H), 2.15 (s, 3 H), 1.98 (s, 2 H), 1.66 (m, 2 H). | 324.1 | 0.039 |

TABLE 7-continued

| | Name | Structure | ¹H NMR | M + H⁺ | $K_I$ |
|---|---|---|---|---|---|
| 10 | N⁴-methyl-5-(trifluoromethyl)-N²-(1,3,5-trimethyl-1H-pyrazol-4-yl)pyrimidine-2,4-diamine | 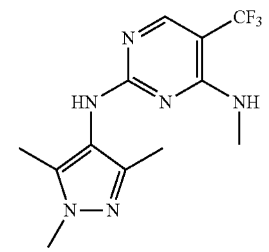 [SMILES: CNc1nc(Nc2c(C)nn(C)c2C)ncc1C(F)(F)F] | ¹H-NMR (DMSO): δ 8.39 (m, 1 H), 7.99 (s, 1 H), 6.79 (s, 1 H), 3.62 (s, 3 H), 2.78 (m, 3 H), 2.03 (s, 3 H), 1.94 (s, 3 H). | 301.1 | 0.096 |
| 11 | 5-Chloro-N-(1-isopropyl-1H-pyrazol-4-yl)-4-(tetrahydro-2H-pyran-4-yloxy)pyrimidin-2-amine | 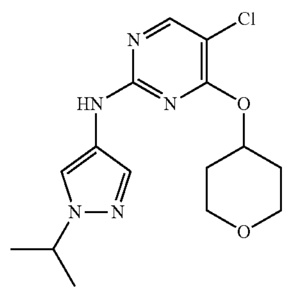 [SMILES: CC(C)n1cc(Nc2ncc(Cl)c(OC3CCOCC3)n2)cn1] | ¹H-NMR (DMSO): δ 9.49 (s, 1 H), 8.23 (s, 1 H), 7.80 (s, 1 H), 7.47 (s, 1 H), 5.31 (m, 1 H), 4.45 (m, 1 H), 3.88 (m, 2 H), 3.53 (m, 2 H), 2.06 (m, 2 H), 1.70 (m, 2 H), 1.40 (d, 6 H). | 338.1 | 0.033 |
| 12 | 5-Chloro-N-(1,5-dimethyl-1H-pyrazol-4-yl)-4-methoxy-pyrimidin-2-amine | 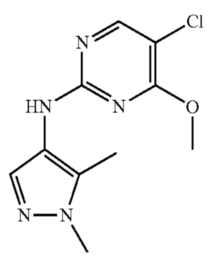 | ¹H-NMR (DMSO): δ 8.82 (s, 1 H), 8.13 (s, 1 H), 7.48 (s, 1 H), 3.91 (s, 3 H), 3.69 (s, 3 H), 2.15 (s, 3 H). | 254.0 | 0.0091 |
| 13 | N-(1,5-dimethyl-1H-pyrazol-4-yl)-4-(pyrrolidin-1-yl)-5-(trifluoromethyl)pyrimidin-2-amine | 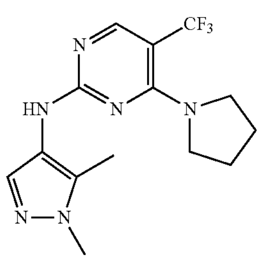 [SMILES: Cc1c(Nc2ncc(C(F)(F)F)c(N3CCCC3)n2)cnn1C] | ¹H-NMR (DMSO): δ 8.88 (s, 1 H), 8.22 (s, 1 H), 7.61 (s, 1 H), 3.69 (s, 3 H), 3.51 (s, 4 H), 2.17 (s, 3 H), 1.87 (s, 4 H). | 327.1 | 0.012 |
| 14 | N²-(1-ethyl-5-methyl-1H-pyrazol-4-yl)-N⁴-methyl-5-(trifluoromethyl)pyrimidine-2,4-diamine | 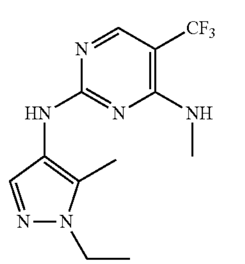 [SMILES: CCn1ncc(Nc2ncc(C(F)(F)F)c(NC)n2)c1C] | ¹H-NMR (DMSO): δ 8.90 (s, 1 H), 8.05 (s, 1 H), 7.67 (s, 1 H), 6.95 (s, 1 H), 4.01 (m, 2 H), 2.82 (s, 3 H), 2.19 (s, 3 H), 1.27 (t, J = 7.2, 3 H). | 301.1 | 0.024 |
| 15 | 5-Chloro-N-(1,3-dimethyl-1H-pyrazol-4-yl)-4-methoxy-pyrimidin-2-amine | 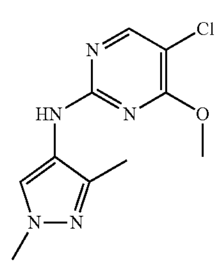 | ¹H-NMR (DMSO): δ 8.87 (s, 1 H), 8.17 (s, 1 H), 7.77 (s, 1 H), 3.95 (s, 3 H), 3.72 (s, 3 H), 2.09 (s, 3 H). | 254.0 | 0.0144 |

TABLE 7-continued

| Name | Structure | $^1$H NMR | M + H$^+$ | K$_I$ |
|---|---|---|---|---|
| 16 N$^4$-methyl-N$^2$-(3-methyl-1-(oxetan-3-yl)-1H-pyrazol-4-yl)-5-(trifluoromethyl)pyrimidine-2,4-diamine | | $^1$H-NMR (DMSO): δ 8.97 (s, 1 H), 8.08 (m, 2 H), 6.96 (s, 1 H), 5.44 (m, 1 H), 4.85 (m, 4 H), 2.89 (d, J = 4.4, 3 H), 2.18 (s, 3 H). | 329.1 | |
| 17 N$^2$-(5-chloro-1-methyl-1H-pyrazol-4-yl)-N$^4$-methyl-5-(trifluoromethyl)pyrimidine-2,4-diamine | | $^1$H-NMR (DMSO): δ 8.87 (s, 1 H), 8.07 (s, 1 H), 7.71 (s, 1 H), 6.98 (s, 1 H), 3.77 (s, 3 H), 2.83 (s, 3 H). | 307.0 | |
| 18 5-Chloro-4-methoxy-N-(3-methyl-1-(oxetan-3-yl)-1H-pyrazol-4-yl)pyrimidin-2-amine | | $^1$H-NMR (DMSO): δ 8.97 (s, 1 H), 8.19 (s, 1 H), 7.98 (s, 1 H), 5.46 (s, 1 H), 4.85 (s, 4 H), 3.96 (s, 3 H), 2.18 (s, 3 H). | 296.0 | 0.022 |
| 19 5-Chloro-4-methoxy-N-(1-(2-methoxyethyl)-3-methyl-1H-pyrazol-4-yl)pyrimidin-2-amine | | $^1$H-NMR (DMSO): δ 8.81 (s, 1 H), 8.13 (s, 1 H), 7.53 (s, 1 H), 4.14 (t, J = 5.4, 2 H), 3.90 (s, 3 H), 3.63 (t, J = 5.4, 2 H), 3.21 (s, 3 H), 2.16 (s, 3 H) | 298.0 | 0.015 |
| 20 5-chloro-4-methoxy-N-(1-(2-methoxyethyl)-5-methyl-1H-pyrazol-4-yl)pyrimidin-2-amine | | 1H-NMR (DMSO): δ 8.90 (s, 1 H), 8.17 (s, 1 H), 7.83 (s, 1 H), 4.13 (t, J = 5.2, 2 H), 3.95 (s, 3 H), 3.63 (t, J = 5.3, 2 H), 3.22 (s, 3 H), 2.11 s, 3 H). | 298.0 | 0.019 |

TABLE 7-continued

| | Name | Structure | ¹H NMR | M + H⁺ | $K_I$ |
|---|---|---|---|---|---|
| 21 | 5-Chloro-N-(5-chloro-1-methyl-1H-pyrazol-4-yl)-4-methoxy-pyrimidin-2-amine | 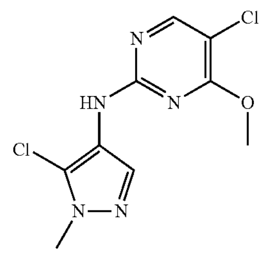 [SMILES: COc1nc(Nc2cnn(C)c2Cl)ncc1Cl] | ¹H-NMR (DMSO): δ 8.99 (s, 1 H), 8.18 (s, 1 H), 7.67 (s, 1 H), 3.91 (s, 3 H), 3.78 (s, 3 H). | 274.0 | 0.020 |
| 22 | 2-Methyl-1-(3-methyl-4-(4-(methylamino)-5-(trifluoromethyl)pyrimidin-2-ylamino)-1H-pyrazol-1-yl)propan-2-ol | 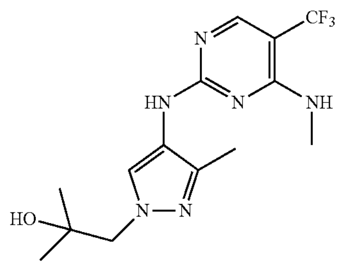 [SMILES: CNc1nc(Nc2cn(CC(C)(C)O)nc2C)ncc1C(F)(F)F] | ¹H-NMR (DMSO): δ 8.89 (s, 1 H), 8.07 (s, 1 H), 7.95 (s, 1 H), 6.93 (s, 1 H), 4.60 (s, 1 H), 3.88 (s, 2 H), 2.87 (d, J = 4.1, 3 H), 2.13 (s, 3 H), 1.05 (s, 6 H). | 345.1 | |
| 23 | 2-Methyl-1-(3-methyl-4-(4-(methylamino)-5-chloro-pyrimidin-2-ylamino)-1H-pyrazol-1-yl)propan-2-ol | 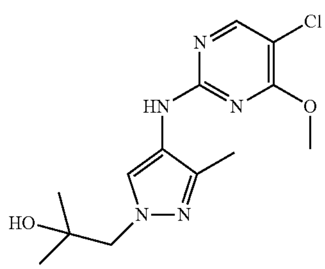 [SMILES: COc1nc(Nc2cn(CC(C)(C)O)nc2C)ncc1Cl] | ¹H-NMR (DMSO): δ 8.92 (s, 1 H), 8.18 (s, 1 H), 7.86 (s, 1 H), 4.61 (s, 1 H), 3.94 (s, 3 H), 3.89 (s, 2 H), 2.12 (s, 3 H), 1.05 (s, 6 H). | 312.1 | 0.027 |
| 24 | N²-(1-(2-methoxyethyl)-3-methyl-1H-pyrazol-4-yl)-N⁴-methyl-5-(trifluoromethyl)pyrimidine-2,4-diamine | 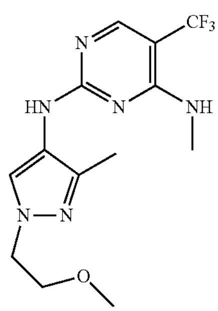 [SMILES: CNc1nc(Nc2cn(CCOC)nc2C)ncc1C(F)(F)F] | ¹H-NMR (DMSO): δ 8.82 (s, 1 H), 8.04 (s, 1 H), 7.64 (s, 1 H), 6.88 (s, 1 H), 4.13 (t, J = 5.4, 2 H), 3.63 (t, J = 5.4, 2 H), 3.21 (s, 3 H), 2.83 (s, 3 H), 2.17 (s, 3 H) | 331.1 | 0.019 |
| 25 | N²-(1-(2-methoxyethyl)-5-methyl-1H-pyrazol-4-yl)-N⁴-methyl-5-(trifluoromethyl)pyrimidine-2,4-diamine | 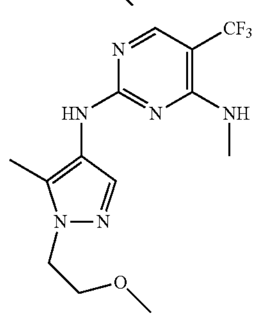 | ¹H-NMR (DMSO): δ 8.89 (s, 1 H), 8.07 (s, 1 H), 7.91 (s, 1 H), 6.94 (s, 1 H), 4.12 (t, J = 5.2, 2 H), 3.63 (t, J = 5.3, 2 H), 3.22 (s, 3 H), 2.88 (d, J = 4.4, 3 H), 2.12 (s, 3 H). | 331.1 | |
| 26 | 5-Chloro-N-(1-ethyl-3-methyl-1H-pyrazol-4-yl)-4-methoxy-pyrimidin-2-amine | 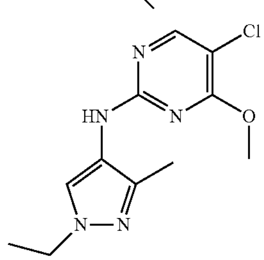 | ¹H-NMR (DMSO): δ 8.87 (s, 1 H), 8.17 (s, 1 H), 7.81 (s, 1 H), 4.01 (q, J = 7.3, 2 H), 3.95 (s, 3 H), 2.10 (s, 3 H), 1.32 (t, J = 7.3, 3 H). | 268.0 | 0.013 |

TABLE 7-continued

| Name | Structure | $^1$H NMR | M + H$^+$ | K$_I$ |
|---|---|---|---|---|
| 27 5-Chloro-N$^4$-methyl-N$^2$-(3-methyl-1-(oxetan-3-yl)-1H-pyrazol-4-yl)pyrimidine-2,4-diamine | | $^1$H-NMR (DMSO): δ 8.36 (s, 1 H), 7.97 (s, 1 H), 7.82 (s, 1 H), 7.01 (d, J = 4.5, 1 H), 5.43 (m, 1 H), 4.85 (m, 4 H), 2.88 (d, J = 4.6, 3 H), 2.17 (s, 3 H). | 295.0 | 0.0088 |
| 28 N$^2$-(1-isopropyl-3-methyl-1H-pyrazol-4-yl)-N$^4$-methyl-5-(trifluoromethyl)pyrimidine-2,4-diamine | | $^1$H-NMR (DMSO): δ 8.89 (s, 1 H), 8.07 (s, 1 H), 7.93 (s, 1 H), 6.95 (s, 1 H), 4.34 (m, 1 H), 2.88 (d, J = 4.4, 3 H), 2.12 (s, 3 H), 1.37 (d, J = 6.7, 6 H). | 315.1 | |
| 29 5-Chloro-N-(1-isopropyl-3-methyl-1H-pyrazol-4-yl)-4-methoxy-pyrimidin-2-amine | | $^1$H-NMR (DMSO): δ 8.87 (s, 1 H), 8.17 (s, 1 H), 7.84 (s, 1 H), 4.36 (m, 1 H), 3.95 (s, 3 H), 2.11 (s, 3 H), 1.37 (d, J = 6.7, 6 H). | 282.1 | 0.022 |
| 30 5-Chloro-N$^2$-(1,3-dimethyl-1H-pyrazol-4-yl)-N$^4$-methylpyrimidine-2,4-diamine | | $^1$H-NMR (DMSO): δ 8.25 (s, 1 H), 7.80 (s, 1 H), 7.74 (s, 1 H), 6.98 (d, J = 4.5, 1 H), 3.70 (s, 3 H), 2.87 (d, J = 4.6, 3 H), 2.08 (s, 3 H). | 253.0 | |
| 31 5-Chloro-N$^2$-(1-isopropyl-3-methyl-1H-pyrazol-4-yl)-N$^4$-methylpyrimidine-2,4-diamine | | $^1$H-NMR (DMSO): δ 8.26 (s, 1 H), 7.83 (s, 1 H), 7.80 (s, 1 H), 6.98 (d, J = 4.3, 1 H), 4.33 (m, 1 H), 2.87 (d, J = 4.6, 3 H), 2.10 (s, 3 H), 1.36 (d, J = 6.7, 7 H). | 281.1 | 0.012 |

TABLE 7-continued

| | Name | Structure | ¹H NMR | M + H⁺ | K$_I$ |
|---|---|---|---|---|---|
| 32 | N⁴-methyl-N²-(3-methyl-1-(tetrahydro-2H-pyran-4-yl)-1H-pyrazol-4-yl)-5-(trifluoromethyl)pyrimidine-2,4-diamine | 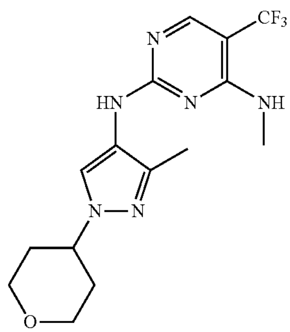 [SMILES: CNc1nc(Nc2cn(C3CCOCC3)nc2C)ncc1C(F)(F)F] | ¹H-NMR (DMSO): δ 8.90 (s, 1 H), 8.07 (s, 1 H), 7.96 (s, 1 H), 6.95 (s, 1 H), 4.24 (s, 1 H), 3.93 (d, J = 10.9, 2 H), 3.44 (t, J = 12.5, 2 H), 2.89 (d, J = 4.3, 3 H), 2.13 (s, 3 H), 1.92 (s, 4 H). | 357.2 | 0.024 |
| 33 | N⁴-methyl-N²-(5-methyl-1-(tetrahydro-2H-pyran-4-yl)-1H-pyrazol-4-yl)-5-(trifluoromethyl)pyrimidine-2,4-diamine | 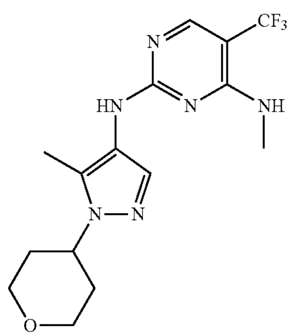 [SMILES: CNc1nc(Nc2cnn(C3CCOCC3)c2C)ncc1C(F)(F)F] | ¹H-NMR (DMSO): δ 8.83 (s, 1 H), 8.04 (s, 1 H), 7.65 (s, 1 H), 6.89 (s, 1 H), 4.33 (m, 1 H), 3.95 (m, 2 H), 3.47 (t, J = 11.2, 2 H), 2.84 (s, 3 H), 2.21 (s, 3 H), 2.02 (m, 2 H), 1.82-1.67 (m, 2 H). | 357.2 | |
| 34 | N²-(2-Ethyl-2H-pyrazol-3-yl)-5-fluoro-N⁴-methyl-pyrimidine-2,4-diamine | 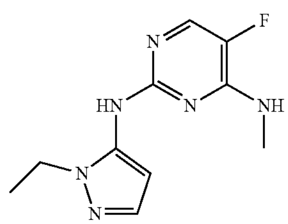 [SMILES: CCn1nccc1Nc1ncc(F)c(NC)n1] | ¹H-NMR (DMSO): δ 8.75 (s, 1 H), 7.78 (d, 1 H), 7.39 (s, 1 H), 7.30 (s, 1 H), 3.17 (s, 1 H), 3.99 (q, 2 H), 2.82 (d, 3 H), 1.26 (t, 3 H). | 237.1 | |
| 35 | 5-Fluoro-N⁴-methyl-N²-(2-methyl-2H-pyrazol-3-yl)-pyrimidine-2,4-diamine | 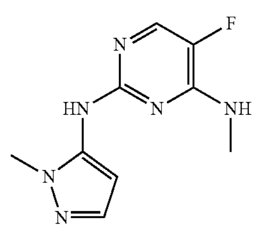 [SMILES: CNc1nc(Nc2ccnn2C)ncc1F] | ¹H-NMR (DMSO): δ 8.77 (s, 1 H), 7.78 (s, 1 H), 7.37 (s, 1 H), 7.26 (s, 1 H), 6.17 (s, 1 H), 3.64 (s, 3 H), 2.82 (d, 3 H). | 223.1 | 0.267 |
| 36 | 5-Fluoro-N⁴-methyl-N⁴-(2-propyl-2H-pyrazol-3-yl)-pyrimidine-2,4-diamine | 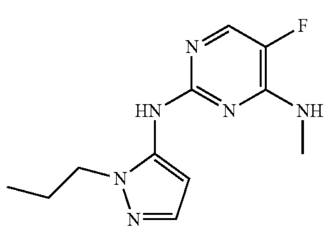 [SMILES: CCCn1nccc1Nc1ncc(F)c(NC)n1] | ¹H-NMR (DMSO): δ 8.79 (s, 1 H), 7.78 (s, 1 H), 7.41 (s, 1 H), 7.29 (s, 1 H), 6.19 (s, 1 H), 3.94 (t, 2 H), 2.82 (d, 3 H), 1.69 (m, 2 H), 0.80 (t, 3 H). | 251.0 | |
| 37 | N²-(2,5-Dimethyl-2H-pyrazol-3-yl)-5-fluoro-N⁴-methyl-pyrimidine-2,4-diamine | 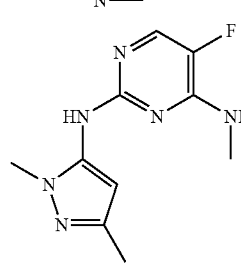 | | 237.0 | |

TABLE 7-continued

| | Name | Structure | $^1$H NMR | M + H$^+$ | K$_I$ |
|---|---|---|---|---|---|
| 38 | N$^2$-(3-isopropyl-1-methyl-1H-pyrazol-5-yl)-N$^4$-methyl-5-(trifluoromethyl)pyrimidine-2,4-diamine | 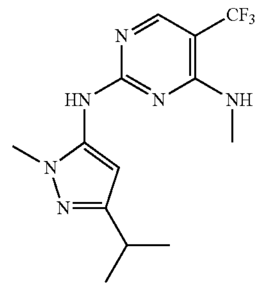 [SMILES: CNc1nc(Nc2cc(C(C)C)nn2C)ncc1C(F)(F)F] | $^1$H-NMR (DMSO): δ 9.36 (s, 1 H), 8.14 (s, 1 H), 7.13 (d, J = 5.2, 1 H), 6.08 (s, 1 H), 3.59 (s, 3 H), 2.86 (d, J = 4.3, 3 H), 2.84-2.73 (m, 1 H), 1.17 (d, J = 6.9, 6 H). | 315 | 0.012 |
| 39 | 5-Chloro-N-(3-cyclopropyl-1-methyl-1H-pyrazol-5-yl)-4-methoxy-pyrimidin-2-amine | 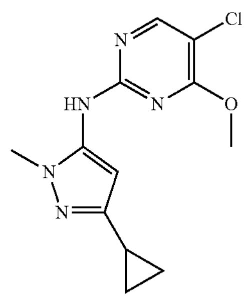 [SMILES: COc1nc(Nc2cc(C3CC3)nn2C)ncc1Cl] | $^1$H-NMR (CDCl$_3$): δ 8.11 (s, 1 H), 6.64 (s, 1 H), 5.94 (s, 1 H), 3.98 (s, 3 H), 3.69 (s, 3 H), 1.93-1.84 (m, 1 H), 0.94-0.84 (m, 2 H), 0.76-0.68 (m, 2 H). | 280 | 0.059 |
| 40 | N$^2$-(3-Cyclopropyl-1-methyl-1H-pyrazol-5-yl)-N$^4$-methyl-5-(trifluoromethyl)pyrimidine-2,4-diamine | 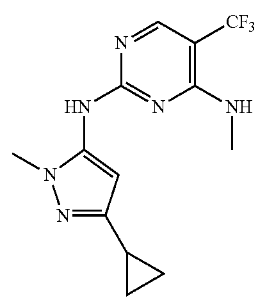 [SMILES: CNc1nc(Nc2cc(C3CC3)nn2C)ncc1C(F)(F)F] | $^1$H-NMR (DMSO): δ 9.35 (s, 1 H), 8.13 (s, 1 H), 7.13 (d, J = 5.2, 1 H), 5.94 (s, 1 H), 3.56 (s, 3 H), 2.85 (d, J = 4.3, 3 H), 1.78 (tt, J = 8.4, J = 5.0, 1 H), 0.84-0.74 (m, 2 H), 0.63-0.55 (m, 2 H). | 313 | |
| 41 | 5-Chloro-N-(3-isopropyl-1-methyl-1H-pyrazol-5-yl)-4-methoxy-pyrimidin-2-amine | 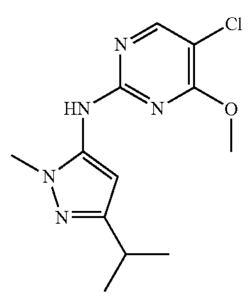 [SMILES: COc1nc(Nc2cc(C(C)C)nn2C)ncc1Cl] | $^1$H-NMR (CDCl$_3$): δ 8.12 (s, 1 H), 6.65 (s, 1 H), 6.11 (s, 1 H), 3.98 (s, 3 H), 3.72 (s, 3 H), 2.98-2.88 (m, 1 H), 1.27 (d, J = 6.9, 6 H). | 282 | 0.070 |
| 42 | 5-Chloro-N$^2$-(5-isopropyl-2-methyl-2H-pyrazol-3-yl)-N$^4$-methyl-pyrimidine-2,4-diamine | 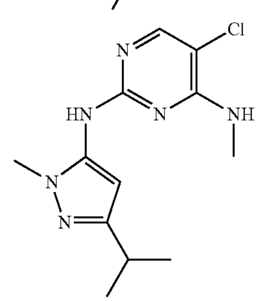 | $^1$H-NMR (CDCl$_3$): δ 7.87 (s, 1 H), 6.44 (s, 1 H), 6.13 (s, 1 H), 5.29 (s, 1 H), 3.71 (s, 3 H), 3.01 (d, J = 4.9, 3 H), 2.97-2.89 (m, 1 H), 1.27 (d, J = 6.9, 6 H). | 281 | 0.016 |

TABLE 7-continued

| | Name | Structure | ¹H NMR | M + H⁺ | K$_I$ |
|---|---|---|---|---|---|
| 43 | 5-Chloro-4-methoxy-N-(1,3,5-trimethyl-1H-pyrazol-4-yl)pyrimidin-2-amine | 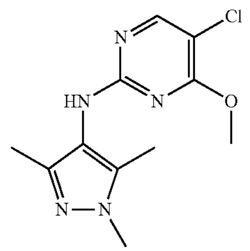 [SMILES: COc1nc(Nc2c(C)nn(C)c2C)ncc1Cl] | ¹H-NMR (CDCl₃): δ 8.04 (s, 1 H), 6.04 (s, 1 H), 3.93 (s, 3 H), 3.73 (s, 3 H), 2.13 (d, J = 5.39, 6 H). | 268 | |
| 44 | 5-Chloro-N⁴-methyl-N²-(1,3,5-trimethyl-1H-pyrazol-4-yl)-pyrimidine-2,4-diamine | 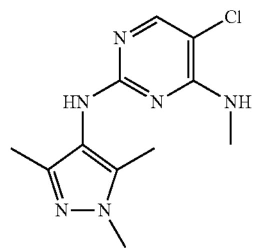 [SMILES: CNc1nc(Nc2c(C)nn(C)c2C)ncc1Cl] | ¹H-NMR (CDCl₃): δ 7.80 (s, 1 H), 5.94 (s, 1 H), 5.18 (s, 1 H), 3.72 (s, 3 H), 2.97 (d, J = 4.9, 3 H), 2.14 (d, J = 2.9, 6 H). | 267 | |
| 45 | 5-Chloro-N²-(5-cyclopropyl-2-methyl-2H-pyrazol-3-yl)-N⁴-methyl-pyrimidine-2,4-diamine | 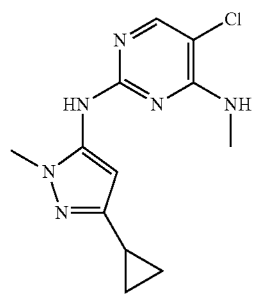 [SMILES: CNc1nc(Nc2cc(C3CC3)nn2C)ncc1Cl] | ¹H-NMR (CDCl₃): δ 7.86 (s, 1 H), 6.41 (s, 1 H), 5.95 (s, 1 H), 5.29 (s, 1 H), 3.69 (s, 3 H), 3.01 (d, J = 4.9, 3 H), 1.92-1.85 (m, 1 H), 0.91-0.85 (m, 2 H), 0.73-0.68 (m, 2 H). | 279 | 0.0134 |
| 46 | N⁴-Methyl-N²-(5-methyl-1-oxetan-3-yl-1H-pyrazol-4-yl)-5-trifluoromethyl-pyrimidine-2,4-diamine | 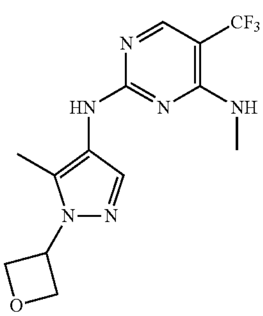 [SMILES: CNc1nc(Nc2cnn(C3COC3)c2C)ncc1C(F)(F)F] | ¹H-NMR (DMSO): δ 8.91 (s, 1 H), 8.05 (s, 1 H), 7.86 (s, 1 H), 6.94 (s, 1 H), 5.53 (m, 1 H), 4.93 (m, 2 H), 4.90-4.83 (m, 2 H), 2.85 (s, 3 H), 2.14 (s, 3 H). | 329 | |
| 47 | N²-(1-isopropyl-1H-pyrazol-5-yl)-N⁴-methyl-5-(trifluoromethyl)pyrimidine-2,4-diamine | 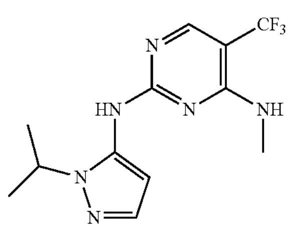 [SMILES: CNc1nc(Nc2ccnn2C(C)C)ncc1C(F)(F)F] | ¹H-NMR (DMSO): δ 9.27 (s, 1 H), 8.12 (s, 1 H), 7.38 (d, J = 1.8, 1 H), 7.11 (d, J = 5.2, 1 H), 6.17 (s, 1 H), 4.54-4.46 (m, 1 H), 2.81 (d, J = 4.3, 3 H), 1.32 (d, J = 6.6, 6 H). | 301 | 0.112 |
| 48 | 5-Chloro-N-(1-ethyl-5-methyl-1H-pyrazol-4-yl)-4-methoxy-pyrimidin-2-amine | 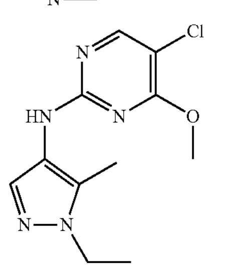 | ¹H-NMR (DMSO): δ 8.81 (s, 1 H), 8.14 (s, 1 H), 7.51 (s, 1 H), 4.02 (q, J = 7.1, 2 H), 3.91 (s, 3 H), 2.17 (s, 3 H), 1.28 (t, J = 7.1, 4 H). | 268.1 | |

TABLE 7-continued

| | Name | Structure | ¹H NMR | M + H⁺ | $K_I$ |
|---|---|---|---|---|---|
| 49 | 5-Chloro-N²-(1-ethyl-5-methyl-1H-pyrazol-4-yl)-N⁴-methyl-pyrimidine-2,4-diamine | 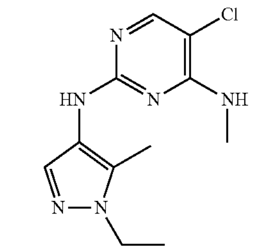 [SMILES: CCn1ncc(Nc2ncc(Cl)c(NC)n2)c1C] | ¹H-NMR (DMSO): δ 8.21 (s, 1 H), 7.76 (s, 1 H), 7.51 (s, 1 H), 6.94 (s, 1 H), 4.0 (q, J = 7.1, 2 H), 2.83 (d, J = 3.7, 3 H), 2.15 (s, 3 H), 1.27 (t, J = 7.2, 3 H). | 267.1 | |
| 50 | N²-(1-ethyl-3-methyl-1H-pyrazol-4-yl)-N⁴-methyl-5-(trifluoromethyl)pyrimidine-2,4-diamine | 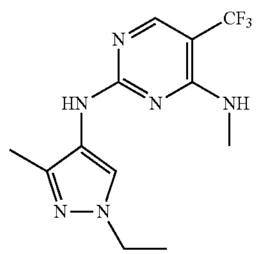 [SMILES: CCn1cc(Nc2ncc(C(F)(F)F)c(NC)n2)c(C)n1] | ¹H-NMR (DMSO): δ 8.88 (s, 1 H), 8.07 (s, 1 H), 7.89 (s, 1 H), 6.94 (s, 1 H), 4.00 (q, J = 7.1, 2 H), 2.88 (d, J = 3.9, 3 H), 2.11 (s, 3 H), 1.32 (t, J = 7.2, 3 H). | 301.1 | |
| 51 | 5-Chloro-N²-(1-ethyl-3-methyl-1H-pyrazol-4-yl)-N⁴-methyl-pyrimidine-2,4-diamine | 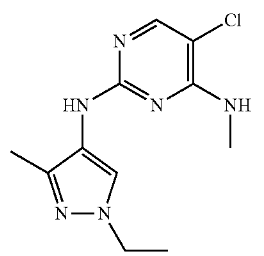 | ¹H-NMR (DMSO): δ 8.26 (s, 1 H), 7.80 (s, 2 H), 6.99 (s, 1 H), 3.98 (q, 2 H), 2.86 (s, 3 H), 2.10 (s, 3 H), 1.32 (t, 3 H). | 267.1 | |
| 52 | 5-chloro-N²-(1-isopropyl-1H-pyrazol-5-yl)-N⁴-methyl-pyrimidine-2,4-diamine | 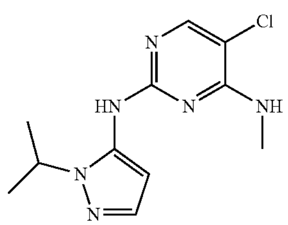 [SMILES: CNc1nc(Nc2ccnn2C(C)C)ncc1Cl] | | | |
| 53 | 5-chloro-N-(1-isopropyl-1H-pyrazol-5-yl)-4-methoxy-pyrimidin-2-amine | 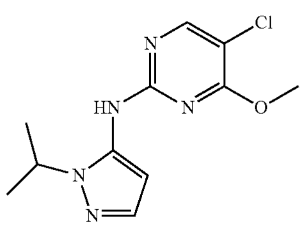 [SMILES: COc1nc(Nc2ccnn2C(C)C)ncc1Cl] | | | |
| 54 | 5-chloro-4-methoxy-N-(3-methyl-1-(methylsulfonyl)-1H-pyrazol-4-yl)pyrimidin-2-amine | 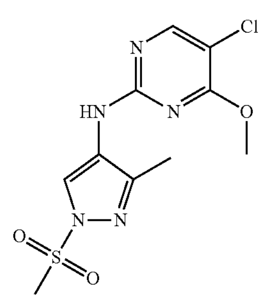 [SMILES: COc1nc(Nc2cn(S(C)(=O)=O)nc2C)ncc1Cl] | ¹H NMR (400 MHz, DMSO) δ 9.44 (s, 1 H), 8.41 (s, 1 H), 8.34 (s, 1 H), 4.01 (s, 3 H), 3.42 (s, 3 H), 2.32 (s, 3 H). | | 0.0078 |

| | Name | Structure | $^1$H NMR | M + H$^+$ | K$_I$ |
|---|---|---|---|---|---|
| 55 | N$^2$-(1-ethyl-1H-pyrazol-3-yl)-N$^4$-methyl-5-(trifluoromethyl)pyrimidine-2,4-diamine | 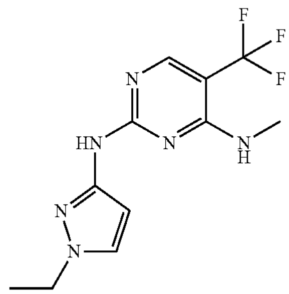 [SMILES: CCn1ccc(Nc2ncc(C(F)(F)F)c(NC)n2)n1] | | | |
| 56 | 5-chloro-4-methoxy-N-(5-methyl-1-phenyl-1H-pyrazol-4-yl)pyrimidin-2-amine | 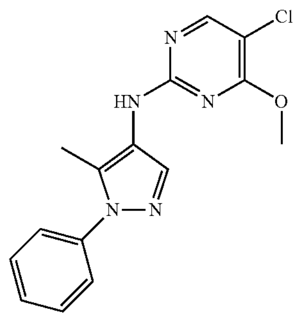 [SMILES: COc1nc(Nc2cnn(-c3ccccc3)c2C)ncc1Cl] | 1H NMR (400 MHz, DMSO) δ 9.17 (s, 1 H), 8.57 (s, 1 H), 8.25 (s, 1 H), 7.73 (d, J = 7.9, 2 H), 7.46 (t, J = 7.9, 2 H), 7.23 (t, J = 7.4, 1 H), 4.01 (s, 3 H), 2.26 (s, 3 H). | 316.1 | 0.027 |
| 57 | N$^2$-(1-isopropyl-1H-pyrazol-3-yl)-N4-methyl-5-(trifluoromethyl)pyrimidine-2,4-diamine | 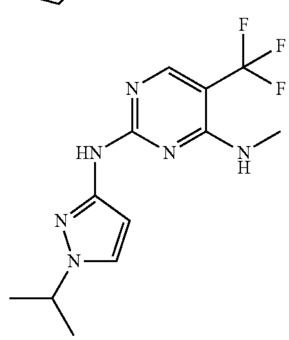 | | | 0.0025 |
| 58 | N$^4$-methyl-N$^2$-(5-methyl-1-(2,2,2-trifluoroethyl)-1H-pyrazol-4-yl)-5-(trifluoromethyl)pyrimidine-2,4-diamine | 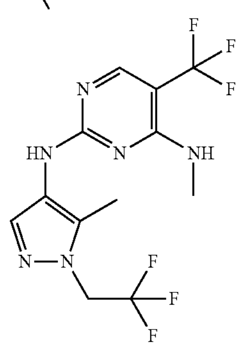 | 1H NMR (400 MHz, DMSO) δ 8.88 (s, 1 H), 8.06 (s, 1 H), 7.74 (s, 1 H), 6.93 (s, 1 H), 5.01 (q, J = 9.2, 2 H), 2.82 (s, 3 H), 2.22 (s, 3 H). | | 0.0036 |
| 59 | N$^2$-(1-(2,2-dimethyl-1,3-dioxan-5-yl)-3-methyl-1H-pyrazol-4-yl)-N4-methyl-5-(trifluoromethyl)pyrimidine-2,4-diamine | 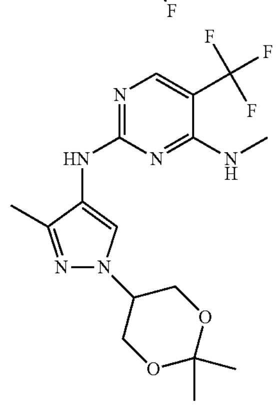 | | 387 | |

TABLE 7-continued

| Name | Structure | ¹H NMR | M + H⁺ | $K_I$ |
|---|---|---|---|---|
| 60 5-chloro-4-methoxy-N-(5-methyl-1-(4-(methylsulfonyl)phenyl)-1H-pyrazol-4-yl)pyrimidin-2-amine | | | | 0.015 |
| 61 N⁴-ethyl-N²-(1-methyl-1H-pyrazol-3-yl)-5-(trifluoromethyl)pyrimidine-2,4-diamine | | | | 0.0046 |
| 62 5-chloro-N-(1,5-dimethyl-1H-pyrazol-4-yl)-4-(oxetan-3-yloxy)pyrimidin-2-amine | | | | 0.039 |
| 63 5-chloro-4-(2,2-difluoroethoxy)-N-(1,5-dimethyl-1H-pyrazol-4-yl)pyrimidin-2-amine | | | | 0.024 |
| 64 5-chloro-N-(1,5-dimethyl-1H-pyrazol-4-yl)-4-(2,2,2-trifluoroethoxy)pyrimidin-2-amine | | | | 0.0586 |

TABLE 7-continued

| Name | Structure | ¹H NMR | M + H⁺ | K$_I$ |
|---|---|---|---|---|
| 65 5-chloro-4-methoxy-N-(3-methyl-1-(tetrahydro-2H-pyran-4-yl)-1H-pyrazol-4-yl)pyrimidin-2-amine | | 1H NMR (400 MHz, DMSO) δ 8.82 (s, 1 H), 8.14 (s, 1 H), 7.57 (s, 1 H), 4.41-4.26 (m, 1 H), 4.03-3.82 (m, 5 H), 3.47 (t, J = 11.3, 2 H), 2.20 (s, 3 H), 2.01 (qd, J = 12.4, 4.5, 2 H), 1.76 (dd, J = 12.5, 2.1, 2 H). | | 0.0029 |
| 66 (4-(4-(5-chloro-4-methoxy-pyrimidin-2-ylamino)-3-methyl-1H-pyrazol-1-yl)piperidin-1-yl)(1-methylcyclopropyl)methanone | | 1H NMR (400 MHz, DMSO) δ 8.82 (s, 1 H), 8.14 (s, 1 H), 7.58 (s, 1 H), 4.36 (m, 3 H), 3.91 (s, 2 H), 3.01 (s, 2 H), 2.21 (s, 3 H), 1.87 (m, 4 H), 0.80 (m, 2 H), 0.55 (m, 2 H). | | 0.066 |
| 67 (4-(4-(5-chloro-4-methoxy-pyrimidin-2-ylamino)-5-methyl-1H-pyrazol-1-yl)piperidin-1-yl)(1-methylcyclopropyl)methanone | | 1H NMR (400 MHz, DMSO) δ 8.88 (s, 1 H), 8.17 (s, 1 H), 7.89 (s, 1 H), 4.39-4.24 (m, 4 H), 2.96 (s, 2 H), 2.11 (s, 3 H), 2.01 (m, 3 H), 1.74 (m, 3 H), 1.24 (s, 4 H), 0.81 (t, J = 5.1, 2 H), 0.54 (m, 2 H). | | 0.089 |
| 68 4-(4-(5-chloro-4-methoxy-pyrimidin-2-ylamino)-3-methyl-1H-pyrazol-1-yl)benzonitrile | | 1H NMR (400 MHz, DMSO) δ 9.29 (s, 1 H), 8.71 (s, 1 H), 8.27 (s, 1 H), 7.98-7.86 (m, 4 H), 4.02 (s, 3 H), 2.29 (s, 3 H). | | 0.0024 |

TABLE 7-continued

| Name | Structure | ¹H NMR | M + H⁺ | K₁ |
|---|---|---|---|---|
| 69 5-chloro-4-methoxy-N-(3-methyl-1-(3-methylpyridin-4-yl)-1H-pyrazol-4-yl)pyrimidin-2-amine | | 1H NMR (400 MHz, DMSO) δ 9.25 (s, 1 H), 8.53 (s, 1 H), 8.46 (d, J = 5.4, 1 H), 8.43 (s, 1 H), 8.26 (s, 1 H), 7.47 (d, J = 5.4, 1 H), 4.01 (s, 3 H), 2.45 (s, 3 H), 2.29 (s, 3 H). | | 0.055 |
| 70 5-chloro-N-(1-(cyclopropyl-sulfonyl)-5-methyl-1H-pyrazol-4-yl)-4-methoxy-pyrimidin-2-amine | | | 334.0 | 0.015 |
| 71 5-chloro-N-(1-(cyclopropyl-sulfonyl)-3-methyl-1H-pyrazol-4-yl)-4-methoxy-pyrimidin-2-amine | | 1H NMR (400 MHz, DMSO) δ 9.44 (s, 1 H), 8.39 (s, 1 H), 8.34 (s, 1 H), 4.01 (s, 3 H), 3.10-2.95 (m, 1 H), 2.31 (s, 3 H), 1.17 (m, 4 H). | | 0.020 |
| 72 2-(4-(5-chloro-4-methoxy-pyrimidin-2-ylamino)-5-methyl-1H-pyrazol-1-yl)-2-methylpropane-nitrile | | 1H NMR (400 MHz, DMSO) δ 8.98 (s, 1 H), 7.69 (s, 1 H), 7.06 (s, 1 H), 3.91 (s, 3 H), 2.40 (s, 3 H), 1.95 (s, 6 H). | | 0.016 |
| 73 2-(4-(5-chloro-4-methoxy-pyrimidin-2-ylamino)-3-methyl-1H-pyrazol-1-yl)-2-methylpropane-nitrile | | 1H NMR (400 MHz, DMSO) δ 9.11 (s, 1 H), 8.14 (s, 1 H), 7.07 (s, 1 H), 3.98 (s, 3 H), 2.18 (s, 3 H), 1.93 (s, 7 H). | | 0.014 |

TABLE 7-continued

| Name | Structure | ¹H NMR | M + H⁺ | K_I |
|---|---|---|---|---|
| 74 5-chloro-4-ethoxy-N-(5-methyl-1-(tetrahydro-2H-pyran-4-yl)-1H-pyrazol-4-yl)pyrimidin-2-amine | | 1H NMR (400 MHz, DMSO) δ 8.84 (s, 1 H), 8.17 (s, 1 H), 7.84 (s, 1 H), 4.41 (q, J = 7.0, 2 H), 4.31-4.16 (m, 1 H), 4.06-3.84 (m, 2 H), 3.44 (td, J = 11.5, 2.7, 2 H), 2.11 (s, 3 H), 1.98- 1.77 (m, 4 H), 1.34 (t, J = 7.1, 3 H). | 338.1 | |
| 75 (5-Chloro-4-methoxy-pyrimidin-2-yl)-[1-(4-methanesulfonyl-phenyl)-3-methyl-1H-pyrazol-4-yl]-amine | | | | 0.0022 |
| 76 (5-Chloro-4-methoxy-pyrimidin-2-yl)-(3-methyl-1-phenyl-1H-pyrazol-4-yl)-amine | | | | 0.0023 |
| 77 (4-Methoxy-5-trifluoromethyl-pyrimidin-2-yl)-(3-methyl-1-phenyl-1H-pyrazol-4-yl)-amine | | | | 0.0016 |

TABLE 7-continued

| Name | Structure | ¹H NMR | M + H⁺ | $K_I$ |
|---|---|---|---|---|
| 78 (4-Methoxy-5-trifluoromethyl-pyrimidin-2-yl)-(5-methyl-1-phenyl-1H-pyrazol-4-yl)-amine | | | | 0.0381 |
| 79 (5-Chloro-4-methoxy-pyrimidin-2-yl)-(1-methanesulfonyl-3-methyl-1H-pyrazol-4-yl)-amine | | | | 0.0078 |
| 80 (5-Chloro-4-methoxy-pyrimidin-2-yl)-[5-methyl-1-(tetrahydro-pyran-4-yl)-1H-pyrazol-4-yl]-amine | | | | 0.0663 |
| 81 4-[4-(5-Chloro-4-methoxy-pyrimidin-2-ylamino)-3-methyl-pyrazol-1-yl]-N,N-dimethyl-benzamide | | | | 0.0022 |

TABLE 7-continued

| | Name | Structure | ¹H NMR | M + H⁺ | K$_I$ |
|---|---|---|---|---|---|
| 82 | 4-[4-(5-Chloro-4-methoxy-pyrimidin-2-ylamino)-5-methyl-pyrazol-1-yl]-N,N-dimethyl-benzamide | 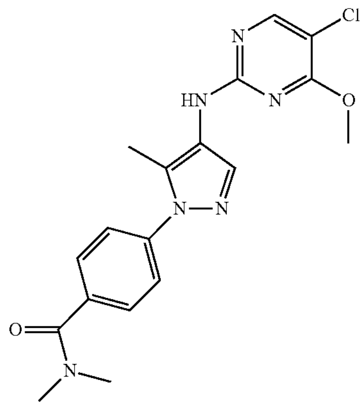 [SMILES: COc1nc(Nc2cnn(-c3ccc(C(=O)N(C)C)cc3)c2C)ncc1Cl] | | | 0.63 |
| 83 | 4-[4-(5-Chloro-4-methoxy-pyrimidin-2-ylamino)-5-methyl-pyrazol-1-yl]-benzonitrile | 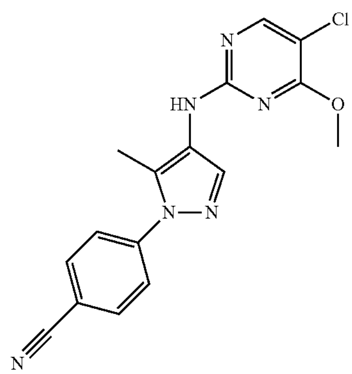 [SMILES: COc1nc(Nc2cnn(-c3ccc(C#N)cc3)c2C)ncc1Cl] | | | 0.0090 |
| 84 | N²-(5-Methoxy-1-methyl-1H-pyrazol-4-yl)-N⁴-methyl-5-trifluoromethyl-pyrimidine-2,4-diamine | 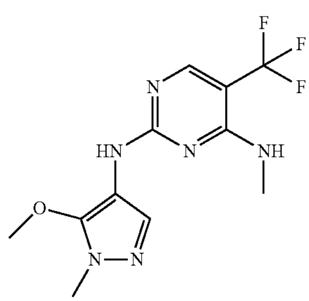 [SMILES: CNc1nc(Nc2cnn(C)c2OC)ncc1C(F)(F)F] | | | 0.0742 |
| 85 | (5-Chloro-4-methoxy-pyrimidin-2-yl)-[5-chloro-1-(tetrahydro-pyran-4-yl)-1H-pyrazol-4-yl]-amine | 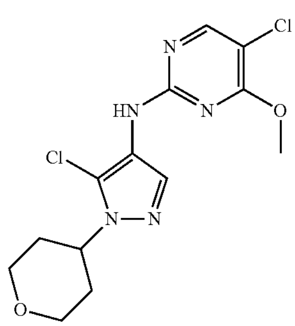 [SMILES: COc1nc(Nc2cnn(C3CCOCC3)c2Cl)ncc1Cl] | | | 0.0066 |

TABLE 7-continued

| Name | Structure | ¹H NMR | M + H⁺ | K$_I$ |
|---|---|---|---|---|
| 86 (5-Chloro-4-methoxy-pyrimidin-2-yl)-{1-[1-(2-fluoro-ethyl)-piperidin-4-yl]-3-methyl-1H-pyrazol-4-yl}-amine | | | | 0.183 |
| 87 N²-[1-(1-[1,3]Dioxolan-2-ylmethyl-piperidin-4-yl)-5-methyl-1H-pyrazol-4-yl]-N⁴-ethyl-5-trifluoromethyl-pyrimidine-2,4-diamine | | | | 0.0008 |
| 88 N²-[1-(1-[1,3]Dioxolan-2-ylmethyl-piperidin-4-yl)-3-methyl-1H-pyrazol-4-yl]-N⁴-ethyl-5-trifluoromethyl-pyrimidine-2,4-diamine | | | | 0.0094 |

Example 89

5-Bromo-N²-(1,5-dimethyl-1H-pyrazol-4-yl)-N⁴-methylpyrimidine-2,4-diamine

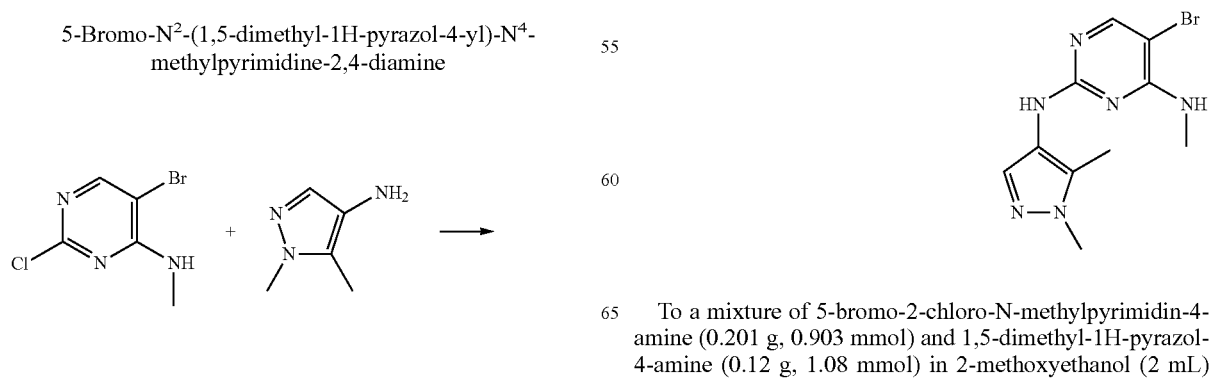

To a mixture of 5-bromo-2-chloro-N-methylpyrimidin-4-amine (0.201 g, 0.903 mmol) and 1,5-dimethyl-1H-pyrazol-4-amine (0.12 g, 1.08 mmol) in 2-methoxyethanol (2 mL)

was added TFA (0.070 mL, 0.9 mmol). The reaction was stirred in a sealed tube at 100° C. for 90 minutes. The resulting precipitate was collected by filtration. The isolated solid was further purified by reverse phase HPLC to give 5-bromo-$N^2$-(1,5-dimethyl-1H-pyrazol-4-yl)-$N^4$-methylpyrimidine-2,4-diamine (46 mg, 17%). LCMS (Method A): [MH$^+$]=297.0 at 2.57 min. $^1$H-NMR (DMSO): δ 8.28 (s, 1H), 7.84 (s, 1H), 7.49 (s, 1H), 6.79 (d, J=3.4, 1H), 3.67 (s, 3H), 2.82 (d, J=3.6, 3H), 2.14 (s, 3H). Ki=0.017 uM.

Compounds made using the above procedure are shown in Table 8 below, together with low resolution mass spectrometry (M+H), proton NMR, and LRRK2 K$_i$ (micromolar) data for selected compounds determined from the assay described below.

TABLE 8

| | Name | Structure | $^1$H NMR | M + H$^+$ | K$_I$ |
|---|---|---|---|---|---|
| 90 | $N^2$-(1,3-Dimethyl-1H-pyrazol-4-yl)-5-iodo-$N^4$-methyl-pyrimidine-2,4-diamine | 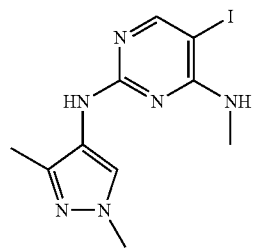 | $^1$H-NMR (DMSO): δ 8.24 (s, 1 H), 7.98 (s, 1 H), 7.73 (s, 1 H), 6.46 (d, J = 4.3, 1 H), 3.70 (s, 3 H), 2.85 (d, J = 4.6, 3 H), 2.08 (s, 3 H). | 345.0 | |
| 91 | N4-methyl-N2-(5-methyl-1-(1-(2,2,2-trifluoroethyl)piperidin-4-yl)-1H-pyrazol-4-yl)-5-(trifluoromethyl)pyrimidine-2,4-diamine | 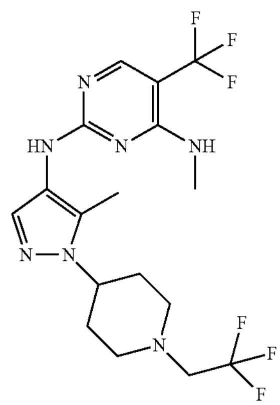 [SMILES: CNc1nc(Nc2cnn(C3CCN(CC(F)(F)F)CC3)c2C)ncc1C(F)(F)F] | | 438.2 | 0.0041 |
| 92 | N4-methyl-N2-(3-methyl-1-(1-(2,2,2-trifluoroethyl)piperidin-4-yl)-1H-pyrazol-4-yl)-5-(trifluoromethyl)pyrimidine-2,4-diamine | 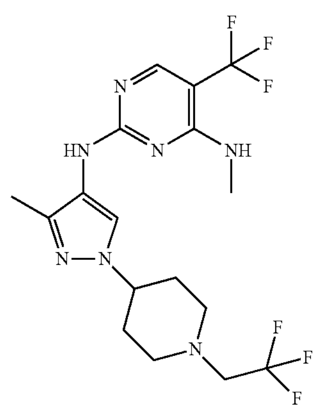 [SMILES: CNc1nc(Nc2cn(C3CCN(CC(F)(F)F)CC3)nc2C)ncc1C(F)(F)F] | | 438.2 | 0.046 |
| 93 | 5-bromo-N4-methyl-N2-(5-methyl-1-(1-(2,2,2-trifluoroethyl)piperidin-4-yl)-1H-pyrazol-4-yl)pyrimidine-2,4-diamine | 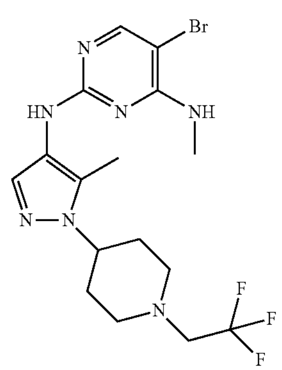 [SMILES: CNc1nc(Nc2cnn(C3CCN(CC(F)(F)F)CC3)c2C)ncc1Br] | 1H NMR (400 MHz, DMSO) δ 8.22 (s, 1 H), 7.84 (s, 1 H), 7.56 (s, 1 H), 6.76 (d, J = 4.6, 1 H), 4.12-4.00 (m, 1 H), 3.22 (q, J = 10.2, 2 H), 3.00 (d, J = 11.9, 2 H), 2.82 (d, J = 4.5, 3 H), 2.56 (d, J = 11.9, 2 H), 2.01 (qd, J = 12.3, 3.7, 2 H), 1.75 (d, J = 13.4, 2 H). | | 0.0014 |

TABLE 8-continued

| Name | Structure | ¹H NMR | M + H⁺ | $K_I$ |
|---|---|---|---|---|
| 94 5-bromo-N4-methyl-N2-(3-methyl-1-(1-(2,2,2-trifluoroethyl)piperidin-4-yl)-1H-pyrazol-4-yl)pyrimidine-2,4-diamine | | 1H NMR (400 MHz, DMSO) δ 8.28 (s, 1 H), 7.86 (d, J = 13.2, 2 H), 6.80 (d, J = 4.6, 1 H), 4.05-3.93 (m, 1 H), 3.21 (dd, J = 20.6, 10.3, 5 H), 2.98 (d, J = 12.0, 2 H), 2.86 (d, J = 4.6, 3 H), 2.00-1.80 (m, 5 H). | | 0.013 |
| 95 5-bromo-N4-methyl-N2-(3-methyl-1-(2,2,2-trifluoroethyl)-1H-pyrazol-4-yl)pyrimidine-2,4-diamine | | 1H NMR (400 MHz, DMSO) δ 8.45 (s, 1 H), 7.98 (s, 1 H), 7.91 (s, 1 H), 6.86 (d, J = 4.4, 1 H), 4.96 (q, J = 9.2, 2 H), 2.87 (d, J = 4.6, 3 H), 2.15 (s, 3 H). | | 0.0012 |
| 96 5-bromo-N4-methyl-N2-(5-methyl-1-(2,2,2-trifluoroethyl)-1H-pyrazol-4-yl)pyrimidine-2,4-diamine | | 1H NMR (400 MHz, DMSO) δ 8.35 (s, 1 H), 7.86 (s, 1 H), 7.68 (s, 1 H), 6.80 (d, J = 4.5, 1 H), 4.99 (q, J = 9.2, 2 H), 2.81 (d, J = 4.5, 3 H), 2.20 (s, 3 H). | | 0.0011 |
| 97 N4-ethyl-N2-(3-methyl-1-(oxetan-3-yl)-1H-pyrazol-4-yl)-5-(trifluoromethyl)pyrimidine-2,4-diamine | | 1H NMR (400 MHz, DMSO) δ 9.06* (br s, 1 H), 8.69† (br s, 1 H), 8.33† (s, 1 H), 8.13* (s, 1 H), 8.09* (br s, 1 H), 7.94† (br s, 1 H), 7.09* (br s, 1 H), 6.95† (br s, 1 H), 5.47 (p, J = 7.0, 1 H), 4.92-4.85 (m, 4 H), 3.68-3.30 (m, 2 H), 2.21 (s, 3 H), 1.17 (t, J = 7.0, 3 H). [* and † denote rotameric peaks.] | 343 | 0.0016 |

TABLE 8-continued

| Name | Structure | ¹H NMR | M + H⁺ | K$_I$ |
| --- | --- | --- | --- | --- |
| 98 5-chloro-N4-ethyl-N2-(3-methyl-1-(oxetan-3-yl)-1H-pyrazol-4-yl)pyrimidine-2,4-diamine | | 1H NMR (400 MHz, DMSO) δ 8.44 (br s, 1 H), 8.01 (s, 1 H), 7.87 (s, 1 H), 7.10 (s, 1 H), 5.46 (t, J = 7.0, 1 H), 4.89 (dt, J = 22.1, 6.7, 4 H), 3.44 (p, J = 6.7, 2 H), 2.20 (s, 3 H), 1.18 (t, J = 7.1, 3 H). | 309 | 0.0031 |
| 99 5-bromo-N4-methyl-N2-(1-methyl-1H-pyrazol-5-yl)pyrimidine-2,4-diamine | | 1H NMR (400 MHz, DMSO) δ 9.04 (s, 1 H), 8.29 (s, 1 H), 7.99 (s, 1 H), 7.32 (d, J = 2.0, 1 H), 7.05 (q, J = 4.7, 1 H), 6.23 (d, J = 2.0, 1 H), 3.68 (s, 3 H), 2.86 (d, J = 4.7, 3 H). Note: formic acid salt. | 283 | 0.0054 |
| 100 2-methyl-1-(5-methyl-4-(4-(methylamino)-5-(trifluoromethyl)pyrimidin-2-ylamino)-1H-pyrazol-1-yl)propan-2-ol | | 1H NMR (400 MHz, CDCl₃) δ 8.08 (s, 1 H), 7.76 (br s, 1 H), 6.69 (br s, 1 H), 5.15 (s, 1 H), 4.49 (s, 1 H), 3.97 (s, 2 H), 2.98 (d, J = 4.6, 3 H), 2.21 (s, 3 H), 1.18 (s, 6 H). | 345 | 0.0085 |
| 101 5-chloro-N4-methyl-N2-(3-methyl-1-(methylsulfonyl)-1H-pyrazol-4-yl)pyrimidine-2,4-diamine | | 1H NMR (400 MHz, DMSO) δ 8.88 (s, 1 H), 8.43 (s, 1 H), 7.95 (s, 1 H), 7.22 (d, J = 4.3, 1 H), 3.38 (s, 3 H), 2.91 (d, J = 4.6, 3 H), 2.31 (s, 3 H). | | 0.0088 |
| 102 N4-methyl-N2-(3-methyl-1-(methylsulfonyl)-1H-pyrazol-4-yl)-5-(trifluoromethyl)pyrimidine-2,4-diamine | | 1H NMR (400 MHz, DMSO) δ 9.35 (s, 1 H), 8.47 (s, 1 H), 8.20 (s, 1 H), 7.17 (s, 1 H), 3.41 (s, 3 H), 2.93 (d, J = 4.4, 3 H), 2.32 (s, 3 H). | | 0.0029 |

TABLE 8-continued

| Name | Structure | ¹H NMR | M + H⁺ | K$_I$ |
|---|---|---|---|---|
| 103 N4-methyl-N2-(3-methyl-1H-pyrazol-4-yl)-5-(trifluoromethyl)pyrimidine-2,4-diamine | | 1H NMR (400 MHz, DMSO) δ 12.20 (d, J = 43.0, 1 H), 8.81 (s, 1 H), 8.06 (s, 1 H), 7.79 (d, J = 67.1, 1 H), 6.90 (s, 1 H), 2.86 (s, 3 H), 2.15 (s, 3 H). | | 0.0090 |
| 104 5-bromo-N4-ethyl-N2-(3-methyl-1-(oxetan-3-yl)-1H-pyrazol-4-yl)pyrimidine-2,4-diamine | | 1H NMR (400 MHz, DMSO) δ 8.46 (br s, 1 H), 8.00 (s, 1 H), 7.94 (s, 1 H), 6.90 (s, 1 H), 5.47-5.45 (m, 1 H), 4.89 (dt, J = 22.8, 6.7, 4 H), 3.44 (p, J = 6.7, 2 H), 2.20 (s, 3 H), 1.18 (t, J = 7.1, 3 H). | 353 | 0.0014 |
| 105 N2-(1-(difluoromethyl)-3-methyl-1H-pyrazol-4-yl)-N4-methyl-5-(trifluoromethyl)pyrimidine-2,4-diamine | | 1H NMR (400 MHz, DMSO) δ 9.04 (s, 1 H), 8.09 (s, 1 H), 7.98 (s, 1 H), 7.71 (t, J = 58.1, 1 H), 7.01 (s, 1 H), 2.84 (s, 3 H), 2.34 (s, 3 H). | | 0.0055 |
| 106 N2-(1-(difluoromethyl)-5-methyl-1H-pyrazol-4-yl)-N4-methyl-5-(trifluoromethyl)pyrimidine-2,4-diamine | | 1H NMR (400 MHz, DMSO) δ 9.20 (s, 1 H), 8.31 (s, 1 H), 8.15 (s, 1 H), 7.66 (t, J = 59.5, 1 H), 7.15 (s, 1 H), 2.91 (d, J = 4.4, 3 H), 2.24 (s, 3 H). | | 0.0019 |
| 107 5-bromo-N4-ethyl-N2-(1-ethyl-5-methyl-1H-pyrazol-4-yl)pyrimidine-2,4-diamine | | 1H NMR (400 MHz, DMSO) δ 8.20 (s, 1 H), 7.85 (s, 1 H), 7.49 (s, 1 H), 6.72 (t, J = 5.5, 1 H), 4.00 (q, J = 7.2, 2 H), 3.35 (p, J = 6.9, 2 H), 2.15 (s, 3 H), 1.27 (t, J = 7.2, 3 H), 1.10 (t, J = 7.1, 3 H). | | 0.00043 |

TABLE 8-continued

| Name | Structure | ¹H NMR | M + H⁺ | K$_I$ |
|---|---|---|---|---|
| 108 5-bromo-N2-(1-(4-fluorophenyl)-3-methyl-1H-pyrazol-4-yl)-N4-methylpyrimidine-2,4-diamine | | 1H NMR (400 MHz, DMSO) δ 8.47 (s, 1 H), 7.88 (m, 2 H), 7.60-7.49 (m, 2 H), 7.34 (t, J = 8.4, 2 H), 6.84 (s, 1 H), 2.86 (d, J = 3.8, 3 H), 2.23 (s, 3 H). | | 0.0003 |
| 109 5-bromo-N4-methyl-N2-(3-methyl-1-phenyl-1H-pyrazol-4-yl)pyrimidine-2,4-diamine | | | 360 | 0.0084 |
| 110 5-bromo-N4-methyl-N2-(5-methyl-1-phenyl-1H-pyrazol-4-yl)pyrimidine-2,4-diamine | | | 360 | |
| 111 5-bromo-N4-methyl-N2-(1-methyl-1H-pyrazol-4-yl)pyrimidine-2,4-diamine | | | | |

TABLE 8-continued

| Name | Structure | ¹H NMR | M + H⁺ | K$_I$ |
|---|---|---|---|---|
| 112 N4-methyl-N2-(3-methyl-1-(1-(methylsulfonyl)azetidin-3-yl)-1H-pyrazol-4-yl)-5-(trifluoromethyl)pyrimidine-2,4-diamine | | ¹H NMR (300MHz, CD$_3$OD) δ 8.12 (s, 1 H), 7.93 (s, 1 H), 5.22-5.13 (m, 1 H), 4.35-4.30 (m, 4 H), , 3.31 (s, 3 H), 3.31 (s, 3 H), 2.24 (s, 3 H) | | |
| 113 5-bromo-N4-methyl-N2-(3-methyl-1-propyl-1H-pyrazol-4-yl)pyrimidine-2,4-diamine | | 1H NMR (400 MHz, DMSO) δ 8.22 (s, 1 H), 7.84 (s, 1 H), 7.51 (s, 1 H), 6.75 (d, J = 4.0, 1 H), 3.92 (t, J = 7.0, 2 H), 2.81 (d, J = 4.3, 3 H), 2.15 (s, 3 H), 1.70 (h, J = 7.2, 2 H), 0.83 (t, J = 7.4, 3 H). | | 0.012 |
| 114 5-chloro-N4-methyl-N2-(3-methyl-1-((3-methyloxetan-3-yl)methyl)-1H-pyrazol-4-yl)pyrimidine-2,4-diamine | | 1H NMR (400 MHz, DMSO) δ 8.36 (s, 1 H), 7.84 (s, 1 H), 7.82 (s, 1 H), 7.04 (q, J = 4.7, 1 H), 4.57 (d, J = 5.8, 2 H), 4.20 (d, J = 6.0, 3 H), 3.44 (br s, 2 H), 2.86 (d, J = 4.6, 3 H), 2.11 (s, 2 H), 1.14 (s, 3 H). | 323 | 0.019 |
| 115 5-bromo-N2-(1-(3,5-difluorophenyl)-5-methyl-1H-pyrazol-4-yl)-N4-methylpyrimidine-2,4-diamine | | 1H NMR (400 MHz, DMSO) δ 8.67 (s, 1 H), 8.61 (s, 1 H), 7.96 (s, 1 H), 7.45 (d, J = 8.2, 2 H), 7.06 (t, J = 9.2, 1 H), 6.93 (d, J = 4.3, 1 H), 2.91 (d, J = 4.5, 3 H), 2.25 (s, 3 H). | | 0.031 |

TABLE 8-continued

| Name | Structure | ¹H NMR | M + H⁺ | $K_I$ |
|---|---|---|---|---|
| 116 5-bromo-N2-(1-(3,5-difluorophenyl)-3-methyl-1H-pyrazol-4-yl)-N4-methylpyrimidine-2,4-diamine | | 1H NMR (400 MHz, DMSO) δ 8.55 (s, 1 H), 7.96 (s, 1 H), 7.90 (s, 1 H), 7.40-7.20 (m, 3 H), 6.86 (d, J = 4.4, 1 H), 2.86 (d, J = 4.5, 3 H), 2.34 (s, 3 H). | | 0.0003 |
| 117 N4-methyl-N2-(3-methyl-1-(pyridin-2-yl)-1H-pyrazol-4-yl)-5-(trifluoromethyl)pyrimidine-2,4-diamine | | 1H NMR (400 MHz, DMSO) δ 9.20 (s, 2 H), 8.40 (d, J = 4.7, 1 H), 8.18 (s, 1 H), 7.91 (t, J = 7.8, 1 H), 7.83 (d, J = 8.2, 1 H), 7.29-7.19 (m, 1 H), 7.08 (s, 1 H), 2.96 (d, J = 3.9, 3 H), 2.32 (s, 3 H). | | 0.0067 |
| 118 N4-methyl-N2-(3-methyl-1-((3-methyloxetan-3-yl)methyl)-1H-pyrazol-4-yl)-5-(trifluoromethyl)pyrimidine-2,4-diamine | | 1H NMR (400 MHz, CDCl₃) δ 8.12 (s, 1 H), 7.83 (s, 1 H), 6.59 (br s, 1 H), 5.18 (br s, 1 H), 4.69 (d, J = 6.1, 2 H), 4.39 (d, J = 6.1, 2 H), 4.24 (s, 2 H), 3.05 (d, J = 4.7, 3 H), 2.24 (s, 3 H), 1.28 (s, 3 H). | 357 | 0.0072 |
| 119 N4-methyl-N2-(5-methyl-1-propyl-1H-pyrazol-4-yl)-5-(trifluoromethyl)pyrimidine-2,4-diamine | | 1H NMR (400 MHz, DMSO) δ 8.86 (s, 1 H), 8.07 (s, 1 H), 7.85 (s, 1 H), 6.93 (s, 1 H), 3.92 (t, J = 6.8, 2 H), 2.87 (d, J = 4.0, 3 H), 2.11 (s, 3 H), 1.73 (h, J = 7.1, 2 H), 0.82 (t, J = 7.3, 3 H). | | 0.0056 |

TABLE 8-continued

| Name | Structure | $^1$H NMR | M + H$^+$ | K$_I$ |
|---|---|---|---|---|
| 120 N4-methyl-N2-(3-methyl-1-propyl-1H-pyrazol-4-yl)-5-(trifluoromethyl)pyrimidine-2,4-diamine | | 1H NMR (400 MHz, DMSO) δ 8.80 (s, 1 H), 8.04 (s, 1 H), 7.61 (s, 1 H), 6.88 (s, 1 H), 3.94 (t, J = 7.0, 2 H), 2.82 (s, 3 H), 2.12 (d, J = 39.3, 3 H), 1.71 (h, J = 7.3, 2 H), 0.84 (t, J = 7.3, 3 H). | | 0.0006 |
| 121 5-bromo-N2-(1-isopropyl-3-methyl-1H-pyrazol-4-yl)-N4-methylpyrimidine-2,4-diamine | | 1H NMR (400 MHz, DMSO) δ 8.28 (s, 1 H), 7.88 (s, 1 H), 7.83 (s, 1 H), 6.80 (d, J = 4.3, 1 H), 4.39-4.26 (m, 1 H), 2.86 (d, J = 4.6, 3 H), 2.10 (s, 3 H), 1.36 (d, J = 6.7, 6 H). | | 0.0031 |
| 122 5-bromo-N2-(1-(4-chlorophenyl)-5-methyl-1H-pyrazol-4-yl)-N4-methylpyrimidine-2,4-diamine | | 1H NMR (400 MHz, DMSO) δ 8.64 (s, 1 H), 8.55 (s, 1 H), 7.95 (s, 1 H), 7.72 (d, J = 8.9, 2 H), 7.49 (d, J = 8.9, 2 H), 6.92 (d, J = 4.4, 1 H), 2.91 (d, J = 4.5, 3 H), 2.25 (s, 3 H). | | 0.014 |
| 123 N2-(1-(4-chlorophenyl)-5-methyl-1H-pyrazol-4-yl)-N4-methyl-5-(trifluoromethyl)pyrimidine-2,4-diamine | | 1H NMR (400 MHz, DMSO) δ 9.03 (s, 1 H), 8.05 (d, J = 33.8, 2 H), 7.57 (s, 4 H), 6.76 (d, J = 171.5, 2 H), 2.88 (d, J = 3.9, 3 H), 2.28 (s, 3 H). | | 0.0003 |

TABLE 8-continued

| Name | Structure | ¹H NMR | M + H⁺ | K$_I$ |
|---|---|---|---|---|
| 124 N4-methyl-N2-(3-methyl-1-(4-(methylsulfonyl)phenyl)-1H-pyrazol-4-yl)-5-(trifluoromethyl)pyrimidine-2,4-diamine | | 1H NMR (400 MHz, DMSO) δ 9.12 (s, 1 H), 8.07 (t, J = 13.9, 3 H), 7.84 (d, J = 11.0, 2 H), 7.00 (s, 1 H), 3.28 (s, 3 H), 2.88 (d, J = 4.0, 3 H), 2.37 (s, 3 H). | | 0.0003 |
| 125 N4-methyl-N2-(5-methyl-1-(4-(methylsulfonyl)phenyl)-1H-pyrazol-4-yl)-5-(trifluoromethyl)pyrimidine-2,4-diamine | | 1H NMR (400 MHz, DMSO) δ 9.24 (s, 1 H), 8.75 (s, 1 H), 8.16 (s, 1 H), 8.02-7.91 (m, 4 H), 7.09 (s, 1 H), 3.23 (s, 3 H), 2.95 (d, J = 4.3, 3 H), 2.31 (s, 3 H). | | 0.0047 |
| 126 N2-(1-((1S,5S)-8-oxabicyclo[3.2.1]octan-3-yl)-3-methyl-1H-pyrazol-4-yl)-N4-methyl-5-(trifluoromethyl)pyrimidine-2,4-diamine | | ¹H NMR (300 MHz, CD₃OD) δ 8.05 (s, 2 H), 4.37-4.46 (m, 3 H), 3.00 (s, 3 H), 2.45-2.42 (m, 4 H), 2.25 (s, 3 H), 1.79-1.77 (m, 4 H) | | 0.113 |
| 127 N2-(1-butyl-5-methyl-1H-pyrazol-4-yl)-N4-methyl-5-(trifluoromethyl)pyrimidine-2,4-diamine | | | 329.2 | 0.0003 |

TABLE 8-continued

| Name | Structure | ¹H NMR | M + H⁺ | K$_I$ |
|---|---|---|---|---|
| 128 N4-methyl-N2-(3-methyl-1-(pyrimidin-2-yl)-1H-pyrazol-4-yl)-5-(trifluoromethyl)pyrimidine-2,4-diamine | | 1H NMR (400 MHz, DMSO) δ 9.28 (s, 1 H), 8.96 (s, 1 H), 8.78 (d, J = 4.8, 2 H), 8.19 (s, 1 H), 7.35 (t, J = 4.8, 1 H), 7.11 (s, 1 H), 2.97 (d, J = 4.0, 3 H), 2.33 (s, 3 H). | | 0.0114 |
| 129 N2-(1-(4-chlorophenyl)-3-methyl-1H-pyrazol-4-yl)-N4-methyl-5-(trifluoromethyl)pyrimidine-2,4-diamine | | 1H NMR (400 MHz, DMSO) δ 9.16 (s, 1 H), 8.60 (s, 1 H), 8.14 (s, 1 H), 7.74 (d, J = 8.8, 2 H), 7.50 (d, J = 8.9, 2 H), 7.05 (s, 1 H), 2.93 (d, J = 4.4, 3 H), 2.26 (s, 3 H). | | 0.028 |
| 130 N2-(1-(2-fluoroethyl)-3-methyl-1H-pyrazol-4-yl)-N4-methyl-5-(trifluoromethyl)pyrimidine-2,4-diamine | | 1H NMR (400 MHz, DMSO) δ 8.97 (s, 1 H), 8.08 (s, 1 H), 7.93 (s, 1 H), 7.25-6.91 (m, 1 H), 4.77 (t, J = 4.7, 1 H), 4.65 (t, J = 4.7, 1 H), 4.33 (t, J = 4.7, 1 H), 4.26 (t, J = 4.7, 1 H), 2.88 (d, J = 4.3, 3 H), 2.13 (s, 3 H). | | 0.0011 |
| 131 N4-methyl-N2-(3-methyl-1-(1-(oxetan-3-yl)piperidin-4-yl)-1H-pyrazol-4-yl)-5-(trifluoromethyl)pyrimidine-2,4-diamine | | 1H NMR (400 MHz, DMSO) δ 8.90 (s, 1 H), 8.07 (s, 1 H), 7.93 (s, 1 H), 6.95 (s, 1 H), 4.54 (t, J = 6.5, 2 H), 4.43 (t, J = 6.1, 2 H), 4.00 (s, 1 H), 3.49-3.38 (m, 1 H), 2.88 (d, J = 4.4, 3 H), 2.76 (d, J = 9.5, 2 H), 2.12 (s, 3 H), 2.04-1.72 (m, 6 H). | | 0.0374 |

TABLE 8-continued

| | Name | Structure | ¹H NMR | M + H⁺ | K$_I$ |
|---|---|---|---|---|---|
| 132 | N4-methyl-N2-(5-methyl-1-(1-(oxetan-3-yl)piperidin-4-yl)-1H-pyrazol-4-yl)-5-(trifluoromethyl)pyrimidine-2,4-diamine | 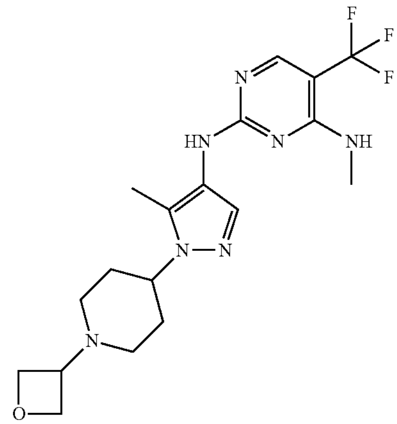 [SMILES: CNc1nc(Nc2cnn(C3CCN(C4COC4)CC3)c2C)ncc1C(F)(F)F] | 1H NMR (400 MHz, DMSO) δ 8.84 (s, 1 H), 8.04 (s, 1 H), 7.71 (s, 1 H), 6.89 (s, 1 H), 4.55 (t, J = 6.3, 2 H), 4.45 (t, J = 5.5, 2 H), 4.07 (s, 1 H), 3.54-3.37 (m, 1 H), 2.84 (t, J = 19.1, 5 H), 2.19 (s, 3 H), 1.99 (td, J = 23.4, 11.5, 4 H), 1.80 (d, J = 11.5, 2 H). | | |
| 133 | N2-(1-(2-fluoroethyl)-5-methyl-1H-pyrazol-4-yl)-N4-methyl-5-(trifluoromethyl)pyrimidine-2,4-diamine | 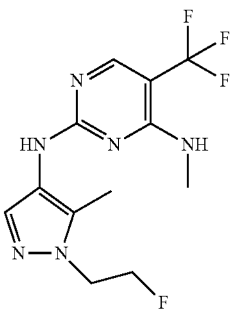 [SMILES: CNc1nc(Nc2cnn(CCF)c2C)ncc1C(F)(F)F] | 1H NMR (400 MHz, DMSO) δ 8.87 (s, 1 H), 8.05 (s, 1 H), 7.69 (s, 1 H), 6.91 (s, 1 H), 4.77 (t, J = 4.8, 1 H), 4.66 (t, J = 4.8, 1 H), 4.35 (t, J = 4.8, 1 H), 4.28 (t, J = 4.8, 1 H), 2.84 (s, 3 H), 2.18 (s, 3 H). | | 0.0018 |
| 134 | 1-(4-(4-(4-(ethylamino)-5-(trifluoromethyl)pyrimidin-2-ylamino)-3-methyl-1H-pyrazol-1-yl)piperidin-1-yl)ethanone | 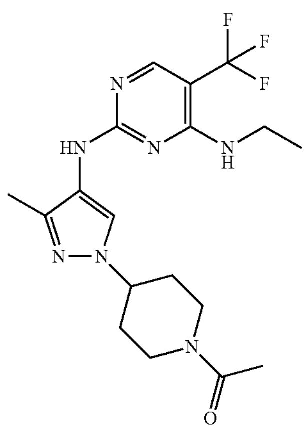 [SMILES: CCNc1nc(Nc2cn(C3CCN(C(C)=O)CC3)nc2C)ncc1C(F)(F)F] | 1H NMR (400 MHz, DMSO) δ 8.78 (s, 1 H), 8.05 (s, 1 H), 7.61 (s, 1 H), 6.87 (s, 1 H), 4.47 (d, J = 13.6, 1 H), 4.42-4.25 (m, 1 H), 3.92 (d, J = 13.6, 1 H), 3.38 (m, 2 H), 3.20 (t, J = 11.5, 1 H), 2.70 (m, 1 H), 2.27 (d, J = 46.8, 3 H), 1.83 (m, 4 H), 1.08 (m, 3 H). | | 0.0022 |
| 135 | cyclopropyl(4-(5-methyl-4-(4-(methylamino)-5-(trifluoromethyl)pyrimidin-2-ylamino)-1H-pyrazol-1-yl)piperidin-1-yl)methanone | 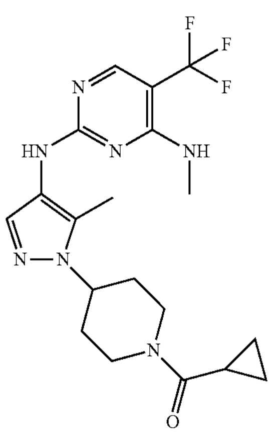 [SMILES: CNc1nc(Nc2cnn(C3CCN(C(=O)C4CC4)CC3)c2C)ncc1C(F)(F)F] | 1H NMR (400 MHz, DMSO) δ 8.85 (s, 1 H), 8.05 (s, 1 H), 7.71 (s, 1 H), 6.89 (s, 1 H), 4.55-4.23 (m, 3 H), 2.84 (s, 4 H), 2.22 (s, 3 H), 1.91 (m, 5 H), 0.79-0.62 (m, 4 H). | | 0.0010 |

TABLE 8-continued

| Name | Structure | ¹H NMR | M + H⁺ | $K_I$ |
|---|---|---|---|---|
| 136 cyclopropyl(4-(3-methyl-4-(4-(methylamino)-5-(trifluoromethyl)pyrimidin-2-ylamino)-1H-pyrazol-1-yl)piperidin-1-yl)methanone | | 1H NMR (400 MHz, DMSO) δ 8.90 (s, 1 H), 8.10 (s, 1 H), 7.95 (s, 1 H), 6.95 (s, 1 H), 4.35 (m, 3 H), 3.24 (m, 1 H), 2.88 (d, J = 4.3, 3 H), 2.74 (m, 1 H), 2.04 (m, 6 H), 1.75 (m, 2 H), 0.72 (m, 4 H). | | 0.0093 |
| 137 1-(4-(4-(4-(ethylamino)-5-(trifluoromethyl)pyrimidin-2-ylamino)-5-methyl-1H-pyrazol-1-yl)piperidin-1-yl)ethanone | | 1H NMR (400 MHz, DMSO) δ 8.78 (s, 1 H), 8.05 (s, 1 H), 7.61 (s, 1 H), 6.87 (s, 1 H), 4.47 (d, J = 13.6, 1 H), 4.42-4.25 (m, 1 H), 3.92 (d, J = 13.6, 1 H), 3.38 (m, 2 H), 3.20 (t, J = 11.5, 1 H), 2.70 (m, 1 H), 2.27 (d, J = 46.8, 3 H), 1.83 (m, 4 H), 1.08 (m, 3 H). | | 0.0004 |
| 138 N2-(5-chloro-1-isopropyl-1H-pyrazol-4-yl)-N4-methyl-5-(trifluoromethyl)pyrimidine-2,4-diamine | | 1H NMR (400 MHz, DMSO) δ 8.98 (br s, 1 H), 8.12 (s, 1 H), 7.85 (s, 1 H), 7.05 (s, 1 H), 4.65 (p, J = 6.6, 1 H), 2.86 (s, 3 H), 1.42 (d, J = 6.6, 6 H). | 335 | 0.0011 |
| 139 N2-(5-chloro-1-ethyl-1H-pyrazol-4-yl)-N4-methyl-5-(trifluoromethyl)pyrimidine-2,4-diamine | | 1H NMR (400 MHz, CDCl₃) δ 8.13 (s, 1 H), 8.08 (s, 1 H), 6.68 (br s, 1 H), 5.21 (s, 1 H), 4.18 (q, J = 7.3, 2 H), 3.07 (d, J = 4.7, 3 H), 1.44 (t, J = 7.3, 3 H). | 321 | 0.0020 |

| Name | Structure | ¹H NMR | M + H⁺ | K_I |
|---|---|---|---|---|
| 140 N4-methyl-N2-(3-methyl-1-(pyrimidin-5-yl)-1H-pyrazol-4-yl)-5-(trifluoromethyl)pyrimidine-2,4-diamine | | 1H NMR (400 MHz, DMSO) δ 9.19 (m, 3 H), 9.06 (s, 1 H), 8.76 (s, 1 H), 8.16 (s, 1 H), 7.10 (s, 1 H), 2.96 (d, J = 4.3, 3 H), 2.31 (s, 3 H). | | 0.0061 |
| 141 N4-methyl-N2-(4-methyl-1-(1-methylpiperidin-4-yl)-1H-pyrazol-3-yl)-5-(trifluoromethyl)pyrimidine-2,4-diamine | | | 370.2 | 0.041 |
| 142 N4-methyl-N2-(5-methyl-1-(2-methylpyridin-4-yl)-1H-pyrazol-4-yl)-5-(trifluoromethyl)pyrimidine-2,4-diamine | | 1H NMR (400 MHz, DMSO) δ 9.11 (s, 1 H), 8.52 (d, J = 5.5, 1 H), 8.10 (s, 2 H), 7.50 (s, 1 H), 7.43 (dd, J = 5.5, 1.9, 1 H), 6.99 (s, 1 H), 2.87 (d, J = 3.5, 3 H), 2.54 (s, 3 H), 2.40 (s, 3 H). | | 0.0003 |
| 143 N4-methyl-N2-(3-methyl-1-(2-methylpyridin-4-yl)-1H-pyrazol-4-yl)-5-(trifluoromethyl)pyrimidine-2,4-diamine | | 1H NMR (400 MHz, DMSO) δ 9.19 (s, 1 H), 8.72 (s, 1 H), 8.42 (d, J = 5.6, 1 H), 8.16 (s, 1 H), 7.59 (s, 1 H), 7.49 (d, J = 4.7, 1 H), 7.09 (s, 1 H), 2.95 (d, J = 4.3, 3 H), 2.29 (s, 3 H). | | 0.0069 |

TABLE 8-continued

| Name | Structure | ¹H NMR | M + H⁺ | K$_I$ |
|---|---|---|---|---|
| 144 N4-ethyl-N2-(3-methyl-1-((3-methyloxetan-3-yl)methyl)-1H-pyrazol-4-yl)-5-(trifluoromethyl)pyrimidine-2,4-diamine | | 1H NMR (400 MHz, CDCl$_3$) δ 8.12 (s, 1 H), 7.79 (s, 1 H), 6.58 (br s, 1 H), 5.10 (br s, 1 H), 4.69 (d, J = 6.0, 2 H), 4.39 (d, J = 6.0, 2 H), 4.24 (s, 2 H), 3.52 (p, J = 6.6, 2 H), 2.23 (s, 3 H), 1.28 (s, 3 H), 1.28 (t, J = 6.6, 3 H). | 371 | 0.0009 |
| 145 N2-(5-chloro-1-cyclopropyl-1H-pyrazol-4-yl)-N4-methyl-5-(trifluoromethyl)pyrimidine-2,4-diamine | | 1H NMR (400 MHz, CDCl$_3$) δ 8.13 (s, 1 H), 8.04 (s, 1 H), 6.76 (br s, 1 H), 5.21 (s, 1 H), 3.48-3.42 (m, 1 H), 3.06 (d, J = 4.7, 3 H), 1.23-1.19 (m, 2 H), 1.10-1.04 (m, 2 H). | 333 | 0.0017 |
| 146 N2-(5-chloro-1-(cyclopropylmethyl)-1H-pyrazol-4-yl)-N4-methyl-5-(trifluoromethyl)pyrimidine-2,4-diamine | | 1H NMR (400 MHz, CDCl$_3$) δ 8.13 (s, 1 H), 8.10 (s, 1 H), 6.72 (br s, 1 H), 5.21 (s, 1 H), 4.00 (d, J = 7.0, 2 H), 3.07 (d, J = 4.7, 3 H), 1.34-1.25 (m, 1 H), 0.62-0.56 (m, 2 H), 0.44-0.39 (m, 2 H). | 347 | 0.0003 |
| 147 4-(5-methyl-4-(4-(methylamino)-5-(trifluoromethyl)pyrimidin-2-ylamino)-1H-pyrazol-1-yl)benzonitrile | | 1H NMR (400 MHz, DMSO) δ 9.20 (s, 1 H), 8.73 (s, 1 H), 8.16 (s, 1 H), 7.91 (s, 4 H), 7.09 (s, 1 H), 2.94 (d, J = 4.3, 3 H), 2.29 (s, 3 H). | | 0.017 |

TABLE 8-continued

| Name | Structure | ¹H NMR | M + H⁺ | K$_I$ |
|---|---|---|---|---|
| 148 4-(3-methyl-4-(4-(methylamino)-5-(trifluoromethyl)pyrimidin-2-ylamino)-1H-pyrazol-1-yl)benzonitrile | | 1H NMR (400 MHz, DMSO) δ 9.07 (s, 1 H), 8.10 (s, 1 H), 7.98 (d, J = 8.6, 2 H), 7.78 (d, J = 8.6, 1 H), 6.99 (s, 1 H), 2.88 (d, J = 3.8, 2 H), 2.36 (s, 2 H). | | 0.0003 |
| 149 N4-methyl-N2-(3-methyl-1-(tetrahydrofuran-3-yl)-1H-pyrazol-4-yl)-5-(trifluoromethyl)pyrimidine-2,4-diamine | | 1H NMR (400 MHz, DMSO) δ 8.95 (s, 1 H), 8.08 (s, 1 H), 7.99 (s, 1 H), 6.96 (s, 1 H), 4.88 (m, 1 H), 3.99-3.74 (m, 4 H), 2.89 (d, J = 4.4, 3 H), 2.33 (m, 1 H), 2.13 (m, 4 H). | | 0.0068 |
| 150 N4-methyl-N2-(5-methyl-1-(tetrahydrofuran-3-yl)-1H-pyrazol-4-yl)-5-(trifluoromethyl)pyrimidine-2,4-diamine | | 1H NMR (400 MHz, DMSO) δ 8.87 (s, 1 H), 8.05 (s, 1 H), 7.61 (d, J = 92.3, 1 H), 6.90 (s, 1 H), 5.10-4.58 (m, 1 H), 4.19-3.69 (m, 4 H), 2.84 (m, 3 H), 2.42-2.04 (m, 5 H). | | 0.0051 |
| 151 5-(4-(4-(ethylamino)-5-(trifluoromethyl)pyrimidin-2-ylamino)-5-methyl-1H-pyrazol-1-yl)-1-methylpiperidin-2-one | | 1H NMR (400 MHz, DMSO) δ 8.84 (s, 1 H), 8.05 (s, 1 H), 7.66 (s, 1 H), 6.89 (s, 1 H), 4.81-4.63 (m, 1 H), 3.61 (m, 1 H), 3.50 (m, 1 H), 3.38 (m, 2 H), 2.82 (m, 3 H), 2.49-2.09 (m, 6 H), 1.99 (m, 1 H), 1.08 (m, 3 H). | | 0.0011 |

TABLE 8-continued

| Name | Structure | ¹H NMR | M + H⁺ | K$_I$ |
|---|---|---|---|---|
| 152 5-(4-(4-(ethylamino)-5-(trifluoromethyl)pyrimidin-2-ylamino)-3-methyl-1H-pyrazol-1-yl)-1-methylpiperidin-2-one | | 1H NMR (400 MHz, DMSO) δ 8.90 (s, 1 H), 8.08 (s, 1 H), 7.90 (s, 1 H), 6.95 (s, 1 H), 4.58 (m, 1 H), 3.68-3.53 (m, 2 H), 3.42 (m, 2 H), 2.82 (m, 3 H), 2.45-2.18 (m, 3 H), 2.13 (m, 4 H), 1.12 (m, 3 H). | | 0.0073 |
| 153 5-(3-methyl-4-(4-(methylamino)-5-(trifluoromethyl)pyrimidin-2-ylamino)-1H-pyrazol-1-yl)piperidin-2-one | | 1H NMR (400 MHz, DMSO) δ 8.95 (s, 1 H), 8.05 (d, J = 23.6, 2 H), 7.50 (s, 1 H), 6.97 (s, 1 H), 4.49 (m, 1 H), 3.47 (m, 2 H), 2.88 (d, J = 4.3, 3 H), 2.39- 1.97 (m, 7 H). | | 0.0097 |
| 154 5-(5-methyl-4-(4-(methylamino)-5-(trifluoromethyl)pyrimidin-2-ylamino)-1H-pyrazol-1-yl)piperidin-2-one | | 1H NMR (400 MHz, DMSO) δ 8.87 (s, 1 H), 8.05 (s, 1 H), 7.62 (d, J = 96.3, 2 H), 6.90 (s, 1 H), 4.59 (m, 1 H), 3.55-3.42 (m, 1 H), 3.36 (m, 1 H), 2.84 (m, 3 H), 2.30 (m, 6 H), 1.99 (m, 1 H). | | 0.0022 |
| 155 N2-(1-isopropyl-5-methyl-1H-pyrazol-4-yl)-N4-methyl-5-(trifluoromethyl)pyrimidine-2,4-diamine | | 1H NMR (500 MHz, DMSO) δ 8.08 (s, 1 H), 7.88 (s, 1 H), 6.80 (s, 1 H), 5.15 (s, 1 H), 4.39-4.44 (m, 1 H), 3.01 (d, J = 5, 3 H), 2.22 (s, 3 H), 1.49 (d, J = 6.5, 6 H). | 315 | 0.0025 |

TABLE 8-continued

| Name | Structure | ¹H NMR | M + H⁺ | K$_I$ |
|---|---|---|---|---|
| 156 N,N-dimethyl-4-(5-methyl-4-(4-(methylamino)-5-(trifluoromethyl)pyrimidin-2-ylamino)-1H-pyrazol-1-yl)benzamide | | 1H NMR (400 MHz, DMSO) δ 9.07 (s, 1 H), 8.10 (s, 1 H), 7.57 (q, J = 8.5, 4 H), 6.98 (s, 1 H), 2.99 (s, 6 H), 2.88 (d, J = 4.0, 3 H), 2.31 (s, 3 H). | | 0.0003 |
| 157 4-(4-(4-(ethylamino)-5-(trifluoromethyl)pyrimidin-2-ylamino)-5-methyl-1H-pyrazol-1-yl)-N,N-dimethylbenzamide | | 1H NMR (400 MHz, DMSO) δ 9.00 (s, 1 H), 8.24-7.78 (m, 2 H), 7.57 (q, J = 8.5, 4 H), 6.95 (s, 1 H), 3.43 (s, 2 H), 2.99 (s, 6 H), 2.31 (s, 3 H), 1.12 (t, J = 6.7, 3 H). | | 0.0003 |
| 158 N4-ethyl-N2-(5-methyl-1-(tetrahydro-2H-pyran-4-yl)-1H-pyrazol-4-yl)-5-(trifluoromethyl)pyrimidine-2,4-diamine | | 1H NMR (400 MHz, DMSO) δ 8.80 (s, 1 H), 8.05 (s, 1 H), 7.63 (s, 1 H), 6.87 (s, 1 H), 4.41-4.24 (m, 1 H), 3.95 (dd, J = 11.2, 4.0, 2 H), 3.47 (t, J = 11.2, 2 H), 3.38 (s, 2 H), 2.20 (s, 3 H), 2.01 (qd, J = 12.4, 4.5, 2 H), 1.85-1.64 (m, 2 H), 1.08 (s, 3 H). | | 0.0003 |
| 159 N4-ethyl-N2-(3-methyl-1-(tetrahydro-2H-pyran-4-yl)-1H-pyrazol-4-yl)-5-(trifluoromethyl)pyrimidine-2,4-diamine | | 1H NMR (400 MHz, DMSO) δ 8.88 (s, 1 H), 8.08 (s, 1 H), 7.87 (s, 1 H), 6.98 (s, 1 H), 4.42-4.15 (m, 1 H), 3.94 (d, J = 11.0, 2 H), 3.44 (t, J = 11.0, 3 H), 2.12 (s, 2 H), 1.89 (s, 3 H), 1.21-1.00 (m, 2 H). | | 0.0039 |

TABLE 8-continued

| | Name | Structure | ¹H NMR | M + H⁺ | K$_I$ |
|---|---|---|---|---|---|
| 160 | N4-ethyl-N2-(3-methyl-1-(methylsulfonyl)-1H-pyrazol-4-yl)-5-(trifluoromethyl)pyrimidine-2,4-diamine | 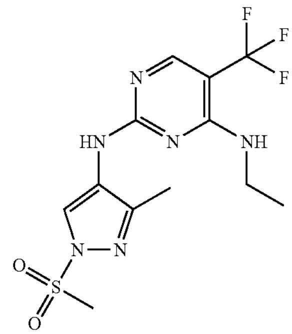 [SMILES: CCNc1nc(Nc2cn(S(C)(=O)=O)nc2C)ncc1C(F)(F)F] | 1H NMR (400 MHz, DMSO) δ 9.38 (s, 1 H), 8.44 (s, 1 H), 8.20 (s, 1 H), 7.24 (s, 1 H), 3.47 (p, J = 6.8, 2 H), 3.40 (s, 3 H), 2.32 (s, 3 H), 1.21-1.09 (m, 3 H). | | 0.0003 |
| 161 | N2-(1-(4-(cyclopropyl-sulfonyl)phenyl)-3-methyl-1H-pyrazol-4-yl)-N4-methyl-5-(trifluoromethyl)pyrimidine-2,4-diamine | 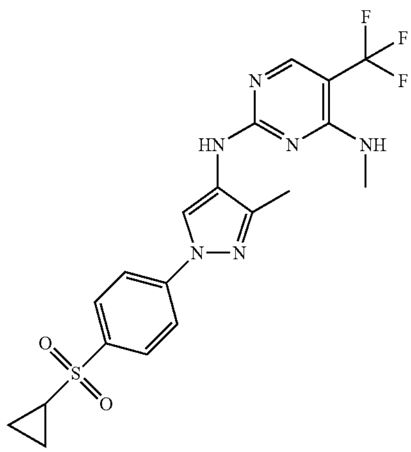 [SMILES: CNc1nc(Nc2cn(-c3ccc(S(=O)(=O)C4CC4)cc3)nc2C)ncc1C(F)(F)F] | 1H NMR (400 MHz, DMSO) δ 9.12 (s, 1 H), 8.11 (s, 1 H), 8.02 (d, J = 8.6, 3 H), 7.84 (d, J = 8.6, 2 H), 7.00 (s, 1 H), 3.01-2.82 (m, 4 H), 2.37 (s, 3 H), 1.22-1.14 (m, 2 H), 1.14-0.94 (m, 2 H). | | 0.0003 |
| 162 | 4-(4-(4-(ethylamino)-5-(trifluoromethyl)pyrimidin-2-ylamino)-5-methyl-1H-pyrazol-1-yl)benzonitrile | 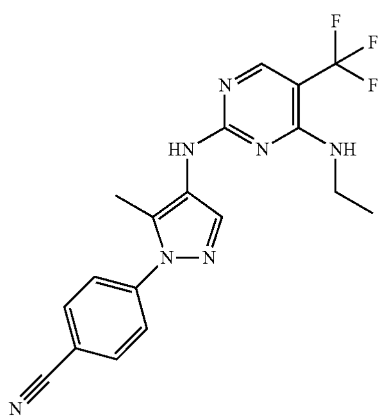 [SMILES: CCNc1nc(Nc2cnn(-c3ccc(C#N)cc3)c2C)ncc1C(F)(F)F] | 1H NMR (400 MHz, DMSO) δ 9.06 (s, 1 H), 8.10 (s, 1 H), 7.99 (d, J = 8.6, 2 H), 7.78 (d, J = 8.6, 2 H), 6.97 (s, 1 H), 3.43 (s, 2 H), 2.36 (s, 3 H), 1.12 (t, J = 6.8, 3 H). | | 0.0003 |
| 163 | N4-ethyl-N2-(5-methyl-1-(4-(methylsulfonyl)phenyl)-1H-pyrazol-4-yl)-5-(trifluoromethyl)pyrimidine-2,4-diamine | 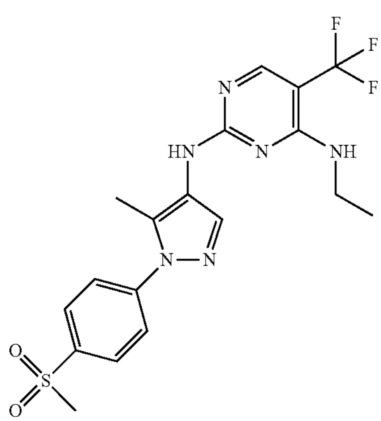 [SMILES: CCNc1nc(Nc2cnn(-c3ccc(S(C)(=O)=O)cc3)c2C)ncc1C(F)(F)F] | 1H NMR (400 MHz, DMSO) δ 9.09 (s, 1 H), 8.15-8.02 (m, 3 H), 7.84 (d, J = 8.7, 2 H), 6.97 (s, 1 H), 3.43 (s, 2 H), 2.37 (s, 3 H), 1.12 (t, J = 7.0, 3 H). | | 0.0003 |

TABLE 8-continued

| Name | Structure | ¹H NMR | M + H⁺ | K_I |
|---|---|---|---|---|
| 164 N,N-dimethyl-4-(3-methyl-4-(4-(methylamino)-5-(trifluoromethyl)pyrimidin-2-ylamino)-1H-pyrazol-1-yl)benzamide | | 1H NMR (400 MHz, DMSO) δ 9.17 (s, 1 H), 8.65 (s, 1 H), 8.14 (s, 1 H), 7.76 (d, J = 8.5, 2 H), 7.50 (d, J = 8.6, 2 H), 7.06 (s, 1 H), 3.06-2.86 (m, 9 H), 2.28 (s, 3 H). | | 0.0057 |
| 165 N2-(1-(cyclopropyl-methyl)-5-methyl-1H-pyrazol-4-yl)-N4-methyl-5-(trifluoromethyl)pyrimidine-2,4-diamine | | ¹H NMR (500 MHz, DMSO) δ 8.41 (d, J = 16.0, 1 H), 8.04 (s, 1 H), 6.59 (s, 1 H), 6.59 (s, 1 H), 3.89 (m, J = 11.0, 1 H), 3.85 (d, J = 7.5, 3 H), 2.17 (s, 1 H), 1.13-1.18 (m, 1 H), 0.44-0.50 (m, 2 H), 0.28-0.32 (s, 2 H). | 327 | 0.0012 |
| 166 N2-(1-(cyclopropyl-methyl)-3-methyl-1H-pyrazol-4-yl)-N4-methyl-5-(trifluoromethyl)pyrimidine-2,4-diamine | | ¹H NMR (500 MHz, DMSO) δ 8.46 (d, J = 2.0, 1 H), 8.14 (s, 1 H), 8.04 (s, 1 H), 6.65 (s, 1 H), 3.82-3.84 (m, 2 H), 2.90 (d, J = 7.5, 3 H), 1.89 (s, 1 H), 1.15-1.20 (m, 1 H), 0.47-0.53 (m, 2 H), 0.28-0.33 (s, 2 H). | | 0.0045 |
| 167 N2-(1-(4-(cyclopropyl-sulfonyl)phenyl)-5-methyl-1H-pyrazol-4-yl)-N4-methyl-5-(trifluoromethyl)pyrimidine-2,4-diamine | | 1H NMR (400 MHz, DMSO) δ 9.24 (s, 1 H), 8.75 (s, 1 H), 8.16 (s, 1 H), 8.02-7.87 (m, 4 H), 7.09 (s, 1 H), 2.96 (d, J = 4.3, 3 H), 2.92-2.81 (m, 1 H), 2.31 (s, 3 H), 1.21-1.11 (m, 2 H), 1.10-0.97 (m, 2 H). | | 0.0188 |

TABLE 8-continued

| | Name | Structure | ¹H NMR | M + H⁺ | K$_I$ |
|---|---|---|---|---|---|
| 168 | N2-(5-chloro-1-(oxetan-3-yl)-1H-pyrazol-4-yl)-N4-methyl-5-(trifluoromethyl)pyrimidine-2,4-diamine | 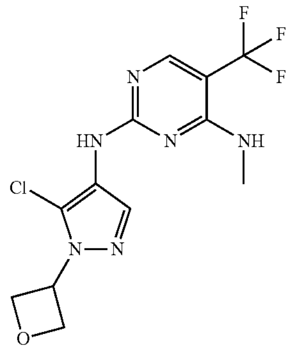 [SMILES: CNc1nc(Nc2cnn(C3COC3)c2Cl)ncc1C(F)(F)F] | 1H NMR (400 MHz, CDCl$_3$) δ 8.25 (s, 1 H), 8.13 (s, 1 H), 6.89 (br s, 1 H), 5.56 (p, J = 7.1, 1 H), 5.25 (s, 1 H), 5.19 (t, J = 6.6, 2 H), 5.00 (t, J = 7.2, 2 H), 3.08 (d, J = 4.7, 3 H). | 349 | 0.0095 |
| 169 | N4-ethyl-N2-(5-methyl-1-((3-methyloxetan-3-yl)methyl)-1H-pyrazol-4-yl)-5-(trifluoromethyl)pyrimidine-2,4-diamine | 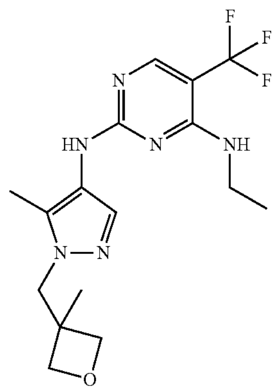 [SMILES: CCNc1nc(Nc2cnn(CC3(C)COC3)c2C)ncc1C(F)(F)F] | 1H NMR (400 MHz, CDCl$_3$) δ 8.09 (s, 1 H), 7.70 (br s, 1 H), 6.41 (br s, 1 H), 5.04 (s, 1 H), 4.78 (d, J = 6.1, 2 H), 4.40 (d, J = 6.1, 2 H), 4.22 (s, 2 H), 3.46 (p, J = 6.6, 2 H), 2.20 (s, 3 H), 1.25 (s, 3 H), 1.21 (t, J = 7.0, 3 H). | 371 | 0.0022 |
| 170 | N2-(1-(cyclopropyl-sulfonyl)-3-methyl-1H-pyrazol-4-yl)-N4-methyl-5-(trifluoromethyl)pyrimidine-2,4-diamine | 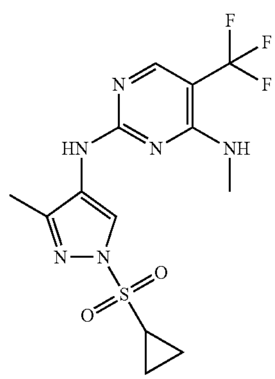 [SMILES: CNc1nc(Nc2cn(S(=O)(=O)C3CC3)nc2C)ncc1C(F)(F)F] | 1H NMR (400 MHz, DMSO) δ 9.36 (s, 1 H), 8.44 (s, 1 H), 8.19 (s, 1 H), 7.18 (s, 1 H), 3.07-2.96 (m, 1 H), 2.92 (d, J = 4.4, 3 H), 2.32 (s, 3 H), 1.24-1.07 (m, 4 H). | | 0.002 |
| 171 | N2-(1-(cyclopropyl-sulfonyl)-3-methyl-1H-pyrazol-4-yl)-N4-ethyl-5-(trifluoromethyl)pyrimidine-2,4-diamine | 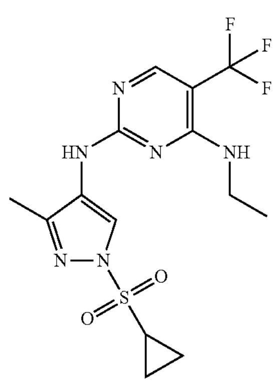 [SMILES: CCNc1nc(Nc2cn(S(=O)(=O)C3CC3)nc2C)ncc1C(F)(F)F] | 1H NMR (400 MHz, DMSO) δ 9.36 (s, 1 H), 8.41 (s, 1 H), 8.19 (s, 1 H), 7.23 (s, 1 H), 3.47 (m, 2 H), 2.99 (m, 1 H), 2.32 (s, 3 H), 1.23-1.04 (m, 7 H). | | 0.0009 |

| Name | Structure | ¹H NMR | M + H⁺ | K₁ |
|---|---|---|---|---|
| 172 5-chloro-N4-(2,2-difluoroethyl)-N2-(1,5-dimethyl-1H-pyrazol-4-yl)pyrimidine-2,4-diamine | | | | 0.0070 |
| 173 5-chloro-4-methyl-N-(3-methyl-1-(4-(methylsulfonyl)phenyl)-1H-pyrazol-4-yl)pyrimidin-2-amine | | 1H NMR (400 MHz, DMSO) δ 9.10 (s, 1 H), 8.31 (s, 1 H), 8.06 (d, J = 8.6, 2 H), 7.93 (s, 1 H), 7.85 (d, J = 8.6, 2 H), 3.28 (s, 6 H), 2.40 (s, 3 H), 2.34 (s, 3 H). | | 0.484 |
| 174 N2-(1-(4-(cyclopropyl-sulfonyl)phenyl)-5-methyl-1H-pyrazol-4-yl)-N4-ethyl-5-(trifluoromethyl)pyrimidine-2,4-diamine | | 1H NMR (400 MHz, DMSO) δ 9.21 (s, 1 H), 8.68 (s, 1 H), 8.17 (s, 1 H), 7.95 (q, J = 9.0, 4 H), 7.09 (s, 1 H), 3.58-3.43 (m, 2 H), 2.95-2.79 (m, 1 H), 2.31 (s, 3 H), 1.12 (ddd, J = 34.8, 14.3, 8.6, 7 H). | | 0.0011 |
| 175 2-methyl-1-(4-(5-methyl-4-(4-(methylamino)-5-(trifluoromethyl)pyrimidin-2-ylamino)-1H-pyrazol-1-yl)piperidin-1-yl)propan-1-one | | | 426 | 0.0068 |

| Name | Structure | ¹H NMR | M + H⁺ | K$_I$ |
|---|---|---|---|---|
| 176 N4-ethyl-N2-(1-methyl-1H-pyrazol-5-yl)-5-(trifluoromethyl)pyrimidine-2,4-diamine | | | | 0.011 |
| 177 N2-(3-cyclopropyl-1-methyl-1H-pyrazol-4-yl)-N4-methyl-5-(trifluoromethyl)pyrimidine-2,4-diamine | | | | 0.0067 |
| 178 N2-(5-cyclopropyl-1-methyl-1H-pyrazol-4-yl)-N4-methyl-5-(trifluoromethyl)pyrimidine-2,4-diamine | | | | 0.012 |
| 179 N4-methyl-N2-(5-methyl-1-((3-methyloxetan-3-yl)methyl)-1H-pyrazol-4-yl)-5-(trifluoromethyl)pyrimidine-2,4-diamine | | 1H NMR (400 MHz, CDCl$_3$) δ 8.09 (s, 1 H), 7.73 (br s, 1 H), 6.50 (br s, 1 H), 5.13 (s, 1 H), 4.78 (d, J = 6.1, 2 H), 4.40 (d, J = 6.1, 2 H), 4.22 (s, 2 H), 2.99 (d, J = 4.7, 3 H), 2.20 (s, 3 H), 1.25 (s, 3 H). | 357 | 0.0090 |

TABLE 8-continued

| Name | Structure | ¹H NMR | M + H⁺ | K$_I$ |
|---|---|---|---|---|
| 180 N2-(5-chloro-1-((3-methyloxetan-3-yl)methyl)-1H-pyrazol-4-yl)-N4-methyl-5-(trifluoromethyl)pyrimidine-2,4-diamine | | 1H NMR (400 MHz, CDCl$_3$) δ 8.13 (s, 1 H), 8.11 (s, 1 H), 6.68 (br s, 1 H), 5.22 (s, 1 H), 4.78 (d, J = 6.2, 2 H), 4.40 (d, J = 6.2, 2 H), 4.33 (s, 2 H), 3.06 (d, J = 4.7, 3 H), 1.28 (s, 3 H). | 377 | 0.0056 |
| 181 1-(4-(4-(4-(ethylamino)-5-(trifluoromethyl)pyrimidin-2-ylamino)-5-methyl-1H-pyrazol-1-yl)piperidin-1-yl)-2-methylpropan-1-one | | 1H NMR (400 MHz, DMSO) δ 8.78 (s, 1 H), 8.05 (s, 1 H), 7.62 (s, 1 H), 6.88 (s, 1 H), 4.51 (d, J = 11.9, 1 H), 4.45-4.30 (m, 1 H), 4.06 (d, J = 12.8, 1 H), 3.37 (s, 2 H), 3.20 (m, 1 H), 2.92 (m, 1 H), 2.80-2.60 (m, 1 H), 2.21 (s, 3 H), 1.88 (m, 4 H), 1.02 (m, 8 H). | | 0.00082 |
| 182 N4-ethyl-N2-(3-methyl-1-(1-(oxetan-3-yl)azetidin-3-yl)-1H-pyrazol-4-yl)-5-(trifluoromethyl)pyrimidine-2,4-diamine | | 1H NMR (400 MHz, DMSO) δ 8.83 (s, 1 H), 8.05 (s, 1 H), 7.73 (s, 1 H), 6.87 (s, 1 H), 4.98 (p, J = 7.2, 1 H), 4.60 (t, J = 6.6, 2 H), 4.43 (t, J = 5.8, 2 H), 3.88-3.77 (m, 1 H), 3.70 (t, J = 7.3, 2 H), 3.56 (t, J = 7.3, 2 H), 3.39 (s, 2 H), 2.16 (s, 3 H), 1.09 (s, 3 H). | | 0.0015 |

TABLE 8-continued

| Name | Structure | ¹H NMR | M + H⁺ | K_I |
|---|---|---|---|---|
| 183 cyclopropyl(4-(4-(4-(ethylamino)-5-(trifluoromethyl)pyrimidin-2-ylamino)-3-methyl-1H-pyrazol-1-yl)piperidin-1-yl)methanone | | | 438.3 | 0.0006 |
| 184 cyclopropyl(4-(4-(4-(ethylamino)-5-(trifluoromethyl)pyrimidin-2-ylamino)-5-methyl-1H-pyrazol-1-yl)piperidin-1-yl)methanone | | | 438.3 | 0.0047 |
| 185 1-(5-chloro-4-(4-(methylamino)-5-(trifluoromethyl)pyrimidin-2-ylamino)-1H-pyrazol-1-yl)-2-methylpropan-2-ol | | 1H NMR (400 MHz, CDCl₃) δ 8.16 (s, 1 H), 8.13 (s, 1 H), 6.81 (br s, 1 H), 5.23 (s, 1 H), 4.09 (s, 2 H), 3.99 (s, 1 H), 3.06 (d, J = 4.7, 3 H), 1.19 (s, 6 H). | 365 | 0.0069 |
| 186 N4-ethyl-N2-(1-ethyl-1H-pyrazol-3-yl)-5-(trifluoromethyl)pyrimidine-2,4-diamine | | 1H NMR (400 MHz, DMSO) δ 9.66 (s, 1 H), 8.10 (s, 1 H), 7.58 (d, J = 2.0, 1 H), 7.02 (s, 0 H), 7.00 (s, 1 H), 6.54 (d, J = 2.0, 1 H), 4.02 (q, J = 7.2, 2 H), 3.57-3.37 (m, 2 H), 1.35 (t, J = 7.2, 3 H), 1.15 (t, J = 7.1, 3 H). | | 0.0019 |

TABLE 8-continued

| Name | Structure | ¹H NMR | M + H⁺ | K$_I$ |
|---|---|---|---|---|
| 187 (S)-N2-(1-(2-methoxypropyl)-5-methyl-1H-pyrazol-4-yl)-N4-methyl-5-(trifluoromethyl)pyrimidine-2,4-diamine | | | 345 | 0.0188 |
| 188 N2-(1-(2-methoxycyclopentyl)-3-methyl-1H-pyrazol-4-yl)-N4-methyl-5-(trifluoromethyl)pyrimidine-2,4-diamine | | ¹H NMR (500 MHz, DMSO) δ 8.49 (s, 1 H), 8.07 (s, 1 H), 6.68 (d, J = 2.5, 1 H), 4.41 (m, 1 H), 3.95 (m, 1 H), 3.18 (s, 1 H), 2.91 (d, J = 8.0, 3 H), 2.09 (s, 3 H), 1.64-192 (m, 6 H). | | 0.012 |
| 189 (S)-N2-(1-(2-methoxypropyl)-3-methyl-1H-pyrazol-4-yl)-N4-methyl-5-(trifluoromethyl)pyrimidine-2,4-diamine | | ¹H NMR (500 MHz, DMSO) δ 8.11 (s, 1 H), 7.90 (s, 1 H), 6.71 (s, 1 H), 5.20 (s, 1 H), 3.00-4.07 (m, 2 H), 3.68-3.74 (m, 1 H), 3.32 (s, 3 H), 3.00-3.06 (t, J = 3 Hz, 3 H), 2.25 (d, J = 3 Hz, 3 H), 1.14-1.18 (m, 3 H). | | 0.0118 |
| 190 N2-(1-(1-methoxy-2-methylpropan-2-yl)-3-methyl-1H-pyrazol-4-yl)-N4-methyl-5-(trifluoromethyl)pyrimidine-2,4-diamine | | ¹H NMR (500 MHz, MeOD) δ 8.01 (s, 1 H), 7.79 (s, 1 H), 3.58 (s, 2 H), 3.27 (s, 3 H), 2.99 (s, 3 H), 2.22 (s, 3 H), 1.55 (s, 6 H). | | 0.0069 |

TABLE 8-continued

| Name | Structure | ¹H NMR | M + H⁺ | K$_I$ |
|---|---|---|---|---|
| 191 N2-(1-(2,6-dimethyltetrahydro-2H-pyran-4-yl)-3-methyl-1H-pyrazol-4-yl)-N4-methyl-5-(trifluoromethyl)pyrimidine-2,4-diamine | | ¹H NMR (500 MHz, CDCl3) δ 8.54 (s, 1 H), 8.08 (s, 1 H), 7.98 (s, 1 H), 6.70 (s, 1 H), 4.47 (s, 1 H), 3.70-3.80 (m, 2 H), 2.90 (d, J = 7.5, 3 H), 2.13-2.24 (m, 5 H), 1.56-1.66 (m, 2 H), 1.16 (d, J = 6.5, 6 H). | | 0.0846 |
| 192 (R)-N2-(1-(2-methoxypropyl)-5-methyl-1H-pyrazol-4-yl)-N4-methyl-5-(trifluoromethyl)pyrimidine-2,4-diamine | | | 345 | 0.0063 |
| 193 N2-(1-(3-methoxycyclopentyl)-3-methyl-1H-pyrazol-4-yl)-N4-methyl-5-(trifluoromethyl)pyrimidine-2,4-diamine | | ¹H-NMR (500 MHz, DMSO) δ 8.46 (br s, 1 H), 8.04 (s, 1 H), 7.85 (s, 1 H), 6.85 (br s, 1 H), 4.48-4.54 (m, 1 H), 3.80-3.84 (m, 1 H), 3.20 (s, 3 H), 2.89 (d, J = 7.0, 3 H), 2.35-2.45 (m, 1 H), 2.10 (s, 3 H), 1.84-2.08 (m, 3 H), 1.74-1.81 (m, 2 H). | | 0.019 |
| 194 N4-methyl-N2-(1-methyl-5-(methylamino)-1H-pyrazol-4-yl)-5-(trifluoromethyl)pyrimidine-2,4-diamine | | 1H NMR (400 MHz, DMSO) δ 8.75-8.24 (m, 1 H), 8.06 (s, 1 H), 7.56-7.06 (m, 1 H), 7.01-6.82 (m, 1 H), 4.89-4.66 (m, 1 H), 3.59 (s, 3 H), 2.87 (br s, 3 H), 2.68 (d, J = 5.1, 3 H). | 302 | 0.0522 |

TABLE 8-continued

| | Name | Structure | ¹H NMR | M + H⁺ | K$_I$ |
|---|---|---|---|---|---|
| 195 | N4-methyl-N2-(5-methyl-1-(methylsulfonyl)-1H-pyrazol-4-yl)-5-(trifluoromethyl)pyrimidine-2,4-diamine | 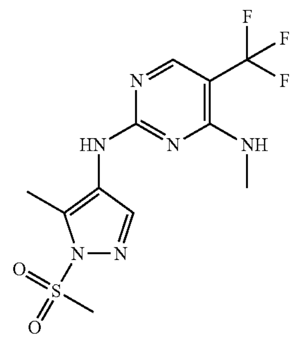 [SMILES: CNc1nc(Nc2cnn(S(C)(=O)=O)c2C)ncc1C(F)(F)F] | 1H NMR (400 MHz, DMSO) δ 9.43 (s, 1 H), 8.47 (s, 1 H), 8.20 (s, 1 H), 7.20 (s, 1 H), 3.41 (s, 3 H), 2.93 (d, J = 4.4, 3 H), 2.32 (s, 3 H). | | 0.010 |
| 196 | N4-methyl-N2-(5-methyl-1-(tetrahydro-2H-1,1-dioxo-thiopyran-4-yl)-1H-pyrazol-4-yl)-5-(trifluoromethyl)pyrimidine-2,4-diamine | 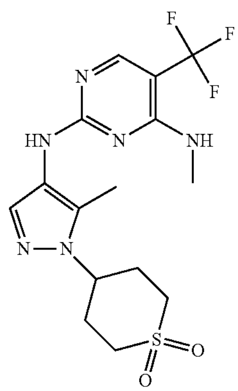 [SMILES: CNc1nc(Nc2cnn(C3CCS(=O)(=O)CC3)c2C)ncc1C(F)(F)F] | 1H NMR (500 MHz, DMSO) δ 8.45 (d, J = 12, 1 H), 8.01 (d, J = 7.5, 1 H), 7.59 (s, 1 H), 6.59-6.64 (m, 1 H), 4.49-4.56 (m, 1 H), 3.26-3.35 (t, J = 20.5, 2 H), 3.16 (d, J = 20.5, 2 H), 2.82 (d, J = 6.0, 3 H), 2.34-2.45 (m, 2 H), 2.11-2.17 (m, 5 H). | | 0.047 |
| 197 | 2-methyl-1-(4-(4-(methylamino)-5-(trifluoromethyl)pyrimidin-2-ylamino)-5-(trifluoromethyl)-1H-pyrazol-1-yl)propan-2-ol | 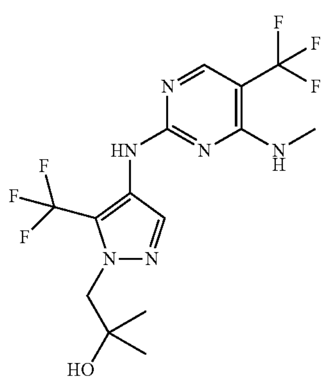 [SMILES: CNc1nc(Nc2cnn(CC(C)(C)O)c2C(F)(F)F)ncc1C(F)(F)F] | | 399.1 | 0.026 |
| 198 | 2-methyl-1-(4-(4-(methylamino)-5-(trifluoromethyl)pyrimidin-2-ylamino)-3-(trifluoromethyl)-1H-pyrazol-1-yl)propan-2-ol | 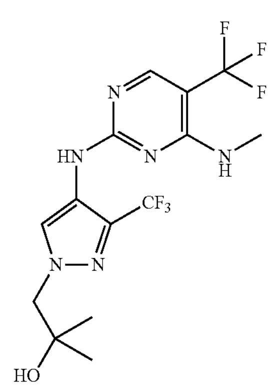 [SMILES: CNc1nc(Nc2cn(CC(C)(C)O)nc2C(F)(F)F)ncc1C(F)(F)F] | | 399.1 | 0.027 |

TABLE 8-continued

| Name | Structure | ¹H NMR | M + H⁺ | K$_I$ |
|---|---|---|---|---|
| 199 N2-(1-(3-fluoro-1-(oxetan-3-yl)piperidin-4-yl)-3-methyl-1H-pyrazol-4-yl)-N4-methyl-5-(trifluoromethyl)pyrimidine-2,4-diamine | | | 430.2 | 0.0022 |
| 200 (R)-N2-(1-(1-methoxypropan-2-yl)-3-methyl-1H-pyrazol-4-yl)-N4-methyl-5-(trifluoromethyl)pyrimidine-2,4-diamine | | | 345 | 0.0128 |
| 201 1-(3-tert-butyl-4-(4-(ethylamino)-5-(trifluoromethyl)pyrimidin-2-ylamino)-1H-pyrazol-1-yl)-2-methylpropan-2-ol | | | 401.2 | 0.42 |
| 202 N4-methyl-N2-(3-methyl-1-(1-(2,2,2-trifluoroethyl)azetidin-3-yl)-1H-pyrazol-4-yl)-5-(trifluoromethyl)pyrimidine-2,4-diamine | | 1H NMR (400 MHz, DMSO) δ 9.01 (s, 1 H), 8.13 (d, J = 36.8, 2 H), 7.01 (s, 2 H), 4.93 (p, J = 6.9, 1 H), 3.82 (t, J = 7.6, 2 H), 3.58 (d, J = 6.9, 2 H), 2.90 (d, J = 4.4, 3 H), 2.15 (s, 4 H). | | 0.034 |

TABLE 8-continued

| Name | Structure | ¹H NMR | M + H⁺ | $K_I$ |
|---|---|---|---|---|
| 203 N2-(1-(1-methoxy-2-methylpropan-2-yl)-5-methyl-1H-pyrazol-4-yl)-N4-methyl-5-(trifluoromethyl)pyrimidine-2,4-diamine | | ¹H NMR (500 MHz, MeOD) δ 7.97 (s, 1 H), 7.49 (s, 1 H), 3.67 (s, 2 H), 3.31 (s, 3 H), 2.96 (s, 3 H), 2.36 (s, 3 H), 1.65 (s, 6 H). | | 0.042 |
| 204 (R)-N4-methyl-N2-(3-methyl-1-(1-(oxetan-3-yl)pyrrolidin-3-yl)-1H-pyrazol-4-yl)-5-(trifluoromethyl)pyrimidine-2,4-diamine | | ¹H NMR (500 MHz, DMSO) δ 9.01 (s, 1 H), 8.12 (d, J = 19.5 Hz, 2 H), 7.04 (s, 1 H), 4.75-4.80 (m, 1 H), 4.55-4.59 (m, 2 H), 4.42-4.47 (m, 2 H), 3.61 (t, J = 6.0 Hz, 1 H), 2.92 (s, 3 H), 2.75 (s, 3 H), 2.32-2.42 (m, 2 H), 1.97-2.14 (m, 4 H). | | 0.029 |
| 205 (R)-N2-(1-(1-methoxypropan-2-yl)-5-methyl-1H-pyrazol-4-yl)-N4-methyl-5-(trifluoromethyl)pyrimidine-2,4-diamine | | ¹H-NMR (Bruker, 500 MHz, MeOD) δ 7.98 (s, 1 H), 4.54-4.58 (m, 1 H), 3.60-3.72 (m, 2 H), 3.342 (s, 3 H), 2.96 (s, 3 H), 2.23 (s, 3 H), 1.45 (d, J = 6.5, 3 H). | | 0.019 |
| 206 N4-methyl-N2-(4-methyl-1H-pyrazol-5-yl)-5-(trifluoromethyl)pyrimidine-2,4-diamine | | 1H NMR (400 MHz, CDCl₃) δ 8.18 (s, 1 H), 7.33 (s, 1 H), 5.33 (s, 1 H), 3.08 (d, J = 4.8, 3 H), 2.05 (s, 3 H). | 273 | 0.2324 |

TABLE 8-continued

| Name | Structure | ¹H NMR | M + H⁺ | K$_I$ |
|---|---|---|---|---|
| 207 N4-ethyl-N2-(5-methyl-1-(1-methylpiperidin-4-yl)-1H-pyrazol-4-yl)-5-(trifluoromethyl)pyrimidine-2,4-diamine | | 1H NMR (400 MHz, DMSO) δ 8.80 (s, 1 H), 8.04 (s, 1 H), 7.61 (s, 1 H), 6.90 (s, 1 H), 4.02 (m, 1 H), 3.39 (m, 2 H), 2.93-2.76 (m, 2 H), 2.20 (m, 6 H), 2.10-1.93 (m, 4 H), 1.75 (m, 2 H), 1.07 (m, 3 H). | | 0.0026 |
| 208 N4-ethyl-N2-(3-methyl-1-(1-methylpiperidin-4-yl)-1H-pyrazol-4-yl)-5-(trifluoromethyl)pyrimidine-2,4-diamine | | 1H NMR (400 MHz, DMSO) δ 8.90 (s, 1 H), 8.08 (s, 1 H), 7.88 (s, 1 H), 7.02 (s, 1 H), 4.01-3.83 (m, 1 H), 3.43 (s, 2 H), 2.82 (d, J = 11.6, 2 H), 2.16-1.76 (m, 9 H), 1.12 (t, J = 7.0, 3 H). | | 0.0102 |
| 209 N4-methyl-N2-(3-methyl-1-(1-methylpiperidin-4-yl)-1H-pyrazol-4-yl)-5-(trifluoromethyl)pyrimidine-2,4-diamine | | | 370.2 | 0.041 |
| 210 N4-methyl-N2-(5-methyl-1-(1-methylpiperidin-4-yl)-1H-pyrazol-4-yl)-5-(trifluoromethyl)pyrimidine-2,4-diamine | | | 370.2 | 0.0071 |

TABLE 8-continued

| Name | Structure | $^1$H NMR | M + H$^+$ | K$_I$ |
|---|---|---|---|---|
| 211 (R)-N4-methyl-N2-(5-methyl-1-(1-(oxetan-3-yl)pyrrolidin-3-yl)-1H-pyrazol-4-yl)-5-(trifluoromethyl)pyrimidine-2,4-diamine | | $^1$H NMR (500 MHz, DMSO) δ 9.00 (s, 1 H), 8.12 (d, J = 18, 1 H), 7.85 (s, 1 H), 7.05 (s, 1 H), 4.77-4.80 (m, 1 H), 4.46-4.59 (m, 2 H), 4.43-4.48 (m, 2 H), 3.62 (t, J = 5.5, 1 H), 2.93 (s, 3 H), 2.76 (s, 3 H), 2.44 (s, 1 H), 2.36 (t, J = 2, 1 H), 1.99-2.15 (m, 4 H). | | 0.0033 |
| 212 N4-methyl-N2-(5-methyl-1-(pyridin-2-ylmethyl)-1H-pyrazol-4-yl)-5-(trifluoromethyl)pyrimidine-2,4-diamine | | $^1$H NMR (500 MHz, DMSO) δ 8.57 (d, J = 5, 8.11 (s, 1 H), 7.97 (s, 1 H), 7.62-7.66 (m, 1 H), 7.21 (t, J = 1.5, 1 H), 7.04 (d, J = 8, 1 H), 6.62 (s, 1 H), 5.37 (s, 2 H), 5.16 (d, J = 4.5, 1 H), 2.98 (s, 3 H), 2.29 (s, 3 H). | | 0.0029 |
| 213 N4-methyl-N2-(3-methyl-1-(pyridin-2-ylmethyl)-1H-pyrazol-4-yl)-5-(trifluoromethyl)pyrimidine-2,4-diamine | | $^1$H NMR (500 MHz, DMSO) δ 8.56 (d, J = 4.5 Hz), 8.09 (s, 1 H), 7.82-7.85 (m, 1 H), 7.60-7.64 (m, 1 H), 7.19-7.21 (m, 1 H), 7.89 (3, 1 H), 6.62 (s, 1 H), 5.42 (s, 2 H), 5.14 (s, 1 H), 2.98 (d, J = 4, 3 H), 2.18 (s, 3 H). | | 0.0029 |
| 214 N2-(1-(1-isopropylazetidin-3-yl)-3-methyl-1H-pyrazol-4-yl)-N4-methyl-5-(trifluoromethyl)pyrimidine-2,4-diamine | | 1H NMR (400 MHz, DMSO) δ 8.91 (s, 1 H), 8.05 (s, 1 H), 7.78 (s, 1 H), 6.93 (s, 1 H), 4.82 (dd, J = 14.4, 7.2, 1 H), 3.64 (t, J = 7.2, 2 H), 2.84 (s, 2 H), 2.36 (dt, J = 12.4, 6.2, 1 H), 2.16 (s, 3 H). | | 0.064 |

TABLE 8-continued

| Name | Structure | ¹H NMR | M + H⁺ | K_I |
|---|---|---|---|---|
| 215 1-methyl-4-(4-(methylamino)-5-(trifluoromethyl)pyrimidin-2-ylamino)-1H-pyrazole-5-carbonitrile | | 1H NMR (400 MHz, CDCl₃) δ 8.18 (s, 1 H), 8.14 (s, 1 H), 7.20 (br s, 1 H), 5.29 (s, 1 H), 4.01 (s, 3 H), 3.09 (d, J = 4.7, 3 H). | 298 | 0.0032 |
| 216 N4-ethyl-N2-(1-(isopropylsulfonyl)-3-methyl-1H-pyrazol-4-yl)-5-(trifluoromethyl)pyrimidine-2,4-diamine | | 1H NMR (400 MHz, DMSO) δ 9.41 (s, 1 H), 8.44 (s, 1 H), 8.19 (s, 1 H), 7.26 (s, 1 H), 3.76 (m, 1 H), 3.54-3.39 (m, 2 H), 2.31 (s, 3 H), 1.24-1.10 (m, 10 H). | | 0.0039 |
| 217 N2-(1-(isopropylsulfonyl)-3-methyl-1H-pyrazol-4-yl)-N4-methyl-5-(trifluoromethyl)pyrimidine-2,4-diamine | | 1H NMR (400 MHz, DMSO) δ 9.39 (s, 1 H), 8.47 (s, 1 H), 8.20 (s, 1 H), 7.20 (s, 1 H), 3.77 (dq, J = 13.6, 6.8, 1 H), 2.90 (d, J = 4.4, 3 H), 2.31 (s, 3 H), 1.19 (d, J = 6.8, 6 H). | | 0.0099 |
| 218 N2-(1-(isopropylsulfonyl)-5-methyl-1H-pyrazol-4-yl)-N4-methyl-5-(trifluoromethyl)pyrimidine-2,4-diamine | | 1H NMR (400 MHz, DMSO) δ 9.08 (s, 1 H), 8.14 (d, J = 21.1, 2 H), 7.06 (s, 1 H), 3.85-3.74 (m, 1 H), 2.82 (s, 3 H), 2.39 (s, 3 H), 1.20 (d, J = 6.8, 6 H). | | 0.0081 |

TABLE 8-continued

| Name | Structure | ¹H NMR | M + H⁺ | $K_I$ |
|---|---|---|---|---|
| 219 N2-(1-(sec-butylsulfonyl)-5-methyl-1H-pyrazol-4-yl)-N4-methyl-5-(trifluoromethyl)pyrimidine-2,4-diamine | | 1H NMR (400 MHz, DMSO) δ 9.08 (s, 1 H), 8.13 (d, J = 14.5, 2 H), 7.06 (s, 1 H), 3.70-3.57 (m, 1 H), 2.82 (s, 3 H), 1.84-1.69 (m, 1 H), 1.56-1.41 (m, 1 H), 1.16 (d, J = 6.8, 3 H), 0.93 (t, J = 7.5, 3 H). | | 0.0067 |
| 220 N2-(1-(sec-butylsulfonyl)-3-methyl-1H-pyrazol-4-yl)-N4-methyl-5-(trifluoromethyl)pyrimidine-2,4-diamine | | 1H NMR (400 MHz, DMSO) δ 9.39 (s, 1 H), 8.47 (s, 1 H), 8.19 (s, 1 H), 7.20 (s, 1 H), 3.60 (dq, J = 13.7, 6.9, 1 H), 2.90 (d, J = 4.3, 3 H), 2.31 (s, 3 H), 1.87-1.70 (m, 1 H), 1.45 (dt, J = 14.0, 7.7, 1 H), 1.16 (d, J = 6.9, 3 H), 0.92 (t, J = 7.5, 3 H). | | 0.0117 |
| 221 1-(4-(4-(ethylamino)-5-(trifluoromethyl)pyrimidin-2-ylamino)-3-isopropyl-1H-pyrazol-l-yl)-2-methylpropan-2-ol | | | | 0.0061 |
| 222 N2-(1-(3-fluoro-1-methylpiperidin-4-yl)-3-methyl-1H-pyrazol-4-yl)-N4-methyl-5-(trifluoromethyl)pyrimidine-2,4-diamine | | 1H NMR (400 MHz, DMSO) δ 8.88 (s, 1 H), 8.05 (s, 1 H), 7.78 (s, 1 H), 6.93 (s, 1 H), 4.91 (m, 1 H), 4.77 (m, 1 H), 4.35-4.05 (m, 1 H), 3.26-3.10 (m, 1 H), 2.83 (s, 4 H), 2.28 (m, 3 H), 2.26-2.00 (m, 5 H), 1.86 (m, 1 H). | | 0.0016 |

TABLE 8-continued

| Name | Structure | ¹H NMR | M + H⁺ | K$_I$ |
|---|---|---|---|---|
| 223 N2-(5-isopropyl-1-methyl-1H-pyrazol-4-yl)-N4-methyl-5-(trifluoromethyl)pyrimidine-2,4-diamine | | | 315.1 | 0.014 |
| 224 N4-methyl-N2-(3-methyl-1-(1-(pyridin-2-yl)ethyl)-1H-pyrazol-4-yl)-5-(trifluoromethyl)pyrimidine-2,4-diamine | | 1H-NMR (500 MHz, CDCl$_3$) δ 8.54 (d, J = 4.0, 1 H), 7.97-8.12 (m, 2 H), 7.78-7.81 (m, 1 H), 7.32-7.35 (m, 1 H), 7.12 (d, J = 7.5, 1 H), 5.53-5.57 (m, 1 H), 5.90-5.91 (m, 3 H), 2.23 (s, 3 H), 1.91 (d, J = 7.0, 3 H). | | 0.0024 |
| 225 N4-methyl-N2-(5-methyl-1-(1-(pyridin-2-yl)ethyl)-1H-pyrazol-4-yl)-5-(trifluoromethyl)pyrimidine-2,4-diamine | | 1H-NMR (500 MHz, CDCl$_3$) δ 8.53 (t, J = 4.0, 1 H), 7.98 (s, 1 H), 7.72-7.78 (m, 2 H), 7.31-7.34 (m, 1 H), 6.96 (s, 1 H), 5.62-5.67 (m, 1 H), 2.86-2.96 (m, 3 H), 2.15 (s, 3 H), 1.95 (d, J = 7.5, 3 H). | | 0.0038 |
| 226 N2-(5-chloro-1-(tetrahydro-2H-pyran-4-yl)-1H-pyrazol-4-yl)-N4-methyl-5-(trifluoromethyl)pyrimidine-2,4-diamine | | 1H NMR (400 MHz, DMSO) δ 8.91 (s, 1 H), 8.08 (s, 1 H), 7.82 (s, 1 H), 7.00 (s, 1 H), 4.50 (tt, J = 11.4, 4.3, 1 H), 3.97 (dd, J = 11.3, 4.0, 2 H), 3.49 (t, J = 11.4, 2 H), 2.83 (s, 3 H), 2.01 (qd, J = 12.4, 4.6, 2 H), 1.81 (dd, J = 12.8, 2.4, 2 H). | | 0.0007 |
| 227 N2-(3-isopropyl-1-methyl-1H-pyrazol-4-yl)-N4-methyl-5-(trifluoromethyl)pyrimidine-2,4-diamine | | | 315.1 | 0.069 |

TABLE 8-continued

| Name | Structure | ¹H NMR | M + H⁺ | K_I |
|---|---|---|---|---|
| 228 N2-(3-cyclobutyl-1-methyl-1H-pyrazol-4-yl)-N4-methyl-5-(trifluoromethyl)pyrimidine-2,4-diamine | | | 327.1 | 0.0034 |
| 229 N2-(5-cyclobutyl-1-methyl-1H-pyrazol-4-yl)-N4-methyl-5-(trifluoromethyl)pyrimidine-2,4-diamine | | 1H NMR (400 MHz, CDCl₃) δ 8.21-7.98 (s, 1 H), 7.82-7.34 (s, 1 H), 6.58- 6.18 (s, 1 H), 5.22-5.01 (s, 1 H), 3.82-3.70 (s, 3 H), 3.67-3.50 (m, 1 H), 3.06-2.94 (d, J = 4.7 Hz, 3 H), 2.54-2.26 (m, 4 H), 2.16-1.99 (m, 1 H), 1.97-1.81 (m, 1 H) | 327.1 | 0.011 |
| 230 N4-methyl-N2-(3-methyl-1-(tetrahydro-2H-pyran-3-yl)-1H-pyrazol-4-yl)-5-(trifluoromethyl)pyrimidine-2,4-diamine | | 1H NMR (400 MHz, DMSO) δ 8.95 (s, 1 H), 8.08 (s, 2 H), 6.98 (s, 1 H), 4.22-4.07 (m, 1 H), 3.92 (dd, J = 10.9, 3.6, 1 H), 3.77 (d, J = 11.1, 1 H), 3.55 (t, J = 9.8, 1 H), 3.41 (t, J = 9.7, 1 H), 2.89 (d, J = 4.4, 3 H), 2.21-1.92 (m, 5 H), 1.79-1.53 (m, 2 H). | | 0.0096 |
| 231 N4-methyl-N2-(5-methyl-1-(tetrahydro-2H-pyran-3-yl)-1H-pyrazol-4-yl)-5-(trifluoromethyl)pyrimidine-2,4-diamine | | 1H NMR (400 MHz, DMSO) δ 8.89 (s, 1 H), 8.05 (s, 1 H), 7.73 (s, 1 H), 6.92 (s, 1 H), 4.26-4.11 (m, 1 H), 3.86 (dd, J = 10.7, 2.4, 2 H), 3.51 (t, J = 10.6, 1 H), 2.83 (s, 3 H), 2.21 (s, 3 H), 2.12-1.94 (m, 2 H), 1.85-1.58 (m, 2 H). | | 0.0018 |
| 232 N2-(1,5-dimethyl-1H-pyrazol-4-yl)-N4-((tetrahydro-2H-pyran-4-yl)methyl)-5-(trifluoromethyl)pyrimidine-2,4-diamine | | | | 0.0096 |

TABLE 8-continued

| Name | Structure | $^1$H NMR | M + H$^+$ | K$_I$ |
|---|---|---|---|---|
| 233 (R)-N4-methyl-N2-(3-methyl-1-(1-methylpyrrolidin-3-yl)-1H-pyrazol-4-yl)-5-(trifluoromethyl)pyrimidine-2,4-diamine | | $^1$H NMR (500 MHz, DMSO) δ 9.00 (s, 1 H), 8.13 (s, 1 H), 8.08 (s, 1H ), 7.03 (s, 1 H), 4.74 (m, 1 H), 2.90 (d, J = 4.5 Hz, 3 H), 2.75-2.80 (m, 3 H), 2.30 (m, 5 H), 2.14 (s, 3 H), 1.96 (s, 2 H). | | 0.061 |
| 234 1-(5-chloro-4-(4-(ethylamino)-5-(trifluoromethyl)pyrimidin-2-ylamino)-1H-pyrazol-1-yl)-2-methylpropan-2-ol | | 1H NMR (400 MHz, CDCl$_3$) δ 8.06 (s, 1 H), 8.02 (s, 1 H), 6.81 (br s, 1 H), 5.62 (br s, 1 H), 4.10 (s, 2 H), 3.84 (s, 1 H), 3.59 (p, J = 6.6, 2 H), 1.31 (t, J = 7.2, 3 H), 1.19 (s, 6 H). | 379 | 0.0031 |
| 235 1-(3-cyclopropyl-4-(4-(methylamino)-5-(trifluoromethyl)pyrimidin-2-ylamino)-1H-pyrazol-1-yl)-2-methylpropan-2-ol | | 1H NMR (400 MHz, CDCl$_3$) δ 8.18-8.09 (s, 1 H), 7.93-7.82 (s, 1 H), 3.98-3.92 (s, 2 H), 3.10-3.01 (d, J = 4.7 Hz, 3 H), 1.80-1.68 (td, J = 8.3, 4.2 Hz, 1 H), 1.19-1.09 (s, 6 H), 0.98-0.77 (m, 4 H) | 371.2 | 0.0051 |
| 236 1-(3-cyclopropyl-4-(4-(ethylamino)-5-(trifluoromethyl)pyrimidin-2-ylamino)-1H-pyrazol-1-yl)-2-methylpropan-2-ol | | 1H NMR (400 MHz, CDCl$_3$) δ 8.15-8.10 (s, 1 H), 7.86-7.81 (s, 1 H), 3.95-3.92 (s, 2 H), 3.59-3.49 (m, 2 H), 1.77-1.67 (td, J = 8.3, 4.1 Hz, 1 H), 1.32-1.23 (t, J = 7.2 Hz, 3 H), 1.18-1.12 (s, 6 H), 0.95-0.75 (m, 4 H) | 385.2 | 0.0015 |

| Name | Structure | ¹H NMR | M + H⁺ | K_I |
|------|-----------|--------|--------|-----|
| 237 2-(5-chloro-4-(4-(methylamino)-5-(trifluoromethyl)pyrimidin-2-ylamino)-1H-pyrazol-1-yl)-N,2-dimethylpropanamide | | 1H NMR (400 MHz, DMSO) δ 8.90 (s, 1 H), 8.09 (s, 1 H), 7.85 (s, 1 H), 7.67 (d, J = 4.4, 1 H), 7.02 (s, 1 H), 2.84 (d, J = 3.8, 3 H), 2.60 (d, J = 4.5, 3 H), 1.66 (s, 6 H). | | 0.045 |
| 238 N2-(1-(1-(2-methoxyethyl)piperidin-4-yl)-3-methyl-1H-pyrazol-4-yl)-N4-methyl-5-(trifluoromethyl)pyrimidine-2,4-diamine | | 1H NMR (400 MHz, DMSO) δ 8.92 (s, 1 H), 8.07 (s, 1 H), 7.94 (s, 1 H), 6.97 (s, 1 H), 3.95 (dt, J = 15.5, 5.6, 1 H), 3.43 (t, J = 5.8, 2 H), 3.24 (s, 3 H), 2.93 (d, J = 11.8, 2 H), 2.88 (d, J = 4.4, 3 H), 2.10 (d, J = 11.8, 5 H), 2.02-1.72 (m, 4 H). | | 0.016 |
| 239 N2-(1-(1-(2-methoxyethyl)piperidin-4-yl)-5-methyl-1H-pyrazol-4-yl)-N4-methyl-5-(trifluoromethyl)pyrimidine-2,4-diamine | | 1H NMR (400 MHz, DMSO) δ 8.86 (s, 1 H), 8.04 (s, 1 H), 7.71 (s, 1 H), 6.91 (s, 1 H), 4.12-3.88 (m, 1 H), 3.44 (t, J = 5.9, 2 H), 3.24 (s, 3 H), 2.96 (d, J = 11.6, 2 H), 2.84 (s, 3 H), 2.15 (dd, J = 22.8, 10.9, 4 H), 1.98 (qd, J = 12.2, 3.4, 2 H), 1.75 (d, J = 12.3, 2 H). | | 0.006 |

TABLE 8-continued

| Name | Structure | ¹H NMR | M + H⁺ | K_I |
|---|---|---|---|---|
| 240 (R)-N4-methyl-N2-(5-methyl-1-(1-methylpyrrolidin-3-yl)-1H-pyrazol-4-yl)-5-(trifluoromethyl)pyrimidine-2,4-diamine | | | | |
| 241 N2-(5-chloro-1-(3-fluoro-1-methylpiperidin-4-yl)-1H-pyrazol-4-yl)-N4-methyl-5-(trifluoromethyl)pyrimidine-2,4-diamine | | 1H NMR (400 MHz, DMSO) δ 8.94 (s, 1 H), 8.08 (s, 1 H), 7.85 (s, 1 H), 7.00 (s, 1 H), 4.87 (dtd, J = 49.9, 9.8, 5.1, 1 H), 4.34 (qd, J = 11.2, 4.9, 1 H), 3.27-3.15 (m, 1 H), 2.82 (s, 4 H), 2.22-2.04 (m, 3 H), 1.91 (s, 1 H). | | 0.0018 |
| 242 N2-(5-chloro-1-(1-ethyl-3-fluoropiperidin-4-yl)-1H-pyrazol-4-yl)-N4-methyl-5-(trifluoromethyl)pyrimidine-2,4-diamine | | 1H NMR (400 MHz, DMSO) δ 8.95 (s, 1 H), 8.08 (s, 1 H), 7.87 (s, 1 H), 7.00 (s, 1 H), 4.86 (m, 1 H), 4.36 (m, 1 H), 3.08-2.71 (m, 4 H), 2.25-1.81 (m, 5 H), 1.03 (t, J = 7.1, 3 H). | | 0.0021 |
| 243 N4-ethyl-N2-(1-(ethylsulfonyl)-3-methyl-1H-pyrazol-4-yl)-5-(trifluoromethyl)pyrimidine-2,4-diamine | | 1H NMR (400 MHz, DMSO) δ 9.40 (s, 1 H), 8.45 (s, 1 H), 8.20 (s, 1 H), 7.28 (s, 1 H), 3.58 (q, J = 7.3, 2 H), 3.53-3.37 (m, 2 H), 2.31 (s, 3 H), 1.16 (t, J = 7.0, 3 H), 1.07 (t, J = 7.3, 3 H). | | 0.0005 |

TABLE 8-continued

| Name | Structure | ¹H NMR | M + H⁺ | $K_I$ |
|---|---|---|---|---|
| 244 N4-ethyl-N2-(1-(ethylsulfonyl)-5-methyl-1H-pyrazol-4-yl)-5-(trifluoromethyl)pyrimidine-2,4-diamine | | 1H NMR (400 MHz, DMSO) δ 9.07 (s, 1 H), 8.11 (s, 2 H), 7.05 (s, 1 H), 3.62 (q, J = 7.3, 2 H), 3.37 (s, 2 H), 2.39 (s, 3 H), 1.09 (t, J = 7.3, 6 H). | | 0.0047 |
| 245 N4-methyl-N2-(3-methyl-1-(2-methyl-2-morpholinopropyl)-1H-pyrazol-4-yl)-5-(trifluoromethyl)pyrimidine-2,4-diamine | | | 414.2 | |
| 246 N2-(1-(1-ethyl-3-fluoropiperidin-4-yl)-3-methyl-1H-pyrazol-4-yl)-N4-methyl-5-(trifluoromethyl)pyrimidine-2,4-diamine | | 1H NMR (400 MHz, DMSO) δ 8.92 (s, 1 H), 8.05 (s, 1 H), 7.79 (s, 1 H), 6.95 (s, 1 H), 5.22-4.55 (m, 1 H), 4.22 (dd, J = 21.0, 11.1, 1 H), 2.85 (d, J = 21.1, 3 H), 2.33-1.97 (m, 5 H), 1.03 (t, J = 7.1, 3 H). | 402.2 | |
| 247 N2-(5-(dimethylamino)-1-methyl-1H-pyrazol-4-yl)-N4-methyl-5-(trifluoromethyl)pyrimidine-2,4-diamine | | 1H NMR (400 MHz, CDCl₃) δ 8.10 (s, 1 H), 7.74 (br s, 1 H), 6.52 (br s, 1 H), 5.13 (s, 1 H), 3.74 (s, 3 H), 3.02 (d, J = 4.7, 3 H), 2.80 (s, 6 H). | 316 | 0.0779 |

TABLE 8-continued

| Name | Structure | ¹H NMR | M + H⁺ | K_I |
|---|---|---|---|---|
| 248 2-(5-chloro-4-(4-(methylamino)-5-(trifluoromethyl)pyrimidin-2-ylamino)-1H-pyrazol-1-yl)-2-methylpropan-1-ol | | 1H NMR (400 MHz, DMSO) δ 8.75 (s, 1 H), 8.08 (s, 1 H), 7.73 (s, 1 H), 6.99 (s, 1 H), 4.92 (t, J = 5.7, 1 H), 3.77 (d, J = 5.6, 2 H), 2.83 (d, J = 3.0, 3 H), 1.57 (s, 6 H). | 365.1 | |
| 249 N²-(1-(ethylsulfonyl)-3-methyl-1H-pyrazol-4-yl)-N4-methyl-5-(trifluoromethyl)pyrimidine-2,4-diamine | | 1H NMR (400 MHz, DMSO) δ 9.41 (s, 1 H), 8.48 (s, 1 H), 8.20 (s, 1 H), 7.20 (s, 1 H), 3.58 (q, J = 7.3, 2 H), 2.91 (d, J = 4.4, 3 H), 2.31 (s, 3 H), 1.08 (t, J = 7.3, 3 H). | 365.1 | 0.0033 |
| 250 2-Methyl-1-[3-methyl-4-(4-methylamino-5-trifluoromethyl-pyrimidin-2-ylamino)-pyrazol-1-yl]-propan-2-ol | | | | 0.0122 |
| 251 N2-[1-(2-Methoxy-ethyl)-3-methyl-1H-pyrazol-4-yl]-N4-methyl-5-trifluoromethyl-pyrimidine-2,4-diamine | | | | 0.0026 |

TABLE 8-continued

| Name | Structure | ¹H NMR | M + H⁺ | K$_I$ |
|---|---|---|---|---|
| 252 N2-[1-(2-Methoxy-ethyl)-5-methyl-1H-pyrazol-4-yl]-N4-methyl-5-trifluoromethyl-pyrimidine-2,4-diamine | | | | 0.0061 |
| 253 5-Bromo-N2-(1-ethyl-3-methyl-1H-pyrazol-4-yl)-N4-methyl-pyrimidine-2,4-diamine | | | | 0.0022 |
| 254 N4-Methyl-N2-[3-methyl-1-(2,2,2-trifluoro-ethyl)-1H-pyrazol-4-yl]-5-trifluoromethyl-pyrimidine-2,4-diamine | | | | 0.0077 |
| 255 5-Bromo-N2-(1-difluoromethyl-5-methyl-1H-pyrazol-4-yl)-N4-methyl-pyrimidine-2,4-diamine | | | | 0.0007 |

TABLE 8-continued

| Name | Structure | ¹H NMR | M + H⁺ | K₁ |
|---|---|---|---|---|
| 256 5-Bromo-N2-(1-difluoromethyl-3-methyl-1H-pyrazol-4-yl)-N4-methyl-pyrimidine-2,4-diamine | | | | 0.0022 |
| 257 5-Bromo-N2-(1,5-dimethyl-1H-pyrazol-4-yl)-N4-ethyl-pyrimidine-2,4-diamine | | | | 0.0015 |
| 258 5-Bromo-N2-[1-(4-fluoro-phenyl)-5-methyl-1H-pyrazol-4-yl]-N4-methyl-pyrimidine-2,4-diamine | | | | |
| 259 5-Bromo-N4-methyl-N2-(5-methyl-1-propyl-1H-pyrazol-4-yl)-pyrimidine-2,4-diamine | | | | 0.0057 |
| 260 5-Bromo-N2-[1-(4-chloro-phenyl)-3-methyl-1H-pyrazol-4-yl]-N4-methyl-pyrimidine-2,4-diamine | | | | 0.0003 |

TABLE 8-continued

| Name | Structure | ¹H NMR | M + H⁺ | K$_I$ |
|---|---|---|---|---|
| 261 N2-(1,5-Dimethyl-1H-pyrazol-4-yl)-N4-ethyl-5-trifluoromethyl-pyrimidine-2,4-diamine | | | | 0.0013 |
| 262 5-[4-(4-Ethylamino-5-trifluoromethyl-pyrimidin-2-ylamino)-3-methyl-pyrazol-1-yl]-piperidin-2-one | | | | 0.0013 |
| 263 4-[4-(4-Ethylamino-5-trifluoromethyl-pyrimidin-2-ylamino)-3-methyl-pyrazol-1-yl]-N,N-dimethyl-benzamide | | | | 0.0018 |
| 264 N2-[1-(4-Cyclopropane-sulfonyl-phenyl)-3-methyl-1H-pyrazol-4-yl]-N4-ethyl-5-trifluoromethyl-pyrimidine-2,4-diamine | | | | 0.0032 |

TABLE 8-continued

| | Name | Structure | ¹H NMR | M + H⁺ | K$_I$ |
|---|---|---|---|---|---|
| 265 | 4-[4-(4-Ethylamino-5-trifluoromethyl-pyrimidin-2-ylamino)-3-methyl-pyrazol-1-yl]-benzonitrile | 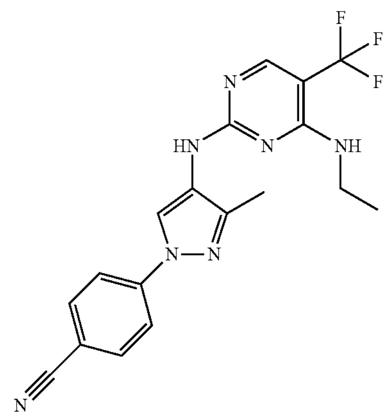 [SMILES: CCNc1nc(Nc2cn(-c3ccc(C#N)cc3)nc2C)ncc1C(F)(F)F] | | | 0.0048 |
| 266 | N4-Ethyl-N2-[1-(4-methanesulfonyl-phenyl)-3-methyl-1H-pyrazol-4-yl]-5-trifluoromethyl-pyrimidine-2,4-diamine | 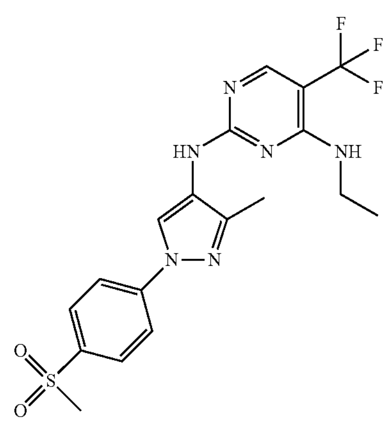 [SMILES: CCNc1nc(Nc2cn(-c3ccc(S(C)(=O)=O)cc3)nc2C)ncc1C(F)(F)F] | | | 0.0021 |
| 267 | 1-{4-[4-(4-Ethylamino-5-trifluoromethyl-pyrimidin-2-ylamino)-5-methyl-pyrazol-1-yl]-piperidin-1-yl}-2-methyl-propan-1-one | 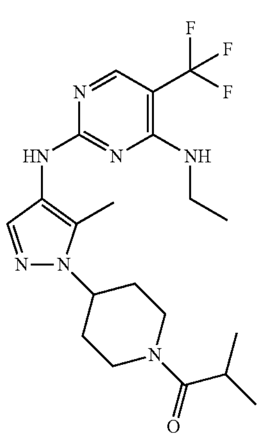 [SMILES: CCNc1nc(Nc2cnn(C3CCN(C(=O)C(C)C)CC3)c2C)ncc1C(F)(F)F] | | | 0.0008 |

TABLE 8-continued

| Name | Structure | ¹H NMR | M + H⁺ | K_I |
|---|---|---|---|---|
| 268 1-{4-[4-(4-Ethylamino-5-trifluoromethyl-pyrimidin-2-ylamino)-3-methyl-pyrazol-1-yl]-piperidin-1-yl}-2-methyl-propan-1-one | | | | 0.0077 |
| 269 N4-Methyl-N2-[3-methyl-1-(3-methyl-pyridin-4-yl)-1H-pyrazol-4-yl]-5-trifluoromethyl-pyrimidine-2,4-diamine | | | | 0.0091 |
| 270 N2-[1-((R)-2-Methoxy-propyl)-3-methyl-1H-pyrazol-4-yl]-N4-methyl-5-trifluoromethyl-pyrimidine-2,4-diamine | | | | 0.017 |
| 272 N2-[1-(2,6-Dimethyl-tetrahydro-pyran-4-yl)-5-methyl-1H-pyrazol-4-yl]-N4-methyl-5-trifluoromethyl-pyrimidine-2,4-diamine | | | | 0.0051 |

TABLE 8-continued

| | Name | Structure | ¹H NMR | M + H⁺ | K₁ |
|---|---|---|---|---|---|
| 273 | N2-[1-(1,1-Dioxo-hexahydro-1$1%6&-thiopyran-4-yl)-3-methyl-1H-pyrazol-4-yl]-N4-methyl-5-trifluoromethyl-pyrimidine-2,4-diamine | 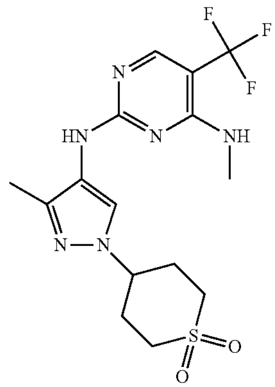 [SMILES: CNc1nc(Nc2cn(C3CCS(=O)(=O)CC3)nc2C)ncc1C(F)(F)F] | | | 0.037 |
| 274 | N2-[1-((R)-2-Methoxy-1-methyl-ethyl)-5-methyl-1H-pyrazol-4-yl]-N4-methyl-5-trifluoromethyl-pyrimidine-2,4-diamine | 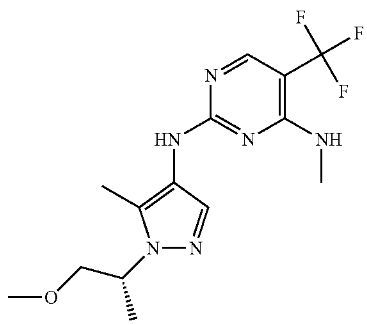 [SMILES: CNc1nc(Nc2cnn([C@H](C)COC)c2C)ncc1C(F)(F)F] | | | 0.0185 |
| 275 | N2-[1-((S)-2-Methoxy-1-methyl-ethyl)-3-methyl-1H-pyrazol-4-yl]-N4-methyl-5-trifluoromethyl-pyrimidine-2,4-diamine | 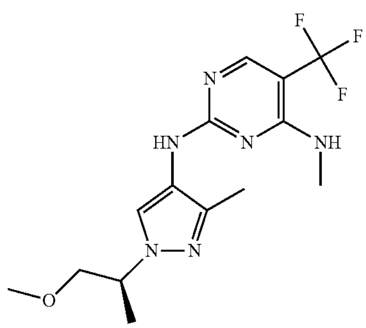 [SMILES: CNc1nc(Nc2cn([C@@H](C)COC)nc2C)ncc1C(F)(F)F] | | | 0.0089 |
| 276 | N4-Methyl-N2-[3-methyl-1-((S)-1-oxetan-3-yl-pyrrolidin-3-yl)-1H-pyrazol-4-yl]-5-trifluoromethyl-pyrimidine-2,4-diamine | 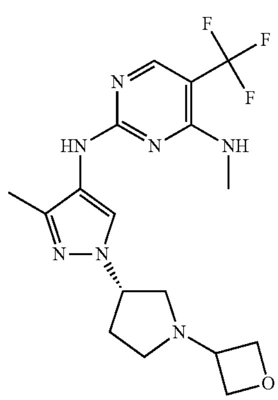 [SMILES: CNc1nc(Nc2cn([C@H]3CCN(C4COC4)C3)nc2C)ncc1C(F)(F)F] | | | 0.0039 |

TABLE 8-continued

| Name | Structure | ¹H NMR | M + H⁺ | K$_I$ |
|---|---|---|---|---|
| 277 N4-Methyl-N2-[5-methyl-1-((S)-1-oxetan-3-yl-pyrrolidin-3-yl)-1H-pyrazol-4-yl]-5-trifluoromethyl-pyrimidine-2,4-diamine | | | | 0.058 |
| 278 N2-[1-(1-Isopropyl-azetidin-3-yl)-5-methyl-1H-pyrazol-4-yl]-N4-methyl-5-trifluoromethyl-pyrimidine-2,4-diamine | | | | 0.0012 |
| 279 N4-Ethyl-N2-[5-methyl-1-(propane-2-sulfonyl)-1H-pyrazol-4-yl]-5-trifluoromethyl-pyrimidine-2,4-diamine | | | | 0.0047 |
| 280 N2-(5-Cyclobutyl-1-methyl-1H-pyrazol-4-yl)-N4-ethyl-5-trifluoromethyl-pyrimidine-2,4-diamine | | | | 0.0036 |
| 281 N2-(3-Cyclobutyl-1-methyl-1H-pyrazol-4-yl)-N4-ethyl-5-trifluoromethyl-pyrimidine-2,4-diamine | | | | 0.0013 |

TABLE 8-continued

| Name | Structure | ¹H NMR | M + H⁺ | K_I |
|---|---|---|---|---|
| 282 N4-Ethyl-N2-{1-[1-(2-methoxy-ethyl)-piperidin-4-yl]-3-methyl-1H-pyrazol-4-yl}-5-trifluoromethyl-pyrimidine-2,4-diamine | | | | 0.0054 |
| 283 N4-Ethyl-N2-{1-[1-(2-methoxy-ethyl)-piperidin-4-yl]-5-methyl-1H-pyrazol-4-yl}-5-trifluoromethyl-pyrimidine-2,4-diamine | | | | 0.002 |
| 284 N2-{1-[1-(2-Fluoro-ethyl)-piperidin-4-yl]-5-methyl-1H-pyrazol-4-yl}-N4-methyl-5-trifluoromethyl-pyrimidine-2,4-diamine | | | | 0.0042 |

TABLE 8-continued

| Name | Structure | ¹H NMR | M + H⁺ | K_I |
|---|---|---|---|---|
| 285 N2-{1-[1-(2-Fluoro-ethyl)-piperidin-4-yl]-3-methyl-1H-pyrazol-4-yl}-N4-methyl-5-trifluoromethyl-pyrimidine-2,4-diamine | | | | 0.0283 |
| 286 N2-[5-Chloro-1-(3-fluoro-1-methyl-piperidin-4-yl)-1H-pyrazol-4-yl]-N4-methyl-5-trifluoromethyl-pyrimidine-2,4-diamine | | 1H NMR (400 MHz, DMSO) δ 8.95 (s, 1 H), 8.08 (s, 1 H), 7.88 (s, 1 H), 7.00 (s, 1 H), 4.87 (dtd, J = 49.9, 9.8, 5.1, 1 H), 4.34 (qd, J = 11.3, 4.9, 1 H), 3.29-3.13 (m, 1 H), 2.82 (s, 4 H), 2.28 (s, 3 H), 2.25-1.99 (m, 3 H), 1.92 (d, J = 6.8, 1 H). | | 0.0018 |
| 287 N2-(1-Ethanesulfonyl-5-methyl-1H-pyrazol-4-yl)-N4-methyl-5-trifluoromethyl-pyrimidine-2,4-diamine | | | | 0.0072 |
| 288 N4-Methyl-N2-[5-methyl-1-(2-methyl-2-morpholin-4-yl-propyl)-1H-pyrazol-4-yl]-5-trifluoromethyl-pyrimidine-2,4-diamine | | | | 0.0077 |

TABLE 8-continued

| Name | Structure | ¹H NMR | M + H⁺ | K_I |
|---|---|---|---|---|
| 289 N4-Methyl-N2-(3-methyl-1-pyridin-3-ylmethyl-1H-pyrazol-4-yl)-5-trifluoromethyl-pyrimidine-2,4-diamine | | | | 0.025 |
| 290 N2-(1-Cyclopropane-sulfonyl-3-cyclopropyl-1H-pyrazol-4-yl)-N4-methyl-5-trifluoromethyl-pyrimidine-2,4-diamine | | | | |
| 291 N4-Methyl-N2-(5-methyl-1-pyridin-3-ylmethyl-1H-pyrazol-4-yl)-5-trifluoromethyl-pyrimidine-2,4-diamine | | | | |
| 292 (5-Chloro-4-methoxy-pyrimidin-2-yl)-{1-[1-(2-fluoro-ethyl)-piperidin-4-yl]-5-methyl-1H-pyrazol-4-yl}-amine | | | | 0.0042 |

TABLE 8-continued

| Name | Structure | ¹H NMR | M + H⁺ | K$_I$ |
|---|---|---|---|---|
| 293 N4-Methyl-N2-[3-methyl-1-(6-methyl-pyridin-2-ylmethyl)-1H-pyrazol-4-yl]-5-trifluoromethyl-pyrimidine-2,4-diamine | | | | 0.0006 |
| 294 N4-Ethyl-N2-[1-(2-methoxy-ethyl)-3-methyl-1H-pyrazol-4-yl]-5-trifluoromethyl-pyrimidine-2,4-diamine | | | | 0.0011 |
| 295 N4-Ethyl-N2-[1-(2-methoxy-ethyl)-5-methyl-1H-pyrazol-4-yl]-5-trifluoromethyl-pyrimidine-2,4-diamine | | | | 0.0004 |
| 296 1-[4-(4-Ethylamino-5-trifluoromethyl-pyrimidin-2-ylamino)-5-methyl-pyrazol-1-yl]-2-methyl-propan-2-ol | | 1H NMR (400 MHz, DMSO) δ 8.75 (s, 1 H), 8.05 (s, 1 H), 7.57 (s, 1 H), 6.86 (s, 1 H), 4.63 (s, 1 H), 3.90 (s, 2 H), 3.36 (s, 2 H), 2.19 (s, 3 H), 1.08 (s, 7 H). | | 0.0023 |

TABLE 8-continued

| Name | Structure | ¹H NMR | M + H⁺ | K_I |
|---|---|---|---|---|
| 297 1-[4-(4-Ethylamino-5-trifluoromethyl-pyrimidin-2-ylamino)-3-methyl-pyrazol-1-yl]-2-methyl-propan-2-ol | | 1H NMR (400 MHz, DMSO) δ 8.83 (s, 1 H), 8.07 (s, 1 H), 7.85 (s, 1 H), 6.91 (s, 1 H), 4.60 (s, 1 H), 3.79 (d, J = 64.3, 2 H), 3.42 (s, 2 H), 2.27-1.82 (m, 3 H), 1.35-1.05 (m, 3 H), 0.97 (d, J = 63.4, 6 H). | | 0.0021 |
| 298 N2-[1-(1,1-Dimethyl-2-morpholin-4-yl-ethyl)-3-methyl-1H-pyrazol-4-yl]-N4-ethyl-5-trifluoromethyl-pyrimidine-2,4-diamine | | | | 0.0506 |
| 299 N2-[1-(1,1-Dimethyl-2-morpholin-4-yl-ethyl)-3-methyl-1H-pyrazol-4-yl]-N4-methyl-5-trifluoromethyl-pyrimidine-2,4-diamine | | | | 0.0228 |
| 300 N4-Cyclopropyl-N2-(1-methanesulfonyl-3-methyl-1H-pyrazol-4-yl)-5-trifluoromethyl-pyrimidine-2,4-diamine | | 1H NMR (400 MHz, DMSO) δ 9.55 (s, 1 H), 8.83 (s, 1 H), 8.22 (s, 1 H), 7.27 (s, 1 H), 3.39 (s, 3 H), 2.79 (s, 1 H), 2.34 (s, 3 H), 0.95-0.58 (m, 4 H). | | 0.0004 |

TABLE 8-continued

| Name | Structure | ¹H NMR | M + H⁺ | K$_I$ |
|---|---|---|---|---|
| 301 N4-Cyclopropyl-N2-(1-methanesulfonyl-5-methyl-1H-pyrazol-4-yl)-5-trifluoromethyl-pyrimidine-2,4-diamine | | 1H NMR (400 MHz, DMSO) δ 9.25 (s, 1 H), 8.40 (s, 1 H), 8.14 (s, 1 H), 7.04 (s, 1 H), 3.46 (s, 3 H), 2.79 (s, 1 H), 2.43 (s, 3 H), 0.68 (dd, J = 13.9, 9.3, 4 H). | | 0.0021 |
| 302 1-[3-Chloro-4-(4-methylamino-5-trifluoromethyl-pyrimidin-2-ylamino)-pyrazol-1-yl]-2-methyl-propan-2-ol | | | | 0.016 |
| 303 2-[4-(4-Ethylamino-5-trifluoromethyl-pyrimidin-2-ylamino)-3-methyl-pyrazol-1-yl]-N-methyl-isobutyramide | | | | 0.0013 |
| 304 N4-Methyl-N2-(3-methyl-1-pyrimidin-2-ylmethyl-1H-pyrazol-4-yl)-5-trifluoromethyl-pyrimidine-2,4-diamine | | | | 0.0051 |

TABLE 8-continued

| Name | Structure | ¹H NMR | M + H⁺ | K$_I$ |
|---|---|---|---|---|
| 305 N2-[5-Chloro-1-(3-fluoro-1-oxetan-3-yl-piperidin-4-yl)-1H-pyrazol-4-yl]-N4-methyl-5-trifluoromethyl-pyrimidine-2,4-diamine | | 1H NMR (400 MHz, DMSO) δ 8.91 (s, 1 H), 8.08 (s, 1 H), 7.86 (s, 1 H), 7.00 (s, 1 H), 4.97 (td, J = 9.8, 5.0, 0 H), 4.90-4.74 (m, 1 H), 4.63-4.52 (m, 2 H), 4.46 (dt, J = 21.3, 7.5, 3 H), 3.71-3.53 (m, 1 H), 3.26-3.11 (m, 1 H), 2.94-2.71 (m, 4 H), 2.16-1.85 (m, 4 H). | | 0.0022 |
| 306 N2-[5-Chloro-1-(3-fluoro-1-oxetan-3-yl-piperidin-4-yl)-1H-pyrazol-4-yl]-N4-ethyl-5-trifluoromethyl-pyrimidine-2,4-diamine | | 1H NMR (400 MHz, DMSO) δ 8.84 (s, 1 H), 8.08 (s, 1 H), 7.80 (s, 1 H), 6.98 (s, 1 H), 5.02-4.79 (m, 1 H), 4.56 (t, J = 6.5, 3 H), 4.46 (dt, J = 20.4, 7.0, 4 H), 3.65-3.53 (m, 2 H), 3.24-3.15 (m, 1 H), 2.77 (s, 1 H), 2.20-1.85 (m, 5 H), 1.05 (s, 4 H). | | 0.0006 |
| 307 N4-Ethyl-N2-[5-methyl-1-((S)-1-oxetan-3-yl-piperidin-3-yl)-1H-pyrazol-4-yl]-5-trifluoromethyl-pyrimidine-2,4-diamine | | | | 0.0003 |

TABLE 8-continued

| Name | Structure | ¹H NMR | M + H⁺ | K$_I$ |
|---|---|---|---|---|
| 308 N4-Ethyl-N2-[3-methyl-1-((S)-1-oxetan-3-yl-piperidin-3-yl)-1H-pyrazol-4-yl]-5-trifluoromethyl-pyrimidine-2,4-diamine | | | | 0.0085 |
| 309 N4-Methyl-N2-(5-methyl-1-pyridazin-3-ylmethyl-1H-pyrazol-4-yl)-5-trifluoromethyl-pyrimidine-2,4-diamine | | | | 0.0028 |
| 310 N4-Methyl-N2-(3-methyl-1-pyridazin-3-ylmethyl-1H-pyrazol-4-yl)-5-trifluoromethyl-pyrimidine-2,4-diamine | | | | 0.0093 |
| 311 N4-Ethyl-N2-[5-methyl-1-((S)-1-methyl-piperidin-3-yl)-1H-pyrazol-4-yl]-5-trifluoromethyl-pyrimidine-2,4-diamine | | | | 0.0012 |

TABLE 8-continued

| Name | Structure | ¹H NMR | M + H⁺ | $K_I$ |
|---|---|---|---|---|
| 312 N4-Ethyl-N2-[3-methyl-1-((S)-1-methyl-piperidin-3-yl)-1H-pyrazol-4-yl]-5-trifluoromethyl-pyrimidine-2,4-diamine | | | | 0.0156 |
| 313 3-[5-Chloro-4-(4-methylamino-5-trifluoromethyl-pyrimidin-2-ylamino)-pyrazol-1-yl]-2,2-dimethyl-propionitrile | | 1H NMR (400 MHz, DMSO) δ 8.92 (s, 1 H), 8.09 (s, 1 H), 7.86 (s, 1 H), 7.00 (s, 1 H), 4.29 (s, 2 H), 2.82 (s, 3 H), 1.38 (s, 6 H). | | 0.0017 |
| 314 N4-Methyl-N2-[5-methyl-1-(6-methyl-pyridin-2-ylmethyl)-1H-pyrazol-4-yl]-5-trifluoromethyl-pyrimidine-2,4-diamine | | | | 0.0015 |
| 315 N4-Methyl-N2-(5-methyl-1-pyrimidin-2-ylmethyl-1H-pyrazol-4-yl)-5-trifluoromethyl-pyrimidine-2,4-diamine | | | | 0.0014 |

TABLE 8-continued

| Name | Structure | ¹H NMR | M + H⁺ | $K_I$ |
|------|-----------|--------|--------|-------|
| 316 N4-Methyl-N2-(5-methyl-1-pyrazin-2-ylmethyl-1H-pyrazol-4-yl)-5-trifluoromethyl-pyrimidine-2,4-diamine | | | | 0.0026 |
| 317 N4-Methyl-N2-(3-methyl-1-pyrazin-2-ylmethyl-1H-pyrazol-4-yl)-5-trifluoromethyl-pyrimidine-2,4-diamine | | | | 0.0012 |
| 318 3-[5-Chloro-4-(4-ethylamino-5-trifluoromethyl-pyrimidin-2-ylamino)-pyrazol-1-yl]-2,2-dimethyl-propionitrile | | 1H NMR (400 MHz, DMSO) δ 8.87 (s, 1 H), 8.09 (s, 1 H), 7.80 (s, 1 H), 6.98 (s, 1 H), 4.30 (s, 2 H), 3.35 (s, 2 H), 1.38 (s, 6 H), 1.05 (s, 3 H). | | 0.0007 |
| 319 N4-Ethyl-N2-[1-(3-fluoro-1-oxetan-3-yl-piperidin-4-yl)-3-methyl-1H-pyrazol-4-yl]-5-trifluoromethyl-pyrimidine-2,4-diamine | | 1H NMR (400 MHz, DMSO) δ 8.79 (s, 1 H), 8.05 (s, 1 H), 7.67 (s, 1 H), 6.87 (s, 1 H), 5.06-4.73 (m, 1 H), 4.56 (td, J = 6.5, 2.5, 2 H), 4.46 (dt, J = 12.0, 6.1, 2 H), 4.26 (dd, J = 21.1, 11.2, 1 H), 3.58 (p, J = 6.3, 1 H), 3.38 (s, 2 H), 3.22-3.07 (m, 1 H), 2.77 (d, J = 9.0, 1 H), 2.26 -1.99 (m, 6 H), 1.90 (s, 1 H), 1.08 (s, 3 H). | | 0.0003 |

TABLE 8-continued

| Name | Structure | ¹H NMR | M + H⁺ | K_I |
|---|---|---|---|---|
| 320 3-Methyl-1-[5-methyl-4-(4-methylamino-5-trifluoromethyl-pyrimidin-2-ylamino)-pyrazol-1-yl]-butan-2-ol | | 1H NMR (400 MHz, DMSO) δ 8.82 (s, 1 H), 8.04 (s, 1 H), 7.65 (s, 1 H), 6.88 (s, 1 H), 4.71 (d, J = 5.2, 1 H), 3.93 (ddd, J = 21.6, 14.0, 6.1, 2 H), 3.59 (dd, J = 7.4, 4.5, 1 H), 2.83 (s, 3 H), 2.19 (s, 3 H), 1.58 (dd, J = 12.0, 6.5, 1 H), 0.90 (t, J = 7.0, 6 H). | | 0.0030 |
| 321 3-Methyl-1-[3-methyl-4-(4-methylamino-5-trifluoromethyl-pyrimidin-2-ylamino)-pyrazol-1-yl]-butan-2-ol | | | | 0.0108 |
| 322 N2-[1-(1-[1,3]Dioxolan-2-ylmethyl-pyrrolidin-3-yl)-3-methyl-1H-pyrazol-4-yl]-N4-ethyl-5-trifluoromethyl-pyrimidine-2,4-diamine | | | | 0.0049 |
| 323 N4-Methyl-N2-(5-methyl-1-pyrimidin-4-ylmethyl-1H-pyrazol-4-yl)-5-trifluoromethyl-pyrimidine-2,4-diamine | | | | 0.0022 |

TABLE 8-continued

| Name | Structure | ¹H NMR | M + H⁺ | K$_I$ |
|------|-----------|--------|--------|-------|
| 324 N4-Methyl-N2-[5-methyl-1-(1-methyl-1H-pyrazol-3-ylmethyl)-1H-pyrazol-4-yl]-5-trifluoromethyl-pyrimidine-2,4-diamine | | | | 0.0006 |
| 325 N4-Methyl-N2-[3-methyl-1-(1-methyl-1H-pyrazol-3-ylmethyl)-1H-pyrazol-4-yl]-5-trifluoromethyl-pyrimidine-2,4-diamine | | | | 0.0038 |
| 326 3-[3-Chloro-4-(4-methylamino-5-trifluoromethyl-pyrimidin-2-ylamino)-pyrazol-1-yl]-2,2-dimethyl-propionitrile | | | | 0.0082 |
| 327 N4-Ethyl-N2-{3-methyl-1-[1-methyl-1-(4H-[1,2,4]triazol-3-yl)-ethyl]-1H-pyrazol-4-yl}-5-trifluoromethyl-pyrimidine-2,4-diamine | | | | 0.0005 |

TABLE 8-continued

| Name | Structure | ¹H NMR | M + H⁺ | $K_I$ |
|---|---|---|---|---|
| 328 N2-[1-(1-[1,3]Dioxolan-2-ylmethyl-pyrrolidin-3-yl)-5-methyl-1H-pyrazol-4-yl]-N4-ethyl-5-trifluoromethyl-pyrimidine-2,4-diamine | | | | 0.0004 |
| 329 N4-Methyl-N2-(3-methyl-1-pyrimidin-4-ylmethyl-1H-pyrazol-4-yl)-5-trifluoromethyl-pyrimidine-2,4-diamine | | | | 0.0052 |
| 330 N2-(5-Fluoromethyl-1-methyl-1H-pyrazol-4-yl)-N4-methyl-5-trifluoromethyl-pyrimidine-2,4-diamine | | | | 0.0245 |
| 331 N4-Ethyl-N2-{3-methyl-1-[1-methyl-1-(5-methyl-4H-[1,2,4]triazol-3-yl)-ethyl]-1H-pyrazol-4-yl}-5-trifluoromethyl-pyrimidine-2,4-diamine | | 1H NMR (400 MHz, DMSO) δ 13.49 (d, J = 53.3, 1 H), 8.89 (s, 1 H), 8.07 (s, 1 H), 7.78 (s, 1 H), 6.96 (s, 1H ), 2.31 (s, 3 H), 2.13 (s, 3 H), 1.83 (s, 6 H), 1.06 (s, 3 H). | | 0.0008 |

TABLE 8-continued

| Name | Structure | ¹H NMR | M + H⁺ | K_I |
|---|---|---|---|---|
| 332 N4-Methyl-N2-{3-methyl-1-[1-methyl-1-(4H-[1,2,4]triazol-3-yl)-ethyl]-1H-pyrazol-4-yl}-5-trifluoromethyl-pyrimidine-2,4-diamine | | | | 0.0023 |
| 333 N4-Ethyl-N2-[1-(3-fluoro-piperidin-4-yl)-3-methyl-1H-pyrazol-4-yl]-5-trifluoromethyl-pyrimidine-2,4-diamine | | | | 0.0007 |
| 334 2-[5-Methyl-4-(4-methylamino-5-trifluoromethyl-pyrimidin-2-ylamino)-pyrazol-1-yl]-cyclopentanol | | | | 0.0063 |
| 335 2-[3-Methyl-4-(4-methylamino-5-trifluoromethyl-pyrimidin-2-ylamino)-pyrazol-1-yl]-cyclopentanol | | | | 0.0033 |

TABLE 8-continued

| Name | Structure | ¹H NMR | M + H⁺ | K$_I$ |
|---|---|---|---|---|
| 336 N4-ethyl-N2-(3-methyl-1-(2-(5-methyl-1,3,4-oxadiazol-2-yl)propan-2-yl)-1H-pyrazol-4-yl)-5-(trifluoromethyl)pyrimidine-2,4-diamine | | | | 0.0012 |
| 337 N4-ethyl-N2-(3-methyl-1-(2-(4-methyl-4H-1,2,4-triazol-3-yl)propan-2-yl)-1H-pyrazol-4-yl)-5-(trifluoromethyl)pyrimidine-2,4-diamine | | | | 0.0076 |
| 338 N4-ethyl-N2-(3-methyl-1-(2-(1-methyl-1H-1,2,4-triazol-3-yl)propan-2-yl)-1H-pyrazol-4-yl)-5-(trifluoromethyl)pyrimidine-2,4-diamine | | | | 0.0003 |
| 339 N4-methyl-N2-(3-methyl-1-(2-(5-methyl-1,3,4-oxadiazol-2-yl)propan-2-yl)-1H-pyrazol-4-yl)-5-(trifluoromethyl)pyrimidine-2,4-diamine | | | | 0.0117 |

TABLE 8-continued

| Name | Structure | ¹H NMR | M + H⁺ | $K_I$ |
|---|---|---|---|---|
| 340 N4-methyl-N2-(3-methyl-1-(2-(1-methyl-1H-pyrazol-4-yl)propan-2-yl)-1H-pyrazol-4-yl)-5-(trifluoromethyl)pyrimidine-2,4-diamine | | | | 0.0003 |
| 341 N4-methyl-N2-(5-methyl-1-(2-(1-methyl-1H-pyrazol-4-yl)propan-2-yl)-1H-pyrazol-4-yl)-5-(trifluoromethyl)pyrimidine-2,4-diamine | | | | 0.0061 |
| 342 N4-ethyl-N2-(3-methyl-1-(2-(1-methyl-1H-pyrazol-3-yl)propan-2-yl)-1H-pyrazol-4-yl)-5-(trifluoromethyl)pyrimidine-2,4-diamine | | | | 0.0217 |
| 343 N4-ethyl-N2-(3-methyl-1-(2-(1-methyl-1H-pyrazol-5-yl)propan-2-yl)-1H-pyrazol-4-yl)-5-(trifluoromethyl)pyrimidine-2,4-diamine | | | | 0.0003 |

TABLE 8-continued

| Name | Structure | ¹H NMR | M + H⁺ | K$_I$ |
|---|---|---|---|---|
| 344 N4-methyl-N2-(3-methyl-1-(2-(1-methyl-1H-pyrazol-5-yl)propan-2-yl)-1H-pyrazol-4-yl)-5-(trifluoromethyl)pyrimidine-2,4-diamine | | | | 0.0014 |
| 345 N4-methyl-N2-(3-methyl-1-(2-(1-methyl-1H-pyrazol-3-yl)propan-2-yl)-1H-pyrazol-4-yl)-5-(trifluoromethyl)pyrimidine-2,4-diamine | | | | 0.115 |
| 346 N2-(1',5-dimethyl-1'H-1,4'-bipyrazol-4-yl)-N4-methyl-5-(trifluoromethyl)pyrimidine-2,4-diamine | | | | |
| 347 N2-(1',3-dimethyl-1'H-1,4'-bipyrazol-4-yl)-N4-methyl-5-(trifluoromethyl)pyrimidine-2,4-diamine | | | | |

TABLE 8-continued

| Name | Structure | $^1$H NMR | M + H$^+$ | K$_I$ |
|---|---|---|---|---|
| 348 N2-(1-(2-(4H-1,2,4-triazol-3-yl)propan-2-yl)-3-methyl-1H-pyrazol-4-yl)-N4-methyl-5-(trifluoromethyl)pyrimidine-2,4-diamine | | | | |

Example 349

2-(1,5-Dimethyl-1H-pyrazol-4-ylamino)-4-(methylamino)pyrimidine-5-carbonitrile

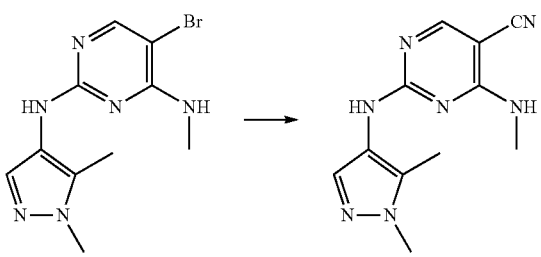 [SMILES: CNc1nc(Nc2cnn(C)c2C)ncc1Br ; CNc1nc(Nc2cnn(C)c2C)ncc1C#N]

To a mixture of 5-bromo-N$^2$-(1,5-dimethyl-1H-pyrazol-4-yl)-N$^4$-methylpyrimidine-2,4-diamine (95 mg, 0.32 mmol), zinc cyanide (70 mg, 0.60 mmol), Pd$_2$(dba)$_3$ (11 mg, 0.012 mmol), DPPF (13 mg, 0.023 mmol) was added DMF (3.5 mL). The reaction was then heated in a sealed tube at 105° C. for 18 h. The reaction mixture was filtered and concentrated. The crude product was purified by reverse phase HPLC to give 2-(1,5-dimethyl-1H-pyrazol-4-ylamino)-4-(methylamino)pyrimidine-5-carbonitrile (19 mg, 25%). LCMS (Method A): [MH$^+$]=244.1 at 2.53 min. $^1$H-NMR (DMSO): δ 8.96 (m, 1H), 8.21 (m, 1H), 7.49 (m, 2H), 3.69 (s, 3H), 2.84 (m, 3H), 2.14 (m, 3H). K$_I$=0.025.

Compounds made using the above procedure are shown in Table 9 below, together with low resolution mass spectrometry (M+H), proton NMR, and LRRK2 K$_I$ (micromolar) data for selected compounds determined from the assay described below.

TABLE 9

| Name | Structure | $^1$H NMR | M + H$^+$ | K$_I$ |
|---|---|---|---|---|
| 350 2-(1,3-Dimethyl-1H-pyrazol-4-ylamino)-4-methylamino-pyrimidine-5-carbonitrile | | $^1$H-NMR (DMSO): δ 9.15 (s, 1H), 8.23 (s, 1H), 7.84 (s, 1H), 7.53 (s, 1H), 3.72 (s, 3H), 2.86 (d, J = 4.4, 3H), 2.12 (s, 3H). | 244.1 | 0.029 |
| 351 2-(1-ethyl-5-methyl-1H-pyrazol-4-ylamino)-4-(methylamino)pyrimidine-5-carbonitrile | | 1H NMR (400 MHz, DMSO) δ 9.12 (s, 1H), 8.21 (s, 1H), 7.73-7.27 (m, 2H), 4.01 (q, J = 7.2, 2H), 2.80 (m, 3H), 2.20 (m, 3H), 1.27 (t, J = 7.2, 3H). | | 0.0097 |

TABLE 9-continued

| Name | Structure | ¹H NMR | M + H⁺ | K₁ |
|---|---|---|---|---|
| 352 2-(1-isopropyl-3-methyl-1H-pyrazol-4-ylamino)-4-(methylamino)pyrimidine-5-carbonitrile | | 1H NMR (400 MHz, DMSO) δ 9.18 (s, 1H), 8.23 (s, 1H), 7.95 (s, 1H), 7.55 (s, 1H), 4.35 (m, 1H), 2.86 (d, J = 4.5, 3H), 2.14 (m, 3H), 1.36 (d, J = 6.6, 6H). | | 0.048 |
| 353 2-(1-ethyl-3-methyl-1H-pyrazol-4-ylamino)-4-(methylamino)pyrimidine-5-carbonitrile | | 1H NMR (400 MHz, DMSO) δ 8.10 (s, 0H), 7.58 (d, J = 2.1, 0H), 7.01 (d, J = 3.6, 0H), 6.60 (s, 0H), 4.02 (q, J = 7.2, 1H), 2.91 (d, J = 4.4, 1H), 1.35 (t, J = 7.2, 1H). | | 0.036 |
| 354 2-(3-methyl-1-phenyl-1H-pyrazol-4-ylamino)-4-(methylamino)pyrimidine-5-carbonitrile | | 1H NMR (400 MHz, DMSO) δ 9.43 (s, 1H), 8.62 (s, 1H), 8.30 (s, 1H), 7.71 (d, J = 8.0, 2H), 7.46 (t, J = 7.9, 2H), 7.24 (t, J = 7.4, 1H), 2.92 (d, J = 3.5, 3H), 2.27 (s, 3H). | | 0.12 |
| 355 2-(3-methyl-1-(1-(2,2,2-trifluoroethyl)piperidin-4-yl)-1H-pyrazol-4-ylamino)-4-(methylamino)pyrimidine-5-carbonitrile | | | | 0.299 |

TABLE 9-continued

| | Name | Structure | ¹H NMR | M + H⁺ | $K_I$ |
|---|---|---|---|---|---|
| 356 | 2-(5-methyl-1-(1-(2,2,2-trifluoroethyl)piperidin-4-yl)-1H-pyrazol-4-ylamino)-4-(methylamino)pyrimidine-5-carbonitrile | 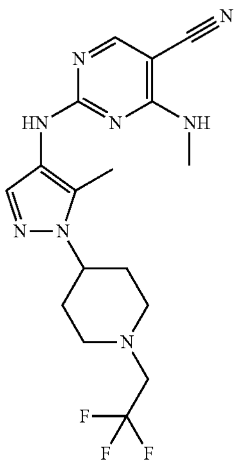 [SMILES: CNc1nc(Nc2cnn(C3CCN(CC(F)(F)F)CC3)c2C)ncc1C#N] | | | 0.0225 |
| 357 | 2-(1-methyl-1H-pyrazol-4-ylamino)-4-(methylamino)pyrimidine-5-carbonitrile | 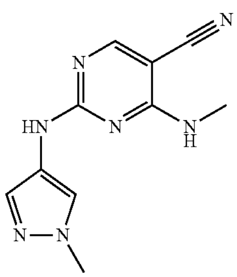 [SMILES: CNc1nc(Nc2cnn(C)c2)ncc1C#N] | | | |
| 358 | 2-(5-methyl-1-(2,2,2-trifluoroethyl)-1H-pyrazol-4-ylamino)-4-(methylamino)pyrimidine-5-carbonitrile | 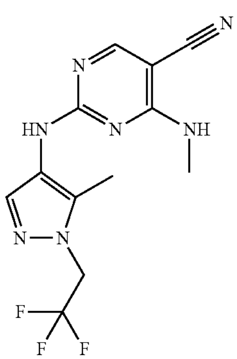 [SMILES: CNc1nc(Nc2cnn(CC(F)(F)F)c2C)ncc1C#N] | 1H NMR (400 MHz, DMSO) δ 9.18 (s, 1H), 8.23 (s, 1H), 7.78 (s, 1H), 7.53 (s, 1H), 5.02 (q, J = 9.2, 2H), 2.79 (s, 3H), 2.23 (s, 3H). | | 0.032 |
| 359 | 2-(3-methyl-1-(2,2,2-trifluoroethyl)-1H-pyrazol-4-ylamino)-4-(methylamino)pyrimidine-5-carbonitrile | 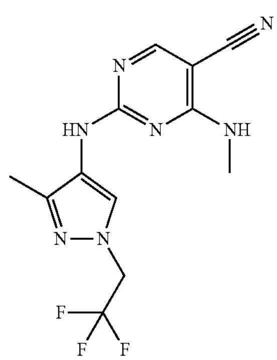 [SMILES: CNc1nc(Nc2cn(CC(F)(F)F)nc2C)ncc1C#N] | 1H NMR (400 MHz, DMSO) δ 9.28 (s, 1H), 8.26 (s, 1H), 8.06 (s, 1H), 7.59 (s, 1H), 5.00 (q, J = 9.0, 2H), 2.86 (d, J = 4.0, 3H), 2.17 (s, 3H). | | 0.053 |

TABLE 9-continued

| Name | Structure | ¹H NMR | M + H⁺ | K$_I$ |
|---|---|---|---|---|
| 360 2-(5-methyl-1-phenyl-1H-pyrazol-4-ylamino)-4-(methylamino)pyrimidine-5-carbonitrile | | 1H NMR (400 MHz, DMSO) δ 9.32 (s, 1H), 8.26 (s, 1H), 7.84 (d, J = 116.0, 1H), 7.46 (d, J = 37.7, 6H), 2.86 (s, 3H), 2.28 (s, 3H). | | 0.0013 |
| 361 2-(5-methyl-1-(tetrahydro-2H-pyran-4-yl)-1H-pyrazol-4-ylamino)-4-(methylamino)pyrimidine-5-carbonitrile | | 1H NMR (400 MHz, DMSO) δ 8.96 (d, J = 136.9, 1H), 8.20 (d, J = 5.4, 1H), 7.73 (s, 1H), 7.44 (d, J = 34.8, 1H), 4.41-4.24 (m, 1H), 3.95 (dd, J = 11.3, 3.8, 2H), 3.47 (t, J = 11.4, 2H), 2.81 (s, 3H), 2.19 (d, J = 30.4, 3H), 2.07-1.93 (m, 2H), 1.75 (d, J = 12.7, 2H). | | 0.0087 |
| 362 2-(3-methyl-1-(tetrahydro-2H-pyran-4-yl)-1H-pyrazol-4-ylamino)-4-(methylamino)pyrimidine-5-carbonitrile | | | 314.1 | 0.086 |
| 363 2-(1-ethyl-5-methyl-1H-pyrazol-4-ylamino)-4-(ethylamino)pyrimidine-5-carbonitrile | | 1H NMR (400 MHz, DMSO) δ 9.08 (m, 1H), 8.21 (m, 1H), 7.70-7.28 (m, 2H), 4.01 (q, J = 7.2, 2H), 3.33 (m, 2H), 2.19 (m, 3H), 1.27 (t, J = 7.2, 3H), 1.08 (m, 3H). | | 0.0060 |

TABLE 9-continued

| Name | Structure | ¹H NMR | M + H⁺ | $K_i$ |
|---|---|---|---|---|
| 364 2-(1-(4-fluorophenyl)-3-methyl-1H-pyrazol-4-ylamino)-4-(ethylamino)pyrimidine-5-carbonitrile | | 1H NMR (400 MHz, DMSO) δ 9.17 (d, J = 125.4, 1H), 8.12 (d, J = 107.0, 2H), 7.55 (s, 3H), 7.35 (t, J = 8.7, 2H), 2.86 (s, 3H), 2.26 (s, 3H). | | 0.0019 |
| 365 2-(1-(difluoromethyl)-3-methyl-1H-pyrazol-4-ylamino)-4-(methylamino)pyrimidine-5-carbonitrile | | | 280.1 | 0.035 |
| 366 2-(5-methyl-1-propyl-1H-pyrazol-4-ylamino)-4-(methylamino)pyrimidine-5-carbonitrile | | | 272.2 | 0.0054 |
| 367 2-(1-(3,5-difluorophenyl)-3-methyl-1H-pyrazol-4-ylamino)-4-(methylamino)pyrimidine-5-carbonitrile | | | 342.2 | 0.0018 |

TABLE 9-continued

| Name | Structure | ¹H NMR | M + H⁺ | K$_I$ |
|---|---|---|---|---|
| 368 2-(1-(4-chlorophenyl)-3-methyl-1H-pyrazol-4-ylamino)-4-(methylamino)pyrimidine-5-carbonitrile | | 1H NMR (400 MHz, DMSO) δ 9.45 (s, 1H), 8.62 (s, 1H), 8.30 (s, 1H), 7.75 (d, J = 8.6, 2H), 7.67 (s, 1H), 7.50 (d, J = 8.9, 2H), 2.91 (d, J = 4.4, 3H), 2.26 (s, 3H). | | 0.082 |
| 369 2-(1-(4-chlorophenyl)-5-methyl-H-pyrazol-4-ylamino)-4-(methylamino)pyrimidine-5-carbonitrile | | | 340.1 | 0.0025 |
| 370 2-(3-methyl-1-(pyridin-2-yl)-1H-pyrazol-4-ylamino)-4-(methylamino)pyrimidine-5-carbonitrile | | 1H NMR (400 MHz, DMSO) δ 9.51 (s, 1H), 8.94 (s, 1H), 8.53-8.24 (m, 2H), 7.92 (t, J = 7.7, 1H), 7.84 (t, J = 6.7, 1H), 7.69 (s, 1H), 7.32-7.21 (m, 1H), 2.93 (s, 3H), 2.31 (s, 3H). | | 0.0415 |
| 371 4-(ethylamino)-2-(5-methyl-1-(tetrahydro-2H-pyran-4-yl)-1H-pyrazol-4-ylamino)pyrimidine-5-carbonitrile | | 1H NMR (400 MHz, DMSO) δ 8.92 (d, J = 137.5, 1H), 8.21 (s, 1H), 7.77-7.30 (m, 2H), 4.41-4.27 (m, 1H), 3.95 (dd, J = 11.2, 4.0, 2H), 3.47 (t, J = 11.3, 2H), 2.23 (s, 3H), 2.00 (qd, J = 12.4, 4.5, 2H), 1.75 (dd, J = 12.6, 2.2, 2H), 1.08 (s, 3H). | | 0.0052 |

TABLE 9-continued

| Name | Structure | ¹H NMR | M + H⁺ | K$_i$ |
|---|---|---|---|---|
| 372 4-(ethylamino)-2-(3-methyl-1-(tetrahydro-2H-pyran-4-yl)-1H-pyrazol-4-ylamino)pyrimidine-5-carbonitrile | | 1H NMR (400 MHz, DMSO) δ 8.97 (d, J = 158.8, 1H), 8.24 (s, 1H), 7.84 (d, J = 58.8, 1H), 7.52 (d, J = 79.5, 1H), 4.31-4.17 (m, 1H), 4.01-3.86 (m, 2H), 3.43 (dd, J = 23.6, 12.1, 4H), 2.10 (d, J = 27.9, 3H), 1.89 (dt, J = 20.4, 11.9, 4H), 1.13 (t, J = 7.1, 3H). | | 0.024 |
| 373 4-(ethylamino)-2-(3-methyl-1-(oxetan-3-yl)-1H-pyrazol-4-ylamino)pyrimidine-5-carbonitrile | | 1H NMR (400 MHz, DMSO) δ 9.32* (s, 1H), 8.94† (s, 1H), 8.29 (s, 1H), 8.10* (s, 1H), 7.89† (s, 1H), 7.71* (s, 1H), 7.54† (s, 1H), 5.48 (p, J = 7.0, 1H), 4.90-4.87 (m, 4H), 3.43 (br s, 2H), 2.28-2.11 (m, 3H), 1.17 (t, J = 7.1, 3H). [* and † denote rotameric peaks.] | 300 | 0.0228 |
| 374 2-(1-isopropyl-5-methyl-1H-pyrazol-4-ylamino)-4-(methylamino)pyrimidine-5-carbonitrile | | ¹H NMR (500 MHz, DMSO) δ 8.68 (s, 1H), 8.15 (s, 1H), 7.54 (s, 1H), 7.17-7.19 (m, 1H), 4.40-4.47 (m, 1H), 2.84 (d, J = 7.5, 3H), 2.16 (s, 3H), 1.29-1.36 (m, 6H). | | 0.0158 |
| 375 2-(1,5-dimethyl-1H-pyrazol-4-ylamino)-4-methoxy-pyrimidine-5-carbonitrile | | | | 0.145 |
| 376 2-(1,5-dimethyl-1H-pyrazol-4-ylamino)-4-(2,2,2-trifluoroethylamino)pyrimidine-5-carbonitrile | | | 312 | 0.0275 |

TABLE 9-continued

| Name | Structure | ¹H NMR | M + H⁺ | K$_i$ |
|---|---|---|---|---|
| 377 2-(1-ethyl-5-methyl-1H-pyrazol-4-ylamino)-4-methoxypyrimidine-5-carbonitrile | | | 259 | 0.075 |
| 378 4-(2,2-difluoroethylamino)-2-(1,5-dimethyl-1H-pyrazol-4-ylamino)pyrimidine-5-carbonitrile | | | 294 | 0.033 |
| 378 2-(1,5-dimethyl-1H-pyrazol-4-ylamino)-4-(2,2,2-trifluoroethoxy)pyrimidine-5-carbonitrile | | | | 0.54 |
| 380 2-(1-(cyclopropylmethyl)-3-methyl-1H-ylamino)-4-(methylamino)pyrimidine-5-carbonitrile | | H NMR (500 MHz, DMSO) δ 8.74 (s, 1H), 8.21 (s, 1H), 7.85 (s, 1H), 7.23 (s, 1H), 3.90 (d, J = 11.5, 2H), 2.89 (d, J = 7.5, 2H), 2.17 (s, 3H), 1.14-1.22 (m, 1H), 0.48-0.54 (m, 2H), 0.28-0.33 (m, 2H). | | 0.045 |
| 381 2-(1-(4,4-difluorocyclohexyl)-5-methyl-1H-pyrazol-4-ylamino)-4-(methylamino)pyrimidine-5-carbonitrile | | ¹H NMR (500 MHz, DMSO) δ 8.71 (m, 1H), 8.32 (s, 1H), 7.58 (s, 1H), 7.19 (m, 1H), 4.33 (m, 1H), 2.83 (d, J = 8.0, 3H), 1.90-2.19 (m, 11H). | | 0.011 |

TABLE 9-continued

| Name | Structure | ¹H NMR | M + H⁺ | K_I |
|---|---|---|---|---|
| 382 2-(3-methyl-1-(oxetan-3-yl)-1H-pyrazol-4-ylamino)-4-(2,2,2-trifluoroethylamino)pyrimidine-5-carbonitrile | | | 354.1 | 0.066 |
| 383 2-(5-chloro-1-(tetrahydro-2H-pyran-4-yl)-1H-pyrazol-4-ylamino)-4-(methylamino)pyrimidine-5-carbonitrile | | 1H NMR (400 MHz, DMSO) δ 9.12 (m, 1H), 8.25 (s, 1H), 7.73 (m, 2H), 4.59-4.41 (m, 1H), 3.96 (m, 2H), 3.49 (m, 2H), 2.80 (s, 3H), 2.13-1.92 (m, 2H), 1.81 (m, 2H). | | 0.0096 |
| 384 2-(1-Difluoromethyl-5-methyl-1H-pyrazol-4-ylamino)-4-methylamino-pyrimidine-5-carbonitrile | | | | 0.0191 |
| 385 2-(1,5-Dimethyl-1H-pyrazol-4-ylamino)-4-ethylamino-pyrimidine-5-carbonitrile | | | | 0.0127 |

TABLE 9-continued

| Name | Structure | ¹H NMR | M + H⁺ | K_I |
|---|---|---|---|---|
| 386 2-[1-(4-Fluoro-phenyl)-5-methyl-1H-pyrazol-4-ylamino]-4-methylamino-pyrimidine-5-carbonitrile | | | | 0.0959 |
| 387 4-Methylamino-2-(3-methyl-1-propyl-1H-pyrazol-4-ylamino)-pyrimidine-5-carbonitrile | | | | 0.0054 |
| 388 4-Methylamino-2-(5-methyl-1-oxetan-3-yl-1H-pyrazol-4-ylamino)-pyrimidine-5-carbonitrile | | | | 0.0322 |
| 389 4-Methylamino-2-(3-methyl-1-oxetan-3-yl-1H-pyrazol-4-ylamino)-pyrimidine-5-carbonitrile | | | | 0.0372 |

TABLE 9-continued

| Name | Structure | ¹H NMR | M + H⁺ | K_I |
|---|---|---|---|---|
| 390 2-[1-(3,5-Difluoro-phenyl)-5-methyl-1H-pyrazol-4-ylamino]-4-methylamino-pyrimidine-5-carbonitrile | | | | 0.241 |
| 391 4-(2,2-Difluoro-ethoxy)-2-(1,5-dimethyl-1H-pyrazol-4-ylamino)-pyrimidine-5-carbonitrile | | | | 0.211 |
| 392 2-[1-(4,4-Difluoro-cyclohexyl)-3-methyl-1H-pyrazol-4-ylamino]-4-methylamino-pyrimidine-5-carbonitrile | | | | 0.266 |

Example 393

(5-(5-chloro-4-(methylamino)pyrimidin-2-ylamino)-1-methyl-1H-pyrazol-3-yl)(morpholino)methanone

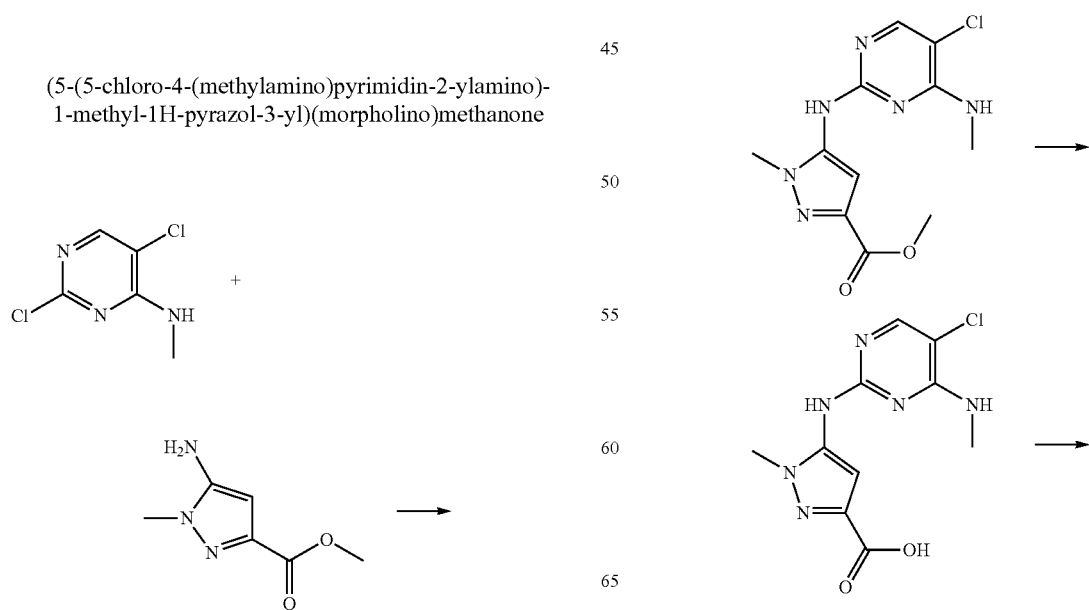

-continued

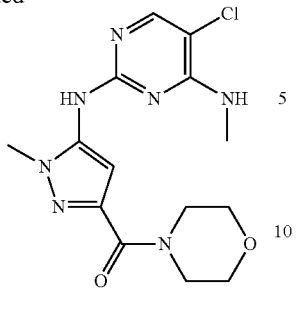

Step 1 Methyl 5-(5-chloro-4-(methylamino)pyrimidin-2-ylamino)-1-methyl-1H-pyrazole-3-carboxylate To a 30 mL microwave vial was added 0.98 g of 2,5-dichloro-N-methylpyrimidin-4-amine, 0.78 g of methyl 5-amino-1-methyl-1H-pyrazole-3-carboxylate, 10 mL of 1-butanol and 0.13 mL of 4M hydrogen chloride in dioxane. The vial was capped and the reaction was heated in a microwave for 30 minutes at 130° C. As the reaction cooled, a precipitate fell out. Filter the precipitate and rinse with a small amount of n-butanol. Drying the cake yielded 0.964 g of methyl 5-(5-chloro-4-(methylamino)pyrimidin-2-ylamino)-1-methyl-1H-pyrazole-3-carboxylate which was used without further purification.

Step 2 5-(5-Chloro-4-(methylamino)pyrimidin-2-ylamino)-1-methyl-1H-pyrazole-3-carboxylic acid To a 100 mL round bottom flask equipped with a stir bar was added 0.964 g of methyl 5-(5-chloro-4-(methylamino)pyrimidin-2-ylamino)-1-methyl-1H-pyrazole-3-carboxylate, 0.28 g of LiOH, 15 mL of tetrahydrofuran and 10 mL of water. The reaction was stirred at room temperature for 18 hours. The tetrahydrofuran was removed in vacuo and the aqueous layer was acidified to pH 5 with 1N HCl. The aqueous layer was partitioned with ethyl acetate and the organic layer washed with brine, dried over MgSO₄, filtered and concentrated to give 0.58 g of 5-(5-chloro-4-(methylamino)pyrimidin-2-ylamino)-1-methyl-1H-pyrazole-3-carboxylic acid which was used without further purification.

Step 3 (5-(5-chloro-4-(methylamino)pyrimidin-2-ylamino)-1-methyl-1H-pyrazol-3-yl)(morpholino)methanone To a 100 mL round bottom flask equipped with a stir bar was added 0.116 g of 5-(5-chloro-4-(methylamino)pyrimidin-2-ylamino)-1-methyl-1H-pyrazole-3-carboxylic acid, 0.19 g of o-benzotriazol-1-yl-tetramethyluronium hexafluorophosphate, 0.14 mL of diisopropylethylamine and 2 mL of dimethylformamide. After pre-activating for 10 minutes, 0.05 mL of morpholine was added and the reaction stirred at room temperature for 2 hours. The reaction was concentrated and purified by preparative reverse phase HPLC to yield 53.2 mg of (5-(5-chloro-4-(methylamino)pyrimidin-2-ylamino)-1-methyl-1H-pyrazol-3-yl)(morpholino)methanone. LCMS (Method A): [MH⁺]=352.0 at 2.80 min. ¹H-NMR (DMSO): δ 9.47 (s, 1H), 7.86 (s, 1H), 7.15 (s, 1H), 6.78 (s, 1H), 3.74 (s, 3H), 3.61 (m, 8H), 2.88 (d, 3H). $K_1$=0.16.

Example 394

2-methyl-2-(3-methyl-4-(4-(methylamino)-5-(trifluoromethyl)pyrimidin-2-ylamino)-1H-pyrazol-1-yl)propanenitrile

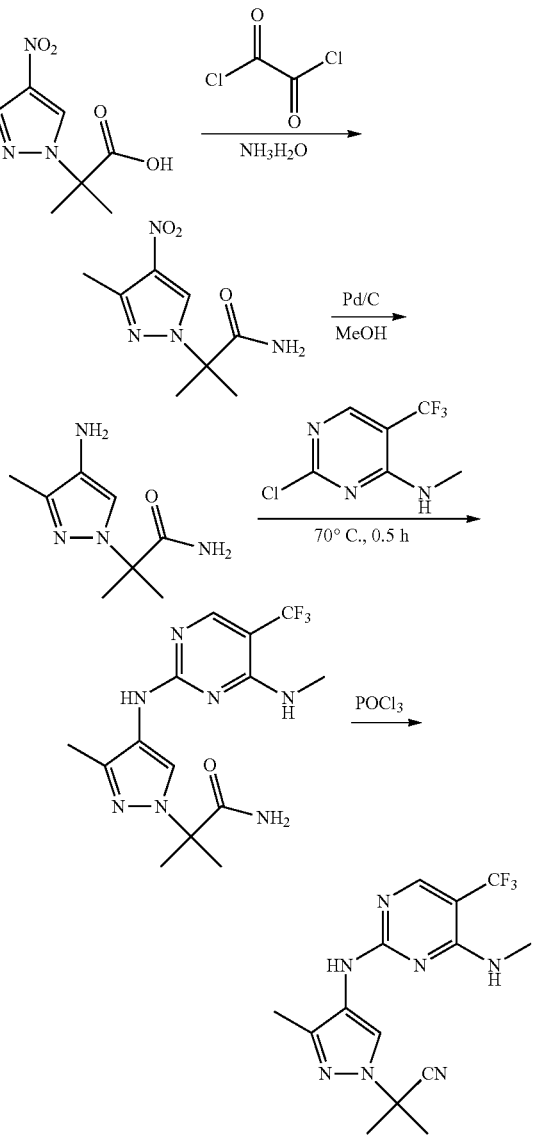

Step 1: 2-methyl-2-(3-methyl-4-nitro-1H-pyrazol-1-yl)propanamide

To a solution of 2-methyl-2-(3-methyl-4-nitro-1H-pyrazol-1-yl)propanoic acid (2.5 g, 11.7 mmol) in CH₂Cl₂ (50 mL) was added dropwise of oxalyl chloride (2.97 g, 23.4 mmol). The reaction was stirred at ambient temperature for about 2 hours, then concentrated under reduced pressure to remove the solvent, the remained solid was dissolved in THF (30 mL) and was added dropwise into NH₄OH (50 mL), the reaction was stirred at ambient temperature for 1 hour. The solution was concentrated under reduced pressure and portioned between EtOAc (50 mL) and water (100 mL), the aqueous phase was extracted with EtOAc, and the combined organic was washed with sat. NH₄Cl (50 mL), dried over anhydrous Na₂SO₄, filleted and concentrated to give crude 2-methyl-2-(3-methyl-4-nitro-1H-pyrazol-1-yl)propanamide (2.5 g, 100%) as white solid which was used in the next step without further purification.

Step 2: 2-(4-amino-3-methyl-1H-pyrazol-1-yl)-2-methylpropanamide

To a solution of 2-methyl-2-(3-methyl-4-nitro-1H-pyrazol-1-yl)propanamide (2.5 g, 11.7 mmol) in MeOH (50 mL) was added Pd/C (1 g), exchanged with nitrogen for three times then with hydrogen, and the reaction was stirred at hydrogen atmosphere (1 atm) for 1 h at ambient temperature. The solution was filtered and the filtrate was concentrated under reduced pressure to give crude 2-(4-amino-3-methyl-1H-pyrazol-1-yl)-2-methylpropanamide (2.0 g, 93%) which was used in the next step without further purification.

Step 3: 2-methyl-2-(3-methyl-4-(4-(methylamino)-5-(trifluoromethyl)pyrimidin-2-ylamino)-1H-pyrazol-1-yl)propanamide To a solution of 2-(4-amino-3-methyl-1H-pyrazol-1-yl)-2-methylpropanamide (250 mg, 1.37 mmol) in 2-methoxyethanol (5 mL) was added 2-chloro-N-methyl-5-(trifluoromethyl)pyrimidin-4-amine (290 mg, 1.37 mmol) and trifluoroaceticacid (156 mg, 1.37 mmol), the reaction was stirred at 70° C. for about 0.5 h. The reaction mixture was cooled to ambient temperature followed with the addition of water (10 mL) and the pH of solution was adjusted to 8 with sat. Na₂CO₃ The aqueous phase was extracted with ethyl acetate (10 mL×3), the combined organic phase was dried over anhydrous sodium sulfate, filtered and concentrated to dry to give a residue which was purified by column chromatography on silica gel (CH₂Cl₂:MeOH=20:1) to give 2-methyl-2-(3-methyl-4-(4-(methylamino)-5-(trifluoromethyl)pyrimidin-2-ylamino)-1H-pyrazol-1-yl)propanamide (250 mg, 51%) as white solid. LCMS (m/z) ES+358 (m+H).

Step 4: 2-methyl-2-(3-methyl-4-(4-(methylamino)-5-(trifluoromethyl)pyrimidin-2-ylamino)-1H-pyrazol-1-yl)propanenitrile A stirred solution of 2-methyl-2-(3-methyl-4-(4-(methylamino)-5-(trifluoromethyl)pyrimidin-2-ylamino)-1H-pyrazol-1-yl)propanamide (250 mg, 0.7 mmol) in POCl₃ (5 mL) was stirred at 90° C. for 1 hour. POCl₃ was removed by evaporation, the mixture was added into ice/H₂O (10 ml) and the pH of the solution was adjusted to 8 with sat.Na₂CO₃, the aqueous phase was extracted with ethyl acetate (5 mL×3). The combined organic phase was washed with sat. sodium chloride (10 mL), dried over anhydrous sodium sulfate, filtered and concentrated to dry to give a residue which was purified by recrystallization to give 2-methyl-2-(3-methyl-4-(4-(methylamino)-5-(trifluoromethyl)pyrimidin-2-ylamino)-1H-pyrazol-1-yl)propanenitrile (100 mg, 42%) as a white solid. ¹H-NMR (300 MHz, DMSO-d₆) δ ppm 9.18 (s, 1H), 8.29 (s, 1H), 8.14 (s, 1H), 7.10 (s, 1H), 2.91 (d, 3H), 2.22 (s, 3H), 1.94 (s, 2H). LCMS (m/z) ES+340 (m+1). Purity, 99.3% (HPLC at 214 nm); $K_i$=0.0005.

Compounds made using the above procedure are shown in Table 10 below, together with low resolution mass spectrometry (M+H), proton NMR, and LRRK2 $K_i$ (micromolar) data for selected compounds determined from the assay described below.

TABLE 10

| Name | Structure | ¹H NMR | M + H⁺ | $K_I$ |
|---|---|---|---|---|
| 395 N,N-dimethyl-2-(5-methyl-4-(4-(methylamino)-5-(trifluoromethyl)pyrimidim-2-ylamino)-1H-pyrazol-1-yl)acetamide | | ¹H NMR (300 MHz, CD₃OD) δ ppm 8.08 (s, 1H), 7.79 (br s, 1H), 5.24 (br s, 1H), 4.92 (s, 2H), 3.12 (s, 3H), 3.04 (s, 3H), 3.00 (s, 3H), 2.24 (s, 3 H) | | 0.015 |
| 396 N,N-dimethyl-2-(3-methyl-4-(4-(methylamino)-5-(trifluoromethyl)pyrimidin-2-ylamino)-1H-pyrazol-1-yl)acetamide | | ¹H NMR (300 MHz, CD₃OD) δ ppm 8.11 (s, 1H), 7.96 (s, 1H), 5.23 (b rs, 1H), 4.90 (s, 2H), 3.08 (s, 3H), 3.07 (s, 3H), 2.99 (s, 3H), 2.27 (s, 3 H) | | 0.004 |

TABLE 10-continued

| Name | Structure | ¹H NMR | M + H⁺ | K_I |
|---|---|---|---|---|
| 397 N-methyl-2-(3-methyl-4-(4-(methylamino)-5-(trifluoromethyl)pyrimidin-2-ylamino)-1H-pyrazol-1-yl)acetamide | 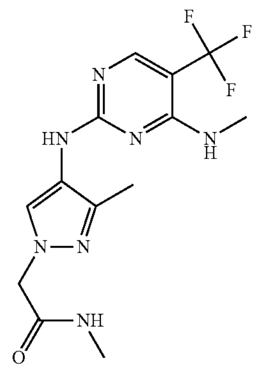 [SMILES: CNC(=O)Cn1cc(Nc2ncc(C(F)(F)F)c(NC)n2)c(C)n1] | ¹H NMR (300 MHz, CD$_3$OD) δ ppm 8.14 (s, 1H), 7.94 (s, 1 H), 6.19 (brs, 1 H), 5.26 (brs, 1 H), 4.73 (s, 2 H), 3.07 (d, J = 4.8 Hz, 3 H), 2.81 (d, J = 4.8 Hz, 3 H), 2.32 (s, 3 H) | | 0.0095 |
| 398 N-methyl-2-(5-methyl-4-(4-(methylamino)-5-(trifluoromethyl)pyrimidin-2-ylamino)-1H-pyrazol-1-yl)acetamide | 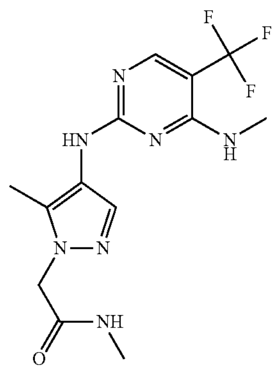 [SMILES: CNC(=O)Cn1ncc(Nc2ncc(C(F)(F)F)c(NC)n2)c1C] | ¹H NMR (300 MHz, CDCl$_3$) δ 8.14 (s, 2H), 6.17 (s, 1H), 5.26 (s, 1H), 3.07 (d, J = 4.6 Hz, 3H), 2.73 (d, J = 4.8 Hz, 3H), 2.32 (s, 3H), 1.84 (s, 6H) | | 0.003 |
| 399 N,N,2-trimethyl-2-(5-methyl-4-(4-(methylamino)-5-(trifluoromethyl)pyrimidin-2-ylamino)-1H-pyrazol-1-yl)propanamide | 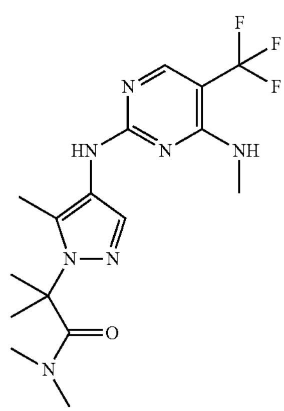 [SMILES: CNc1nc(Nc2cnn(C(C)(C)C(=O)N(C)C)c2C)ncc1C(F)(F)F] | 1H NMR (400 MHz, DMSO) δ 8.79 (s, 1H), 8.06 (s, 1H), 7.68 (s, 1H), 6.85 (s, 1H), 2.84 (s, 6H), 2.38 (s, 3H), 2.02 (s, 3H), 1.67 (s, 6H). | | 0.314 |
| 400 2-methyl-2-(5-methyl-4-(4-(methylamino)-5-(trifluoromethyl)pyrimidin-2-ylamino)-1H-pyrazol-1-yl)-1-(pyrrolidin-1-yl)propan-1-one | 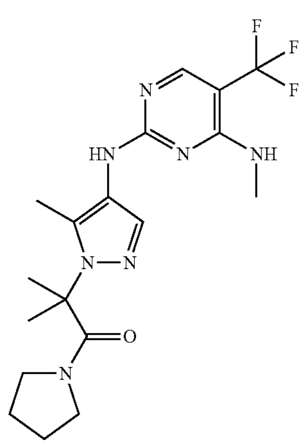 [SMILES: CNc1nc(Nc2cnn(C(C)(C)C(=O)N3CCCC3)c2C)ncc1C(F)(F)F] | 1H NMR (400 MHz, DMSO) δ 8.77 (s, 1H), 8.04 (s, 1H), 7.69 (s, 1H), 6.92 (s, 1H), 3.35 (t, J = 6.6, 2H), 2.81 (s, 3H), 2.53 (s, 1H), 2.03 (s, 3H). | | 0.404 |

TABLE 10-continued

| Name | Structure | $^1$H NMR | M + H$^+$ | K$_I$ |
|---|---|---|---|---|
| 401 2-methyl-2-(5-methyl-4-(4-(methylamino)-5-(trifluoromethyl)pyrimidin-2-ylamino)-1H-pyrazol-1-yl)propanenitrile | | $^1$H-NMR (300 MHz, DMSO-d$_6$) δ ppm 9.18 (s, 1H), 8.29 (s, 1H), 8.14 (s, 1H), 7.10 (s, 1H), 2.91 (d, 3H), 2.22 (s, 3H), 1.94 (s, 2H) | | 0.0007 |
| 402 1-(3-methyl-4-(4-(methylamino)-5-(trifluoromethyl)pyrimidin-2-ylamino)-1H-pyrazol-1-yl)cyclopropanecarbonitrile | | 1H NMR (400 MHz, DMSO) δ 9.09 (s, 1H), 8.12 (s, 2H), 7.03 (s, 1H), 2.91 (d, J = 4.4, 3H), 2.16 (s, 3H), 1.87-1.78 (m, 2H), 1.78-1.70 (m, 2H). | | 0.0037 |
| 403 (R)-2-(3-methyl-4-(4-(methylamino)-5-(trifluoromethyl)pyrimidin-2-ylamino)-1H-pyrazol-1-yl)-1-(pyrrolidin-l-yl)propan-1-one | | | 398 | 0.016 |
| 404 (R)-N,N-dimethyl-2-(3-methyl-4-(4-(methylamino)-5-(trifluoromethyl)pyrimidin-2-ylamino)-1H-pyrazol-1-yl)propanamide | | $^1$H-NMR (500 MHz, DMSO) δ 9.04 (s, 1H), 8.09 (s, 1H), 8.01 (s, 1H), 7.04 (s, 1H), 5.39 (q, J = 6.5 Hz, 1H), 2.97 (s, 3H), 2.87 (s, 3H), 2.82 (s, 3H), 2.14 (s, 3H), 1.45 (d, J = 6.5 Hz, 3H). | | 0.018 |

TABLE 10-continued

| Name | Structure | ¹H NMR | M + H⁺ | K_I |
|---|---|---|---|---|
| 405 (S)-2-(3-methyl-4-(4-(methylamino)-5-(trifluoromethyl)pyrimidin-2-ylamino)-1H-pyrazol-1-yl)-1-(pyrrolidin-1-yl)propan-1-one | | ¹H NMR (500 MHz, DMSO) δ 9.08 (s, 1H), 8.09 (s, 1H), 8.04 (s, 1H), 7.02 (s, 1H), 5.16-5.20 (m, 1H), 3.53-3.57 (m, 1H), 3.23-3.31 (m, 3H), 2.88 (d, J = 4.0, 3H), 2.13 (s, 3H), 1.83-1.88 (m, 2H), 1.67-1.79 (m, 2H), 1.48 (d, J = 6.5, 3H). | | 0.022 |
| 406 3-(5-methyl-4-(4-(methylamino)-5-(trifluoromethyl)pyrimidin-2-ylamino)-1H-pyrazol-1-yl)propanenitrile | | ¹H NMR (500 MHz, MeOD) δ 7.96 (s, 1H), 7.67 (s, 1H), 4.34-4.37 (m, 2H), 2.96-2.99 (m, 2H), 2.91 (s, 3H), 2.27 (s, 3H). | | 0.0073 |
| 407 3-(3-methyl-4-(4-(methylamino)-5-(trifluoromethyl)pyrimidin-2-ylamino)-1H-pyrazol-1-yl)propanenitrile | | ¹H NMR (500 MHz, CDCl₃) δ 8.12 (s, 1H), 7.97 (s, 1H), 4.30-4.33 (m, 2H), 3.07 (s, 3H), 2.90-2.93 (m, 2H), 2.26 (s, 3H), 1.64 (s, 2H). | | 0.0054 |
| 408 methyl 2-methyl-2-(3-methyl-4-(4-(methylamino)-5-(trifluoromethyl)pyrimidin-2-ylamino)-1H-pyrazol-1-yl)propanoate | | 1H NMR (400 MHz, DMSO) δ 9.02 (s, 1H), 8.14 (s, 1H), 8.10 (s, 1H), 7.03 (s, 1H), 3.61 (s, 3H), 2.89 (d, J = 4.4, 3H), 2.14 (s, 3H), 1.71 (s, 6H). | | 0.0047 |

TABLE 10-continued

| Name | Structure | ¹H NMR | M + H⁺ | K$_I$ |
|---|---|---|---|---|
| 409 methyl 2-methyl-2-(5-methyl-4-(4-(methylamino)-5-(trifluoromethyl)pyrimidin-2-ylamino)-1H-pyrazol-1-yl)propanoate | 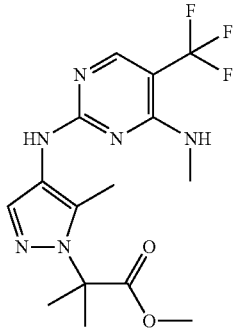 [SMILES: CNc1nc(Nc2cnn(C(C)(C)C(=O)OC)c2C)ncc1C(F)(F)F] | 1H NMR (400 MHz, DMSO) δ 8.86 (s, 1H), 8.06 (s, 1H), 7.69 (s, 1H), 6.94 (s, 1H), 3.70 (s, 3H), 2.83 (s, 3H), 2.05 (s, 3H), 1.71 (s, 6H). | | 0.0076 |
| 410 2-(3-ethyl-4-(4-(methylamino)-5-(trifluoromethyl)pyrimidin-2-ylamino)-1H-pyrazol-1-yl)-2-methylpropanenitrile | 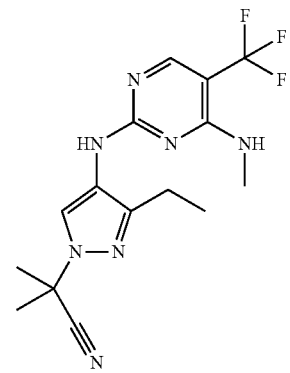 [SMILES: CCc1nn(C(C)(C)C#N)cc1Nc1ncc(C(F)(F)F)c(NC)n1] | 1H NMR (400 MHz, DMSO) δ 8.93 (s, 1H), 8.07 (s, 1H), 7.80 (s, 1H), 6.98 (s, 1H), 2.97 (s, 2H), 2.84 (s, 3H), 1.95 (s, 6H), 1.13 (t, J = 7.4, 3H). | | 0.010 |
| 411 (R)-2-(5-methyl-4-(4-(methylamino)-5-(trifluoromethyl)pyrimidin-2-ylamino)-1H-pyrazol-1-yl)-1-(pyrrolidin-1-yl)propan-1-one | 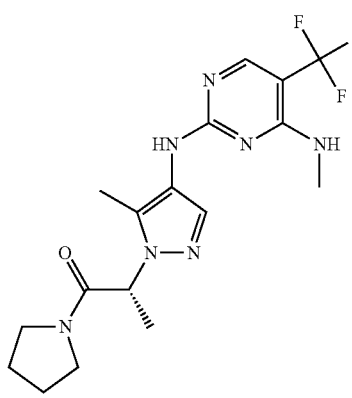 | ¹H-NMR (500 MHz, MeOD) δ 7.88 (s, 1H), 7.53 (s, 1H), 7.49-5.19 (m, 1H), 3.35-3.39 (m, 1H), 2.77-2.81 (m, 3H), 2.69-2.71 (m, 1H), 2.13 (s, 3H), 1.75-1.84 (m, 3H), 1.66-1.71 (m, 1H), 1.50 (d, J = 7.0, 1H). | | 0.039 |
| 412 (R)-N,N-dimethyl-2-(5-methyl-4-(4-(methylamino)-5-(trifluoromethyl)pyrimidin-2-ylamino)-1H-pyrazol-1-yl)propanamide | 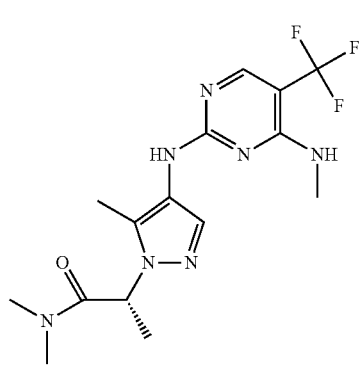 [SMILES: CNc1nc(Nc2cnn([C@H](C)C(=O)N(C)C)c2C)ncc1C(F)(F)F] | ¹H-NMR (500 MHz, DMSO) δ 8.88 (s, 1H), 8.06 (s, 1H), 7.67 (s, 1H), 6.95 (s, 1H), 5.37 (q, J = 6.0 Hz, 1H), 2.79 (s, 6H), 2.74 (s, 3H), 2.15 (s, 3H), 1.43 (d, J = 6.0 Hz, 3H). | | 0.0284 |

TABLE 10-continued

| Name | Structure | ¹H NMR | M + H⁺ | K$_I$ |
|---|---|---|---|---|
| 413 (S)-2-(5-methyl-4-(4-(methylamino)-5-(trifluoromethyl)pyrimidin-2-ylamino)-1H-pyrazol-1-yl)-1-(pyrrolidin-1-yl)propan-1-one | | ¹H NMR (500 MHz, DMSO) δ 8.08 (s, 1H), 7.79 (d, J = 10.0, 1H), 6.56-6.52 (m, 1H), 5.15 (s, 1H), 5.08-5.12 (m, 1H), 3.48-3.56 (m, 2H), 3.27-3.32 (m, 1H), 2.99 (d, J = 4.5, 3H), 2.84 (d, J = 4.0, 1H), 2.21 (t, J = 9.5, 3H), 1.81-1.88 (m, 4H), 1.74-1.79 (m, 3H). | | 0.040 |
| 414 (S)-N,N-dimethyl-2-(5-methyl-4-(4-(methylamino)-5-(trifluoromethyl)pyrimidin-2-ylamino)-1H-pyrazol-1-yl)propanamide | | ¹H NMR (500 MHz, DMSO) δ 8.48 (s, 1H), 8.06 (s, 1H), 7.57 (s, 1H), 6.64-6.66 (m, 1H), 5.33-5.36 (m, 1H), 2.77-2.85 (m, 9H), 2.16 (s, 3H), 1.48-1.51 (m, 3H). | | 0.030 |
| 415 (S)-2-(5-methyl-4-(4-(methylamino)-5-(trifluoromethyl)pyrimidin-2-ylamino)-1H-pyrazol-1-yl)propanenitrile | | ¹H NMR (500 MHz, DMSO) δ 8.60 (s, 1H), 8.06 (s, 1H), 7.75 (s, 1H), 6.71 (s, 1H), 5.73-5.75 (m, 1H), 2.87-2.98 (m, 3H), 2.26 (s, 3H), 1.75-1.78 (s, 3H). | | 0.0095 |
| 416 (S)-2-(3-methyl-4-(4-(methylamino)-5-(trifluoromethyl)pyrimidin-2-ylamino)-1H-pyrazol-1-yl)propanenitrile | | ¹H NMR (500 MHz, DMSO) δ 8.25-8.26 (m, 1H), 8.10 (s, 1H), 8.03 (s, 1H), 6.75 (s, 1H), 5.68-5.69 (m, 1H), 2.92-2.93 (m, 3H), 2.19 (s, 3H), 1.76-1.78 (m, 3H). | | 0.0019 |

TABLE 10-continued

| Name | Structure | ¹H NMR | M + H⁺ | $K_I$ |
|---|---|---|---|---|
| 417 2-(4-(5-chloro-4-(methylamino)pyrimidin-2-ylamino)-3-methyl-1H-pyrazol-1-yl)-2-methylpropanenitrile | | 1H NMR (400 MHz, DMSO) δ 8.53 (s, 1H), 8.15 (s, 1H), 7.85 (s, 1H), 7.09 (d, J = 4.5, 1H), 2.89 (d, J = 4.6, 3H), 2.18 (s, 3H), 1.91 (s, 6H). | | 0.0021 |
| 418 2-(5-chloro-4-(4-(methylamino)-5-(trifluoromethyl)pyrimidin-2-ylamino)-1H-pyrazol-1-yl)-2-methylpropanenitrile | | 1H NMR (400 MHz, DMSO) δ 9.05 (s, 1H), 8.11 (s, 1H), 7.92 (s, 1H), 7.06 (s, 1H), 2.83 (s, 3H), 2.01 (s, 6H). | | 0.0019 |
| 419 2-(3-cyclopropyl-4-(4-(methylamino)-5-(trifluoromethyl)pyrimidin-2-ylamino)-1H-pyrazol-1-yl)-2-methylpropanenitrile | | 1H NMR (400 MHz, DMSO) δ 9.19 (s, 1H), 8.22 (s, 1H), 8.12 (s, 1H), 7.05 (s, 1H), 2.91 (d, J = 4.4, 3H), 2.12 (s, 1H), 1.89 (s, 6H), 0.92-0.80 (m, 2H), 0.80-0.64 (m, 2H). | | 0.0010 |
| 420 2,2-dimethyl-3-(3-methyl-4-(4-(methylamino)-5-(trifluoromethyl)pyrimidin-2-ylamino)-1H-pyrazol-1-yl)propanenitrile | | ¹H-NMR (500 MHz, CDCl₃) δ 8.03 (s, 2H), 7.05 (br, s, 1H), 5.20 (d, J = 1.5 Hz, 1H), 4.08 (s, 2H), 3.01 (s, 3H), 2.18 (s, 3H), 1.40 (m, 6H) | | 0.0028 |

TABLE 10-continued

| Name | Structure | ¹H NMR | M + H⁺ | K$_I$ |
|---|---|---|---|---|
| 421 2,2-dimethyl-3-(5-methyl-4-(4-(methylamino)-5-(trifluoromethyl)pyrimidin-2-ylamino)-1H-pyrazol-1-yl)propanenitrile | 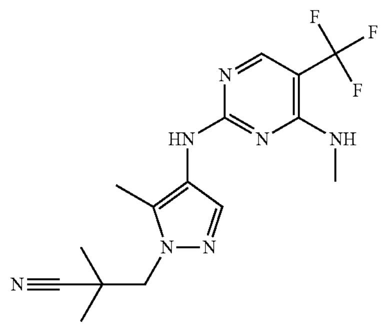 [SMILES: CNc1nc(Nc2cnn(CC(C)(C)C#N)c2C)ncc1C(F)(F)F] | ¹H-NMR (500 MHz, CDCl$_3$) δ 8.01 (s, 1H), 7.73 (br, s, 1H), 5.10 (s, 1H), 4.09 (s, 2H), 2.93 J = 4.5 Hz, 3H), 2.27 (s, 3H), 1.40 (s, 6H) | | 0.0068 |
| 422 1-(5-chloro-4-(4-(methylamino)-5-(trifluoromethyl)pyrimidin-2-ylamino)-1H-pyrazol-1-yl)cyclopropane-carbonitrile | 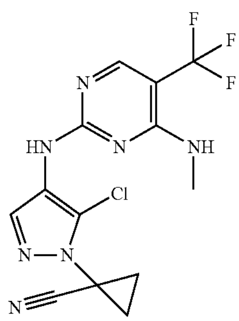 [SMILES: CNc1nc(Nc2cnn(C3(C#N)CC3)c2Cl)ncc1C(F)(F)F] | 1H NMR (400 MHz, DMSO) δ 9.12 (s, 1H), 8.11 (s, 1H), 7.94 (s, 1H), 7.06 (t, J = 6.9, 1H), 2.84 (s, 2H), 2.10-1.98 (m, 1H), 1.89-1.76 (m, 1H). | | 0.0023 |
| 423 N-tert-butyl-2-methyl-2-(3-methyl-4-(4-(methylamino)-5-(trifluoromethyl)pyrimidin-2-ylamino)-1H-pyrazol-1-yl)propanamide | 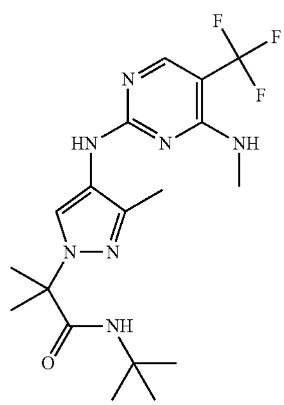 [SMILES: CNc1nc(Nc2cn(C(C)(C)C(=O)NC(C)(C)C)nc2C)ncc1C(F)(F)F] | 1H-NMR (500 MHz, DMSO) δ 9.101 (s, 1H) 8.081-8.143 (m, 2H), 7.025-7.049 (m, 1H), 6.348 (s, 1H), 2.877 (d, J = 4.0, 3H), 2.193 (s, 3H), 1.644 (s, 6H), 1.177 (s, 9H). | | 0.073 |
| 424 2-methyl-2-(3-methyl-4-(4-(methylamino)-5-(trifluoromethyl)pyrimidin-2-ylamino)-1H-pyrazol-1-yl)-N-trifluoroethyl)propanamide | 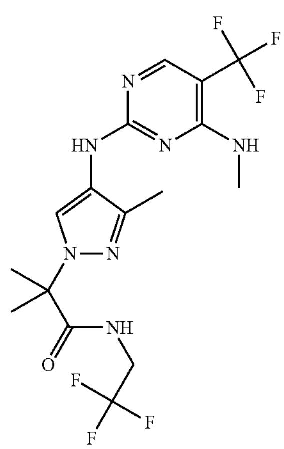 [SMILES: CNc1nc(Nc2cn(C(C)(C)C(=O)NCC(F)(F)F)nc2C)ncc1C(F)(F)F] | | | 0.0063 |

TABLE 10-continued

| Name | Structure | ¹H NMR | M + H⁺ | K_I |
|---|---|---|---|---|
| 425 2-(5-chloro-4-(4-(methylamino)-5-(trifluoromethyl) pyrimidin-2-ylamino)-1H-pyrazol-1-yl)-N-ethyl-2-methyl propanamide | | 1H NMR (400 MHz, DMSO) δ 8.35 (d, J = 9.1, 1H), 8.22 (s, 1H), 8.16 (s, 1H), 7.34 (d, J = 8.5, 2H), 6.32 (t, J = 9.5, 1H), 3.54 (s, 3H), 2.94 (d, J = 4.4, 3H). | | 0.0355 |
| 426 N-(cyclopropylmethyl)-2-methyl-2-(5-methyl-4-(4-(methylamino)-5-(trifluoromethyl) pyrimidin-2-ylamino)-1H-pyrazol-1-yl)propanamide | | 1H-NMR (500 MHz, MeOD) δ 7.50-8.10 (m, 2H), 3.05 (d, J = 7.0 Hz, 3H), 2.97 (s, 3H), 2.16 (s, 3H), 1.76 (s, 6H), 0.99-1.23 (m, 1H), 0.43-0.47 (m, 2H), 0.19-0.22 (m, 2H). | | 0.009 |
| 427 N-(cyclopropylmethyl)-2-methyl-2-(3-methyl-4-(4-(methylamino)-5-(trifluoromethyl) pyrimidin-2-ylamino)-1H-pyrazol-1-yl)propanamide | | 1H-NMR (500 MHz, MeOD) δ 7.82-8.20 (m, 2H), 3.03 (d, J = 6.5 Hz, 3H), 2.98 (s, 3H), 2.20 (s, 3H), 1.76 (s, 6H), 0.93-0.94 (m, 1H), 0.39-0.44 (m, 2H), 0.13-0.18 (m, 2H). | | 0.052 |
| 428 N-ethyl-1-(3-methyl-4-(4-(methylamino)-5-(trifluoromethyl) pyrimidin-2-yl)cyclobutane-carboxamide | | | 398.2 | 0.024 |

TABLE 10-continued

| Name | Structure | ¹H NMR | M + H⁺ | K$_I$ |
|---|---|---|---|---|
| 429 N-isopropyl-2-methyl-2-(5-methyl-4-(4-(methylamino)-5-(trifluoromethyl)pyrimidin-2-ylamino)-1H-pyrazol-1-yl)propanamide | 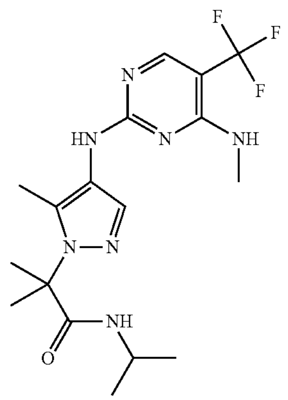 | | | |
| 430 1-(3-methyl-4-(4-(methylamino)-5-(trifluoromethyl)pyrimidin-2-ylamino)-1H-pyrazol-1-yl)cyclobutane-carbonitrile | 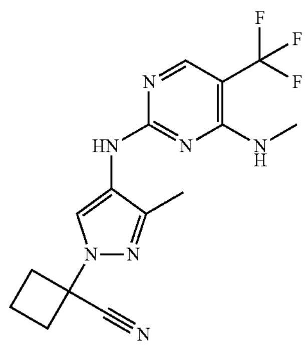 [SMILES: CNc1nc(Nc2cn(C3(C#N)CCC3)nc2C)ncc1C(F)(F)F] | | 352.1 | |
| 431 2-(4-(4-(cyclopropylamino)-5-(trifluoromethyl)pyrimidin-2-ylamino)-3-methyl-1H-pyrazol-1-yl)-2-methylpropanenitrile | 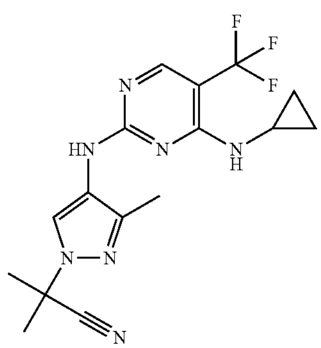 [SMILES: Cc1nn(C(C)(C)C#N)cc1Nc1ncc(C(F)(F)F)c(NC2CC2)n1] | | | |
| 432 N,2-dimethyl-2-(3-methyl-4-(4-(methylamino)-5-(trifluoromethyl)pyrimidin-2-ylamino)-1H-pyrazol-1-yl)propanamide | 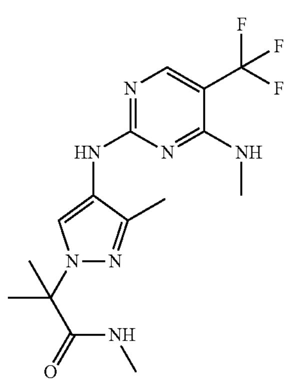 [SMILES: CNC(=O)C(C)(C)n1cc(Nc2ncc(C(F)(F)F)c(NC)n2)c(C)n1] | 1H NMR (400 MHz, DMSO) δ 9.04 (s, 1H), 8.13 (s, 1H), 8.10 (s, 1H), 7.17 (s, 1H), 7.01 (s, 1H), 2.93 (d, 3H), 2.55 (d, 3H), 2.17 (s, 3H). 1.64 (s, 6H). | 372.1 | 0.0184 |

TABLE 10-continued

| Name | Structure | ¹H NMR | M + H⁺ | K$_I$ |
|---|---|---|---|---|
| 433 1-(5-chloro-4-(4-(methylamino)-5-(trifluoromethyl)pyrimidin-2-ylamino)-1H-pyrazol-1-yl)cyclopropane-carbonitrile | | | 358.1 | |
| 434 2-[4-(5-Chloro-4-methoxy-pyrimidin-2-ylamino)-5-methyl-pyrazol-1-yl]-2-methyl-propionic acid methyl ester | | | | 0.0122 |
| 435 2-[4-(5-Chloro-4-methoxy-pyrimidin-2-ylamino)-3-methyl-pyrazol-1-yl]-2-methyl-propionic acid methyl ester | | | | 0.0355 |
| 436 (S)-N,N-Dimethyl-2-[3-methyl-4-(4-methylamino-5-trifluoromethyl-pyrimidin-2-ylamino)-pyrazol-1-yl]-propionamide | | | | 0.0303 |
| 437 R)-2-[3-Methyl-4-(4-methylamino-5-trifluoromethyl-pyrimidin-2-ylamino)-pyrazol-1-yl]-propionitrile | | | | 0.0065 |

TABLE 10-continued

| Name | Structure | ¹H NMR | M + H⁺ | K$_I$ |
|---|---|---|---|---|
| 438 2-[4-(5-Chloro-4-methoxy-pyrimidin-2-ylamino)-3-cyclopropyl-pyrazol-1-yl]-2-methyl-propionitrile | 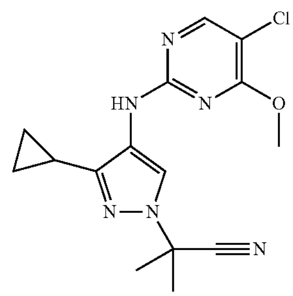 [SMILES: COc1nc(Nc2cn(C(C)(C)C#N)nc2C2CC2)ncc1Cl] | | | 0.0058 |
| 439 (R)-2-[5-Methyl-4-(4-methylamino-5-trifluoromethyl-pyrimidin-2-ylamino)-pyrazol-1-yl]-propionitrile | 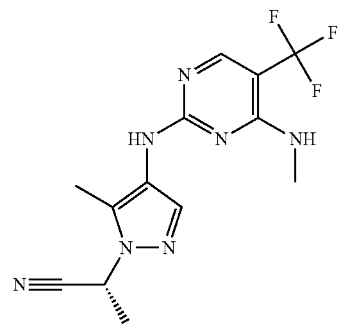 [SMILES: CNc1nc(Nc2cnn([C@H](C)C#N)c2C)ncc1C(F)(F)F] | | | 0.0016 |
| 440 N-Ethyl-2-[3-methyl-4-(4-methylamino-5-trifluoromethyl-pyrimidin-2-ylamino)-pyrazol-1-yl]-isobutyramide | 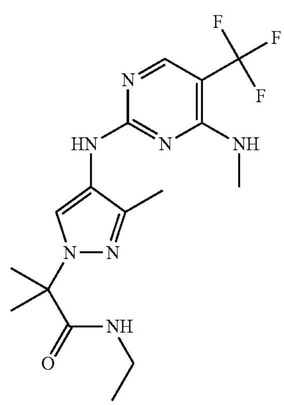 [SMILES: CCNC(=O)C(C)(C)n1cc(Nc2ncc(C(F)(F)F)c(NC)n2)c(C)n1] | | | 0.0095 |
| 441 N-Ethyl-2-[5-ethyl-4-(4-methylamino-5-trifluoromethyl-pyrimidin-2-ylamino)-pyrazol-1-yl]-isobutyramide | 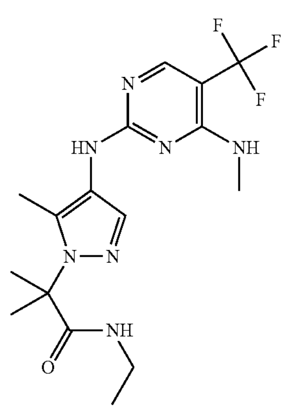 [SMILES: CCNC(=O)C(C)(C)n1ncc(Nc2ncc(C(F)(F)F)c(NC)n2)c1C] | | | 0.0237 |

| Name | Structure | ¹H NMR | M + H⁺ | K_I |
|---|---|---|---|---|
| 442 1-[5-Methyl-4-(4-methylamino-5-trifluoromethyl-pyrimidin-2-ylamino)-pyrazol-1-yl]-cyclobutane-carboxylic acid ethylamide | | | | 0.0156 |
| 443 2-[5-Methyl-4-(4-methylamino-5-trifluoromethyl-pyrimidin-2-ylamino)-pyrazol-1-yl]-N-(2,2,2-trifluoro-ethyl)-isobutyramide | | | | 0.0666 |
| 444 N-Isopropyl-2-[3-ethyl-4-(4-methylamino-5-trifluoromethyl-pyrimidin-2-ylamino)-pyrazol-1-yl]-isobutyramide | | | | 0.0246 |

TABLE 10-continued

| Name | Structure | $^1$H NMR | M + H$^+$ | K$_I$ |
|---|---|---|---|---|
| 445 N-Methyl-2-[5-ethyl-4-(4-methylamino-5-trifluoromethyl-pyrimidin-2-ylamino)-pyrazol-1-yl]-isobutyramide | | | | 0.0926 |
| 446 1-[5-Methyl-4-(4-methylamino-5-trifluoromethyl-pyrimidin-2-ylamino)-pyrazol-1-yl]-cyclobutane-carbonitrile | | | | 0.0024 |
| 447 N-tert-Butyl-2-[5-methyl-4-(4-methylamino-5-trifluoromethyl-pyrimidin-2-ylamino)-pyrazol-1-yl]-isobutyramide | | | | 0.067 |
| 448 2-[4-(4-Ethylamino-5-trifluoromethyl-pyrimidin-2-ylamino)-5-methyl-pyrazol-1-yl]-N-methyl-isobutyramide | | | | 0.0153 |

TABLE 10-continued

| Name | Structure | ¹H NMR | M + H⁺ | $K_I$ |
|---|---|---|---|---|
| 449 2-[4-(4-Cyclopropylamino-5-trifluoromethyl-pyrimidin-2-ylamino)-3-methyl-pyrazol-1-yl]-N-methyl-isobutyramide | | 1H NMR (400 MHz, DMSO) δ 9.10 (s, 1H), 8.22 (s, 1H), 8.13 (s, 1H), 7.21 (d, J = 4.1, 1H), 6.98 (s, 1H), 2.83 (s, 1H), 2.54 (d, J = 4.3, 3H), 2.20 (s, 3H), 1.61 (s, 6H), 0.69 (dd, J = 35.4, 4.3, 4H). | | 0.0013 |
| 450 2-[4-(4-Cyclopropylamino-5-trifluoromethyl-pyrimidin-2-ylamino)-5-methyl-pyrazol-1-yl]-N-methyl-isobutyramide | | | | 0.0071 |
| 451 2-[4-(4-Ethylamino-5-trifluoromethyl-pyrimidin-2-ylamino)-3-methyl-pyrazol-1-yl]-2-methyl-propionitrile | | 1H NMR (400 MHz, DMSO) δ 9.07 (s, 1H), 8.15 (d, J = 26.9, 2H), 7.05 (s, 1H), 3.51-3.42 (m, 2H), 2.19 (s, 3H), 1.92 (s, 6H), 1.13 (t, J = 7.1, 3H). | | 0.0003 |
| 452 2-(3-chloro-4-(4-(methylamino)-5-(trifluoromethyl)pyrimidin-2-ylamino)-1H-pyrazol-1-yl)-2-methylpropanenitrile | | | | |

TABLE 10-continued

| Name | Structure | $^1$H NMR | M + H$^+$ | K$_I$ |
|---|---|---|---|---|
| 453 2-[4-(4-Ethylamino-5-trifluoromethyl-pyrimidin-2-ylamino)-3-methyl-pyrazol-1-yl]-N-methyl-isobutyramide | | | | 0.0092 |

Example 454

In Vitro LRRK2 Lanthascreen Binding Assay

This assay was used to determine a compound's potency in inhibiting activity of LRRK2 by determining, Ki$_{app}$, IC$_{50}$, or percent inhibition values. In 384 well proxiplates F black, shallow well plates LRRK2, Eu-anti-GST-antibody, Alexa Fluor® Kinase tracer 236 and test compound were incubated together.

Binding of the Alexa Fluor® "tracer" to a kinase is detected by addition of a Eu-labeled anti-GST antibody. Binding of the tracer and antibody to a kinase results in a high degree of FRET, whereas displacement of the tracer with a kinase inhibitor results in a loss of FRET.

Assay conditions and materials used were as follows:
Final Assay Conditions:

| | |
|---|---|
| GST-LRRK2 G2019S | 10 nM |
| Eu-anti-GST-antibody | 2 nM |
| Kinase tracer 236 | 8.5 nM |
| Kinase reaction time: | 1 hour |
| Temperature: | ambient |
| Total volume: | 15 μl |
| DMSO | 1% |

Materials:

| | |
|---|---|
| 384 well proxiplates F black shallow well | Perkin Elmer cat# 6008260 |
| Kinase: LRRK2G2019S, | Invitrogen cat # PV4882 (LOT 567054A). |
| Eu-labeled anti-GST antibody | Invitrogen cat # PV5594 |
| Alexa Fluor ® Kinase tracer 236 | Invitrogen cat #PV5592 |
| TRIS- HCl | Sigma cat # T3253 |
| EGTA | Sigma cat # E3889 |
| Brij-35: | Sigma cat # B4184(30% w/v) |
| DMSO: | Sigma cat # D8418 |
| MgCl$_2$ | Sigma cat # M9272 |
| Reaction Buffer: | H$_2$O/50 mM Tris, pH 7.4/10 mM MgCl$_2$/1 mM EGTA/0.01% Brij 35 |

Compound Plate Preparation:

Serially dilute test compounds (10 mM stock) 1:3.16 (20 ul+43.2 ul) in 100% DMSO. 12 pt curve. Dilute each concentration 1:33.3 (3 ul+97 ul) in reaction buffer. Stamp 5 ul to assay plate. Final top test concentration 100 uM Total and Blank Preparation:

In Reaction Buffer, 5 ul of DMSO (3%) was added to total and blank wells and 5 ul of Eu-labeled anti-GST antibody (6 nM) was added to blank wells. Add 5 ul LRRK2 (30 nM)/Eu-labeled anti-GST antibody (6 nM) mix to compound and total wells.

Assay Procedure:

Add 5 ul kinase tracer (25.5 nM) to all wells. Incubate plates at room temperature for 1 hour on a plate shaker (gentle shaking). Read on Perkin Elmer EnVision reader HTRF protocol Data Handling:

Calculate ratio: (665/620)*10000. Subtract mean background values from all data points. Calculate % of control for each test value. Plot % of control vs Compound concentration. Calculate Ki Value (xlfit curve fitting—Morrison equation). Results expressed as a Ki in μM. Equation for Ki:

$$Y = V0 * (1 - ((x + Ki*(1 + S/Km) + Et)/(2*Et) - (((x + Ki*(1 + S/Km) + Et)^2 - (4*Et*x))^0.5)/(2*Et)))$$

Where Et=4 nM
kd (Tracer)=8.5 nM
Tracer concentration (S)=8.5 nM

Example 455

In Vitro LRRK2 Assay

This assay was used to determine a compound's potency in inhibiting activity of LRRK2 by determining, Ki$_{app}$, IC$_{50}$, or percent inhibition values. In a polypropylene plate, LRRK2, fluorescently-labeled peptide substrate, ATP and test compound were incubated together. Using a LabChip 3000 (Caliper Life Sciences), after the reaction the substrate was separated by capillary electrophoresis into two populations: phosphorylated and unphosphorylated. The relative amounts of each were quantitated by fluorescence intensity. LRRK2 Ki was determined according to the equation:

$$Y = V0 * (1 - (x + Ki*(1 + S/Km) + Et)/(2*Et) - (((x + Ki*(1 + S/Km) + Et)^2 - (4*Et*x))^0.5)/(2*Et))).$$

Ki values in Table 4 and elsewhere herein are shown in μM.
Assay conditions and materials used were as follows:
Final Assay Conditions:

| | |
|---|---|
| LRRK2 G2019S in 5 mM MgCl$_2$: | 5.2 nM (Invitrogen lot # 567054A) |
| LRRK2 G2019S in 1 mM MnCl$_2$: | 11 nM (Invitrogen lot # 567054A) |
| LRRK2 Wild type in 5 mM MgCl$_2$: | 15 nM (Invitrogen lot # 500607F) |

-continued

| | |
|---|---|
| LRRK2 I2020T in 5 mM MgCl$_2$: | 25 nM (Invitrogen lot # 43594) |
| Substrate: | 1 µM |
| ATP: | 130 µM |
| Kinase reaction time: | 2 hours |
| Temperature: | ambient |
| Total volume: | 20 µl |

ATP$^{app}$ Kms:

| | |
|---|---|
| G2019S in 5 mM MgCl$_2$: | 130 µM |
| G2019S in 1 mM MnCl$_2$: | 1 µM |
| Wild type in 5 mM MgCl$_2$: | 80 µM |
| I2020T in 5 mM MgCl$_2$: | 14 µM |

Materials:

| | |
|---|---|
| Solid Support: | Black 50 µL volume polypropylene 384 well plate (MatriCal cat # MP101-1-PP) |
| Kinase: | LRRK2 G2019S (Invitrogen cat # PV4882). LRRK2 Wild type (Invitrogen cat # PV4874). |
| Substrate: | 5FAM-GAGRLGRDKYKTLRQIRQ-CONH$_2$ |
| Non-binding plate: | 384 well clear V-bottom polypropylene plates (Greiner cat # 781280). |
| ATP: | 10 mM ATP (Cell Signaling cat # 9804). |
| Triton X-100: | Triton X-100. |
| Brij-35: | Brij-35 (Pierce cat # 20150). |
| Coating Reagent #3: | Coating Reagent #3 (Caliper). |
| DMSO: | DMSO (Sigma cat # 34869-100ML). |
| Complete Reaction Buffer: | H$_2$O/25 mM Tris, pH 8.0/5 mM MgCl$_2$/2 mM DTT/0.01% Triton X-100. |
| Stop Solution: | H$_2$O/100 mM HEPES, pH 7.2/0.015% Brij-35/0.2% Coating Reagent #3/20 mM EDTA. |
| Separation Buffer: | H$_2$O/100 mM HEPES, pH 7.2/0.015% Brij-35/0.1% Coating Reagent #3/1:200 Coating Reagent #8/10 mM EDTA/5% DMSO. |

Compound Plate Preparation:

For serial dilutions, 34.6 µl DMSO was added to columns 3-24. For the assay controls, 37.5 µl DMSO was added to columns 1 and 2 of rows A and P. a, d and 50 µl 25 µM G-028831 (Staurosporine) was added to columns 1 and 2, row B. For the samples: to start at 100 µM, 37.5 µl DMSO was to columns 1 and 2, then 12.5 µl 10 mM compound; to start at 10 µM, 78 µl DMSO was added to columns 1 & 2, then 2 µl 10 mM compound; and to start at 1 µM, 25 µM compound (2 µl 10 mM cmpd+798 µl DMSO) was added to empty columns 1 and 2. A Precision instrument was used to perform 1:3.16 serial dilutions ("PLK_BM_serial_halflog").

ATP Preparation:

ATP was diluted to 282.1 µM in Complete Kinase Buffer (final concentration was 130 µM).

Total and Blank Preparation:

In Complete Reaction Buffer, substrate was diluted to 4 µM. Equal volumes of Complete Reaction Buffer and 4 µM substrate were combined to obtain the blank. Equal volumes of Complete Reaction Buffer and 4 µM substrate were combined and to the combined solution was added 2× final LRRK2 concentration.

Assay Procedure:

To a 50 µl polypropylene plate, 5 µl/well buffer/substrate was added by hand to Blank wells. A Biomek FX was used to start the kinase reaction ("PLK SAR 23 ATP"). The following were added to the appropriate wells:

2 µl compound+23 µl ATP;
5 µl/well compound/ATP in Assay Plate;
5 µl/well kinase/substrate in Assay Plate;

The plate was incubated for 2 hours in the dark. Biomek FX was used to stop the kinase reaction ("PLK Stop"), and 10 µl/well Stop solution was added to the Assay Plate. Results were read on the LabChip 3000.

Lab Chip 3000 Protocol:

The LabChip 3000 was run using the job "LRRK2 IC50" with the following job settings:

| | |
|---|---|
| Pressure: | −1.4 psi |
| Downstream voltage: | −500 V |
| Upstream voltage: | −2350 V |
| Post sample buffer sip time: | 75 seconds |
| Post dye buffer sip time: | 75 seconds |
| Final delay time: | 200 seconds |

Example 456

Parkinson's Disease Mouse Model

Parkinson's disease can be replicated in mice and in primates by administration of 1-methyl-4-phenyul tetrahydropyridine (MPTP), a selective nigrostriatal dopaminergic neurotoxin that produces a loss of striatal dopamine (DA) nerve terminal markers. Compounds of the invention may be evaluated for effectiveness in treatment of Parkinson's disease using MPTP induced neurodegeneration following generally the protocol described by Saporito et al., *J. Pharmacology* (1999) Vol. 288, pp. 421-427.

Briefly, MPTP is dissolved in PBS at concentrations of 2-4 mg/ml, and mice (male C57 weighing 20-25 g) are given a subcutaneous injection of 20 to 40 mg/kg. Compounds of the invention are solubilized with polyethylene glycol hydroxystearate and dissolved in PBS. Mice are administered 10 ml/kg of compound solution by subcutaneous injection 4 to 6 h before MPTP administration, and then daily for 7 days. On the day of the last injection, mice are sacrificed and the midbrain blocked and postfixed in paraformaldehyde. Striata are dissected free, weighed, and stored at −70° C.

The striata thus collected are evaluated for content of dopamine and its metabolites dihydroxyphenylacetic acid and homovanillic acid, by HPLC with electrochemical detection as described by Sonsalla et al., *J. Pharmacol. Exp. Ther.* (1987) Vol. 242, pp. 850-857. The striata may also be evaluated using the tyrosine hydroxylase assay of Okunu et al., *Anal Biochem* (1987) Vol. 129, pp. 405-411 by measuring $^{14}CO_2$ evolution associated with tyrosine hydroxylase-mediated conversion of labeled tyrosine to L-dopa. The striata may further be evaluated using the Monoamine oxidase-B assay as described by White et al., *Life Sci.* (1984), Vol. 35, pp. 827-833, and by monitoring dopamine uptake as described by Saporito et al., (1992) Vol. 260, pp. 1400-1409.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of the formula I:

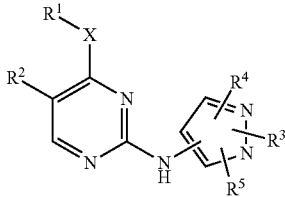

or a pharmaceutically acceptable salt thereof,
wherein:
X is: —$NR^a$—; or —O— wherein $R^a$ is hydrogen or $C_{1-6}$alkyl;
$R^1$ is: $C_{1-6}$alkyl; $C_{2-6}$alkenyl; $C_{2-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted one or more times with $C_{1-6}$alkyl; $C_{3-6}$cycloalkyl-$C_{1-6}$alkyl wherein the $C_{3-6}$cycloalkyl portion is optionally substituted one or more times with $C_{1-6}$alkyl; heterocyclyl optionally substituted one or more times with $R^7$; or heterocyclyl-$C_{1-6}$alkyl optionally substituted one or more times with $R^7$, wherein the heterocyclyl is piperidinyl, piperazinyl, morpholinyl, tetrahydropyranyl, pyrrolidinyl, tetrahydrofuranyl or oxetanyl;
or X and $R^1$ together form $C_{1-6}$alkyl; $C_{1-6}$alkoxy-$C_{1-6}$alkyl; $C_{3-6}$cycloalkyl optionally substituted one or more times with $R^6$; or $C_{3-6}$cycloalkyl-$C_{1-6}$alkyl wherein the $C_{3-6}$cycloalkyl portion is optionally substituted one or more times with $R^6$;
or $R^1$ and $R^a$ together with the atoms to which they are attached may form a three- to six-membered ring optionally substituted one or more times with $R^7$;
$R^2$ is: halo; cyano; or halo-$C_{1-6}$alkyl;
$R^3$ is: hydrogen; $C_{1-6}$alkyl; halo-$C_{1-6}$alkyl; $C_{2-6}$alkenyl; $C_{2-6}$alkynyl; hydroxy-$C_{1-6}$alkyl; $C_{1-6}$alkoxy-$C_{1-6}$alkyl; cyano-$C_{1-6}$alkyl; $C_{1-6}$alkylsulfonyl; $C_{1-6}$alkylsulfonyl$C_{1-6}$alkyl; amino-$C_{1-6}$alkyl; $C_{3-6}$cycloalkyl optionally substituted one or more times with $R^6$; $C_{3-6}$cycloalkyl-$C_{1-6}$alkyl wherein the $C_{3-6}$cycloalkyl portion is optionally substituted one or more times with $R^6$; $C_{3-6}$cycloalkyl-sulfonyl wherein the $C_{3-6}$cycloalkyl portion is optionally substituted one or more times with $R^6$; heterocyclyl optionally substituted one or more times with $R^7$; heterocyclyl-$C_{1-6}$alkyl wherein the heterocyclyl portion is optionally substituted one or more times with $R^7$, wherein the heterocyclyl is piperidinyl, pyrrolidinyl, oxetanyl, tetrahydropyranyl, tetrahydrofuranyl, azetidinyl, [1,3]dioxolanyl or tetrahydrothiopyranyl; aryl optionally substituted one or more times with $R^8$; aryl-$C_{1-6}$alkyl wherein the aryl portion is optionally substituted one or more times with $R^8$; heteroaryl optionally substituted one or more times with $R^8$; heteroaryl-$C_{1-6}$alkyl wherein the heteroaryl portion is optionally substituted one or more times with $R^8$; or —Y—C(O)—$R^d$;
Y is $C_{2-6}$alkylene or a bond;
$R^d$ is $C_{1-6}$alkyl, $C_{1-6}$alkoxy, amino, $C_{1-6}$alkyl-amino, di-$C_{1-6}$alkyl-amino, halo-$C_{1-6}$alkyl-amino, di-halo-$C_{1-6}$alkyl-amino, halo-$C_{1-6}$alkyl, hydroxy-$C_{1-6}$alkyl, hydroxy, $C_{1-6}$alkoxy-$C_{1-6}$alkyl, cyano-$C_{1-6}$alkyl, $C_{1-6}$alkylsulfonyl$C_{1-6}$alkyl, amino-$C_{1-6}$alkyl, $C_{3-6}$cycloalkyl optionally substituted one or more times with $R^6$, $C_{3-6}$cycloalkyl-$C_{1-6}$alkyl wherein the $C_{3-6}$cycloalkyl portion is optionally substituted one or more times with $R^6$-heterocyclyl optionally substituted one or more times with $R^7$, or heterocyclyl-$C_{1-6}$alkyl wherein the heterocyclyl portion is optionally substituted one or more times with $R^7$, wherein the heterocyclyl is piperidinyl, piperazinyl, morpholinyl, tetrahydropyranyl, pyrrolidinyl, azetidinyl, tetrahydrofuranyl or oxetanyl;
$R^4$ is: chloro; or methyl;
$R^5$ is: hydrogen; or $C_{1-6}$alkyl;
each $R^6$ is independently: $C_{1-6}$alkyl; halo-$C_{1-6}$alkyl; $C_{1-6}$alkoxy; oxo; cyano; halo; or Y—C(O)—$R^d$;
each $R^7$ is independently: $C_{1-6}$alkyl; halo-$C_{1-6}$alkyl; halo; oxo; $C_{1-6}$alkoxy; $C_{1-6}$alkylsulfonyl; $C_{1-6}$alkoxy-$C_{1-6}$alkyl; cyano; —Y—C(O)—$R^d$; heterocyclyl; heterocyclyl-$C_{1-6}$alkyl; $C_{3-6}$cycloalkyl; $C_{3-6}$cycloalkyl-$C_{1-6}$alkyl; or $C_{3-6}$cycloalkylsulfonyl, wherein the heterocyclyl is piperidinyl, pyrrolidinyl, oxetanyl, tetrahydropyranyl, tetrahydrofuranyl, azetidinyl, [1,3]dioxolanyl or tetrahydrothiopyranyl; and
each $R^8$ is independently: oxo; $C_{1-6}$alkyl; halo-$C_{1-6}$alkyl; halo; $C_{1-6}$alkyl-sulfonyl; $C_{1-6}$alkoxy; $C_{1-6}$alkoxy-$C_{1-6}$alkyl; cyano; heterocyclyl; heterocyclyl-$C_{1-6}$ alkyl; —Y—C(O)—$R^d$; $C_{3-6}$cycloalkyl, $C_{3-6}$cycloalkyl-$C_{1-6}$alkyl, or $C_{3-6}$cycloalkyl-sulfonyl, wherein the heterocyclyl moiety is piperidinyl, piperazinyl, morpholinyl, thiomorpholinyl, pyrrolidinyl, oxetanyl, tetrahydropyranyl, tetrahydrofuranyl, azetidinyl, [1,3]dioxolanyl or tetrahydrothiopyranyl.

2. The compound of claim 1, wherein X is —NH— or —O—.

3. The compound of claim 1, wherein $R^1$ is: $C_{1-6}$alkyl; halo-$C_{1-6}$alkyl; $C_{1-6}$alkoxy-$C_{1-6}$alkyl; amino-$C_{1-6}$alkyl; $C_{1-6}$alkylsulfonyl-$C_{1-6}$alkyl; $C_{3-6}$cycloalkyl; or $C_{3-6}$cycloalkyl-$C_{1-6}$alkyl.

4. The compound of claim 1, wherein $R^1$ is $C_{1-6}$alkyl.

5. The compound of claim 1, wherein $R^2$ is: fluoro; bromo; chloro; iodo; trifluoromethyl; or cyano.

6. The compound of claim 1, wherein $R^3$ is: methyl; ethyl; propyl; isopropyl; butyl; cyclopropyl; cyclopropylmethyl; cyclobutyl; methanesulfonyl; ethylsulfonyl; cyclopropylsulfonyl; sec-butylsulfonyl; morpholin-4-yl-ethyl; oxetan-3-yl; 2-methoxyethyl; 2-hydroxy-2-methyl-propyl; 3-hydroxy-2-methyl-propan-2-yl; 2-methoxy-propyl; tetrahydro-2H-pyran-4-yl; tetrahydrofuran-3-yl; 2,6-dimethyltetrahydro-2H-pyran-4-yl; tetrahydro-2H-pyran-3-yl); phenyl; 4-(methylsulfonyl)phenyl); 4-cyano-phenyl; 4-fluoro-phenyl; 4-chloro-phenyl; 3,5-difluorophenyl; 4-(dimethylaminocarbonyl)-phenyl); 4-(cyclopropylsulfonyl)phenyl; 2,2,2-trifluoroethyl; 2-fluoroethyl; difluoromethyl; 2-dimethyl-1,3-dioxan-5-yl; 1-methyl-cyclopropyl-carbonyl; 3-methylpyridin-4-yl; 2-methylpyridin-4-yl; pyridin-2-yl; pyrimidin-2-yl; pyrimidin-5-yl; pyridin-2-ylmethyl; 1-(pyridin-2-yl)ethyl; cyclopropylsulfonyl; 1-cyano-1-methylethyl; 2-cyano-ethyl; 1-cyano-ethyl; 2-cyano-2-methyl-propyl; 1-(2,2,2-trifluoroethyl)piperidin-4-yl; 1-(methylsulfonyl)azetidin-3-yl; (3-methyloxetan-3-yl)methyl; (1S,5S)-8-oxabicyclo[3.2.1]octan-3-yl; 1-(oxetan-3-yl)piperidin-4-yl; 1-acetyl-piperidin-4-yl; 1-(cyclopropyl-carbonyl)-piperidin-4-yl; 1-methyl-piperidin-4-yl; 1-methyl-2-oxo-piperidin-5-yl; 2-oxo-piperidin-5-yl; 1-(isopropyl-carbonyl)-piperidin-4-yl; 1-(oxetan-3-yl)azetidin-3-yl; 1-(cyclopropyl-carbonyl)-piperidin-4-yl; 2-methoxycyclopentyl; 3-methoxycyclopentyl; 1-methoxy-2-methylpropan-2-yl; tetrahydro-2H-1,1-dioxo-thiopyran-4-yl; 3-fluoro-1-(oxetan-3-yl)piperidin-4-yl; 1-methoxypropan-2-yl; 1-(2,2,2-trifluoroethyl)azetidin-3-yl); 1-(oxetan-3-yl)pyrrolidin-3-yl; 1-isopropylazetidin-3-yl; 3-fluoro-1-methylpiperidin-4-yl; 1-ethyl-3-fluoropiperidin-4-yl; 1-methylpyrrolidin-3-yl;

2-methoxyethyl)piperidin-4-yl); 1-methyl-1-(methylamino-carbonyl)-ethyl; 2-methyl-2-morpholino-propyl; 4,4-difluorocyclohexyl; morpholin-4-yl-carbonyl; dimethylamino-carbonyl-methyl; 1-methyl-1-(dimethylamino-carbonyl)-ethyl; pyrrolidin-'-yl-carbonyl; 1-cyamo-cyclopropyl; 1-(pyrrolidin-'-yl-carbonyl)-ethyl; 1-(dimethylamino-carbonyl)-ethyl; 1-(methoxy-carbonyl)-ethyl; 1-(tert-butylamino-carbonyl)-1-methyl-ethyl; 1-(2,2,2-trifluoroethyllamino-carbonyl)-1-methyl-ethyl; 1-(ethylamino-carbonyl)-1-methyl-ethyl; 1-(cyclopropylmethylamino-carbonyl)-1-methyl-ethyl; 1-(ethylamino-carbonyl)-cyclobutyl; 1-(isopropylamino-carbonyl)-1-methyl-ethyl; 1-cyano-cyclobutyl; 2-methoxy-1-methyl-ethyl; 1-methyl-1-(methoxy-carbonyl)-ethyl; 2-methoxy-2-methyl-propan-1-yl; 1-(oxetan-3-yl)-pyrrolidin-3-yl; isopropylsulfonyl; butane-2-sulfonyl; 1-(2-fluoro-ethyl)-piperidin-4-yl; 3-fluoro-1-methyl-piperidin-4-yl; 1-ethyl-3-fluoro-piperidin-4-yl; pyridin-3-ylmethyl; 6-methyl-pyridin-2-ylmethyl; 2-(morpholin-1-yl)-1,1,dimethyl-ethyl; pyrimdin-2-yl-methyl; 3-fluoro-1-(oxetan-3-yl)-piperidin-4-yl; 1-(oxetan-3-yl)-piperidin-3-yl; 1-([1,3]Dioxolan-2-ylmethyl)-piperidin-4-yl; pyridazin-3-ylmethyl; piperidin-3-yl; pyrazin-2-ylmethyl; 2-hydroxy-3-methyl-butan-1-yl; 1-([1,3]Dioxolan-2-ylmethyl)-pyrrolidin-3-yl; pyrimidin-4-ylmethyl; 1-methyl-1H-pyrazol-3-ylmethyl; 1-methyl-1-(4H-[1,2,4]triazol-3-yl)-ethyl; 1-methyl-1-(5-methyl-4H-[1,2,4]triazol-3-yl)-ethyl; 3-fluoro-piperidin-4-yl; 2-hydroxy-cyclopentyl; dimethyl-[1,3]dioxan-5-yl; 2-(5-methyl-1,3,4-oxadiazol-2-yl)propan-2-yl; 2-(4-methyl-4H-1,2,4-triazol-3-yl)propan-2-yl; 2-(1-methyl-1H-1,2,4-triazol-3-yl)propan-2-yl; 2-(1-methyl-1H-pyrazol-4-yl)propan-2-yl; 2-(1-methyl-1H-pyrazol-3-yl)propan-2-yl; 2-(1-methyl-1H-pyrazol-5-yl; 2-(4H-1,2,4-triazol-3-yl)propan-2-yl; or 1-methyl-1H-pyrazole-4-yl.

7. The compound of claim 1, wherein $R^5$ is $C_{1-6}$alkyl.

8. The compound of claim 1, wherein $R^5$ is hydrogen or methyl.

9. The compound of claim 1, wherein said compounds are of formula II

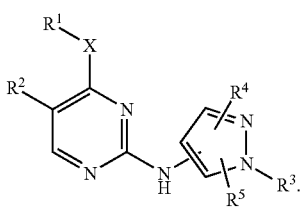

10. The compound of claim 1, wherein said compound is of formula III

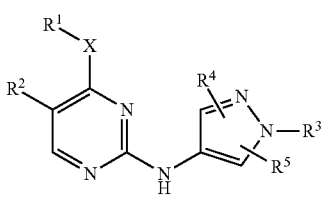

and wherein X, $R^1$, R, $R^2$, $R^3$, $R^4$ and $R^5$ are as recited in claim 1.

11. The compound of claim 1, wherein said compound is of formula IV

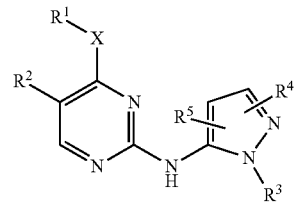

and wherein X, $R^1$, R, $R^2$, $R^3$, $R^4$ and $R^5$ are as recited in claim 1.

12. The compound of claim 1, wherein said compound is of formula V

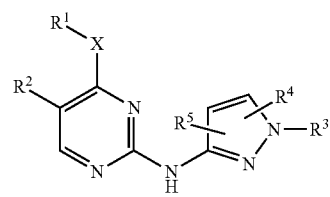

and wherein X, $R^1$, R, $R^2$, $R^3$, $R^4$ and $R^5$ are as recited in claim 1.

13. A composition comprising:
(a) a pharmaceutically acceptable carrier; and
(b) a compound of claim 1.

14. The compound of claim 10, wherein $R^1$ is methyl, ethyl or isopropyl.

15. The compound of claim 14, wherein $R^2$ is chloro; trifluoromethyl; or cyano.

16. The compound of claim 15, wherein $R^3$ is: methyl; ethyl; propyl; isopropyl; butyl; cyclopropyl; cyclopropylmethyl; cyclobutyl; methanesulfonyl; ethylsulfonyl; cyclopropylsulfonyl; sec-butylsulfonyl; morpholin-4-yl-ethyl; oxetan-3-yl; 2-methoxyethyl; 2-hydroxy-2-methyl-propyl; 3-hydroxy-2-methyl-propan-2-yl; 2-methoxy-propyl; tetrahydro-2H-pyran-4-yl; tetrahydrofuran-3-yl; 2,6-dimethyltetrahydro-2H-pyran-4-yl; tetrahydro-2H-pyran-3-yl); phenyl; 4-(methylsulfonyl)phenyl); 4-cyano-phenyl; 4-fluoro-phenyl; 4-chloro-phenyl; 3,5-difluorophenyl; 4-(dimethylamino-carbonyl)-phenyl); 4-(cyclopropylsulfonyl)phenyl; 2,2,2-trifluoroethyl; 2-fluoroethyl; difluoromethyl; 2-dimethyl-1,3-dioxan-5-yl; 1-methyl-cyclopropyl-carbonyl; 3-methylpyridin-4-yl; 2-methylpyridin-4-yl; pyridin-2-yl; pyrimidin-2-yl; pyrimidin-5-yl; pyridin-2-ylmethyl; 1-(pyridin-2-yl)ethyl; cyclopropylsulfonyl; 1-cyano-1-methyl-ethyl; 2-cyano-ethyl; 1-cyano-ethyl; 2-cyano-2-methyl-propyl; 1-(2,2,2-trifluoroethyl)piperidin-4-yl; 1-(methylsulfonyl)azetidin-3-yl; (3-methyloxetan-3-yl)methyl; (1S,5S)-8-oxabicyclo[3.2.1]octan-3-yl; 1-(oxetan-3-yl)piperidin-4-yl; 1-acetyl-piperidin-4-yl; 1-(cyclopropyl-carbonyl)-piperidin-4-yl; 1-methyl-piperidin-4-yl; 1-methyl-2-oxo-piperidin-5-yl; 2-oxo-piperidin-5-yl; 1-(isopropyl-carbonyl)-piperidin-4-yl; 1-(oxetan-3-yl)azetidin-3-yl; 1-(cyclopropyl-carbonyl)-piperidin-4-yl; 2-methoxycyclopentyl; 3-methoxycyclopentyl; 1-methoxy-2-methylpropan-2-yl; tetrahydro-2H-1,1-dioxo-thiopyran-4-yl; 3-fluoro-1-(oxetan-3-yl)piperidin-4-yl; 1-methoxypropan-2-yl; 1-(2,2,2-trifluoroethyl)azetidin-3-yl); 1-(oxetan-3-yl)pyrrolidin-3-yl; 1-isopropylazetidin-3-yl; 3-fluoro-1-methylpiperidin-4-yl; 1-ethyl-3-fluoropiperidin-4-yl; 1-methylpyrrolidin-3-yl;

2-methoxyethyl)piperidin-4-yl); 1-methyl-1-(methylaminocarbonyl)-ethyl; 2-methyl-2-morpholino-propyl; 4,4-difluorocyclohexyl; morpholin-4-yl-carbonyl; dimethylamino-carbonyl-methyl; methylamino-carbonyl-methyl; 1-methyl-1-(dimethylamino-carbonyl)-ethyl; pyrrolidin-'-yl-carbonyl; 1-cyamo-cyclopropyl; 1-(pyrrolidin-'-yl-carbonyl)-ethyl; 1-(dimethylamino-carbonyl)-ethyl; 1-(methoxy-carbonyl)-ethyl; 1-(tert-butylamino-carbonyl)-1-methyl-ethyl; 1-(2,2,2-trifluoroethyllamino-carbonyl)-1-methyl-ethyl; 1-(ethylamino-carbonyl)-1-methyl-ethyl; 1-(cyclopropylmethylamino-carbonyl)-1-methyl-ethyl; 1-(ethylamino-carbonyl)-cyclobutyl; 1-(isopropylamino-carbonyl)-1-methyl-ethyl; 1-cyano-cyclobutyl; 2-methoxy-1-methyl-ethyl; 1-methyl-1-(methoxy-carbonyl)-ethyl; 2-methoxy-2-methyl-propan-1-yl; 1-(oxetan-3-yl)-pyrrolidin-3-yl; isopropylsulfonyl; butane-2-sulfonyl; 1-(2-fluoroethyl)-piperidin-4-yl; 3-fluoro-1-methyl-piperidin-4-yl; 1-ethyl-3-fluoro-piperidin-4-yl; pyridin-3-ylmethyl; 6-methyl-pyridin-2-ylmethyl; 2-(morpholin-1-yl)-1,1,dimethyl-ethyl; pyrimdin-2-yl-methyl; 3-fluoro-1-(oxetan-3-yl)-piperidin-4-yl; 1-(oxetan-3-yl)-piperidin-3-yl; 1-([1,3]Dioxolan-2-ylmethyl)-piperidin-4-yl; pyridazin-3-ylmethyl; piperidin-3-yl; pyrazin-2-ylmethyl; 2-hydroxy-3-methyl-butan-1-yl; 1-([1,3]Dioxolan-2-ylmethyl)-pyrrolidin-3-yl; pyrimidin-4-ylmethyl; 1-methyl-1H-pyrazol-3-ylmethyl; 1-methyl-1-(4H-[1,2,4]triazol-3-yl)-ethyl; 1-methyl-1-(5-methyl-4H[1,2,4]triazol-3-yl)-ethyl; 3-fluoro-piperidin-4-yl; 2-hydroxy-cyclopentyl; dimethyl-[1,3]dioxan-5-yl; 2-(5-methyl-1,3,4-oxadiazol-2-yl)propan-2-yl; 2-(4-methyl-4H-1,2,4-triazol-3-yl)propan-2-yl; 2-(1-methyl-1H-1,2,4-triazol-3-yl)propan-2-yl; 2-(1-methyl-1H-pyrazol-4-yl)propan-2-yl; 2-(1-methyl-1H-pyrazol-3-yl)propan-2-yl; 2-(1-methyl-1H-pyrazol-5-yl; 2-(4H-1,2,4-triazol-3-yl)propan-2-yl; or 1-methyl-1H-pyrazole-4-yl.

17. The compound of claim 15, wherein $R^5$ is hydrogen or methyl.

18. A compound selected from:
$N^2$-(1-isopropyl-1H-pyrazol-4-yl)-$N^4$-methyl-5-(trifluoromethyl)pyrimidine-2,4-diamine;
$N^2$-(1,5-dimethyl-1H-pyrazol-4-yl)-$N^4$-methyl-5-(trifluoromethyl)pyrimidine-2,4-diamine;
$N^4$-methyl-$N^2$-(1-(2-morpholinoethyl)-1H-pyrazol-4-yl)-5-(trifluoromethyl)pyrimidine-2,4-diamine;
$N^4$-methyl-$N^2$-(1-methyl-1H-pyrazol-4-yl)-5-(trifluoromethyl)pyrimidine-2,4-diamine;
5-chloro-$N^2$-(1-isopropyl-1H-pyrazol-4-yl)-$N^4$-methylpyrimidine-2,4-diamine;
$N^4$-methyl-$N^2$-(1-methyl-1H-pyrazol-5-yl)-5-(trifluoromethyl)pyrimidine-2,4-diamine;
$N^4$-methyl-$N^2$-(1-methyl-1H-pyrazol-3-yl)-5-(trifluoromethyl)pyrimidine-2,4-diamine;
$N^2$-(1,3-dimethyl-1H-pyrazol-4-yl)-$N^4$-methyl-5-(trifluoromethyl)pyrimidine-2,4-diamine;
5-Chloro-N-(1,5-dimethyl-1H-pyrazol-4-yl)-4-(tetrahydro-2H-pyran-4-yloxy)pyrimidin-2-amine;
$N^4$-methyl-5-(trifluoromethyl)-$N^2$-(1,3,5-trimethyl-1H-pyrazol-4-yl)pyrimidine-2,4-diamine;
5-Chloro-N-(1-isopropyl-1H-pyrazol-4-yl)-4-(tetrahydro-2H-pyran-4-yloxy)pyrimidin-2-amine;
5-Chloro-N-(1,5-dimethyl-1H-pyrazol-4-yl)-4-methoxypyrimidin-2-amine;
N-(1,5-dimethyl-1H-pyrazol-4-yl)-4-(pyrrolidin-1-yl)-5-(trifluoromethyl)pyrimidin-2-amine;
$N^2$-(1-ethyl-5-methyl-1H-pyrazol-4-yl)-$N^4$-methyl-5-(trifluoromethyl)pyrimidine-2,4-diamine;
5-Chloro-N-(1,3-dimethyl-1H-pyrazol-4-yl)-4-methoxypyrimidin-2-amine;
$N^4$-methyl-$N^2$-(3-methyl-1-(oxetan-3-yl)-1H-pyrazol-4-yl)-5-(trifluoromethyl)pyrimidine-2,4-diamine;
$N^2$-(5-chloro-1-methyl-1H-pyrazol-4-yl)-$N^4$-methyl-5-(trifluoromethyl)pyrimidine-2,4-diamine;
5-Chloro-4-methoxy-N-(3-methyl-1-(oxetan-3-yl)-1H-pyrazol-4-yl)pyrimidin-2-amine;
5-Chloro-4-methoxy-N-(1-(2-methoxyethyl)-3-methyl-1H-pyrazol-4-yl)pyrimidin-2-amine;
5-chloro-4-methoxy-N-(1-(2-methoxyethyl)-5-methyl-1H-pyrazol-4-yl)pyrimidin-2-amine;
5-Chloro-N-(5-chloro-1-methyl-1H-pyrazol-4-yl)-4-methoxypyrimidin-2-amine;
2-Methyl-1-(3-methyl-4-(4-(methylamino)-5-(trifluoromethyl)pyrimidin-2-ylamino)-1H-pyrazol-1-yl)propan-2-ol;
2-Methyl-1-(3-methyl-4-(4-(methylamino)-5-chloro-pyrimidin-2-ylamino)-1H-pyrazol-1-yl)propan-2-ol;
$N^2$-(1-(2-methoxyethyl)-3-methyl-1H-pyrazol-4-yl)-$N^4$-methyl-5-(trifluoromethyl)pyrimidine-2,4-diamine;
$N^2$-(1-(2-methoxyethyl)-5-methyl-1H-pyrazol-4-yl)-$N^4$-methyl-5-(trifluoromethyl)pyrimidine-2,4-diamine;
5-Chloro-N-(1-ethyl-3-methyl-1H-pyrazol-4-yl)-4-methoxypyrimidin-2-amine;
5-Chloro-$N^4$-methyl-$N^2$-(3-methyl-1-(oxetan-3-yl)-1H-pyrazol-4-yl)pyrimidine-2,4-diamine;
$N^2$-(1-isopropyl-3-methyl-1H-pyrazol-4-yl)-$N^4$-methyl-5-(trifluoromethyl)pyrimidine-2,4-diamine;
5-Chloro-N-(1-isopropyl-3-methyl-1H-pyrazol-4-yl)-4-methoxypyrimidin-2-amine;
5-Chloro-$N^2$-(1,3-dimethyl-1H-pyrazol-4-yl)-$N^4$-methylpyrimidine-2,4-diamine;
5-Chloro-$N^2$-(1-isopropyl-3-methyl-1H-pyrazol-4-yl)-$N^4$-methylpyrimidine-2,4-diamine;
$N^4$-methyl-$N^2$-(3-methyl-1-(tetrahydro-2H-pyran-4-yl)-1H-pyrazol-4-yl)-5-(trifluoromethyl)pyrimidine-2,4-diamine;
$N^4$-methyl-$N^2$-(5-methyl-1-(tetrahydro-2H-pyran-4-yl)-1H-pyrazol-4-yl)-5-(trifluoromethyl)pyrimidine-2,4-diamine;
$N^2$-(2-Ethyl-2H-pyrazol-3-yl)-5-fluoro-$N^4$-methyl-pyrimidine-2,4-diamine;
5-Fluoro-$N^4$-methyl-$N^2$-(2-methyl-2H-pyrazol-3-yl)-pyrimidine-2,4-diamine;
5-Fluoro-$N^4$-methyl-$N^4$-(2-propyl-2H-pyrazol-3-yl)-pyrimidine-2,4-diamine;
$N^2$-(2,5-Dimethyl-2H-pyrazol-3-yl)-5-fluoro-$N^4$-methyl-pyrimidine-2,4-diamine;
$N^2$-(3-isopropyl-1-methyl-1H-pyrazol-5-yl)-$N^4$-methyl-5-(trifluoromethyl)pyrimidine-2,4-diamine;
5-Chloro-N-(3-cyclopropyl-1-methyl-1H-pyrazol-5-yl)-4-methoxypyrimidin-2-amine;
$N^2$-(3-Cyclopropyl-1-methyl-1H-pyrazol-5-yl)-$N^4$-methyl-5-(trifluoromethyl)pyrimidine-2,4-diamine;
5-Chloro-N-(3-isopropyl-1-methyl-1H-pyrazol-5-yl)-4-methoxypyrimidin-2-amine;
5-Chloro-$N^2$-(5-isopropyl-2-methyl-2H-pyrazol-3-yl)-$N^4$-methyl-pyrimidine-2,4-diamine;
5-Chloro-4-methoxy-N-(1,3,5-trimethyl-1H-pyrazol-4-yl)pyrimidin-2-amine;
5-Chloro-$N^4$-methyl-$N^2$-(1,3,5-trimethyl-1H-pyrazol-4-yl)-pyrimidine-2,4-diamine;
5-Chloro-$N^2$-(5-cyclopropyl-2-methyl-2H-pyrazol-3-yl)-$N^4$-methyl-pyrimidine-2,4-diamine;
$N^4$-Methyl-$N^2$-(5-methyl-1-oxetan-3-yl-1H-pyrazol-4-yl)-5-trifluoromethyl-pyrimidine-2,4-diamine;
$N^2$-(1-isopropyl-1H-pyrazol-5-yl)-$N^4$-methyl-5-(trifluoromethyl)pyrimidine-2,4-diamine;

5-Chloro-N-(1-ethyl-5-methyl-1H-pyrazol-4-yl)-4-methoxypyrimidin-2-amine;
5-Chloro-$N^2$-(1-ethyl-5-methyl-1H-pyrazol-4-yl)-$N^4$-methylpyrimidine-2,4-diamine;
$N^2$-(1-ethyl-3-methyl-1H-pyrazol-4-yl)-$N^4$-methyl-5-(trifluoromethyl)pyrimidine-2,4-diamine;
5-Chloro-$N^2$-(1-ethyl-3-methyl-1H-pyrazol-4-yl)-$N^4$-methylpyrimidine-2,4-diamine;
5-chloro-$N^2$-(1-isopropyl-1H-pyrazol-5-yl)-$N^4$-methylpyrimidine-2,4-diamine;
5-chloro-N-(1-isopropyl-1H-pyrazol-5-yl)-4-methoxypyrimidin-2-amine;
5-chloro-4-methoxy-N-(3-methyl-1-(methylsulfonyl)-1H-pyrazol-4-yl)pyrimidin-2-amine;
$N^2$-(1-ethyl-1H-pyrazol-3-yl)-$N^4$-methyl-5-(trifluoromethyl)pyrimidine-2,4-diamine;
5-chloro-4-methoxy-N-(5-methyl-1-phenyl-1H-pyrazol-4-yl)pyrimidin-2-amine;
$N^2$-(1-isopropyl-1H-pyrazol-3-yl)-N4-methyl-5-(trifluoromethyl)pyrimidine-2,4-diamine;
$N^4$-methyl-$N^2$-(5-methyl-1-(2,2,2-trifluoroethyl)-1H-pyrazol-4-yl)-5-(trifluoromethyl)pyrimidine-2,4-diamine;
$N^2$-(1-(2,2-dimethyl-1,3-dioxan-5-yl)-3-methyl-1H-pyrazol-4-yl)-N4-methyl-5-(trifluoromethyl)pyrimidine-2,4-diamine;
5-chloro-4-methoxy-N-(5-methyl-1-(4-(methylsulfonyl)phenyl)-1H-pyrazol-4-yl)pyrimidin-2-amine;
$N^4$-ethyl-$N^2$-(1-methyl-1H-pyrazol-3-yl)-5-(trifluoromethyl)pyrimidine-2,4-diamine;
5-chloro-N-(1,5-dimethyl-1H-pyrazol-4-yl)-4-(oxetan-3-yloxy)pyrimidin-2-amine;
5-chloro-4-(2,2-difluoroethoxy)-N-(1,5-dimethyl-1H-pyrazol-4-yl)pyrimidin-2-amine;
5-chloro-N-(1,5-dimethyl-1H-pyrazol-4-yl)-4-(2,2,2-trifluoroethoxy)pyrimidin-2-amine;
5-chloro-4-methoxy-N-(3-methyl-1-(tetrahydro-2H-pyran-4-yl)-1H-pyrazol-4-yl)pyrimidin-2-amine;
(4-(4-(5-chloro-4-methoxypyrimidin-2-ylamino)-3-methyl-1H-pyrazol-1-yl)piperidin-1-yl)(1-methylcyclopropyl)methanone;
(4-(4-(5-chloro-4-methoxypyrimidin-2-ylamino)-5-methyl-1H-pyrazol-1-yl)piperidin-1-yl)(1-methylcyclopropyl)methanone;
4-(4-(5-chloro-4-methoxypyrimidin-2-ylamino)-3-methyl-1H-pyrazol-1-yl)benzonitrile;
5-chloro-4-methoxy-N-(3-methyl-1-(3-methylpyridin-4-yl)-1H-pyrazol-4-yl)pyrimidin-2-amine;
5-chloro-N-(1-(cyclopropylsulfonyl)-5-methyl-1H-pyrazol-4-yl)-4-methoxypyrimidin-2-amine;
5-chloro-N-(1-(cyclopropylsulfonyl)-3-methyl-1H-pyrazol-4-yl)-4-methoxypyrimidin-2-amine;
2-(4-(5-chloro-4-methoxypyrimidin-2-ylamino)-5-methyl-1H-pyrazol-1-yl)-2-methylpropanenitrile;
2-(4-(5-chloro-4-methoxypyrimidin-2-ylamino)-3-methyl-1H-pyrazol-1-yl)-2-methylpropanenitrile;
5-chloro-4-ethoxy-N-(5-methyl-1-(tetrahydro-2H-pyran-4-yl)-1H-pyrazol-4-yl)pyrimidin-2-amine;
(5-Chloro-4-methoxy-pyrimidin-2-yl)-[1-(4-methanesulfonyl-phenyl)-3-methyl-1H-pyrazol-4-yl]-amine;
(5-Chloro-4-methoxy-pyrimidin-2-yl)-(3-methyl-1-phenyl-1H-pyrazol-4-yl)-amine;
(4-Methoxy-5-trifluoromethyl-pyrimidin-2-yl)-(3-methyl-1-phenyl-1H-pyrazol-4-yl)-amine;
(4-Methoxy-5-trifluoromethyl-pyrimidin-2-yl)-(5-methyl-1-phenyl-1H-pyrazol-4-yl)-amine;
(5-Chloro-4-methoxy-pyrimidin-2-yl)-(1-methanesulfonyl-3-methyl-1H-pyrazol-4-yl)-amine;
(5-Chloro-4-methoxy-pyrimidin-2-yl)-[5-methyl-1-(tetrahydro-pyran-4-yl)-1H-pyrazol-4-yl]-amine;
4-[4-(5-Chloro-4-methoxy-pyrimidin-2-ylamino)-3-methyl-pyrazol-1-yl]-N,N-dimethyl-benzamide;
4-[4-(5-Chloro-4-methoxy-pyrimidin-2-ylamino)-5-methyl-pyrazol-1-yl]-N,N-dimethyl-benzamide;
4-[4-(5-Chloro-4-methoxy-pyrimidin-2-ylamino)-5-methyl-pyrazol-1-yl]-benzonitrile;
$N^2$-(5-Methoxy-1-methyl-1H-pyrazol-4-yl)-$N^4$-methyl-5-trifluoromethyl-pyrimidine-2,4-diamine;
(5-Chloro-4-methoxy-pyrimidin-2-yl)-[5-chloro-1-(tetrahydro-pyran-4-yl)-1H-pyrazol-4-yl]-amine;
(5-Chloro-4-methoxy-pyrimidin-2-yl)-{1-[1-(2-fluoro-ethyl)-piperidin-4-yl]-3-methyl-1H-pyrazol-4-yl}-amine;
$N^2$-[1-(1-[1,3]Dioxolan-2-ylmethyl-piperidin-4-yl)-5-methyl-1H-pyrazol-4-yl]-$N^4$-ethyl-5-trifluoromethyl-pyrimidine-2,4-diamine;
$N^2$-[1-(1-[1,3]Dioxolan-2-ylmethyl-piperidin-4-yl)-3-methyl-1H-pyrazol-4-yl]-$N^4$-ethyl-5-trifluoromethyl-pyrimidine-2,4-diamine;
5-bromo-$N^2$-(1,5-dimethyl-1H-pyrazol-4-yl)-$N^4$-methylpyrimidine-2,4-diamine;
$N^2$-(1,3-Dimethyl-1H-pyrazol-4-yl)-5-iodo-$N^4$-methyl-pyrimidine-2,4-diamine;
N4-methyl-N2-(5-methyl-1-(1-(2,2,2-trifluoroethyl)piperidin-4-yl)-1H-pyrazol-4-yl)-5-(trifluoromethyl)pyrimidine-2,4-diamine;
N4-methyl-N2-(3-methyl-1-(1-(2,2,2-trifluoroethyl)piperidin-4-yl)-1H-pyrazol-4-yl)-5-(trifluoromethyl)pyrimidine-2,4-diamine;
5-bromo-N4-methyl-N2-(5-methyl-1-(1-(2,2,2-trifluoroethyl)piperidin-4-yl)-1H-pyrazol-4-yl)pyrimidine-2,4-diamine;
5-bromo-N4-methyl-N2-(3-methyl-1-(1-(2,2,2-trifluoroethyl)piperidin-4-yl)-1H-pyrazol-4-yl)pyrimidine-2,4-diamine;
5-bromo-N4-methyl-N2-(3-methyl-1-(2,2,2-trifluoroethyl)-1H-pyrazol-4-yl)pyrimidine-2,4-diamine;
5-bromo-N4-methyl-N2-(5-methyl-1-(2,2,2-trifluoroethyl)-1H-pyrazol-4-yl)pyrimidine-2,4-diamine;
N4-ethyl-N2-(3-methyl-1-(oxetan-3-yl)-1H-pyrazol-4-yl)-5-(trifluoromethyl)pyrimidine-2,4-diamine;
5-chloro-N4-ethyl-N2-(3-methyl-1-(oxetan-3-yl)-1H-pyrazol-4-yl)pyrimidine-2,4-diamine;
5-bromo-N4-methyl-N2-(1-methyl-1H-pyrazol-5-yl)pyrimidine-2,4-diamine;
2-methyl-1-(5-methyl-4-(4-(methylamino)-5-(trifluoromethyl)pyrimidin-2-ylamino)-1H-pyrazol-1-yl)propan-2-ol;
5-chloro-N4-methyl-N2-(3-methyl-1-(methylsulfonyl)-1H-pyrazol-4-yl)pyrimidine-2,4-diamine;
N4-methyl-N2-(3-methyl-1-(methylsulfonyl)-1H-pyrazol-4-yl)-5-(trifluoromethyl)pyrimidine-2,4-diamine;
N4-methyl-N2-(3-methyl-1H-pyrazol-4-yl)-5-(trifluoromethyl)pyrimidine-2,4-diamine;
5-bromo-N4-ethyl-N2-(3-methyl-1-(oxetan-3-yl)-1H-pyrazol-4-yl)pyrimidine-2,4-diamine;
N2-(1-(difluoromethyl)-3-methyl-1H-pyrazol-4-yl)-N4-methyl-5-(trifluoromethyl)pyrimidine-2,4-diamine;
N2-(1-(difluoromethyl)-5-methyl-1H-pyrazol-4-yl)-N4-methyl-5-(trifluoromethyl)pyrimidine-2,4-diamine;
5-bromo-N4-ethyl-N2-(1-ethyl-5-methyl-1H-pyrazol-4-yl)pyrimidine-2,4-diamine;

5-bromo-N2-(1-(4-fluorophenyl)-3-methyl-1H-pyrazol-4-yl)-N4-methylpyrimidine-2,4-diamine;
5-bromo-N4-methyl-N2-(3-methyl-1-phenyl-1H-pyrazol-4-yl)pyrimidine-2,4-diamine;
5-bromo-N4-methyl-N2-(5-methyl-1-phenyl-1H-pyrazol-4-yl)pyrimidine-2,4-diamine;
5-bromo-N4-methyl-N2-(1-methyl-1H-pyrazol-4-yl)pyrimidine-2,4-diamine;
N4-methyl-N2-(3-methyl-1-(1-(methylsulfonyl)azetidin-3-yl)-1H-pyrazol-4-yl)-5-(trifluoromethyl)pyrimidine-2,4-diamine;
5-bromo-N4-methyl-N2-(3-methyl-1-propyl-1H-pyrazol-4-yl)pyrimidine-2,4-diamine;
5-chloro-N4-methyl-N2-(3-methyl-1-methyloxetan-3-yl)methyl)-1H-pyrazol-4-yl)pyrimidine-2,4-diamine;
5-bromo-N2-(1-(3,5-difluorophenyl)-5-methyl-1H-pyrazol-4-yl)-N4-methylpyrimidine-2,4-diamine;
5-bromo-N2-(1-(3,5-difluorophenyl)-3-methyl-1H-pyrazol-4-yl)-N4-methylpyrimidine-2,4-diamine;
N4-methyl-N2-(3-methyl-1-(pyridin-2-yl)-1H-pyrazol-4-yl)-5-(trifluoromethyl)pyrimidine-2,4-diamine;
N4-methyl-N2-(3-methyl-1-((3-methyloxetan-3-yl)methyl)-1H-pyrazol-4-yl)-5-(trifluoromethyl)pyrimidine-2,4-diamine;
N4-methyl-N2-(5-methyl-1-propyl-1H-pyrazol-4-yl)-5-(trifluoromethyl)pyrimidine-2,4-diamine;
N4-methyl-N2-(3-methyl-1-propyl-1H-pyrazol-4-yl)-5-(trifluoromethyl)pyrimidine-2,4-diamine;
5-bromo-N2-(1-isopropyl-3-methyl-1H-pyrazol-4-yl)-N4-methylpyrimidine-2,4-diamine;
5-bromo-N2-(1-(4-chlorophenyl)-5-methyl-1H-pyrazol-4-yl)-N4-methylpyrimidine-2,4-diamine;
N2-(1-(4-chlorophenyl)-5-methyl-1H-pyrazol-4-yl)-N4-methyl-5-(trifluoromethyl)pyrimidine-2,4-diamine;
N4-methyl-N2-(3-methyl-1-(4-(methylsulfonyl)phenyl)-1H-pyrazol-4-yl)-5-(trifluoromethyl)pyrimidine-2,4-diamine;
N4-methyl-N2-(5-methyl-1-(4-(methylsulfonyl)phenyl)-1H-pyrazol-4-yl)-5-(trifluoromethyl)pyrimidine-2,4-diamine;
N2-(1-((1S,5S)-8-oxabicyclo[3.2.1]octan-3-yl)-3-methyl-1H-pyrazol-4-yl)-N4-methyl-5-(trifluoromethyl)pyrimidine-2,4-diamine;
N2-(1-butyl-5-methyl-1H-pyrazol-4-yl)-N4-methyl-5-(trifluoromethyl)pyrimidine-2,4-diamine;
N4-methyl-N2-(3-methyl-1-(pyrimidin-2-yl)-1H-pyrazol-4-yl)-5-(trifluoromethyl)pyrimidine-2,4-diamine;
N2-(1-(4-chlorophenyl)-3-methyl-1H-pyrazol-4-yl)-N4-methyl-5-(trifluoromethyl)pyrimidine-2,4-diamine;
N2-(1-(2-fluoroethyl)-3-methyl-1H-pyrazol-4-yl)-N4-methyl-5-(trifluoromethyl)pyrimidine-2,4-diamine;
N4-methyl-N2-(3-methyl-1-(1-(oxetan-3-yl)piperidin-4-yl)-1H-pyrazol-4-yl)-5-(trifluoromethyl)pyrimidine-2,4-diamine;
N4-methyl-N2-(5-methyl-1-(1-(oxetan-3-yl)piperidin-4-yl)-1H-pyrazol-4-yl)-5-(trifluoromethyl)pyrimidine-2,4-diamine;
N2-(1-(2-fluoroethyl)-5-methyl-1H-pyrazol-4-yl)-N4-methyl-5-(trifluoromethyl)pyrimidine-2,4-diamine;
1-(4-(4-(4-(ethylamino)-5-(trifluoromethyl)pyrimidin-2-ylamino)-3-methyl-1H-pyrazol-1-yl)piperidin-1-yl)ethanone;
Cyclopropyl(4-(5-methyl-4-(4-(methylamino)-5-(trifluoromethyl)pyrimidin-2-ylamino)-1H-pyrazol-1-yl)piperidin-1-yl)methanone;
Cyclopropyl(4-(3-methyl-4-(4-(methylamino)-5-(trifluoromethyl)pyrimidin-2-ylamino)-1H-pyrazol-1-yl)piperidin-1-yl)methanone;
1-(4-(4-(4-(ethylamino)-5-(trifluoromethyl)pyrimidin-2-ylamino)-5-methyl-1H-pyrazol-1-yl)piperidin-1-yl)ethanone;
N2-(5-chloro-1-isopropyl-1H-pyrazol-4-yl)-N4-methyl-5-(trifluoromethyl)pyrimidine-2,4-diamine;
N2-(5-chloro-1-ethyl-1H-pyrazol-4-yl)-N4-methyl-5-(trifluoromethyl)pyrimidine-2,4-diamine;
N4-methyl-N2-(3-methyl-1-(pyrimidin-5-yl)-1H-pyrazol-4-yl)-5-(trifluoromethyl)pyrimidine-2,4-diamine;
N4-methyl-N2-(4-methyl-1-(1-methylpiperidin-4-yl)-1H-pyrazol-3-yl)-5-(trifluoromethyl)pyrimidine-2,4-diamine;
N4-methyl-N2-(5-methyl-1-(2-methylpyridin-4-yl)-1H-pyrazol-4-yl)-5-(trifluoromethyl)pyrimidine-2,4-diamine;
N4-methyl-N2-(3-methyl-1-(2-methylpyridin-4-yl)-1H-pyrazol-4-yl)-5-(trifluoromethyl)pyrimidine-2,4-diamine;
N4-ethyl-N2-(3-methyl-1-((3-methyloxetan-3-yl)methyl)-1H-pyrazol-4-yl)-5-(trifluoromethyl)pyrimidine-2,4-diamine;
N2-(5-chloro-1-cyclopropyl-1H-pyrazol-4-yl)-N4-methyl-5-(trifluoromethyl)pyrimidine-2,4-diamine;
N2-(5-chloro-1-(cyclopropylmethyl)-1H-pyrazol-4-yl)-N4-methyl-5-(trifluoromethyl)pyrimidine-2,4-diamine;
4-(5-methyl-4-(4-(methylamino)-5-(trifluoromethyl)pyrimidin-2-ylamino)-1H-pyrazol-1-yl)benzonitrile;
4-(3-methyl-4-(4-(methylamino)-5-(trifluoromethyl)pyrimidin-2-ylamino)-1H-pyrazol-1-yl)benzonitrile;
N4-methyl-N2-(3-methyl-1-(tetrahydrofuran-3-yl)-1H-pyrazol-4-yl)-5-(trifluoromethyl)pyrimidine-2,4-diamine;
N4-methyl-N2-(5-methyl-1-(tetrahydrofuran-3-yl)-1H-pyrazol-4-yl)-5-(trifluoromethyl)pyrimidine-2,4-diamine;
5-(4-(4-(ethylamino)-5-(trifluoromethyl)pyrimidin-2-ylamino)-5-methyl-1H-pyrazol-1-yl)-1-methylpiperidin-2-one;
5-(4-(4-(ethylamino)-5-(trifluoromethyl)pyrimidin-2-ylamino)-3-methyl-1H-pyrazol-1-yl)-1-methylpiperidin-2-one;
5-(3-methyl-4-(4-(methylamino)-5-(trifluoromethyl)pyrimidin-2-ylamino)-1H-pyrazol-1-yl)piperidin-2-one;
5-(5-methyl-4-(4-(methylamino)-5-(trifluoromethyl)pyrimidin-2-ylamino)-1H-pyrazol-1-yl)piperidin-2-one;
N2-(1-isopropyl-5-methyl-1H-pyrazol-4-yl)-N4-methyl-5-(trifluoromethyl)pyrimidine-2,4-diamine;
N,N-dimethyl-4-(5-methyl-4-(4-(methylamino)-5-(trifluoromethyl)pyrimidin-2-ylamino)-1H-pyrazol-1-yl)benzamide;
4-(4-(4-(ethylamino)-5-(trifluoromethyl)pyrimidin-2-ylamino)-5-methyl-1H-pyrazol-1-yl)-N,N-dimethylbenzamide;
N4-ethyl-N2-(5-methyl-1-(tetrahydro-2H-pyran-4-yl)-1H-pyrazol-4-yl)-5-(trifluoromethyl)pyrimidine-2,4-diamine;
N4-ethyl-N2-(3-methyl-1-(tetrahydro-2H-pyran-4-yl)-1H-pyrazol-4-yl)-5-(trifluoromethyl)pyrimidine-2,4-diamine;
N4-ethyl-N2-(3-methyl-1-(methylsulfonyl)-1H-pyrazol-4-yl)-5-(trifluoromethyl)pyrimidine-2,4-diamine;
N2-(1-(4-(cyclopropylsulfonyl)phenyl)-3-methyl-1H-pyrazol-4-yl)-N4-methyl-5-(trifluoromethyl)pyrimidine-2,4-diamine;

4-(4-(4-(ethylamino)-5-(trifluoromethyl)pyrimidin-2-ylamino)-5-methyl-1H-pyrazol-1-yl)benzonitrile;
N4-ethyl-N2-(5-methyl-1-(4-(methylsulfonyl)phenyl)-1H-pyrazol-4-yl)-5-(trifluoromethyl)pyrimidine-2,4-diamine;
N,N-dimethyl-4-(3-methyl-4-(4-(methylamino)-5-(trifluoromethyl)pyrimidin-2-ylamino)-1H-pyrazol-1-yl)benzamide;
N2-(1-(cyclopropylmethyl)-5-methyl-1H-pyrazol-4-yl)-N4-methyl-5-(trifluoromethyl)pyrimidine-2,4-diamine;
N2-(1-(cyclopropylmethyl)-3-methyl-1H-pyrazol-4-yl)-N4-methyl-5-(trifluoromethyl)pyrimidine-2,4-diamine;
N2-(1-(4-(cyclopropylsulfonyl)phenyl)-5-methyl-1H-pyrazol-4-yl)-N4-methyl-5-(trifluoromethyl)pyrimidine-2,4-diamine;
N2-(5-chloro-1-(oxetan-3-yl)-1H-pyrazol-4-yl)-N4-methyl-5-(trifluoromethyl)pyrimidine-2,4-diamine;
N4-ethyl-N2-(5-methyl-1-((3-methyloxetan-3-yl)methyl)-1H-pyrazol-4-yl)-5-(trifluoromethyl)pyrimidine-2,4-diamine;
N2-(1-(cyclopropylsulfonyl)-3-methyl-1H-pyrazol-4-yl)-N4-methyl-5-(trifluoromethyl)pyrimidine-2,4-diamine;
N2-(1-(cyclopropylsulfonyl)-3-methyl-1H-pyrazol-4-yl)-N4-ethyl-5-(trifluoromethyl)pyrimidine-2,4-diamine;
5-chloro-N4-(2,2-difluoroethyl)-N2-(1,5-dimethyl-1H-pyrazol-4-yl)pyrimidine-2,4-diamine;
5-chloro-4-methyl-N-(3-methyl-1-(4-(methylsulfonyl)phenyl)-1H-pyrazol-4-yl)pyrimidin-2-amine;
N2-(1-(4-(cyclopropylsulfonyl)phenyl)-5-methyl-1H-pyrazol-4-yl)-N4-ethyl-5-(trifluoromethyl)pyrimidine-2,4-diamine;
2-methyl-1-(4-(5-methyl-4-(4-(methylamino)-5-(trifluoromethyl)pyrimidin-2-ylamino)-1H-pyrazol-1-yl)piperidin-1-yl)propan-1-one;
N4-ethyl-N2-(1-methyl-1H-pyrazol-5-yl)-5-(trifluoromethyl)pyrimidine-2,4-diamine;
N2-(3-cyclopropyl-1-methyl-1H-pyrazol-4-yl)-N4-methyl-5-(trifluoromethyl)pyrimidine-2,4-diamine;
N2-(5-cyclopropyl-1-methyl-1H-pyrazol-4-yl)-N4-methyl-5-(trifluoromethyl)pyrimidine-2,4-diamine;
N4-methyl-N2-(5-methyl-1-((3-methyloxetan-3-yl)methyl)-1H-pyrazol-4-yl)-5-(trifluoromethyl)pyrimidine-2,4-diamine;
N2-(5-chloro-1-((3-methyloxetan-3-yl)methyl)-1H-pyrazol-4-yl)-N4-methyl-5-(trifluoromethyl)pyrimidine-2,4-diamine;
1-(4-(4-(4-(ethylamino)-5-(trifluoromethyl)pyrimidin-2-ylamino)-5-methyl-1H-pyrazol-1-yl)piperidin-1-yl)-2-methylpropan-1-one;
N4-ethyl-N2-(3-methyl-1-(1-(oxetan-3-yl)azetidin-3-yl)-1H-pyrazol-4-yl)-5-(trifluoromethyl)pyrimidine-2,4-diamine;
Cyclopropyl(4-(4-(4-(ethylamino)-5-(trifluoromethyl)pyrimidin-2-ylamino)-3-methyl-1H-pyrazol-1-yl)piperidin-1-yl)methanone;
Cyclopropyl(4-(4-(4-(ethylamino)-5-(trifluoromethyl)pyrimidin-2-ylamino)-5-methyl-1H-pyrazol-1-yl)piperidin-1-yl)methanone;
1-(5-chloro-4-(4-(methylamino)-5-(trifluoromethyl)pyrimidin-2-ylamino)-1H-pyrazol-1-yl)-2-methylpropan-2-ol;
N4-ethyl-N2-(1-ethyl-1H-pyrazol-3-yl)-5-(trifluoromethyl)pyrimidine-2,4-diamine;
(S)—N2-(1-(2-methoxypropyl)-5-methyl-1H-pyrazol-4-yl)-N4-methyl-5-(trifluoromethyl)pyrimidine-2,4-diamine;
N2-(1-(2-methoxycyclopentyl)-3-methyl-1H-pyrazol-4-yl)-N4-methyl-5-(trifluoromethyl)pyrimidine-2,4-diamine;
(S)—N2-(1-(2-methoxypropyl)-3-methyl-1H-pyrazol-4-yl)-N4-methyl-5-(trifluoromethyl)pyrimidine-2,4-diamine;
N2-(1-(1-methoxy-2-methylpropan-2-yl)-3-methyl-1H-pyrazol-4-yl)-N4-methyl-5-(trifluoromethyl)pyrimidine-2,4-diamine;
N2-(1-(2,6-dimethyltetrahydro-2H-pyran-4-yl)-3-methyl-1H-pyrazol-4-yl)-N4-methyl-5-(trifluoromethyl)pyrimidine-2,4-diamine;
(R)—N2-(1-(2-methoxypropyl)-5-methyl-1H-pyrazol-4-yl)-N4-methyl-5-(trifluoromethyl)pyrimidine-2,4-diamine;
N2-(1-(3-methoxycyclopentyl)-3-methyl-1H-pyrazol-4-yl)-N4-methyl-5-(trifluoromethyl)pyrimidine-2,4-diamine;
N4-methyl-N2-(1-methyl-5-(methylamino)-1H-pyrazol-4-yl)-5-(trifluoromethyl)pyrimidine-2,4-diamine;
N4-methyl-N2-(5-methyl-1-(methylsulfonyl)-1H-pyrazol-4-yl)-5-(trifluoromethyl)pyrimidine-2,4-diamine;
N4-methyl-N2-(5-methyl-1-(tetrahydro-2H-1,1-dioxothiopyran-4-yl)-1H-pyrazol-4-yl)-5-(trifluoromethyl)pyrimidine-2,4-diamine;
2-methyl-1-(4-(4-(methylamino)-5-(trifluoromethyl)pyrimidin-2-ylamino)-5-(trifluoromethyl)-1H-pyrazol-1-yl)propan-2-ol;
2-methyl-1-(4-(4-(methylamino)-5-(trifluoromethyl)pyrimidin-2-ylamino)-3-(trifluoromethyl)-1H-pyrazol-1-yl)propan-2-ol;
N2-(1-(3-fluoro-1-(oxetan-3-yl)piperidin-4-yl)-3-methyl-1H-pyrazol-4-yl)-N4-methyl-5-(trifluoromethyl)pyrimidine-2,4-diamine;
(R)—N2-(1-(1-methoxypropan-2-yl)-3-methyl-1H-pyrazol-4-yl)-N4-methyl-5-(trifluoromethyl)pyrimidine-2,4-diamine;
1-(3-tert-butyl-4-(4-(ethylamino)-5-(trifluoromethyl)pyrimidin-2-ylamino)-1H-pyrazol-1-yl)-2-methylpropan-2-ol;
N4-methyl-N2-(3-methyl-1-(1-(2,2,2-trifluoroethyl)azetidin-3-yl)-1H-pyrazol-4-yl)-5-(trifluoromethyl)pyrimidine-2,4-diamine;
N2-(1-(1-methoxy-2-methylpropan-2-yl)-5-methyl-1H-pyrazol-4-yl)-N4-methyl-5-(trifluoromethyl)pyrimidine-2,4-diamine;
(R)—N4-methyl-N2-(3-methyl-1-(1-(oxetan-3-yl)pyrrolidin-3-yl)-1H-pyrazol-4-yl)-5-(trifluoromethyl)pyrimidine-2,4-diamine;
(R)—N2-(1-(1-methoxypropan-2-yl)-5-methyl-1H-pyrazol-4-yl)-N4-methyl-5-(trifluoromethyl)pyrimidine-2,4-diamine;
N4-methyl-N2-(4-methyl-1H-pyrazol-5-yl)-5-(trifluoromethyl)pyrimidine-2,4-diamine;
N4-ethyl-N2-(5-methyl-1-(1-methylpiperidin-4-yl)-1H-pyrazol-4-yl)-5-(trifluoromethyl)pyrimidine-2,4-diamine;
N4-ethyl-N2-(3-methyl-1-(1-methylpiperidin-4-yl)-1H-pyrazol-4-yl)-5-(trifluoromethyl)pyrimidine-2,4-diamine;
N4-methyl-N2-(3-methyl-1-(1-methylpiperidin-4-yl)-1H-pyrazol-4-yl)-5-(trifluoromethyl)pyrimidine-2,4-diamine;
N4-methyl-N2-(5-methyl-1-(1-methylpiperidin-4-yl)-1H-pyrazol-4-yl)-5-(trifluoromethyl)pyrimidine-2,4-diamine;

(R)—N4-methyl-N2-(5-methyl-1-(1-(oxetan-3-yl)pyrrolidin-3-yl)-1H-pyrazol-4-yl)-5-(trifluoromethyl)pyrimidine-2,4-diamine;
N4-methyl-N2-(5-methyl-1-(pyridin-2-ylmethyl)-1H-pyrazol-4-yl)-5-(trifluoromethyl)pyrimidine-2,4-diamine;
N4-methyl-N2-(3-methyl-1-(pyridin-2-ylmethyl)-1H-pyrazol-4-yl)-5-(trifluoromethyl)pyrimidine-2,4-diamine;
N2-(1-(1-isopropylazetidin-3-yl)-3-methyl-1H-pyrazol-4-yl)-N4-methyl-5-(trifluoromethyl)pyrimidine-2,4-diamine;
1-methyl-4-(4-(methylamino)-5-(trifluoromethyl)pyrimidin-2-ylamino)-1H-pyrazole-5-carbonitrile;
N4-ethyl-N2-(1-(isopropylsulfonyl)-3-methyl-1H-pyrazol-4-yl)-5-(trifluoromethyl)pyrimidine-2,4-diamine;
N2-(1-(isopropylsulfonyl)-3-methyl-1H-pyrazol-4-yl)-N4-methyl-5-(trifluoromethyl)pyrimidine-2,4-diamine;
N2-(1-(isopropylsulfonyl)-5-methyl-1H-pyrazol-4-yl)-N4-methyl-5-(trifluoromethyl)pyrimidine-2,4-diamine;
N2-(1-(sec-butylsulfonyl)-5-methyl-1H-pyrazol-4-yl)-N4-methyl-5-(trifluoromethyl)pyrimidine-2,4-diamine;
N2-(1-(sec-butylsulfonyl)-3-methyl-1H-pyrazol-4-yl)-N4-methyl-5-(trifluoromethyl)pyrimidine-2,4-diamine;
1-(4-(4-(ethylamino)-5-(trifluoromethyl)pyrimidin-2-ylamino)-3-isopropyl-1H-pyrazol-1-yl)-2-methylpropan-2-ol;
N2-(1-(3-fluoro-1-methylpiperidin-4-yl)-3-methyl-1H-pyrazol-4-yl)-N4-methyl-5-(trifluoromethyl)pyrimidine-2,4-diamine;
N2-(5-isopropyl-1-methyl-1H-pyrazol-4-yl)-N4-methyl-5-(trifluoromethyl)pyrimidine-2,4-diamine;
N4-methyl-N2-(3-methyl-1-(1-(pyridin-2-yl)ethyl)-1H-pyrazol-4-yl)-5-(trifluoromethyl)pyrimidine-2,4-diamine;
N4-methyl-N2-(5-methyl-1-(1-(pyridin-2-yl)ethyl)-1H-pyrazol-4-yl)-5-(trifluoromethyl)pyrimidine-2,4-diamine;
N2-(5-chloro-1-(tetrahydro-2H-pyran-4-yl)-1H-pyrazol-4-yl)-N4-methyl-5-(trifluoromethyl)pyrimidine-2,4-diamine;
N2-(3-isopropyl-1-methyl-1H-pyrazol-4-yl)-N4-methyl-5-(trifluoromethyl)pyrimidine-2,4-diamine;
N2-(3-cyclobutyl-1-methyl-1H-pyrazol-4-yl)-N4-methyl-5-(trifluoromethyl)pyrimidine-2,4-diamine;
N2-(5-cyclobutyl-1-methyl-1H-pyrazol-4-yl)-N4-methyl-5-(trifluoromethyl)pyrimidine-2,4-diamine;
N4-methyl-N2-(3-methyl-1-(tetrahydro-2H-pyran-3-yl)-1H-pyrazol-4-yl)-5-(trifluoromethyl)pyrimidine-2,4-diamine;
N4-methyl-N2-(5-methyl-1-(tetrahydro-2H-pyran-3-yl)-1H-pyrazol-4-yl)-5-(trifluoromethyl)pyrimidine-2,4-diamine;
N2-(1,5-dimethyl-1H-pyrazol-4-yl)-N4-((tetrahydro-2H-pyran-4-yl)methyl)-5-(trifluoromethyl)pyrimidine-2,4-diamine;
(R)—N4-methyl-N2-(3-methyl-1-(1-methylpyrrolidin-3-yl)-1H-pyrazol-4-yl)-5-(trifluoromethyl)pyrimidine-2,4-diamine;
1-(5-chloro-4-(4-(ethylamino)-5-(trifluoromethyl)pyrimidin-2-ylamino)-1H-pyrazol-1-yl)-2-methylpropan-2-ol;
1-(3-cyclopropyl-4-(4-(methylamino)-5-(trifluoromethyl)pyrimidin-2-ylamino)-1H-pyrazol-1-yl)-2-methylpropan-2-ol;
1-(3-cyclopropyl-4-(4-(ethylamino)-5-(trifluoromethyl)pyrimidin-2-ylamino)-1H-pyrazol-1-yl)-2-methylpropan-2-ol;
2-(5-chloro-4-(4-(methylamino)-5-(trifluoromethyl)pyrimidin-2-ylamino)-1H-pyrazol-1-yl)-N,2-dimethylpropanamide;
N2-(1-(1-(2-methoxyethyl)piperidin-4-yl)-3-methyl-1H-pyrazol-4-yl)-N4-methyl-5-(trifluoromethyl)pyrimidine-2,4-diamine;
N2-(1-(1-(2-methoxyethyl)piperidin-4-yl)-5-methyl-1H-pyrazol-4-yl)-N4-methyl-5-(trifluoromethyl)pyrimidine-2,4-diamine;
(R)—N4-methyl-N2-(5-methyl-1-(1-methylpyrrolidin-3-yl)-1H-pyrazol-4-yl)-5-(trifluoromethyl)pyrimidine-2,4-diamine;
N2-(5-chloro-1-(3-fluoro-1-methylpiperidin-4-yl)-1H-pyrazol-4-yl)-N4-methyl-5-(trifluoromethyl)pyrimidine-2,4-diamine;
N2-(5-chloro-1-(1-ethyl-3-fluoropiperidin-4-yl)-1H-pyrazol-4-yl)-N4-methyl-5-(trifluoromethyl)pyrimidine-2,4-diamine;
N4-ethyl-N2-(1-(ethylsulfonyl)-3-methyl-1H-pyrazol-4-yl)-5-(trifluoromethyl)pyrimidine-2,4-diamine;
N4-ethyl-N2-(1-(ethylsulfonyl)-5-methyl-1H-pyrazol-4-yl)-5-(trifluoromethyl)pyrimidine-2,4-diamine;
N4-methyl-N2-(3-methyl-1-(2-methyl-2-morpholinopropyl)-1H-pyrazol-4-yl)-5-(trifluoromethyl)pyrimidine-2,4-diamine;
N2-(1-(1-ethyl-3-fluoropiperidin-4-yl)-3-methyl-1H-pyrazol-4-yl)-N4-methyl-5-(trifluoromethyl)pyrimidine-2,4-diamine;
N2-(5-(dimethylamino)-1-methyl-1H-pyrazol-4-yl)-N4-methyl-5-(trifluoromethyl)pyrimidine-2,4-diamine;
2-(5-chloro-4-(4-(methylamino)-5-(trifluoromethyl)pyrimidin-2-ylamino)-1H-pyrazol-1-yl)-2-methylpropan-1-ol;
$N^2$-(1-(ethylsulfonyl)-3-methyl-1H-pyrazol-4-yl)-N4-methyl-5-(trifluoromethyl)pyrimidine-2,4-diamine;
2-Methyl-1-[3-methyl-4-(4-methylamino-5-trifluoromethyl-pyrimidin-2-ylamino)-pyrazol-1-yl]-propan-2-ol;
N2-[1-(2-Methoxy-ethyl)-3-methyl-1H-pyrazol-4-yl]-N4-methyl-5-trifluoromethyl-pyrimidine-2,4-diamine;
N2-[1-(2-Methoxy-ethyl)-5-methyl-1H-pyrazol-4-yl]-N4-methyl-5-trifluoromethyl-pyrimidine-2,4-diamine;
5-Bromo-N2-(1-ethyl-3-methyl-1H-pyrazol-4-yl)-N4-methyl-pyrimidine-2,4-diamine;
N4-Methyl-N2-[3-methyl-1-(2,2,2-trifluoro-ethyl)-1H-pyrazol-4-yl]-5-trifluoromethyl-pyrimidine-2,4-diamine;
5-Bromo-N2-(1-difluoromethyl-5-methyl-1H-pyrazol-4-yl)-N4-methyl-pyrimidine-2,4-diamine;
5-Bromo-N2-(1-difluoromethyl-3-methyl-1H-pyrazol-4-yl)-N4-methyl-pyrimidine-2,4-diamine;
5-Bromo-N2-(1,5-dimethyl-1H-pyrazol-4-yl)-N4-ethyl-pyrimidine-2,4-diamine;
5-Bromo-N2-[1-(4-fluoro-phenyl)-5-methyl-1H-pyrazol-4-yl]-N4-methyl-pyrimidine-2,4-diamine;
5-Bromo-N4-methyl-N2-(5-methyl-1-propyl-1H-pyrazol-4-yl)-pyrimidine-2,4-diamine;
5-Bromo-N2-[1-(4-chloro-phenyl)-3-methyl-1H-pyrazol-4-yl]-N4-methyl-pyrimidine-2,4-diamine;
N2-(1,5-Dimethyl-1H-pyrazol-4-yl)-N4-ethyl-5-trifluoromethyl-pyrimidine-2,4-diamine;
5-[4-(4-Ethylamino-5-trifluoromethyl-pyrimidin-2-ylamino)-3-methyl-pyrazol-1-yl]-piperidin-2-one;

4-[4-(4-Ethylamino-5-trifluoromethyl-pyrimidin-2-ylamino)-3-methyl-pyrazol-1-yl]-N,N-dimethyl-benzamide;
N2-[1-(4-Cyclopropanesulfonyl-phenyl)-3-methyl-1H-pyrazol-4-yl]-N4-ethyl-5-trifluoromethyl-pyrimidine-2,4-diamine;
4-[4-(4-Ethylamino-5-trifluoromethyl-pyrimidin-2-ylamino)-3-methyl-pyrazol-1-yl]-benzonitrile;
N4-Ethyl-N2-[1-(4-methanesulfonyl-phenyl)-3-methyl-1H-pyrazol-4-yl]-5-trifluoromethyl-pyrimidine-2,4-diamine;
1-{4-[4-(4-Ethylamino-5-trifluoromethyl-pyrimidin-2-ylamino)-5-methyl-pyrazol-1-yl]-piperidin-1-yl}-2-methyl-propan-1-one;
1-{4-[4-(4-Ethylamino-5-trifluoromethyl-pyrimidin-2-ylamino)-3-methyl-pyrazol-1-yl]-piperidin-1-yl}-2-methyl-propan-1-one;
N4-Methyl-N2-[3-methyl-1-(3-methyl-pyridin-4-yl)-1H-pyrazol-4-yl]-5-trifluoromethyl-pyrimidine-2,4-diamine;
N2-[1-((R)-2-Methoxy-propyl)-3-methyl-1H-pyrazol-4-yl]-N4-methyl-5-trifluoromethyl-pyrimidine-2,4-diamine;
N2-[1-(2,6-Dimethyl-tetrahydro-pyran-4-yl)-5-methyl-1H-pyrazol-4-yl]-N4-methyl-5-trifluoromethyl-pyrimidine-2,4-diamine;
N2-[1-(1,1-Dioxo-hexahydro-1$1%6&-thiopyran-4-yl)-3-methyl-1H-pyrazol-4-yl]-N4-methyl-5-trifluoromethyl-pyrimidine-2,4-diamine;
N2-[1-((R)-2-Methoxy-1-methyl-ethyl)-5-methyl-1H-pyrazol-4-yl]-N4-methyl-5-trifluoromethyl-pyrimidine-2,4-diamine;
N2-[1-((S)-2-Methoxy-1-methyl-ethyl)-3-methyl-1H-pyrazol-4-yl]-N4-methyl-5-trifluoromethyl-pyrimidine-2,4-diamine;
N4-Methyl-N2-[3-methyl-1-((S)-1-oxetan-3-yl-pyrrolidin-3-yl)-1H-pyrazol-4-yl]-5-trifluoromethyl-pyrimidine-2,4-diamine;
N4-Methyl-N2-[5-methyl-1-((S)-1-oxetan-3-yl-pyrrolidin-3-yl)-1H-pyrazol-4-yl]-5-trifluoromethyl-pyrimidine-2,4-diamine;
N2-[1-(1-Isopropyl-azetidin-3-yl)-5-methyl-1H-pyrazol-4-yl]-N4-methyl-5-trifluoromethyl-pyrimidine-2,4-diamine;
N4-Ethyl-N2-[5-methyl-1-(propane-2-sulfonyl)-1H-pyrazol-4-yl]-5-trifluoromethyl-pyrimidine-2,4-diamine;
N2-(5-Cyclobutyl-1-methyl-1H-pyrazol-4-yl)-N4-ethyl-5-trifluoromethyl-pyrimidine-2,4-diamine;
N2-(3-Cyclobutyl-1-methyl-1H-pyrazol-4-yl)-N4-ethyl-5-trifluoromethyl-pyrimidine-2,4-diamine;
N4-Ethyl-N2-{1-[1-(2-methoxy-ethyl)-piperidin-4-yl]-3-methyl-1H-pyrazol-4-yl}-5-trifluoromethyl-pyrimidine-2,4-diamine;
N4-Ethyl-N2-{1-[1-(2-methoxy-ethyl)-piperidin-4-yl]-5-methyl-1H-pyrazol-4-yl}-5-trifluoromethyl-pyrimidine-2,4-diamine;
N2-{1-[1-(2-Fluoro-ethyl)-piperidin-4-yl]-5-methyl-1H-pyrazol-4-yl}-N4-methyl-5-trifluoromethyl-pyrimidine-2,4-diamine;
N2-{1-[1-(2-Fluoro-ethyl)-piperidin-4-yl]-3-methyl-1H-pyrazol-4-yl}-N4-methyl-5-trifluoromethyl-pyrimidine-2,4-diamine;
N2-[5-Chloro-1-(3-fluoro-1-methyl-piperidin-4-yl)-1H-pyrazol-4-yl]-N4-methyl-5-trifluoromethyl-pyrimidine-2,4-diamine;
N2-(1-Ethanesulfonyl-5-methyl-1H-pyrazol-4-yl)-N4-methyl-5-trifluoromethyl-pyrimidine-2,4-diamine;
N4-Methyl-N2-[5-methyl-1-(2-methyl-2-morpholin-4-yl-propyl)-1H-pyrazol-4-yl]-5-trifluoromethyl-pyrimidine-2,4-diamine;
N4-Methyl-N2-(3-methyl-1-pyridin-3-ylmethyl-1H-pyrazol-4-yl)-5-trifluoromethyl-pyrimidine-2,4-diamine;
N2-(1-Cyclopropanesulfonyl-3-cyclopropyl-1H-pyrazol-4-yl)-N4-methyl-5-trifluoromethyl-pyrimidine-2,4-diamine;
N4-Methyl-N2-(5-methyl-1-pyridin-3-ylmethyl-1H-pyrazol-4-yl)-5-trifluoromethyl-pyrimidine-2,4-diamine;
(5-Chloro-4-methoxy-pyrimidin-2-yl)-{1-[1-(2-fluoro-ethyl)-piperidin-4-yl]-5-methyl-1H-pyrazol-4-yl}-amine;
N4-Methyl-N2-[3-methyl-1-(6-methyl-pyridin-2-ylmethyl)-1H-pyrazol-4-yl]-5-trifluoromethyl-pyrimidine-2,4-diamine;
N4-Ethyl-N2-[1-(2-methoxy-ethyl)-3-methyl-1H-pyrazol-4-yl]-5-trifluoromethyl-pyrimidine-2,4-diamine;
N4-Ethyl-N2-[1-(2-methoxy-ethyl)-5-methyl-1H-pyrazol-4-yl]-5-trifluoromethyl-pyrimidine-2,4-diamine;
1-[4-(4-Ethylamino-5-trifluoromethyl-pyrimidin-2-ylamino)-5-methyl-pyrazol-1-yl]-2-methyl-propan-2-ol;
1-[4-(4-Ethylamino-5-trifluoromethyl-pyrimidin-2-ylamino)-3-methyl-pyrazol-1-yl]-2-methyl-propan-2-ol;
N2-[1-(1,1-Dimethyl-2-morpholin-4-yl-ethyl)-3-methyl-1H-pyrazol-4-yl]-N4-ethyl-5-trifluoromethyl-pyrimidine-2,4-diamine;
N2-[1-(1,1-Dimethyl-2-morpholin-4-yl-ethyl)-3-methyl-1H-pyrazol-4-yl]-N4-methyl-5-trifluoromethyl-pyrimidine-2,4-diamine;
N4-Cyclopropyl-N2-(1-methanesulfonyl-3-methyl-1H-pyrazol-4-yl)-5-trifluoromethyl-pyrimidine-2,4-diamine;
N4-Cyclopropyl-N2-(1-methanesulfonyl-5-methyl-1H-pyrazol-4-yl)-5-trifluoromethyl-pyrimidine-2,4-diamine;
1-[3-Chloro-4-(4-methylamino-5-trifluoromethyl-pyrimidin-2-ylamino)-pyrazol-1-yl]-2-methyl-propan-2-ol;
2-[4-(4-Ethylamino-5-trifluoromethyl-pyrimidin-2-ylamino)-3-methyl-pyrazol-1-yl]-N-methyl-isobutyramide;
N4-Methyl-N2-(3-methyl-1-pyrimidin-2-ylmethyl-1H-pyrazol-4-yl)-5-trifluoromethyl-pyrimidine-2,4-diamine;
N2-[5-Chloro-1-(3-fluoro-1-oxetan-3-yl-piperidin-4-yl)-1H-pyrazol-4-yl]-N4-methyl-5-trifluoromethyl-pyrimidine-2,4-diamine;
N2-[5-Chloro-1-(3-fluoro-1-oxetan-3-yl-piperidin-4-yl)-1H-pyrazol-4-yl]-N4-ethyl-5-trifluoromethyl-pyrimidine-2,4-diamine;
N4-Ethyl-N2-[5-methyl-1-((S)-1-oxetan-3-yl-piperidin-3-yl)-1H-pyrazol-4-yl]-5-trifluoromethyl-pyrimidine-2,4-diamine;
N4-Ethyl-N2-[3-methyl-1-((S)-1-oxetan-3-yl-piperidin-3-yl)-1H-pyrazol-4-yl]-5-trifluoromethyl-pyrimidine-2,4-diamine;
N4-Methyl-N2-(5-methyl-1-pyridazin-3-ylmethyl-1H-pyrazol-4-yl)-5-trifluoromethyl-pyrimidine-2,4-diamine;

N4-Methyl-N2-(3-methyl-1-pyridazin-3-ylmethyl-1H-pyrazol-4-yl)-5-trifluoromethyl-pyrimidine-2,4-diamine;

N4-Ethyl-N2-[5-methyl-1-((S)-1-methyl-piperidin-3-yl)-1H-pyrazol-4-yl]-5-trifluoromethyl-pyrimidine-2,4-diamine;

N4-Ethyl-N2-[3-methyl-1-((S)-1-methyl-piperidin-3-yl)-1H-pyrazol-4-yl]-5-trifluoromethyl-pyrimidine-2,4-diamine;

3-[5-Chloro-4-(4-methylamino-5-trifluoromethyl-pyrimidin-2-ylamino)-pyrazol-1-yl]-2,2-dimethyl-propionitrile;

N4-Methyl-N2-[5-methyl-1-(6-methyl-pyridin-2-ylmethyl)-1H-pyrazol-4-yl]-5-trifluoromethyl-pyrimidine-2,4-diamine;

N4-Methyl-N2-(5-methyl-1-pyrimidin-2-ylmethyl-1H-pyrazol-4-yl)-5-trifluoromethyl-pyrimidine-2,4-diamine;

N4-Methyl-N2-(5-methyl-1-pyrazin-2-ylmethyl-1H-pyrazol-4-yl)-5-trifluoromethyl-pyrimidine-2,4-diamine;

N4-Methyl-N2-(3-methyl-1-pyrazin-2-ylmethyl-1H-pyrazol-4-yl)-5-trifluoromethyl-pyrimidine-2,4-diamine;

3-[5-Chloro-4-(4-ethylamino-5-trifluoromethyl-pyrimidin-2-ylamino)-pyrazol-1-yl]-2,2-dimethyl-propionitrile;

N4-Ethyl-N2-[1-(3-fluoro-1-oxetan-3-yl-piperidin-4-yl)-3-methyl-1H-pyrazol-4-yl]-5-trifluoromethyl-pyrimidine-2,4-diamine;

3-Methyl-1-[5-methyl-4-(4-methylamino-5-trifluoromethyl-pyrimidin-2-ylamino)-pyrazol-1-yl]-butan-2-ol;

3-Methyl-1-[3-methyl-4-(4-methylamino-5-trifluoromethyl-pyrimidin-2-ylamino)-pyrazol-1-yl]-butan-2-ol;

N2-[1-(1-[1,3]Dioxolan-2-ylmethyl-pyrrolidin-3-yl)-3-methyl-1H-pyrazol-4-yl]-N4-ethyl-5-trifluoromethyl-pyrimidine-2,4-diamine;

N4-Methyl-N2-(5-methyl-1-pyrimidin-4-ylmethyl-1H-pyrazol-4-yl)-5-trifluoromethyl-pyrimidine-2,4-diamine;

N4-Methyl-N2-[5-methyl-1-(1-methyl-1H-pyrazol-3-ylmethyl)-1H-pyrazol-4-yl]-5-trifluoromethyl-pyrimidine-2,4-diamine;

N4-Methyl-N2-[3-methyl-1-(1-methyl-1H-pyrazol-3-ylmethyl)-1H-pyrazol-4-yl]-5-trifluoromethyl-pyrimidine-2,4-diamine;

3-[3-Chloro-4-(4-methylamino-5-trifluoromethyl-pyrimidin-2-ylamino)-pyrazol-1-yl]-2,2-dimethyl-propionitrile;

N4-Ethyl-N2-{3-methyl-1-[1-methyl-1-(4H-[1,2,4]triazol-3-yl)-ethyl]-1H-pyrazol-4-yl}-5-trifluoromethyl-pyrimidine-2,4-diamine;

N2-[1-(1-[1,3]Dioxolan-2-ylmethyl-pyrrolidin-3-yl)-5-methyl-1H-pyrazol-4-yl]-N4-ethyl-5-trifluoromethyl-pyrimidine-2,4-diamine;

N4-Methyl-N2-(3-methyl-1-pyrimidin-4-ylmethyl-1H-pyrazol-4-yl)-5-trifluoromethyl-pyrimidine-2,4-diamine;

N2-(5-Fluoromethyl-1-methyl-1H-pyrazol-4-yl)-N4-methyl-5-trifluoromethyl-pyrimidine-2,4-diamine N4-Ethyl-N2-{3-methyl-1-[1-methyl-1-(5-methyl-4H-[1,2,4]triazol-3-yl)-ethyl]-1H-pyrazol-4-yl}-5-trifluoromethyl-pyrimidine-2,4-diamine;

N4-Methyl-N2-{3-methyl-1-[1-methyl-1-(4H-[1,2,4]triazol-3-yl)-ethyl]-1H-pyrazol-4-yl}-5-trifluoromethyl-pyrimidine-2,4-diamine;

N4-Ethyl-N2-[1-(3-fluoro-piperidin-4-yl)-3-methyl-1H-pyrazol-4-yl]-5-trifluoromethyl-pyrimidine-2,4-diamine;

2-[5-Methyl-4-(4-methylamino-5-trifluoromethyl-pyrimidin-2-ylamino)-pyrazol-1-yl]-cyclopentanol;

2-[3-Methyl-4-(4-methylamino-5-trifluoromethyl-pyrimidin-2-ylamino)-pyrazol-1-yl]-cyclopentanol;

N4-ethyl-N2-(3-methyl-1-(2-(5-methyl-1,3,4-oxadiazol-2-yl)propan-2-yl)-1H-pyrazol-4-yl)-5-(trifluoromethyl)pyrimidine-2,4-diamine;

N4-ethyl-N2-(3-methyl-1-(2-(4-methyl-4H-1,2,4-triazol-3-yl)propan-2-yl)-1H-pyrazol-4-yl)-5-(trifluoromethyl)pyrimidine-2,4-diamine;

N4-ethyl-N2-(3-methyl-1-(2-(1-methyl-1H-1,2,4-triazol-3-yl)propan-2-yl)-1H-pyrazol-4-yl)-5-(trifluoromethyl)pyrimidine-2,4-diamine;

N4-methyl-N2-(3-methyl-1-(2-(5-methyl-1,3,4-oxadiazol-2-yl)propan-2-yl)-1H-pyrazol-4-yl)-5-(trifluoromethyl)pyrimidine-2,4-diamine;

N4-methyl-N2-(3-methyl-1-(2-(1-methyl-1H-pyrazol-4-yl)propan-2-yl)-1H-pyrazol-4-yl)-5-(trifluoromethyl)pyrimidine-2,4-diamine;

N4-methyl-N2-(5-methyl-1-(2-(1-methyl-1H-pyrazol-4-yl)propan-2-yl)-1H-pyrazol-4-yl)-5-(trifluoromethyl)pyrimidine-2,4-diamine;

N4-ethyl-N2-(3-methyl-1-(2-(1-methyl-1H-pyrazol-3-yl)propan-2-yl)-1H-pyrazol-4-yl)-5-(trifluoromethyl)pyrimidine-2,4-diamine;

N4-ethyl-N2-(3-methyl-1-(2-(1-methyl-1H-pyrazol-5-yl)propan-2-yl)-1H-pyrazol-4-yl)-5-(trifluoromethyl)pyrimidine-2,4-diamine;

N4-methyl-N2-(3-methyl-1-(2-(1-methyl-1H-pyrazol-5-yl)propan-2-yl)-1H-pyrazol-4-yl)-5-(trifluoromethyl)pyrimidine-2,4-diamine;

N4-methyl-N2-(3-methyl-1-(2-(1-methyl-1H-pyrazol-3-yl)propan-2-yl)-1H-pyrazol-4-yl)-5-(trifluoromethyl)pyrimidine-2,4-diamine;

N2-(1',5-dimethyl-1'H-1,4'-bipyrazol-4-yl)-N4-methyl-5-(trifluoromethyl)pyrimidine-2,4-diamine;

N2-(1',3-dimethyl-1'H-1,4'-bipyrazol-4-yl)-N4-methyl-5-(trifluoromethyl)pyrimidine-2,4-diamine;

N2-(1-(2-(4H-1,2,4-triazol-3-yl)propan-2-yl)-3-methyl-1H-pyrazol-4-yl)-N4-methyl-5-(trifluoromethyl)pyrimidine-2,4-diamine;

2-(1,5-dimethyl-1H-pyrazol-4-ylamino)-4-(methylamino)pyrimidine-5-carbonitrile;

2-(1,3-Dimethyl-1H-pyrazol-4-ylamino)-4-methylamino-pyrimidine-5-carbonitrile;

2-(1-ethyl-5-methyl-1H-pyrazol-4-ylamino)-4-(methylamino)pyrimidine-5-carbonitrile;

2-(1-isopropyl-3-methyl-1H-pyrazol-4-ylamino)-4-(methylamino)pyrimidine-5-carbonitrile;

2-(1-ethyl-3-methyl-1H-pyrazol-4-ylamino)-4-(methylamino)pyrimidine-5-carbonitrile;

2-(3-methyl-1-phenyl-1H-pyrazol-4-ylamino)-4-(methylamino)pyrimidine-5-carbonitrile;

2-(3-methyl-1-(1-(2,2,2-trifluoroethyl)piperidin-4-yl)-1H-pyrazol-4-ylamino)-4-(methylamino)pyrimidine-5-carbonitrile;

2-(5-methyl-1-(1-(2,2,2-trifluoroethyl)piperidin-4-yl)-1H-pyrazol-4-ylamino)-4-(methylamino)pyrimidine-5-carbonitrile;

2-(1H-pyrazol-4-ylamino)-4-(methylamino)pyrimidine-5-carbonitrile;

2-(5-methyl-1-(2,2,2-trifluoroethyl)-1H-pyrazol-4-ylamino)-4-(methylamino)pyrimidine-5-carbonitrile;

2-(3-methyl-1-(2,2,2-trifluoro ethyl)-1H-pyrazol-4-ylamino)-4-(methylamino)pyrimidine-5-carbonitrile;
2-(5-methyl-1-phenyl-1H-pyrazol-4-ylamino)-4-(methylamino)pyrimidine-5-carbonitrile;
2-(5-methyl-1-(tetrahydro-2H-pyran-4-yl)-1H-pyrazol-4-ylamino)-4-(methylamino)pyrimidine-5-carbonitrile;
2-(3-methyl-1-(tetrahydro-2H-pyran-4-yl)-1H-pyrazol-4-ylamino)-4-(methylamino)pyrimidine-5-carbonitrile;
2-(1-ethyl-5-methyl-1H-pyrazol-4-ylamino)-4-(ethylamino)pyrimidine-5-carbonitrile;
2-(1-(4-fluorophenyl)-3-methyl-1H-pyrazol-4-ylamino)-4-(methylamino)pyrimidine-5-carbonitrile;
2-(1-(difluoromethyl)-3-methyl-1H-pyrazol-4-ylamino)-4-(methylamino)pyrimidine-5-carbonitrile;
2-(5-methyl-1-propyl-1H-pyrazol-4-ylamino)-4-(methylamino)pyrimidine-5-carbonitrile;
2-(1-(3,5-difluorophenyl)-3-methyl-1H-pyrazol-4-ylamino)-4-(methylamino)pyrimidine-5-carbonitrile;
2-(1-(4-chlorophenyl)-3-methyl-1H-pyrazol-4-ylamino)-4-(methylamino)pyrimidine-5-carbonitrile;
2-(1-(4-chlorophenyl)-5-methyl-1H-pyrazol-4-ylamino)-4-(methylamino)pyrimidine-5-carbonitrile;
2-(3-methyl-1-(pyridin-2-yl)-1H-pyrazol-4-ylamino)-4-(methylamino)pyrimidine-5-carbonitrile;
4-(ethylamino)-2-(5-methyl-1-(tetrahydro-2H-pyran-4-yl)-1H-pyrazol-4-ylamino)pyrimidine-5-carbonitrile;
4-(ethylamino)-2-(3-methyl-1-(tetrahydro-2H-pyran-4-yl)-1H-pyrazol-4-ylamino)pyrimidine-5-carbonitrile;
4-(ethylamino)-2-(3-methyl-1-(oxetan-3-yl)-1H-pyrazol-4-ylamino)pyrimidine-5-carbonitrile;
2-(1-isopropyl-5-methyl-1H-pyrazol-4-ylamino)-4-(methylamino)pyrimidine-5-carbonitrile;
2-(1,5-dimethyl-1H-pyrazol-4-ylamino)-4-methoxypyrimidine-5-carbonitrile;
2-(1,5-dimethyl-1H-pyrazol-4-ylamino)-4-(2,2,2-trifluoroethylamino)pyrimidine-5-carbonitrile;
2-(1-ethyl-5-methyl-1H-pyrazol-4-ylamino)-4-methoxypyrimidine-5-carbonitrile;
4-(2,2-difluoroethylamino)-2-(1,5-dimethyl-1H-pyrazol-4-ylamino)pyrimidine-5-carbonitrile;
2-(1,5-dimethyl-1H-pyrazol-4-ylamino)-4-(2,2,2-trifluoroethoxy)pyrimidine-5-carbonitrile;
2-(1-(cyclopropylmethyl)-3-methyl-1H-pyrazol-4-ylamino)-4-(methylamino)pyrimidine-5-carbonitrile;
2-(1-(4,4-difluorocyclohexyl)-5-methyl-1H-pyrazol-4-ylamino)-4-(methylamino) pyrimidine-5-carbonitrile;
2-(3-methyl-1-(oxetan-3-yl)-1H-pyrazol-4-ylamino)-4-(2,2,2-trifluoro ethylamino)pyrimidine-5-carbonitrile;
2-(5-chloro-1-(tetrahydro-2H-pyran-4-yl)-1H-pyrazol-4-ylamino)-4-(methylamino) pyrimidine-5-carbonitrile;
2-(1-Difluoromethyl-5-methyl-1H-pyrazol-4-ylamino)-4-methylamino-pyrimidine-5-carbonitrile;
2-(1,5-Dimethyl-1H-pyrazol-4-ylamino)-4-ethylamino-pyrimidine-5-carbonitrile
2-[1-(4-Fluoro-phenyl)-5-methyl-1H-pyrazol-4-ylamino]-4-methylamino-pyrimidine-5-carbonitrile;
4-Methylamino-2-(3-methyl-1-propyl-1H-pyrazol-4-ylamino)-pyrimidine-5-carbonitrile;
4-Methylamino-2-(5-methyl-1-oxetan-3-yl-1H-pyrazol-4-ylamino)-pyrimidine-5-carbonitrile;
4-Methylamino-2-(3-methyl-1-oxetan-3-yl-1H-pyrazol-4-ylamino)-pyrimidine-5-carbonitrile;
2-[1-(3,5-Difluoro-phenyl)-5-methyl-1H-pyrazol-4-ylamino]-4-methylamino-pyrimidine-5-carbonitrile;
4-(2,2-Difluoro-ethoxy)-2-(1,5-dimethyl-1H-pyrazol-4-ylamino)-pyrimidine-5-carbonitrile;
2-[1-(4,4-Difluoro-cyclohexyl)-3-methyl-1H-pyrazol-4-ylamino]-4-methylamino-pyrimidine-5-carbonitrile;
(5-(5-chloro-4-(methylamino)pyrimidin-2-ylamino)-1-methyl-1H-pyrazol-3-yl)(morpholino)methanone;
2-methyl-2-(3-methyl-4-(4-(methylamino)-5-(trifluoromethyl)pyrimidin-2-ylamino)-1H-pyrazol-1-yl)propanenitrile;
N,N-dimethyl-2-(5-methyl-4-(4-(methylamino)-5-(trifluoromethyl)pyrimidin-2-ylamino)-1H-pyrazol-1-yl)acetamide;
N,N-dimethyl-2-(3-methyl-4-(4-(methylamino)-5-(trifluoromethyl)pyrimidin-2-ylamino)-1H-pyrazol-1-yl)acetamide;
N-methyl-2-(3-methyl-4-(4-(methylamino)-5-(trifluoromethyl)pyrimidin-2-ylamino)-1H-pyrazol-1-yl)acetamide;
N-methyl-2-(5-methyl-4-(4-(methylamino)-5-(trifluoromethyl)pyrimidin-2-ylamino)-1H-pyrazol-1-yl)acetamide;
N,N,2-trimethyl-2-(5-methyl-4-(4-(methylamino)-5-(trifluoromethyl)pyrimidin-2-ylamino)-1H-pyrazol-1-yl)propanamide;
2-methyl-2-(5-methyl-4-(4-(methylamino)-5-(trifluoromethyl)pyrimidin-2-ylamino)-1H-pyrazol-1-yl)-1-(pyrrolidin-1-yl)propan-1-one;
2-methyl-2-(5-methyl-4-(4-(methylamino)-5-(trifluoromethyl)pyrimidin-2-ylamino)-1H-pyrazol-1-yl)propanenitrile;
1-(3-methyl-4-(4-(methylamino)-5-(trifluoromethyl)pyrimidin-2-ylamino)-1H-pyrazol-1-yl)cyclopropanecarbonitrile;
(R)-2-(3-methyl-4-(4-(methylamino)-5-(trifluoromethyl)pyrimidin-2-ylamino)-1H-pyrazol-1-yl)-1-(pyrrolidin-1-yl)propan-1-one;
(R)—N,N-dimethyl-2-(3-methyl-4-(4-(methylamino)-5-(trifluoromethyl)pyrimidin-2-ylamino)-1H-pyrazol-1-yl)propanamide;
(S)-2-(3-methyl-4-(4-(methylamino)-5-(trifluoromethyl)pyrimidin-2-ylamino)-1H-pyrazol-1-yl)-1-(pyrrolidin-1-yl)propan-1-one;
3-(5-methyl-4-(4-(methylamino)-5-(trifluoromethyl)pyrimidin-2-ylamino)-1H-pyrazol-1-yl)propanenitrile;
3-(3-methyl-4-(4-(methylamino)-5-(trifluoromethyl)pyrimidin-2-ylamino)-1H-pyrazol-1-yl)propanenitrile;
methyl 2-methyl-2-(3-methyl-4-(4-(methylamino)-5-(trifluoromethyl)pyrimidin-2-ylamino)-1H-pyrazol-1-yl)propanoate;
methyl 2-methyl-2-(5-methyl-4-(4-(methylamino)-5-(trifluoromethyl)pyrimidin-2-ylamino)-1H-pyrazol-1-yl)propanoate;
2-(3-ethyl-4-(4-(methylamino)-5-(trifluoromethyl)pyrimidin-2-ylamino)-1H-pyrazol-1-yl)-2-methylpropanenitrile;
(R)-2-(5-methyl-4-(4-(methylamino)-5-(trifluoromethyl)pyrimidin-2-ylamino)-1H-pyrazol-1-yl)-1-(pyrrolidin-1-yl)propan-1-one;
(R)—N,N-dimethyl-2-(5-methyl-4-(4-(methylamino)-5-(trifluoromethyl)pyrimidin-2-ylamino)-1H-pyrazol-1-yl)propanamide;
(S)-2-(5-methyl-4-(4-(methylamino)-5-(trifluoromethyl)pyrimidin-2-ylamino)-1H-pyrazol-1-yl)-1-(pyrrolidin-1-yl)propan-1-one;
(S)—N,N-dimethyl-2-(5-methyl-4-(4-(methylamino)-5-(trifluoromethyl)pyrimidin-2-ylamino)-1H-pyrazol-1-yl)propanamide;
(S)-2-(5-methyl-4-(4-(methylamino)-5-(trifluoromethyl)pyrimidin-2-ylamino)-1H-pyrazol-1-yl)propanenitrile;

(S)-2-(3-methyl-4-(4-(methylamino)-5-(trifluoromethyl) pyrimidin-2-ylamino)-1H-pyrazol-1-yl)propanenitrile;
2-(4-(5-chloro-4-(methylamino)pyrimidin-2-ylamino)-3-methyl-1H-pyrazol-1-yl)-2-methylpropanenitrile;
2-(5-chloro-4-(4-(methylamino)-5-(trifluoromethyl)pyrimidin-2-ylamino)-1H-pyrazol-1-yl)-2-methylpropanenitrile;
2-(3-cyclopropyl-4-(4-(methylamino)-5-(trifluoromethyl) pyrimidin-2-ylamino)-1H-pyrazol-1-yl)-2-methylpropanenitrile;
2,2-dimethyl-3-(3-methyl-4-(4-(methylamino)-5-(trifluoromethyl)pyrimidin-2-ylamino)-1H-pyrazol-1-yl)propanenitrile;
2,2-dimethyl-3-(5-methyl-4-(4-(methylamino)-5-(trifluoromethyl)pyrimidin-2-ylamino)-1H-pyrazol-1-yl)propanenitrile;
1-(5-chloro-4-(4-(methylamino)-5-(trifluoromethyl)pyrimidin-2-ylamino)-1H-pyrazol-1-yl)cyclopropanecarbonitrile;
N-tert-butyl-2-methyl-2-(3-methyl-4-(4-(methylamino)-5-(trifluoromethyl)pyrimidin-2-ylamino)-1H-pyrazol-1-yl)propanamide;
2-methyl-2-(3-methyl-4-(4-(methylamino)-5-(trifluoromethyl)pyrimidin-2-ylamino)-1H-pyrazol-1-yl)-N-(2,2,2-trifluoroethyl)propanamide;
2-(5-chloro-4-(4-(methylamino)-5-(trifluoromethyl)pyrimidin-2-ylamino)-1H-pyrazol-1-yl)-N-ethyl-2-methylpropanamide;
N-(cyclopropylmethyl)-2-methyl-2-(5-methyl-4-(4-(methylamino)-5-(trifluoromethyl)pyrimidin-2-ylamino)-1H-pyrazol-1-yl)propanamide;
N-(cyclopropylmethyl)-2-methyl-2-(3-methyl-4-(4-(methylamino)-5-(trifluoromethyl)pyrimidin-2-ylamino)-1H-pyrazol-1-yl)propanamide;
N-ethyl-1-(3-methyl-4-(4-(methylamino)-5-(trifluoromethyl)pyrimidin-2-ylamino)-1H-pyrazol-1-yl)cyclobutanecarboxamide;
N-isopropyl-2-methyl-2-(5-methyl-4-(4-(methylamino)-5-(trifluoromethyl)pyrimidin-2-ylamino)-1H-pyrazol-1-yl)propanamide;
1-(3-methyl-4-(4-(methylamino)-5-(trifluoromethyl)pyrimidin-2-ylamino)-1H-pyrazol-1-yl)cyclobutanecarbonitrile;
2-(4-(4-(cyclopropylamino)-5-(trifluoromethyl)pyrimidin-2-ylamino)-3-methyl-1H-pyrazol-1-yl)-2-methyl-propanenitrile;
N,2-dimethyl-2-(3-methyl-4-(4-(methylamino)-5-(trifluoromethyl)pyrimidin-2-ylamino)-1H-pyrazol-1-yl) propanamide;
1-(5-chloro-4-(4-(methylamino)-5-(trifluoromethyl)pyrimidin-2-ylamino)-1H-pyrazol-1-yl)cyclopropanecarbonitrile;
2-[4-(5-Chloro-4-methoxy-pyrimidin-2-ylamino)-5-methyl-pyrazol-1-yl]-2-methyl-propionic acid methyl ester;
2-[4-(5-Chloro-4-methoxy-pyrimidin-2-ylamino)-3-methyl-pyrazol-1-yl]-2-methyl-propionic acid methyl ester;
(S)—N,N-Dimethyl-2-[3-methyl-4-(4-methylamino-5-trifluoromethyl-pyrimidin-2-ylamino)-pyrazol-1-yl]-propionamide;
R)-2-[3-Methyl-4-(4-methylamino-5-trifluoromethyl-pyrimidin-2-ylamino)-pyrazol-1-yl]-propionitrile;
2-[4-(5-Chloro-4-methoxy-pyrimidin-2-ylamino)-3-cyclopropyl-pyrazol-1-yl]-2-methyl-propionitrile;
(R)-2-[5-Methyl-4-(4-methylamino-5-trifluoromethyl-pyrimidin-2-ylamino)-pyrazol-1-yl]-propionitrile;
N-Ethyl-2-[3-methyl-4-(4-methylamino-5-trifluoromethyl-pyrimidin-2-ylamino)-pyrazol-1-yl]-isobutyramide;
N-Ethyl-2-[5-methyl-4-(4-methylamino-5-trifluoromethyl-pyrimidin-2-ylamino)-pyrazol-1-yl]-isobutyramide;
1-[5-Methyl-4-(4-methylamino-5-trifluoromethyl-pyrimidin-2-ylamino)-pyrazol-1-yl]-cyclobutanecarboxylic acid ethylamide;
2-[5-Methyl-4-(4-methylamino-5-trifluoromethyl-pyrimidin-2-ylamino)-pyrazol-1-yl]-N-(2,2,2-trifluoroethyl)-isobutyramide;
N-Isopropyl-2-[3-methyl-4-(4-methylamino-5-trifluoromethyl-pyrimidin-2-ylamino)-pyrazol-1-yl]-isobutyramide;
N-Methyl-2-[5-methyl-4-(4-methylamino-5-trifluoromethyl-pyrimidin-2-ylamino)-pyrazol-1-yl]-isobutyramide;
1-[5-Methyl-4-(4-methylamino-5-trifluoromethyl-pyrimidin-2-ylamino)-pyrazol-1-yl]-cyclobutanecarbonitrile;
N-tert-Butyl-2-[5-methyl-4-(4-methylamino-5-trifluoromethyl-pyrimidin-2-ylamino)-pyrazol-1-yl]-isobutyramide;
2-[4-(4-Ethylamino-5-trifluoromethyl-pyrimidin-2-ylamino)-5-methyl-pyrazol-1-yl]-N-methyl-isobutyramide;
2-[4-(4-Cyclopropylamino-5-trifluoromethyl-pyrimidin-2-ylamino)-3-methyl-pyrazol-1-yl]-N-methyl-isobutyramide;
2-[4-(4-Cyclopropylamino-5-trifluoromethyl-pyrimidin-2-ylamino)-5-methyl-pyrazol-1-yl]-N-methyl-isobutyramide;
2-[4-(4-Ethylamino-5-trifluoromethyl-pyrimidin-2-ylamino)-3-methyl-pyrazol-1-yl]-2-methyl-propionitrile;
2-(3-chloro-4-(4-(methylamino)-5-(trifluoromethyl)pyrimidin-2-ylamino)-1H-pyrazol-1-yl)-2-methylpropanenitrile; and
2-[4-(4-Ethylamino-5-trifluoromethyl-pyrimidin-2-ylamino)-3-methyl-pyrazol-1-yl]-N-methyl-isobutyramide.

19. The compound N2-[5-chloro-1-(3-fluoro-1-oxetan-3-yl-piperidin-4-yl)-1H-pyrazol-4-yl]-N4-methyl-5-trifluoromethyl-pyrimidine-2,4-diamine, or a pharmaceutical salt thereof.

20. The compound 2-methyl-2-(3-methyl-4-(4-(methylamino)-5-(trifluoromethyl)pyrimidin-2-ylamino)-1H-pyrazol-1-yl)propanenitrile, or a pharmaceutical salt thereof.

21. The compound of claim 15, wherein $R^5$ is hydrogen, and $R^3$ is: $C_{1-6}$alkyl; halo-$C_{1-6}$alkyl; hydroxy-$C_{1-6}$alkyl; cyano-$C_{1-6}$alkyl; $C_{3-6}$cycloalkyl; $C_{3-6}$cycloalkyl-$C_{1-6}$alkyl; heterocyclyl optionally substituted one or more times with $R^7$; or heterocyclyl-$C_{1-6}$alkyl wherein the heterocyclyl portion is optionally substituted one or more times with $R^7$, wherein the heterocyclyl is piperidinyl, pyrrolidinyl, oxetanyl, tetrahydropyranyl, tetrahydrofuranyl, azetidinyl, [1,3] dioxolanyl or tetrahydrothiopyranyl.

22. The compound of claim 21, wherein $R^3$ is cyano-$C_{1-6}$alkyl.

* * * * *